US011253600B2

(12) United States Patent
Mejia Oneto et al.

(10) Patent No.: US 11,253,600 B2
(45) Date of Patent: Feb. 22, 2022

(54) BIOORTHOGONAL COMPOSITIONS

(71) Applicants: TAMBO, INC., San Francisco, CA (US); THE RESEARCH FOUNDATION FOR THE STATE UNIVERSITY OF NEW YORK, Albany, NY (US)

(72) Inventors: Jose Manuel Mejia Oneto, San Francisco, CA (US); Nathan Yee, San Francisco, CA (US); Maksim Royzen, San Francisco, CA (US); Sangeetha Srinivasan, San Francisco, CA (US); Ethan Miller, San Francisco, CA (US)

(73) Assignees: TAMBO, INC., San Francisco, CA (US); THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 138 days.

(21) Appl. No.: 16/603,471

(22) PCT Filed: Apr. 6, 2018

(86) PCT No.: PCT/US2018/026551
§ 371 (c)(1),
(2) Date: Oct. 7, 2019

(87) PCT Pub. No.: WO2018/187740
PCT Pub. Date: Oct. 11, 2018

(65) Prior Publication Data
US 2021/0128733 A1    May 6, 2021

Related U.S. Application Data

(60) Provisional application No. 62/626,978, filed on Feb. 6, 2018, provisional application No. 62/623,329, filed on Jan. 29, 2018, provisional application No. 62/623,245, filed on Jan. 29, 2018, provisional application No. 62/609,943, filed on Dec. 22, 2017, provisional application No. 62/568,586, filed on Oct. 5, 2017, provisional application No. 62/515,948, filed on Jun. 6, 2017, provisional application No. 62/507,973, filed on May 18, 2017, provisional application No. 62/483,163, filed on Apr. 7, 2017, provisional application No. 62/483,121, filed on Apr. 7, 2017, provisional application No. 62/483,081, filed on Apr. 7, 2017.

(51) Int. Cl.
| A61K 47/61 | (2017.01) |
| A61P 35/00 | (2006.01) |
| A61K 49/00 | (2006.01) |
| A61K 47/54 | (2017.01) |
| A61P 31/04 | (2006.01) |
| A61K 45/06 | (2006.01) |

(52) U.S. Cl.
CPC ............ *A61K 47/545* (2017.08); *A61K 45/06* (2013.01); *A61K 47/542* (2017.08); *A61K 47/61* (2017.08); *A61K 49/0041* (2013.01); *A61K 49/0043* (2013.01); *A61K 49/0052* (2013.01); *A61K 49/0054* (2013.01); *A61P 31/04* (2018.01); *A61P 35/00* (2018.01)

(58) Field of Classification Search
CPC ...... A61K 47/61; A61K 47/545; A61K 49/00; A61P 35/00; A61P 31/04
See application file for complete search history.

(56) References Cited

U.S. PATENT DOCUMENTS

| 5,770,229 A | 6/1998 | Tanihara et al. |
| 8,552,183 B2 | 10/2013 | Wiessler et al. |
| 9,421,274 B2 | 8/2016 | Robillard et al. |
| 9,427,482 B2 | 8/2016 | Rossin et al. |
| 9,463,256 B2 | 10/2016 | Lub et al. |
| 10,130,711 B2 | 11/2018 | Mejia Oneto et al. |
| 10,130,723 B2 | 11/2018 | Mejia Oneto et al. |
| 10,342,882 B2 | 7/2019 | Mejia Oneto et al. |
| 2005/0014197 A1 | 1/2005 | Agnew et al. |
| 2006/0153893 A1 | 7/2006 | Matsuno et al. |
| 2009/0023916 A1 | 1/2009 | Fox et al. |

(Continued)

FOREIGN PATENT DOCUMENTS

| EP | 1867638 A1 | 12/2007 |
| EP | 2716662 A1 | 4/2014 |

(Continued)

OTHER PUBLICATIONS

Raffaello Rossin et al., Triggered Drug Release from an Antibody-Drug Conjugate Using Fast "Click-to-Release" Chemistry in Mice, Bioconjugate Chemistry, 27, 1697-1706. (Year: 2016).*
Pretze et al., "Recent Trends in Bioorthogonal Click-Radiolabeling Reactions Using Fluorine-18," Molecules, vol. 18, 2013, pp. 8618-8665; doi:10.3390/molecules18078618.
Reiner et al., "The inverse electron demand Diels-Alder click reaction in radiochemistry," J. Labelled Comp. Radiopharm., 2014, vol. 57, No. 4, pp. 285-290.
Rohatagi et al., "Pharmacokinetic and Pharmacodynamic Evaluation of Triamcinolone Acetonide After Intravenous, Oral, and Inhaled Administration," J. Clin. Pharmacol., 1995, 35: 1187-1193.

(Continued)

*Primary Examiner* — Michael G. Hartley
*Assistant Examiner* — Jagadishwar R Samala
(74) *Attorney, Agent, or Firm* — Michael Best & Friedrich LLP

(57) ABSTRACT

Cyclooctene conjugates of therapeutic or diagnostic agents have improved aqueous solubility and can release the agents upon contact with a tetrazine-containing biomaterial. The cyclooctene conjugates provide site-selective delivery of agents at the location of the tetrazine-containing biomaterial in a subject. The compositions and methods have applications in the treatment of various diseases or conditions including cancer, tumor growths, and bacterial infections.

27 Claims, 46 Drawing Sheets

(56) References Cited

U.S. PATENT DOCUMENTS

| | | |
|---|---|---|
| 2009/0304587 A1 | 12/2009 | Rubinstein et al. |
| 2010/0016545 A1 | 1/2010 | Wiessler et al. |
| 2010/0028435 A1 | 2/2010 | Gavard Molliard |
| 2011/0223257 A1 | 9/2011 | Zhao et al. |
| 2011/0268654 A1 | 11/2011 | Hilderbrand et al. |
| 2012/0034161 A1 | 2/2012 | Robillard et al. |
| 2012/0076727 A1 | 3/2012 | McBride et al. |
| 2013/0281644 A1 | 10/2013 | Kiessling et al. |
| 2013/0302246 A1 | 11/2013 | Hilderbrand et al. |
| 2014/0093450 A1 | 4/2014 | Robillard et al. |
| 2014/0199331 A1 | 7/2014 | Robillard et al. |
| 2014/0303123 A1 | 10/2014 | Baker, Jr. et al. |
| 2015/0037359 A1 | 2/2015 | Schellenberger et al. |
| 2016/0114046 A1 | 4/2016 | Brudno et al. |

FOREIGN PATENT DOCUMENTS

| | | |
|---|---|---|
| EP | 2719400 A2 | 4/2014 |
| JP | 2009513696 A | 4/2009 |
| JP | 2010036032 A | 2/2010 |
| WO | 53000708 A1 | 1/2003 |
| WO | 53084571 A1 | 10/2003 |
| WO | 2010051530 A2 | 5/2010 |
| WO | 2011127149 A1 | 10/2011 |
| WO | 2012012612 A2 | 1/2012 |
| WO | 2012049624 A1 | 4/2012 |
| WO | 2012074840 A2 | 6/2012 |
| WO | 2012085789 A1 | 6/2012 |
| WO | 2012153254 A1 | 11/2012 |
| WO | 2012156918 A1 | 11/2012 |
| WO | 2012156919 A1 | 11/2012 |
| WO | 2012156920 A1 | 11/2012 |
| WO | 2012165462 A1 | 12/2012 |
| WO | 2012168512 A2 | 12/2012 |
| WO | 2013187954 A1 | 12/2013 |
| WO | 2014065860 A1 | 5/2014 |
| WO | 2014081299 A1 | 5/2014 |
| WO | 2014081300 A1 | 5/2014 |
| WO | 2014081301 A1 | 5/2014 |
| WO | 2014081303 A1 | 5/2014 |
| WO | 2014117001 A1 | 7/2014 |
| WO | 2014134689 A1 | 9/2014 |
| WO | 2014138186 A1 | 9/2014 |
| WO | 2014200767 A1 | 12/2014 |
| WO | 2014205126 A1 | 12/2014 |
| WO | 2015117235 A1 | 8/2015 |
| WO | 2015139025 A1 | 9/2015 |
| WO | 2015154082 A1 | 10/2015 |
| WO | 2017044983 A1 | 3/2017 |

OTHER PUBLICATIONS

Rossin et al., "Chemically triggered drug release from an antibody-drug conjugate leads to potent antitumour activity in mice," Nat Commun, 2018, 9:1484, Supplementary Information Included, 120 pages.

Rossin et al., "In Vivo Chemistry for Pretargeted Tumor Imagining in Live Mice," Angew. Chem. Int. Ed., vol. 49, pp. 3375-3378 (2010) Supporting Information Sections S1-S6, pp. S2-S21.

Royzen et al., "A Photochemical Synthesis of Functionalized trans-Cyclooctenes Driven by Metal Complexation," J. Am. Chem. Soc., vol. 130, pp. 3760-3761 (2008).

Seif-Naraghi et al., "Safety and Efficacy of an Injectable Extracellular Matrix Hydrogel for Treating Myocardial Infarction," Science Translation Medicine, 2013, vol. 5, Issue 173, 10 pages.

Selvaraj et al., "Tetrazine-tans-cyclooctene ligation for the rapid construction of integrin αvβ3 targeted PET tracer based on a cyclic RGD peptide," Bioorg. Med. Chem. Lett., 2011; 21 (17), pp. 5011-5014; doi:10.1016/j.omcl.2011.04.116.

Selvaraj et al., "trans-Cyclooctene—a stable, voracious dienophile for bioorthogonal labeling", Current Opinion in Chemical Biology, vol. 17, Issue 5, 2013, pp. 753-760; doi: 10.1016/j.cbpa.2013.07.031.

Shelke et al., "Polysaccharide biomaterials for drug delivery and regenerative engineering," Polym. Adv. Technol., 2014, vol. 25, pp. 448-460; DOI: 10.1002/pat.3266.

Sluyterman et al., "Chromatofocusing: a preparative protein separation method," TIBS, 1982, pp. 168-170.

Thalhammer et al., "Reaktivitat Einfacher Offenkettiger Und Cyclischer Dienophile Bei Diels-Alder-Reaktionen Mit Inversem Elektronenbedarf," Tetrahedron Letters, 1990, vol. 31, No. 47, pp. 3851-6854.

Thomas et al., "Polyvalent Dendrimer-Methotrexate as a Folate Receptor-Targeted Cancer Therapeutic" Molecular Pharmaceutics, 2012, vol. 9 pp. 2669-2676.

Tjwa, "Budesonide inhaled via Turbuhaler: a more effective treatment for asthma than beclomethasone dipropionate via Rotahaler," Ann. Allergy Asthma Immunol, 1995, 75(2): 107-111.

Triton et al., "The anticancer agent adriamycin can be actively cytotoxic without entering cells," Science, 1982, 217(4556):248-250.

Verbeke et al., "Multicomponent Injectable Hydrogels for Antigen-Specific Tolerogenic Immune Modulation," Adv Healthc Mater, 2017, 6 (6), 34 pages.

Versteegen et al., "Click to Release: Instantaneous Doxorubicin Elimination upon Tetrazine Ligation," Angew. Chem. Int. Ed., 2013, vol. 52, pp. 14112-14116.

Versteegen et al., "Click-to-Release from trans-Cyclooctenes: Mechanistic Insights and Expansion of Scope from Established Carbamate to Remarkable Ether Cleavage," Angew. Chem. Int. Ed., 2018, 57:10494-10499.

Zeglis et al., "Modular Strategy for the Construction of Radiometalated Antibodies for Positron Emission Tomography Based on Inverse Electron Demand Diels-Alder Click Chemistry," Bioconjugate Chemistry, 2011, vol. 22, pp. 2048-2059.

Zeglis et al., "Building Blocks for the Construction of Bioorthogonally Reactive Peptides via Solid-Phase Peptide Synthesis," Chemistry Open Communications, 2014, vol. 3, pp. 48-53, DOI: 10.1002/open.201402000.

Zeglis et al., "A Pretargeted PET Imaging Strategy Based on Bioorthogonal Diels-Alder Click Chemistry," J. Nucl. Med., 2013, vol. 54, No. 8, pp. 1389-1396.

Zhang et al., "An ionically crosslinked hydrogel containing vancomycin coating on a porous scaffold for drug delivery and cell culture," International Journal of Pharmaceutics, 2008, vol. 353, pp. 74 87.

Rossin et al., Supplementary Information for "Tetrazine-triggered drug release from an antibody-drug conjugate leads to potent antitumour activity in mice," Nat Commun, 2018, 109 pages.

Jose M. Mejia Oneto et al.: In Vivo Bioorthogonal Chemistry Enables Local Hydrogel and Systemic Pro-Drug to Treat Soft Tissue Sarcoma11, ACS Central Science, vol. 2, No. 7, Jul. 13, 2016 (Jul. 13, 2016), pp. 476-482.

Guo Hua et al: "Functional alginate nanoparticles for efficient intracellular release of doxorubicin and hepatoma carcinoma cell targeting therapy", International Journal of Pharmaceutics, Els ev i er, N L, vol. 451, No. 1, Apr. 22, 2013 (Apr. 22, 2013), pp. 1-11.

Extended European Search Report from the European Patent Office for Application No. 16845300.9 dated Apr. 17, 2019 (13 pages).

Raffaella Rossin et al., "Highly Reactive trans-Cyclooctene Tags with Improved Stability for Diels-Alder Chemistry in Living Systems", Bioconjugate Chemistry, vol. 24, No. 7, Jul. 17, 2013, pp. 1210-1217.

Blackman M L et al., "Tetrazine ligation: Fast bioconjugation based on inverse-electron-demand Diels-Alder reactivity", Journal of the American Chemical Society, American Chemical Society, US, vol. 130, No. 41, Oct. 15, 2008 (Oct. 15, 2008), pp. 13518-13519.

Raffaella Rossin et al., "Triggered Drug Release from an Antibody-Drug Conjugate Using Fast "Click-to-Release" Chemistry in Mice", 2016, Bioconjugate Chemistry, vol. 27, pp. 1697-1706, Tagworks Pharmaceuticals, High Tech Campus 11, 5656 AE Eindhoven, The Netherlands.

International Search Report and Written Opinion for Application No. PCT/US2018/026551 dated Jul. 19, 2018 (10 pages).

International Preliminary Reporton Patentability for Application No. PCT/US2018/026551 dated Oct. 8, 2019 (7 pages).

(56) References Cited

OTHER PUBLICATIONS

Al-Dubai et al., "Biocompatible medical implant materials with binding sites for a biodegradable drug-delivery system," Nanotechnology, Science and AQQlications, vol. 2011, No. 4, pp. 87-94 (2011).

Alge et al., "Synthetically tractable click hydrogels for three-dimensional cell culture formed using tetrazine-norbomene chemistry," Biomacromolecules, 2013, 14(4):949-953.

Altin et al., "Fabrication of "Clickable" Hydrogels via Dendron-Polymer Conjugates," Macromolecules, 2010, vol. 43, No. 8, pp. 3801-3808.

Antoci et al., "The inhibition of Staphylococcus epidermidis biofilm formation by vancomycin-modified titanium alloy and implications for the treatment of periprosthetic infection," Biomaterials, vol. 29, pp. 4684-4690 (2008).

Berge et al., "Pharmaceutical Salts," J. Pharm. Sci., 1977, vol. 66, pp. 1-19.

Brudno et al., "In Vivo Targeting through Click Chemistry," Chem. Med. Chem., 2015, vol. 10, pp. 617-620.

Brudno et al., "On-demand drug delivery from local depots," J. Control. Release, 2015, http://dx.doi.org/10.1016/j.conrel.2015.09.011, 10 pages.

Brudno et al., "Refilling drug delivery depots through the blood," PNAS, 2014, 111(35): 12722-12727.

Brudno et al., "Replenishable drug depot to combat post-resection cancer recurrence," Biomaterials, 2018, 178:373-382.

Burdick et al., "Acellular Biomaterials: An Evolving Alternative to Cell-Based Therapies," Science Translation Medicine, Mar. 13, 2013, vol. 5, Issue 176, 4 pages.

Carlson et al., "Unraveling Tetrazine-Triggered Bioorthogonal Elimination Enables Chemical Tools for Ultrafast Release and Universal Cleavage," J Am. Chem. Soc, 2018, 140(10):3603-3612.

Chung et al., "Ubiquitous Detection of Gram-Positive Bacteria with Bioorthogonal Magnetofluorescent Nanoparticles," ACS Nano, 2011, vol. 5, No. 11, pp. 8834 8841, Supporting Documentation Included.

Cok et al., "Synthesis of Model Network Hydrogels via Tetrazine-Olefin Inverse Electron Demand Diels-Alder Cycloaddition," Macromol Symp, 2013, 329:108-112.

Coviello et al., "Polysaccharide hydrogels for modified release formulations," Journal of Controlled Release, 2007, vol. 119, pp. 5-24.

Deforest et al., "Sequential click reactions for synthesizing and patterning three-dimensional cell microenvironments," Nature materials: Letters, 2009, vol. 8, pp. 659-664.

Desai et al., "Versatile click alginate hydrogels crosslinked via tetrazine-norbornene chemistry," Biomaterials, 2015, vol. 50, pp. 30-37.

Devaraj et al., "Fast and Sensitive Pretargeted Labeling of Cancer Cells through a Tetrazine/trans-Cyclooctene Cycloaddition," Angew. Chem. Int. Ed., 2009, vol. 48, pp. 7013-7016.

Devaraj et al., "Reactive polymer enables efficient in vivo bioorthogonal chemistry," PNAS, 2012, vol. 109, No. 13, pp. 4762-4767.

Eckhouse et al., "Local Hydrogel Release of Recombinant TIMP-3 Attenuates Adverse Left Ventricular Remodeling After Experimental Myocardial Infarction," Science Translation Medicine, 2014, vol. 6, Issue 223, 10 pages.

Eschenhagen et al., "Physiological aspects of cardiac tissue engineering," Am. J. Physiol. Heart Circ. Physiol., vol. 30, 2012, pp. H133-H143.

European Application No. 14813532.0, Extended European Search Report dated Dec. 2, 2016, 9 pages.

Extended European Search Report dated Aug. 10, 2017, for EP Application No. 15761367.0, filed Aug. 10, 2017, 12 pages.

Godoy et al., "Enhanced activity of an immobilized lipase promoted by site-directed chemical modification with polymers," Process Biochemistry, 2010, 45(4):534-541.

Hashida et al., "Timed-Release of Mitomycin C from Its Agarose Bead Conjugate," Chem Pharm Bull, 1977, 25:2456-2458.

Hofmann et al., "Targeted delivery of vancomycin to Staphylococcus epidermidis biofilms using a fibrinogen-derived peptide," J Biomed Mater Res A, 2012, 100(9):2517-2525.

Hu et al., "Mitochondria-Targeted Cancer Therapy Using a Light-Up Probe with Aggregation-Induced-Emission Characteristics," Angew. Chem. Int. Ed., 2014, 53:14225-14229.

International Application No. PCT/US2015/020718, "International Search Report and Written Opinion", dated Jun. 10, 2015, 8 pages.

International Search Report and Written Opinion for Application No. PCT/US2016/051394 dated Feb. 16, 2017 (21 pages).

International Search Report and Written Opinion for International Application No. PCT/US2014/043020 dated Oct. 6, 2014 (9 pages).

IUPAC 1974 Recommendations for Section E, Fundamental Stereochemistry, in Pure Appl. Chem., 1976, 45: 13-30.

Kharkar et al., "Designing degradable hydrogels for orthogonal control of cell microenvironments," Chem. Soc. Rev., vol. 42, No. 17, pp. 7335-7372 (2013).

Kojima et al., "Antitumor activity of timed-release derivative of mitomycin C, agarose bead conjugate," Chem Pharm Bull, 1978, 26(6): 1818-1824.

Koo et al., "Bioorthogonal Copper-Free Click Chemistry In Vivo for Tumor-Targeted Delivery of Nanoparticles," Angew. Chem. Int. Ed., 2012, vol. 51, pp. 11836-11840.

Korpela et al., "A simple method to introduce aldehydic function to agarose," Anal Biochem, 1976, 71 (1):322-323.

Koshy et al., "Click-Crosslinked Injectable Gelatin Hydrogels," Advanced Healthcare Materials, 2016, DOI: 10.1002/adhm.201500757, 7 pages.

Landa et al., "Effect of Injectable Alginate Implant on Cardiac Remodeling and Function After Recent and Old Infarcts in Rat," Circulation, 2008, vol. 117, pp. 1388-1396.

Li et al., "Designing hydrogels for controlled drug delivery," Nature Reviews Materials, 2016, 1(12): 38 pages.

Li et al., "Diels-Alder reaction-triggered bioorthogonal protein decaging in living cells," Natural Chemical Biology, Advanced Online Publication, 2014, vol. 10, 5 pages.

Li et al., "Monodispersed PEG-DOTA Conjugated Anti-Tag-72 Diabody Has Low Kidney Uptake and High Tumor to Blood Ratios Resulting in Inproved 64Cu PET Imaging," J. Nucl. Med., 2010, vol. 51, No. 7, pp. 1139-1146.

Lueckgen et al., "Hydrolytically-degradable click-crosslinked alginate hydrogels," Biomaterials, 2018, 181: 189-198.

Matikonda et al., "Bioorthogonal prodrug activation driven by a strain-promoted 1,3-dipolar cycloaddition," Chem. Sci., 2015, vol. 6, pp. 1212-1218.

Mejia Oneto et al., "Implantable biomaterial based on click chemistry for targeting small molecules," Acta Biomaterialia, 2014, vol. 10, pp. 5099-5105.

Neves et al., "Imaging Cell Surface Glycosylation in Vivo Using "Double Click" Chemistry," Bioconjugate Chem., May 5, 2013, vol. 24, pp. 934-941.

Niska et al., "Vancomycin-rifampin combination therapy has enhanced efficacy against an experimental Staphylococcus aureus prosthetic joint infection," Antimicrob Agents Chemother, 2013, 57(10):5080-5086.

Patterson et al., "Finding the Right (Bioorthogonal) Chemistry," ACS Chem. Biol., 2014, vol. 9, pp. 592-605.

* cited by examiner

| Compound | MW (mg/nmole) | Thermodynamic Solubility (mg/mL) PBS (pH 7.4) | | | [ ] mMol | Mice (0.25 kg) Injection Vol | | | | | | Dog (7.4 kg) | | | | |
|---|---|---|---|---|---|---|---|---|---|---|---|---|---|---|---|---|
| | | Value | Mean | Final pH | µmole/mL | µmoles/ 100 µL | µmoles/kg (µmoles/100 µL)/0.025 kg | mg/kg of pro-drug (mg/100 µL)/0.025 kg | mg/kg of drug *MW Drug/MW Prodrug | Injection Vol µmoles/10 0 mL | µmoles/kg (µmoles/100 mL)/7.4 kg | mg/kg of pro-drug (mg/100 mL)/7.4 kg | mg/kg of drug *MW Drug/MW Prodrug | | |
| Dox-HCl | 579.15 | 2.654 / 2.621 / 2.672 | 2.649 | 5.80 | 4.574 | 0.4574 | 18.295 | 10.596 | 10.596 | 457.37 | 61.81 | 35.80 | 35.80 | | |
| TCO-Dox | 695.26 | 0.000 / 0.000 / 0.000 | 0.001 | 7.42 | 0.001 | 0.0001 | 0.006 | 0.004 | 0.003 | 0.14 | 0.02 | 0.01 | 0.01 | | |
| TCO-Dox-Mor-TFA | 935.8 | 0.073 / 0.071 / 0.071 | 0.072 | 7.27 | 0.077 | 0.0077 | 0.306 | 0.287 | 0.177 | 7.65 | 1.03 | 0.97 | 0.60 | | |
| TCO-Dox-long-NMP | 878.39 | 6.114 / 6.291 / 6.297 | 6.234 | | 7.097 | 0.7097 | 28.388 | 24.936 | 16.441 | 709.71 | 95.91 | 84.24 | 55.54 | | |
| TCO-Dox-acid-TFA | 867 | 2.477 / 2.484 / 2.487 | 2.483 | | 2.864 | 0.2864 | 11.454 | 9.931 | 6.634 | 286.35 | 38.70 | 33.55 | 22.41 | | |
| TCO-Dox-short-NMP | 835.35 | 2.522 / 2.443 / 2.371 | 2.445 | | 2.927 | 0.2927 | 11.709 | 9.781 | 6.781 | 292.73 | 39.56 | 33.05 | 22.91 | | |

FIG. 1

A  In vitro Luminescence (MSSA)
| Group | Gel | Antibiotic | Concentration (µM) 0.25 0.5 1.0 2.0 | MIC (µM) |
|---|---|---|---|---|
| Shasqi Tx | TAG | TCO-vanco | | 2.0 |
| Positive control | TAG | vanco | | 0.5 |
| Negative control | Ctrl Gel | TCO-vanco | | 8.0 |
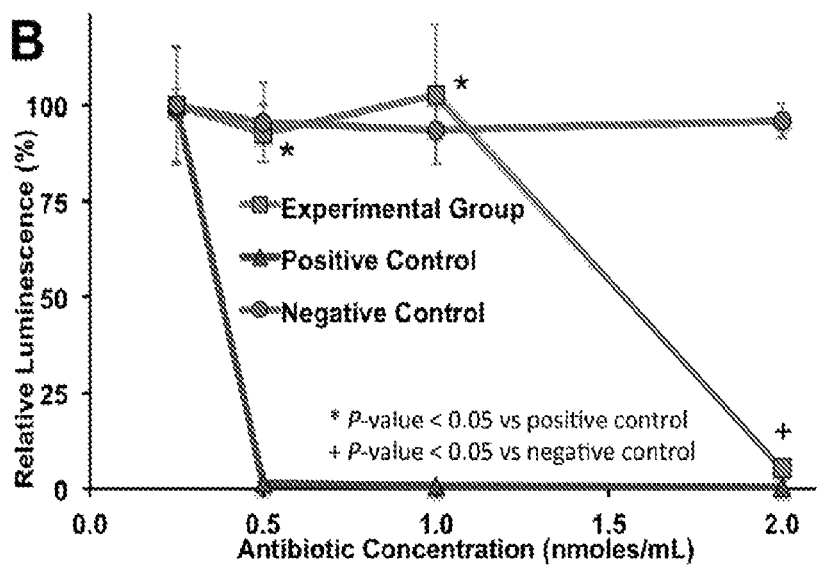
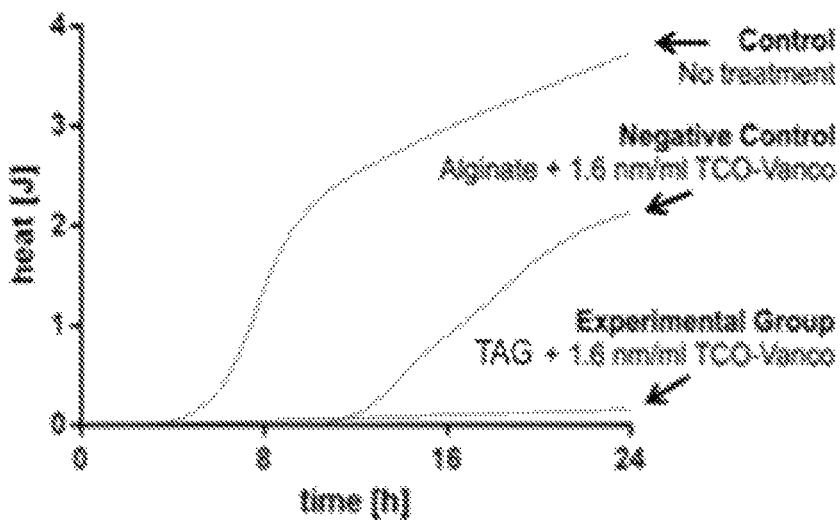
FIG. 9A-9C

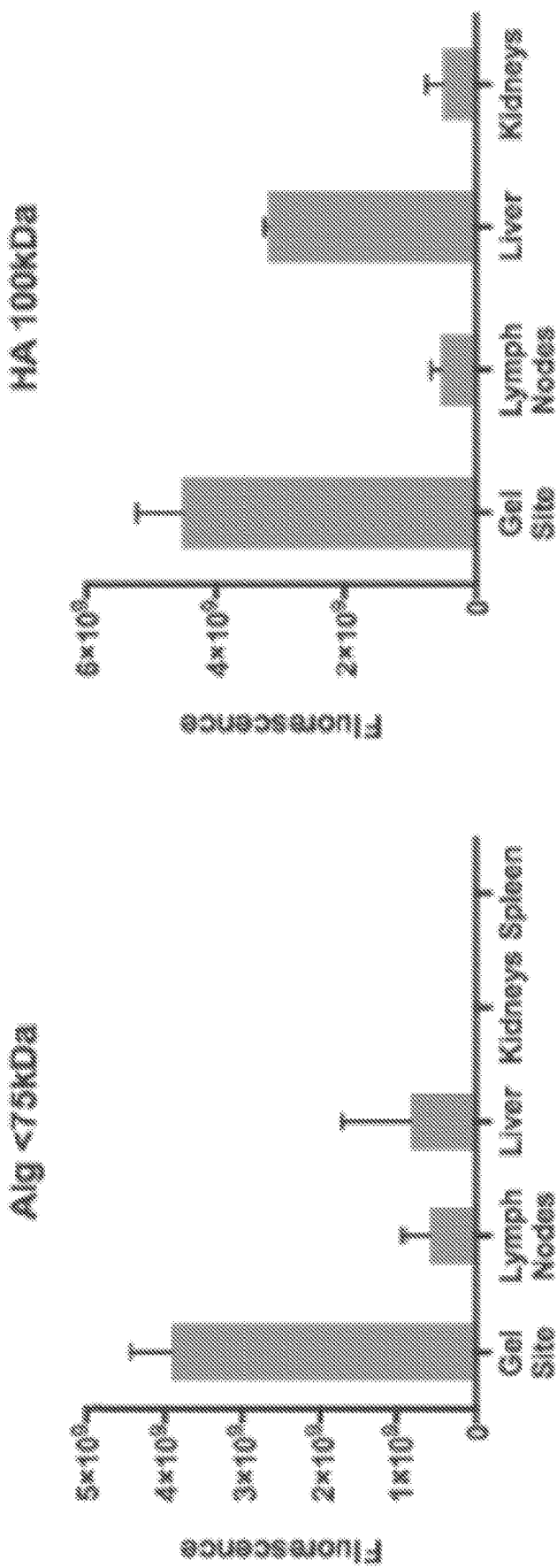
FIG. 20 (Contd.)

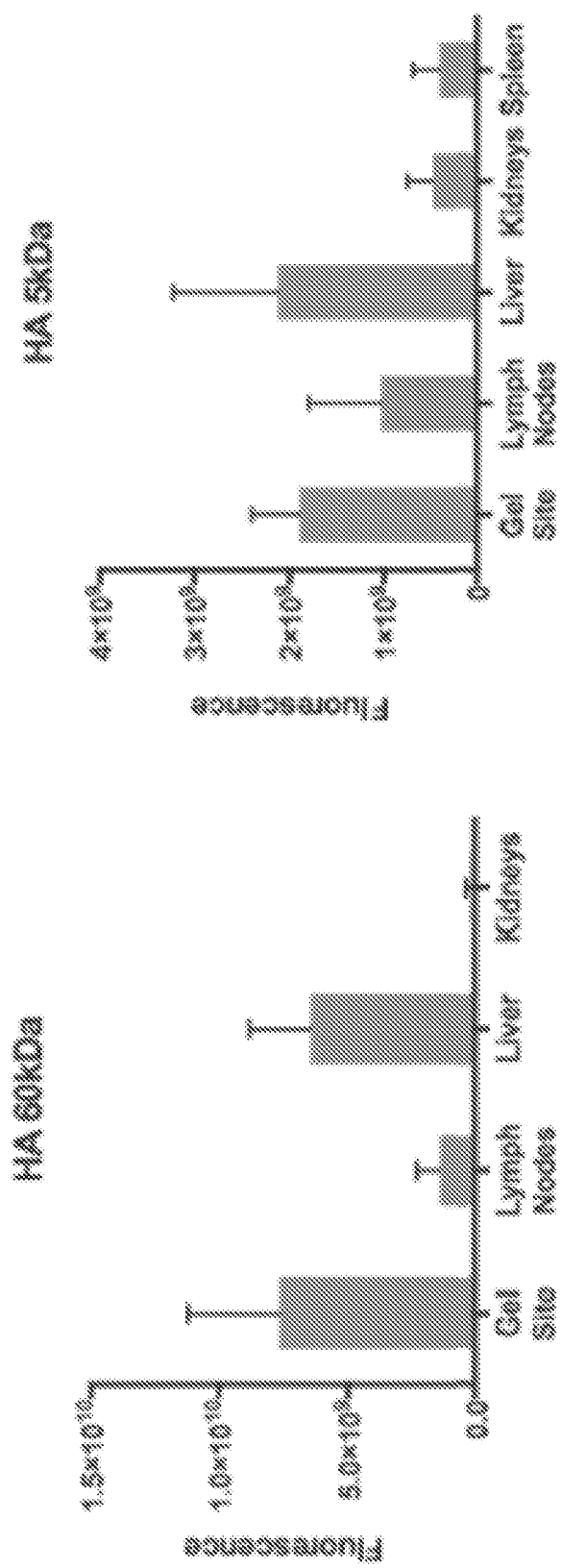
FIG. 20 (Contd.)

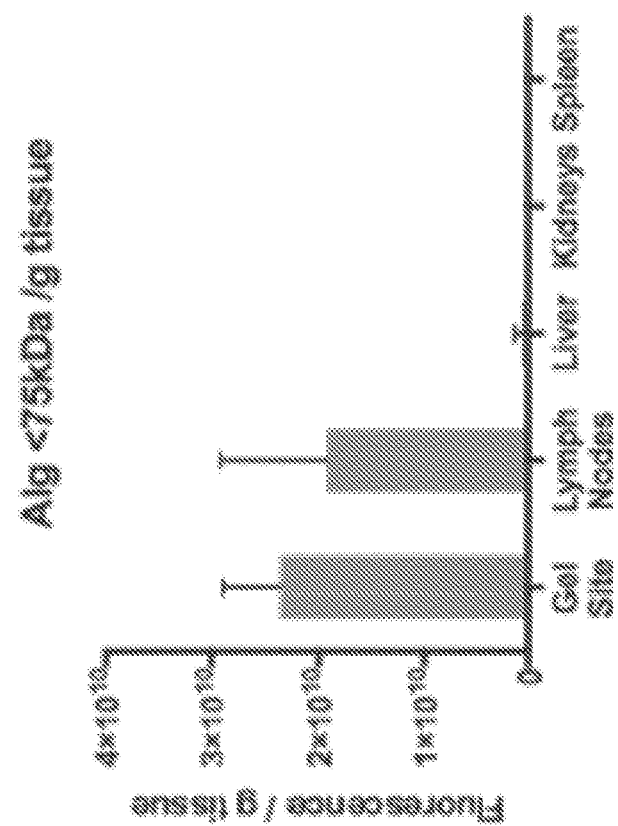
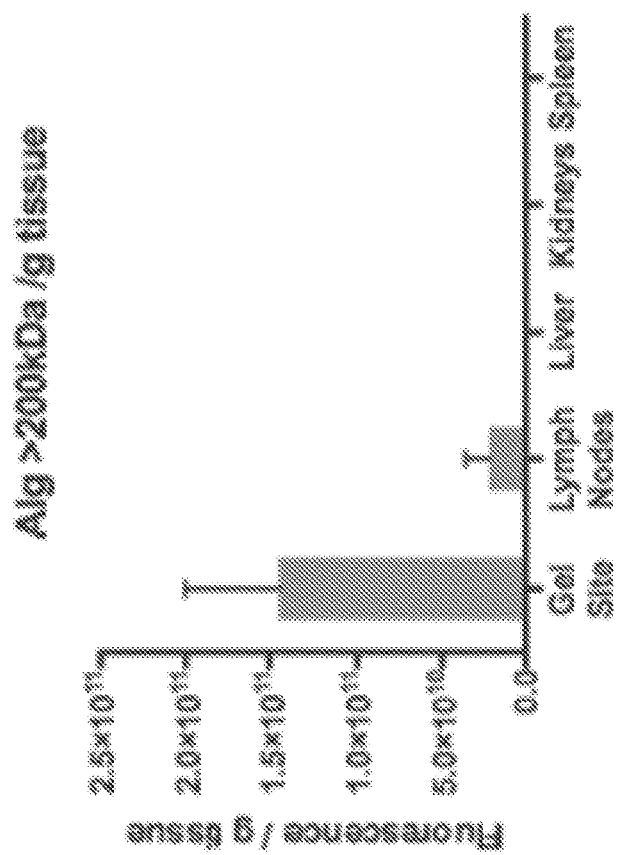
FIG. 21

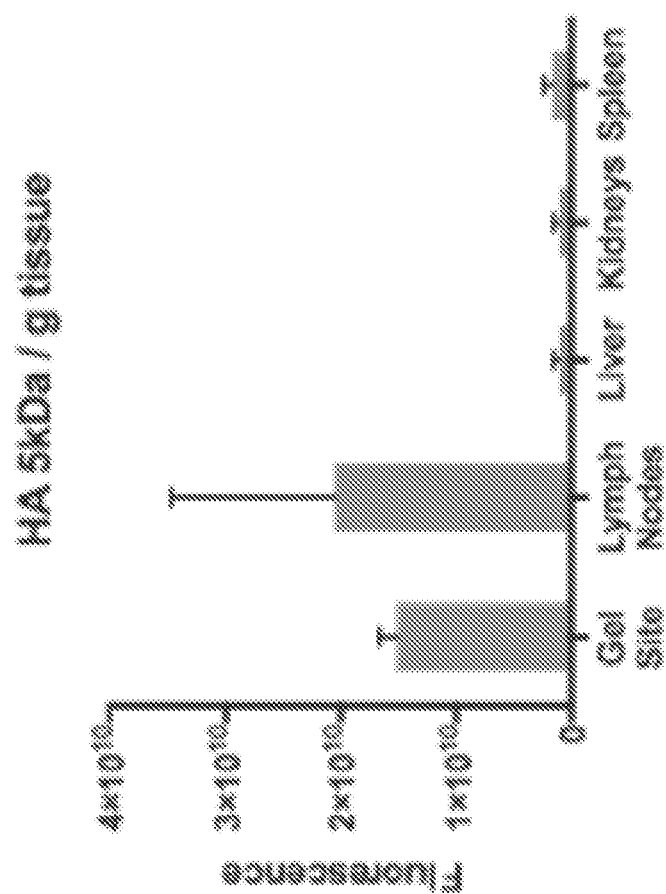
FIG. 21 (Contd.)

FIG. 31
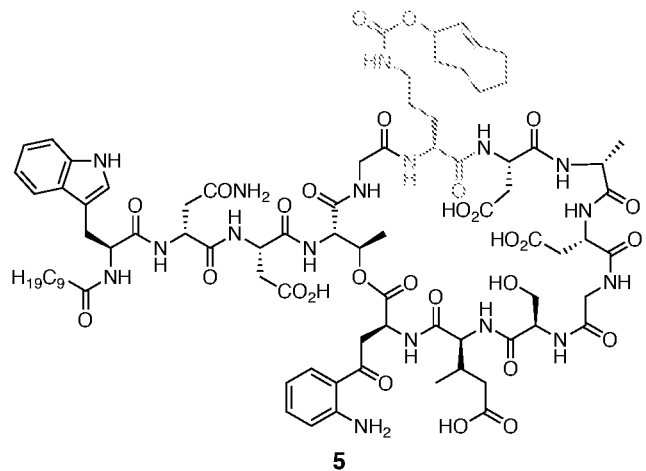
5
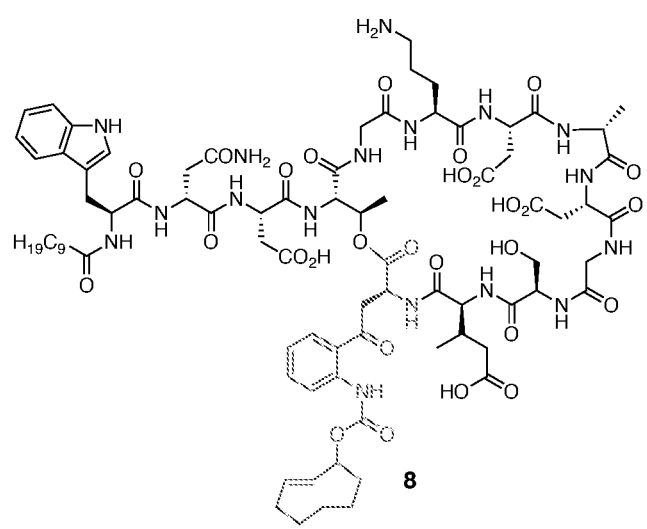
8
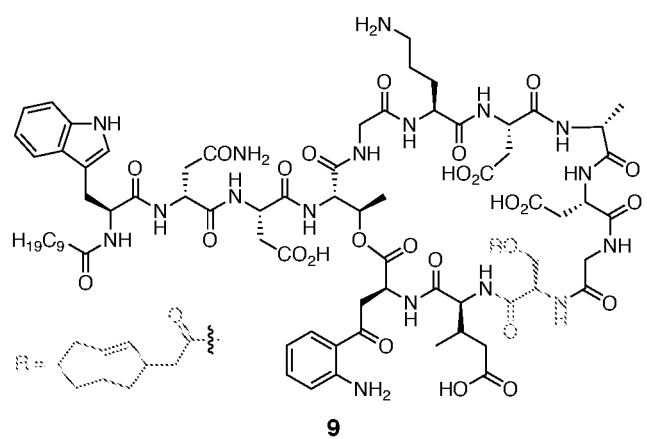
9
The target compounds for the first aim. The releasable is attached to either Orn[6], D-Ser[11], or Kyn[13] residues.

A

B

(A) Synthesis of the compound 8: (a) HCl, NaNO$_2$, then NaN$_3$; (b) Boc$_2$O; (c) InCl$_3$, *p*-nitrophenylcarbonate-TCO; (d) TFA.
(B) Synthesis of the compound 9: (a) 2 equiv Boc$_2$O; (b) *p*-nitrophenylcarbonate-TCO; (c) TFA.

A

B (A) Oligomers of Daptomycin (attachment at the $Orn^6$ residue); (B) The mechanism of release of multiple payloads upon a single trigger step.[39]

Synthesis of the oligomers of daptomycin: (a) *p*-nitrophenyl chloroformate, triethylamine; (b) daptomycin; (c) triethylamine; (d) Amberlyst 15, followed by *p*-nitrophenyl chloroformate; (e) daptomycin; (f) triethylamine; (g) Amberlyst 15, followed by *p*-nitrophenyl chloroformate; (h) daptomycin.

Dog Data

Table 1  Subject Characteristics

| Subject No. | Age (years) | Prior Chemotherapy (drugs) | Prior Radiation (dose) | Shasqi Amount of Dose (mg/kg) | (μmoles/kg) | Doses No. |
|---|---|---|---|---|---|---|
| 1 | 9 | Doxorubicin: 1 mg/kg (1.74 μmoles/kg) Q3Wk x 4 | None | 7.28 | 10.5 | 3 (W,F,M) |

Table 2  Drug Related Toxicities by Shasqi Doxo

| | 10.5 μmoles/kg (per cycle) | |
|---|---|---|
| Adverse Events | Dose 1 | All 3 Doses |
| Neutrophils | normal | normal |
| Febrile neutropenia | none | none |
| Platelets | normal | normal |
| Vomiting | none | none |
| Hemoglobin | normal | normal |
| Anorexia | none | none |
| Diarrhea | none | none |
| ALT | normal | normal |
| AST | normal | transient grade 1 (2x ULN @ 16d, nl after 23d) |
| Alopecia | none | none |

FIG. 37

BIOORTHOGONAL COMPOSITIONS

CROSS REFERENCE TO RELATED APPLICATIONS

This application is a U.S. national stage entry of International Patent Application No. PCT/US2018/026551, filed on Apr. 6, 2018, which claims priority to U.S. Provisional Patent Application No. 62/483,163, filed on Apr. 7, 2017, U.S. Provisional Patent Application No. 62/483,081, filed on Apr. 7, 2017, U.S. Provisional Patent Application No. 62/483,121, filed on Apr. 7, 2017, U.S. Provisional Patent Application No. 62/507,973, filed on May 18, 2017, U.S. Provisional Patent Application No. 62/515,948, filed on Jun. 6, 2017, U.S. Provisional Patent Application No. 62/568,586, filed on Oct. 5, 2017, U.S. Provisional Patent Application No. 62/609,943, filed on Dec. 22, 2017, U.S. Provisional Patent Application No. 62/623,245, filed on Jan. 29, 2018, U.S. Provisional Patent Application No. 62/623,329, filed on Jan. 29, 2018, and U.S. Provisional Patent Application No. 62/626,978, filed on Feb. 6, 2018, each of which is incorporated herein by reference in its entirety.

STATEMENT OF GOVERNMENT INTEREST

This invention was made with government support under grant nos. CA228997, GM130240, GM119864, and CA224561 awarded by the National Institutes of Health, and grant no. 1660258 awarded by the National Science Foundation. The government has certain rights in the invention.

TECHNICAL FIELD

The present disclosure provides bioorthogonal compositions and methods of using the bioorthogonal compositions for delivering agents in a subject. Aspects of the bioorthogonal compositions as well as methods of producing the bioorthogonal compositions are also described herein.

BACKGROUND

Typically, physicians rely on systemic medications for the treatment of various medical conditions. The use of physical drug delivery systems may assist the physician in optimizing the delivery of therapeutic agents to specific sites of the body, as well as facilitating the delivery of therapeutic agents at desired times or intervals. However, after the initial intervention, physicians still rely on systemic medications that need frequent dosing and may have noxious side effects. Existing biomaterials can serve as depots for therapeutic agents, which can be released to the body through diffusion or degradation. However, most biomaterials cannot be modulated or modified after implantation, and usually exhibit an initial burst of activity shortly after implantation. These issues may limit the application of biomaterials for medical conditions that require a particular dosing regimen, such as doses that are to be administered at different time points, or for medical conditions where the most effective therapeutic agent is identified hours or days after implantation of the biomaterial, e.g., after culture or pathology results are obtained.

Bioorthogonal conjugation or click reactions are selective and orthogonal (non-interacting with) functionalities found in biological systems, and have found use in various applications in the fields of chemistry, chemical biology, molecular diagnostics, and medicine, where they can be used to facilitate the selective manipulation of molecules, cells, particles and surfaces, and the tagging and tracking of biomolecules in vitro and in vivo. These reactions include the Staudinger ligation, the azide-cyclooctyne cycloaddition, and the inverse-electron-demand Diels-Alder reaction.

SUMMARY OF THE INVENTION

The present disclosure provides bioorthogonal compositions for delivering agents in a subject. The disclosure also provides methods of producing the compositions, as well as methods of using the same. The invention provides novel functionalized payload compositions with improved aqueous solubility.

In one aspect, the invention provides compounds of formula (I-A), or a salt thereof,

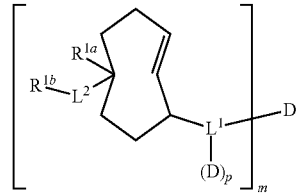

(I-A)

wherein
$R^{1a}$ is selected from the group consisting of $C_{1-4}$alkyl, $C_{1-4}$haloalkyl, and $C_{1-4}$alkoxy;
$R^{1b}$ is selected from the group consisting of $G^1$, OH, —$NR^{1c}$—$C_{1-4}$alkylene-$G^1$, —$NR^{1c}$—$C_{1-4}$alkylene-$N(R^{1d})_2$, —$N(R^{1c})CHR^{1e}CO_2H$, —$N(R^{1c})$—$C_{1-6}$alkylene-$CO_2H$, —$N(R^{1f})$—$C_{2-4}$alkylene-$(N(C_{1-4}$alkylene-$CO_2H)$—$C_{2-4}$alkylene)-$N(C_{1-4}$alkylene-$CO_2H)_2$, —$N(R^{1c})CHR^{1e}C(O)OC_{1-6}$alkyl, —$N(R^{1c})$—$C_{1-6}$alkylene-$C(O)OC_{1-6}$alkyl, and —$N(R^{1f})$—$C_{2-4}$alkylene-$(N(C_{1-4}$alkylene-$C(O)OC_{1-6}$alkyl)-$C_{2-4}$alkylene)$_n$-$N(C_{1-4}$alkylene-$C(O)OC_{1-6}$alkyl)$_2$;
$R^{1c}$ and $R^{1d}$, at each occurrence, are independently hydrogen or $C_{1-4}$alkyl;
$R^{1e}$ is —$C_{1-4}$alkylene-$CO_2H$, —$C_{1-4}$alkylene-$CONH_2$, or —$C_{1-4}$alkylene-$OH$;
$R^{1f}$ is hydrogen, $C_{1-6}$alkyl, or $C_{1-4}$alkylene-$CO_2H$;
D, at each occurrence, is independently a payload;
-$L^1$- is a linker;
-$L^2$- is selected from the group consisting of —C(O)— and $C_{1-3}$alkylene;
$G^1$ is an optionally substituted heterocyclyl;
m is 1, 2, or 3;
n is 0, 1, 2, or 3; and
p is 0, 1, or 2.

In another aspect, the invention provides compounds of formula (I), or a salt thereof,

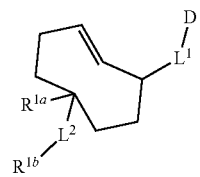

(I)

wherein
$R^{1a}$ is selected from the group consisting of $C_{1-4}$alkyl, $C_{1-4}$haloalkyl, and $C_{1-4}$alkoxy;

-L²- is selected from the group consisting of —C(O)— and $C_{1-3}$alkylene;
$R^{1b}$ is selected from the group consisting of $G^1$, OH, —NR$^{1c}$—C$_{1-4}$alkylene-G$^1$, and —NR$^{1c}$—C$_{1-4}$ alkylene-N(R$^{1d}$)$_2$;
$G^1$ is an optionally substituted heterocyclyl; and
$R^{1c}$ and $R^{1d}$, at each occurrence, are independently hydrogen or $C_{1-4}$alkyl.

In yet another aspect the invention provides compounds of formula

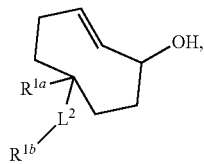

or a salt thereof, wherein
$R^{1a}$ is selected from the group consisting of $C_{1-4}$alkyl, $C_{1-4}$haloalkyl, and $C_{1-4}$alkoxy;
-L²- is selected from the group consisting of —C(O)— and $C_{1-3}$alkylene;
$R^{1b}$ is selected from the group consisting of $G^1$, OH, —NR$^{1c}$—C$_{1-4}$alkylene-G$^1$, and —NR$^{1c}$—C$_{1-4}$ alkylene-N(R$^{1d}$)$_2$;
$G^1$ is an optionally substituted heterocyclyl; and
$R^{1c}$ and $R^{1d}$, at each occurrence, are independently hydrogen or $C_{1-4}$alkyl.

In another aspect, the invention provides a pharmaceutical composition comprising a compound of formula (I) or (I-A), or a pharmaceutically acceptable salt thereof, wherein D is a therapeutic agent, and a pharmaceutically acceptable carrier.

In another aspect, the invention provides a diagnostic composition comprising a compound of formula (I) or (I-A), or a salt thereof, wherein D is a diagnostic agent, and a pharmaceutically acceptable carrier.

In another aspect, the invention provides a therapeutic support composition comprising: a tetrazine-containing group of formula:

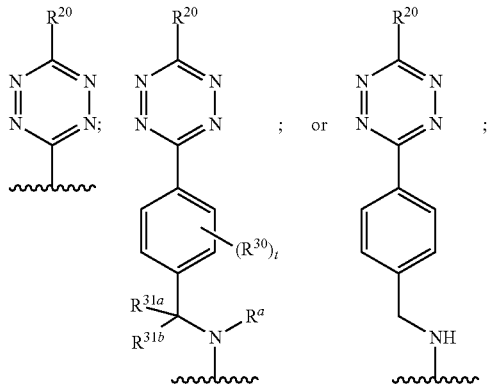

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, CF$_3$, CF$_2$—R', NO$_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S) R'R''', SC(=S)R'R''', NR'C(=O)NR''R''', and NR'C(=S)NR''R''';
R' and R'' at each occurrence are independently selected from hydrogen, aryl and alkyl; and R''' at each occurrence is independently selected from aryl and alkyl; $R^{30}$ is halogen, cyano, nitro, hydroxy, alkyl, haloalkyl; alkenyl, alkynyl, alkoxy; halalkoxy; heteroalkyl, aryl, heteroaryl, heterocycle, cycloalkyl, or cycloalkenyl; $R^a$, $R^{31a}$ and $R^{31b}$ are each independently hydrogen, $C_1$-$C_6$-alkyl, or $C_1$-$C_6$-haloalkyl; and t is 0, 1, 2, 3, or 4; wherein the tetrazine-containing group is linked or directly bonded to a hyaluronic acid.

In another aspect, the invention provides a method of treating or preventing a condition or disorder comprising administering to a subject in need thereof, a therapeutically effective amount of a compound of formula (I) or (I-A), or a pharmaceutically acceptable salt or composition thereof, wherein D is a therapeutic agent; and a therapeutic support composition, the therapeutic support composition comprising a biocompatible support and a tetrazine-containing group of formula

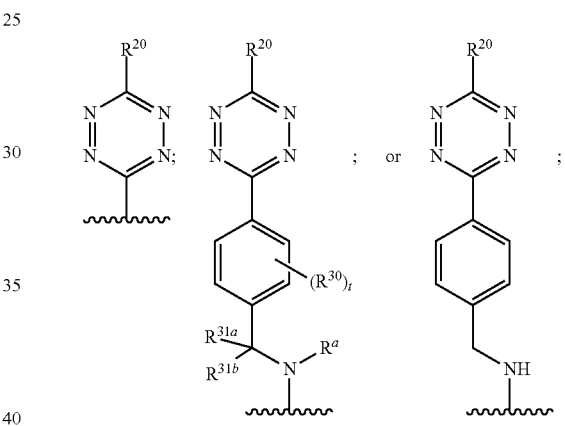

wherein
$R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, CF$_3$, CF$_2$—R', NO$_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S) R'R''', SC(=S)R'R''', NR'C(=O)NR''R''', and NR'C(=S)NR''R''';
R' and R'' at each occurrence are independently selected from hydrogen, aryl and alkyl;
R''' at each occurrence is independently selected from aryl and alkyl;
$R^{30}$ is halogen, cyano, nitro, hydroxy, alkyl, haloalkyl; alkenyl, alkynyl, alkoxy; halalkoxy; heteroalkyl, aryl, heteroaryl, heterocycle, cycloalkyl, or cycloalkenyl;
$R^a$, $R^{31a}$ and $R^{31b}$ are each independently hydrogen, $C_1$-$C_6$-alkyl, or $C_1$-$C_6$-haloalkyl; and
t is 0, 1, 2, 3, or 4.

In another aspect, the invention provides a method of enhancing or eliciting an immune response comprising administering to a subject in need thereof, a therapeutically effective amount of a compound of formula (I) or (I-A), or a pharmaceutically acceptable salt or composition thereof, wherein D is a therapeutic agent, and the therapeutically effective amount enhances or elicits an immune response against a cancer in the subject.

In another aspect, the invention provides a compound of formula (I) or (I-A), or a pharmaceutically acceptable salt, or composition thereof, wherein D is a therapeutic agent; and a therapeutic support composition, the therapeutic support composition comprising a biocompatible support and a tetrazine-containing group of formula

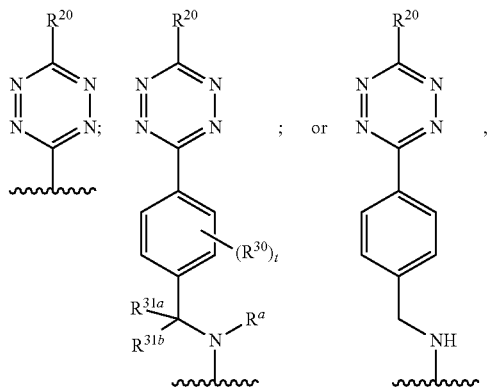

as defined herein for use in the treatment or prevention of a disease or disorder, such as cancer, infections, tissue injury, stenosis, ischemia, re-vascularization, myocardial infarction, arrhythmias, vascular occlusion, inflammation, autoimmune disorders, transplant rejection, macular degeneration, rheumatoid arthritis, osteoarthritis, peri-prosthetic infections, and pigmented villonodular synovitis.

In another aspect, the invention provides a compound of formula (I) or (I-A), or a pharmaceutically acceptable salt, or composition thereof, wherein D is a therapeutic agent, for use in the enhancement or elicitation of an immune response.

In another aspect, the invention provides the use of a compound of formula (I) or (I-A), or a pharmaceutically acceptable salt, or composition thereof, wherein D is a therapeutic agent, in the manufacture of a medicament for the treatment or prevention of a condition or disorder such as cancer, infections, tissue injury, stenosis, ischemia, re-vascularization, myocardial infarction, arrhythmias, vascular occlusion, inflammation, autoimmune disorders, transplant rejection, macular degeneration, rheumatoid arthritis, osteoarthritis, peri-prosthetic infections, and pigmented villonodular synovitis.

In another aspect, the invention provides the use of a compound of formula (I) or (I-A), or a pharmaceutically acceptable salt, or composition thereof, wherein D is a therapeutic agent, in the manufacture of a medicament for the enhancement or elicitation of an immune response.

Aspects of the present disclosure include a support composition that includes a support, where the support is a polymer, a viscous or non-viscous liquid material, a gel, a hydrogel support or a support particle. The support composition also includes a first binding agent attached to the support and comprising a first bioorthogonal functional group that is a member of a first complementary binding pair. In addition, if the support comprises the support particle, then the support composition can comprise a targeting agent attached to the support particle. In some embodiments, the support is a hydrogel support. In some embodiments, the support is a support particle and the support composition includes the targeting agent attached to the support particle. In some embodiments, the support composition includes a first linker covalently linking the first binding agent to the support. In some embodiments, the first bioorthogonal functional group is a tetrazine. In some embodiments, the support particle is a nanoparticle or a microparticle.

In some embodiments, the functionalized payload comprises a first complementary binding agent that selectively binds to the first binding agent, a first payload and a linker covalently linking the first complementary binding agent to the first payload. In some embodiments, the first payload includes a therapeutic agent, a diagnostic agent or a targeting agent. In some embodiments, the linker comprises a releasable linker.

Aspects of the present disclosure include a method for delivering an effective amount of a payload to a target location in a subject, where the method includes administering to the subject a support composition. The support composition includes a support, where the support is a polymer, a viscous or non-viscous liquid material, a gel, a hydrogel support or a support particle. The support composition also includes a first binding agent attached to the support and comprising a first bioorthogonal functional group that is a member of a first complementary binding pair. In addition, if the support comprises the support particle, then the support composition further can comprise a targeting agent attached to the support particle. The method also includes administering to the subject a first functionalized payload comprising a first complementary binding agent that selectively binds to the first binding agent, a first payload, and a linker covalently linking the first complementary binding agent to the first payload, such that the first functionalized payload binds to the support composition.

In some embodiments, the linker includes a releasable linker, and the method also includes releasing the first payload, thereby delivering the first payload to the target location in the subject.

Aspects of the present disclosure also include a kit. The kit includes a support composition that includes a support, where the support is a polymer, a viscous or non-viscous liquid material, a gel, a hydrogel support or a support particle. The support composition also includes a first binding agent attached to the support and comprising a first bioorthogonal functional group that is a member of a first complementary binding pair. In addition, if the support comprises the support particle, then the support composition further comprises a targeting agent attached to the support particle. The kit also includes a packaging containing the support composition.

In some embodiments, the kit includes a first functionalized payload. In some embodiments, the first functionalized payload comprises a first complementary binding agent that selectively binds to the first binding agent, a first payload, and a linker covalently linking the first complementary binding agent to the first payload.

BRIEF DESCRIPTION OF THE DRAWINGS

FIG. 1 shows solubility data.

In FIG. 4A, NCR/nu:nu mice were injected with human HT-1080 fibrosarcoma cells at day 0. Tumors were then injected with alginate tetrazine-modified activating gel (TAG) and started on intravenous doses of either doxorubicin pro-drug (TCO-Dox) or a maximum tolerable dose of doxorubicin or negative controls. Tumor sizes were monitored for more than 16 weeks (n=4-10). FIG. 4B shows evaluation of reticulocyte counts as a surrogate for bone marrow suppression in a xenograft model of soft tissue sarcoma. Mice were given vehicle, doxorubicin or doxorubicin pro-drug after injection of alginate TAG. Samples were collected 3 d after the last treatment. Data are means±SD (n=2). FIG. 4C shows body weight changes in response to therapy. Data are mean body weight changes as a percentage of initial weight±SD (n=5-10). P values were determined by unpaired t-test.

FIG. 8A shows a hyaluronic acid modified with Tz (HAT) injected into the area where the drugs are needed, used as a coating on an implanted or indwelling medical device, or co-implanted with an implanted or indwelling medical device. In FIG. 8B, a drug covalently modified with a TCO carbamate (prodrug) is given to the patient. In FIG. 8C, when the prodrug and the material come in contact, the rapid cycloaddition reaction enhances the amount of drug present at the desired location with the concomitant release of nitrogen. In FIG. 8D, the resulting cycloadduct isomerizes in vivo leading to decomposition of the self-immolable carbamate linker, releasing an equivalent of carbon dioxide and most importantly the drug at the local site to perform its therapeutic function.

FIG. 9A-9C compare antibacterial effects of vacomycin and TCO-vancomycin, with or without tetrazine modification of alginate. FIG. 9A shows the minimum inhibitory concentrations of three treatments on luminescent methicillin-sensitive *Staphylococcus aureus* (MSSA) in vitro. In FIG. 9B, the alginate TAG+TCO-vancomycin was effective at killing MSSA at a MIC of 2.0 nmoles/mL, whereas the negative control did not inhibit bacterial growth at these concentrations. Luminescence was measured 16 hours after addition of the bacteria per standard protocols. In FIG. 9C, results are confirmed by isothermal microcalorimetry, in which TCO-vancomycin and alginate TAG had a significantly greater antibacterial effect compared to controls with unmodified alginate gel or no treatment.

In FIG. 10A, a hydrogel modified with tetrazine (HMT) is injected in the vicinity of infected area. In FIG. 10B, an antibiotic, covalently modified with a TCO (prodrug) is given to the patient. In FIG. 10C, when the pro-drug and the material come in contact, the inverse electron-demand Diels-Alder reaction enhances the amount of antibiotic present near the infected site. In FIG. 10D, the resulting cycloaddition product spontaneously isomerizes, releasing an equivalent of carbon dioxide and most importantly, the active antibiotic.

FIG. 17 shows the bacterial loading of the harvested knee joint from rats injected with MRSA bacteria and TAG (right knee) or unmodified alginate control gel (left knee). Prodrug, TCO-Dapto was delivered systemically via tail vein. Mean SEM of n=3, unpaired two-tailed Welch's t-test, * p<0.05.

FIG. 20A shows the concentration of TCO-Dox and Dox in serum after treatment with Shasqi Tx or Doxorubicin. Shasqi Tx, n=1; Dox, error bar represents SD of n=2. FIG. 20B shows the concentration of active Doxorubicin in heart, liver, and gel in mice treated with Shasqi Tx or Doxorubicin. Mean SEM of n=2.

FIG. 21 is a set of graphs showing fluorescence signal per gram of tissue gel injection site tissue and organs collected post-necropsy per gram of tissue.

50 mg/kg and 75 mg/kg administered once daily days 1-5. 100 mg/kg administered day 1. 125 mg/kg administered one week after.

Figure 23:
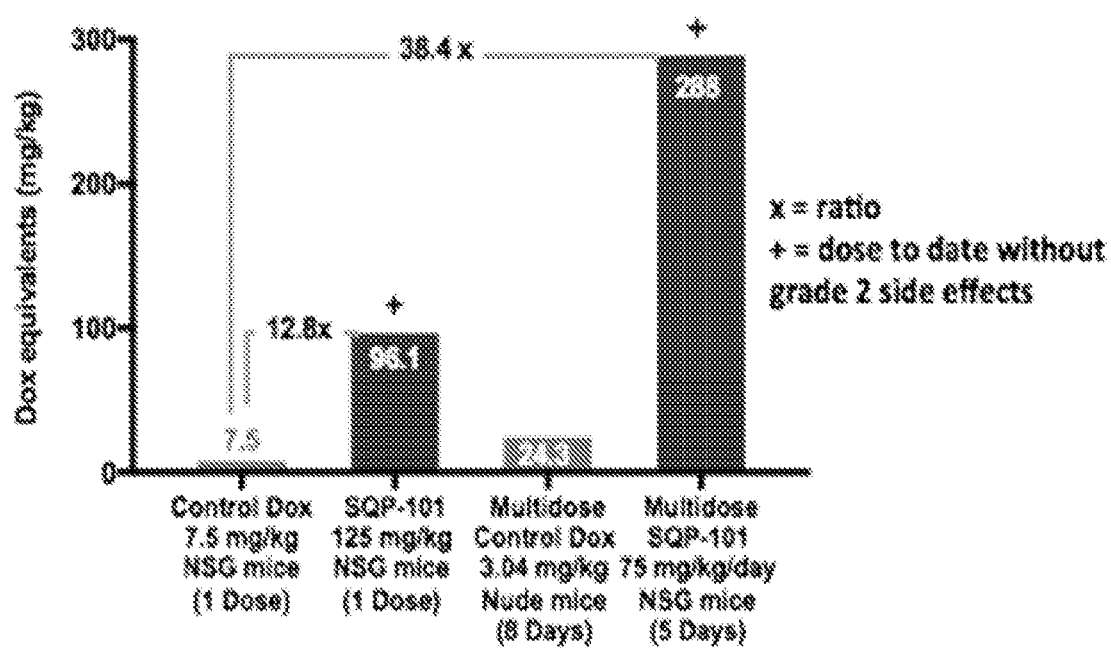

FIG. 23 is a graph showing MTD of TCO-Dox-Acid (SQP-101) in NSG mice injected with alginate TAG. Doxorubicin (DOX) or TCO-Dox-Acid given on the regimens indicated. Dosage in nude mice reproduced from Albright, et al., *Mol. Cancer Ther.* 2005, 4 (5) 751-760.

Figures 24A, 24B, 24C:
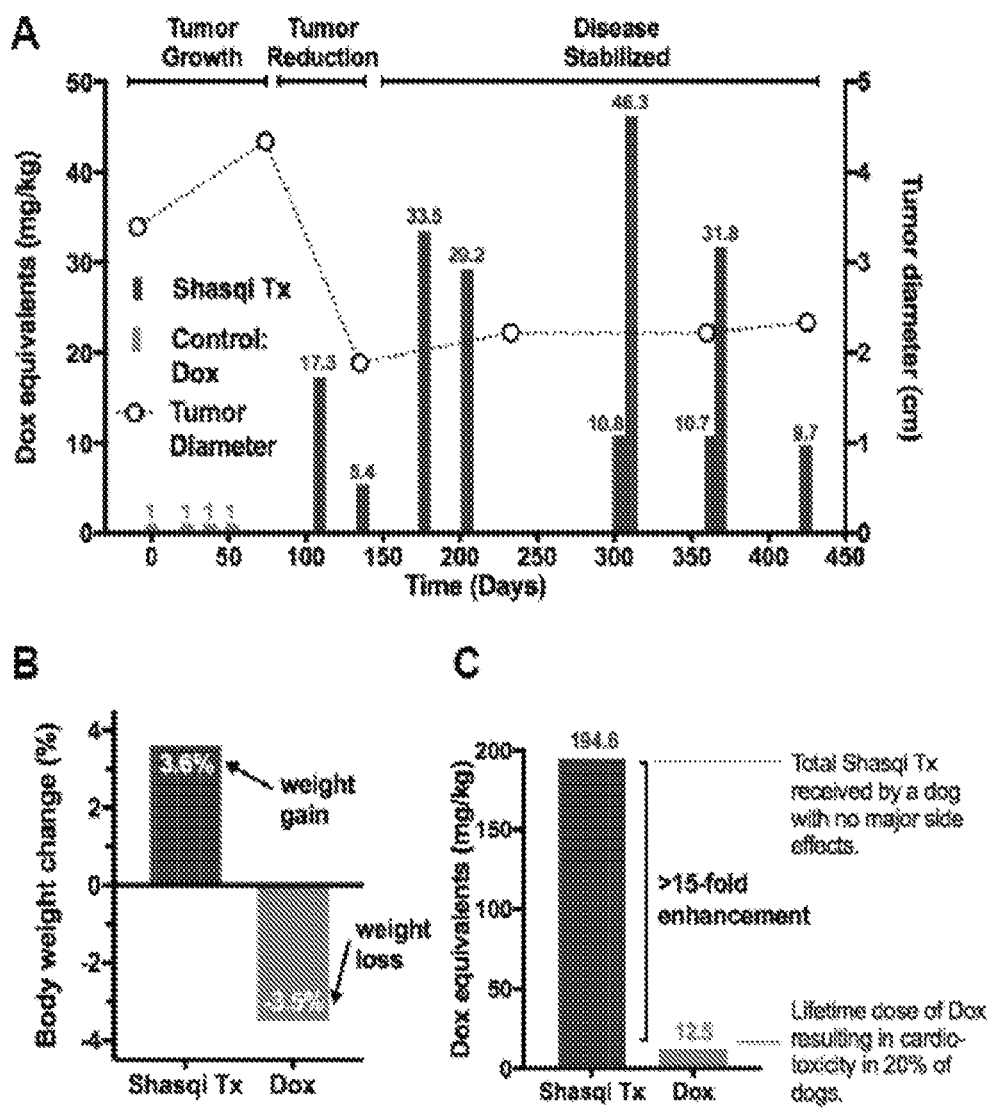

FIG. 24A-24C is a set of graphs showing that Shasqi Tx (tetrazine-modified gel injected locally, followed by TCO-doxorubicin pro-drug injected intravenously) is safer and more effective than Doxorubicin in a canine. A tumor-bearing dog was given multiple treatments of Doxorubicin and Shasqi Tx (gel and doxorubicin pro-drug). FIG. 24A shows tumor response to treatment with cycles of Dox and Shasqi Tx. Longest tumor diameter determined by CT scans. FIG. 24B shows body weight change percentage following treatment cycle with Dox (day 52) and TCO-Dox (day 131). FIG. 24C shows that Shasqi Tx allows over 15 times the maximum lifetime dose of Dox to be given without major side effects (Matus, et al. J. Vet. Int. Med., 1992, 6, 82-88).

Figure 25:
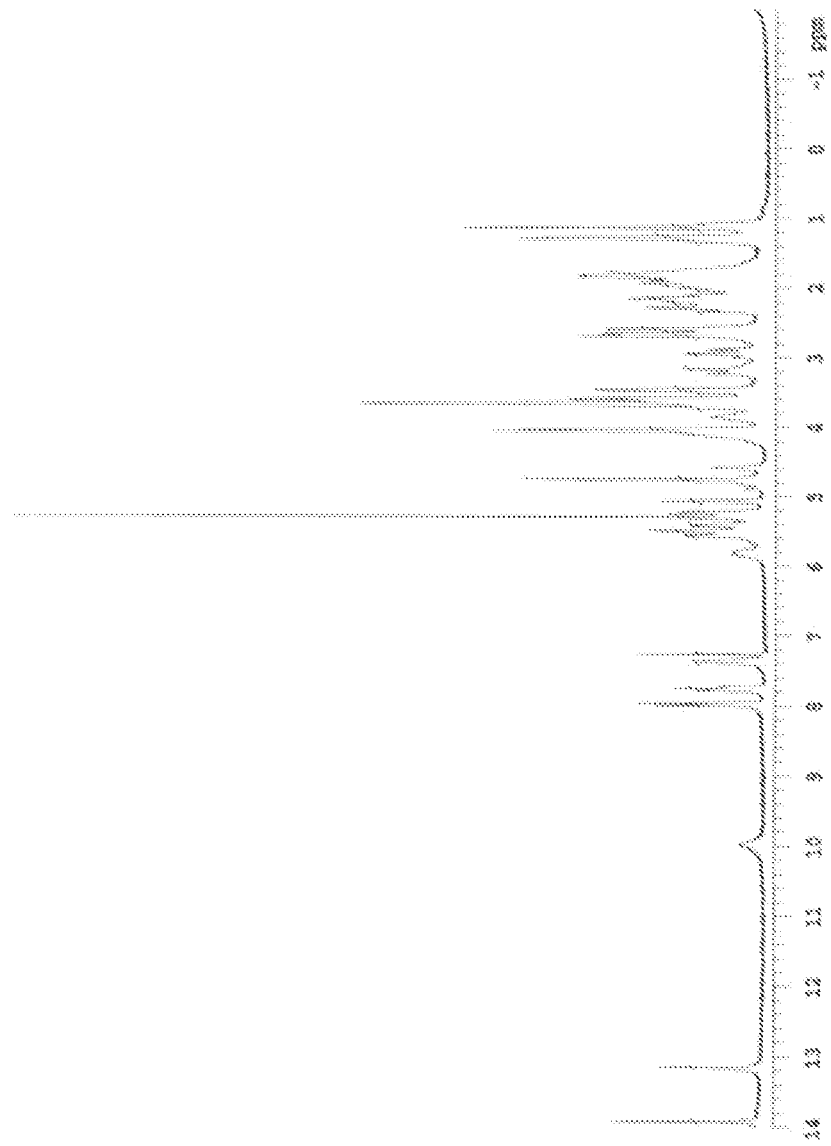

FIG. 25 shows the $^1$H NMR spectrum for the Morpholine-TCO-Doxorubicin of Example 1.

Figure 26:
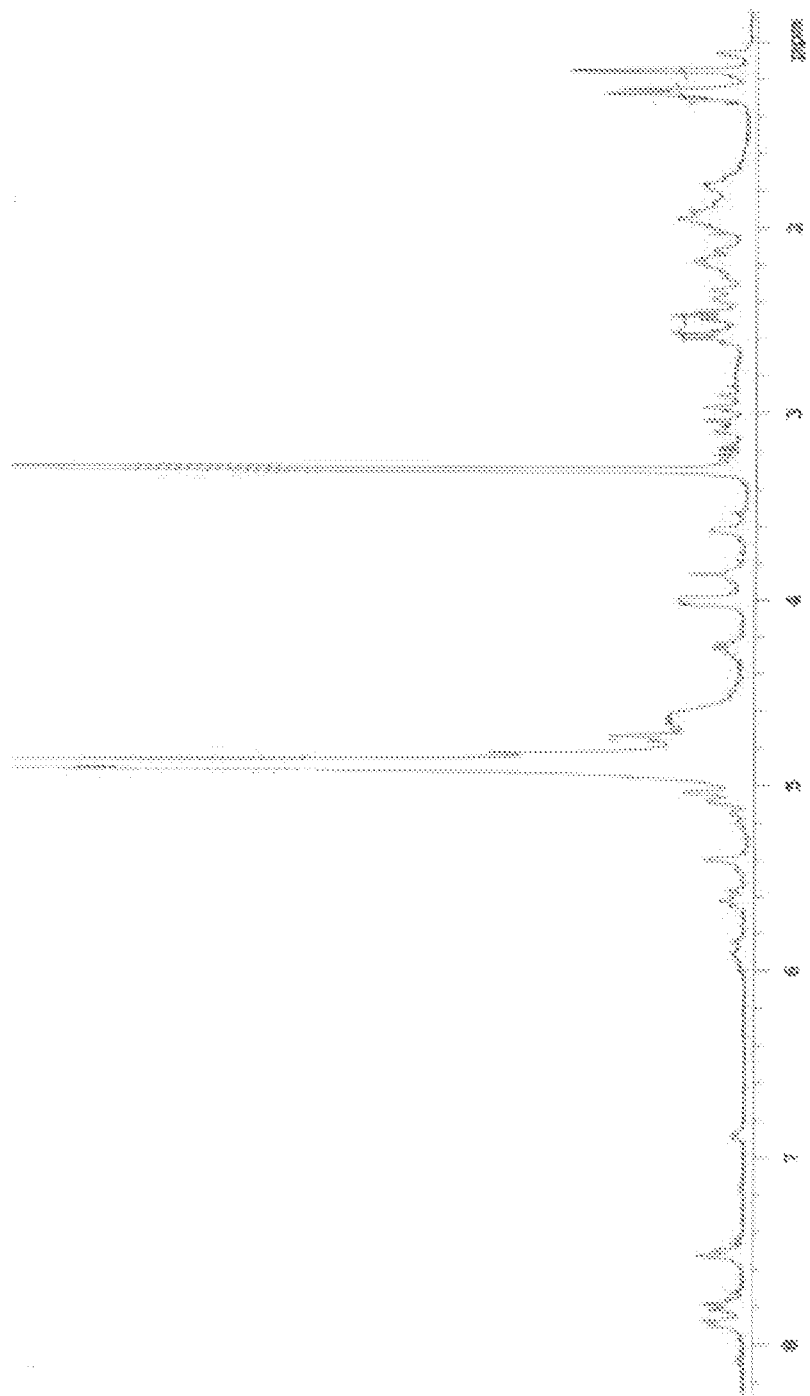

FIG. 26 shows the $^1$H NMR spectrum for the Acid-TCO-Doxorubicin of Example 3.

Figure 27:
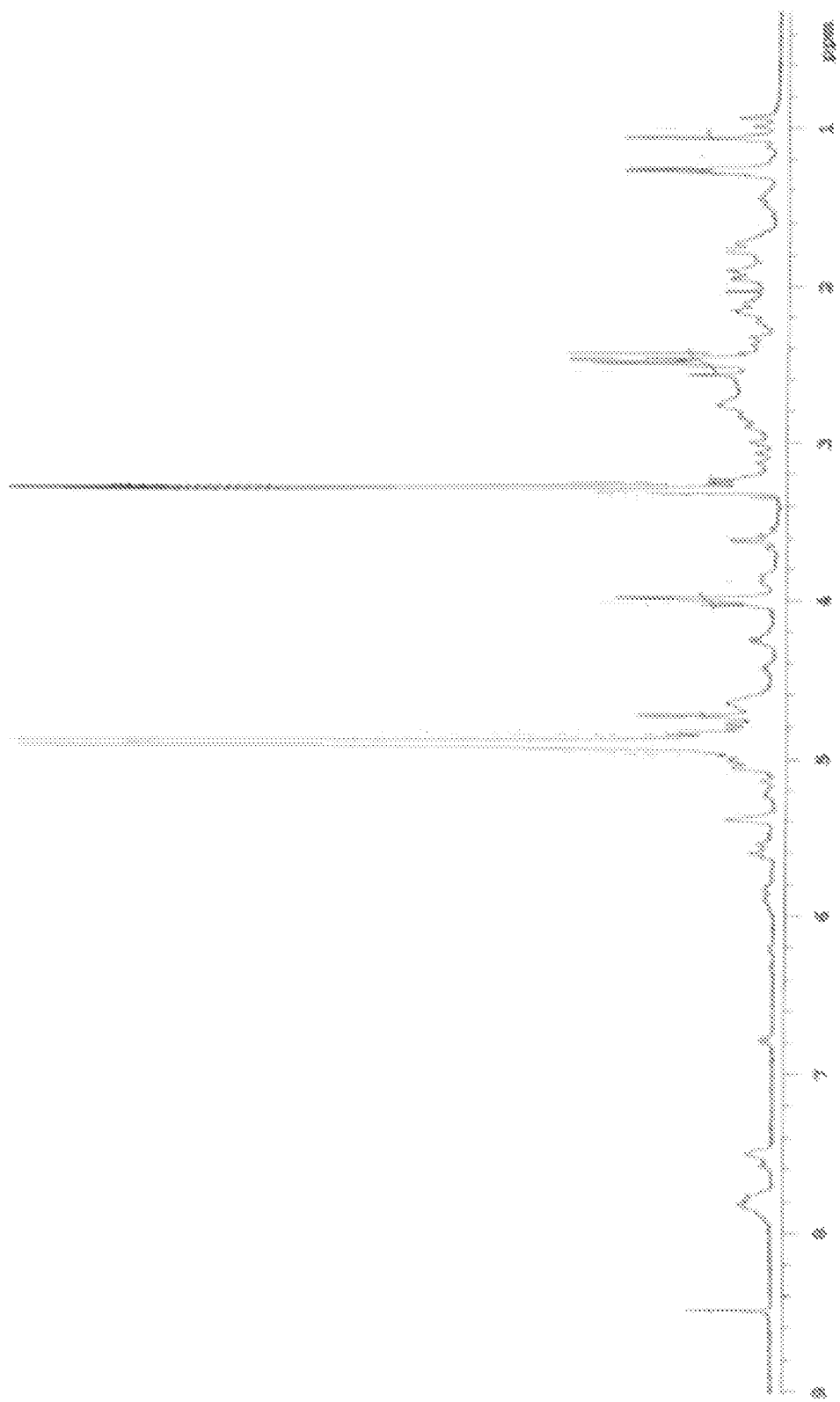

FIG. 27 shows the $^1$H NMR spectrum for the N-Methylpiperazinylethyl-TCO-doxorubicin of Example 4.

Figure 28:
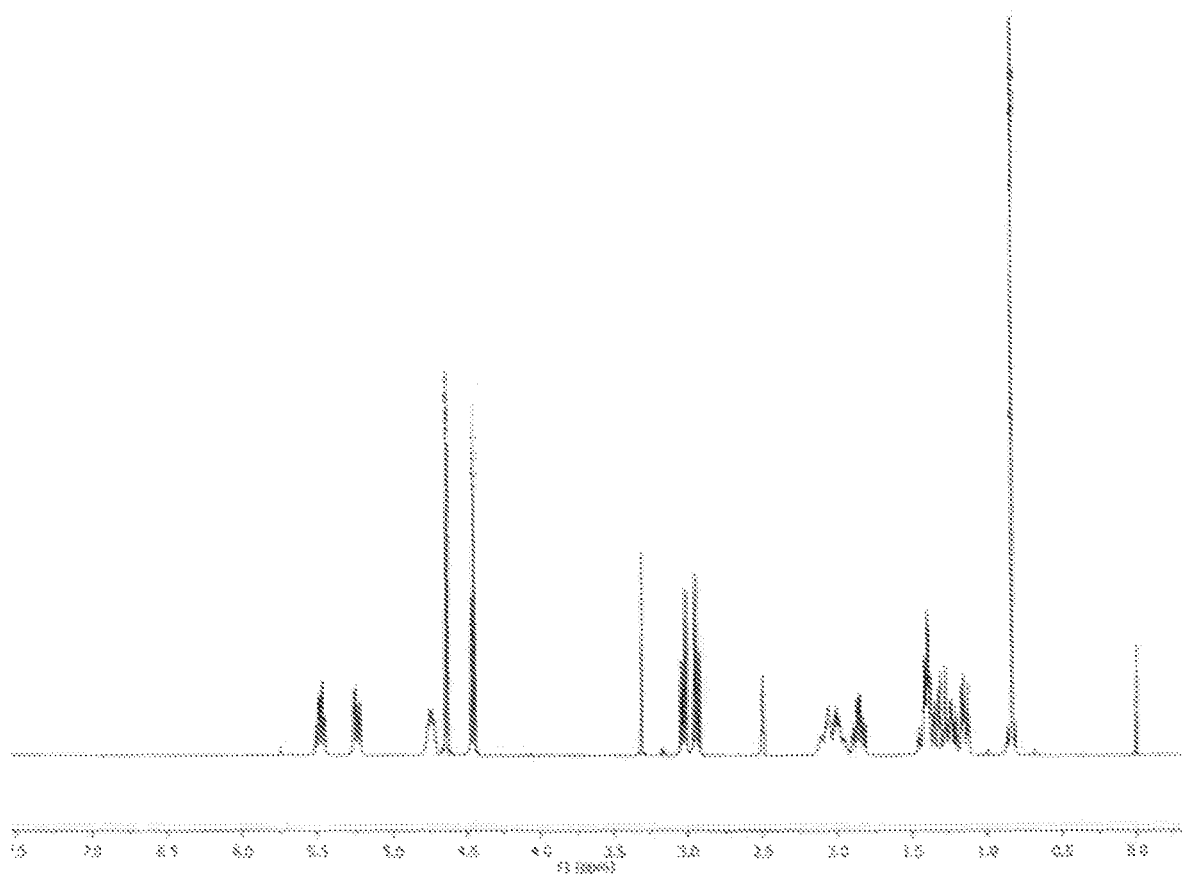

FIG. 28 shows the $^1$H NMR spectrum for the diol 3 of Example 6.

Figure 29:
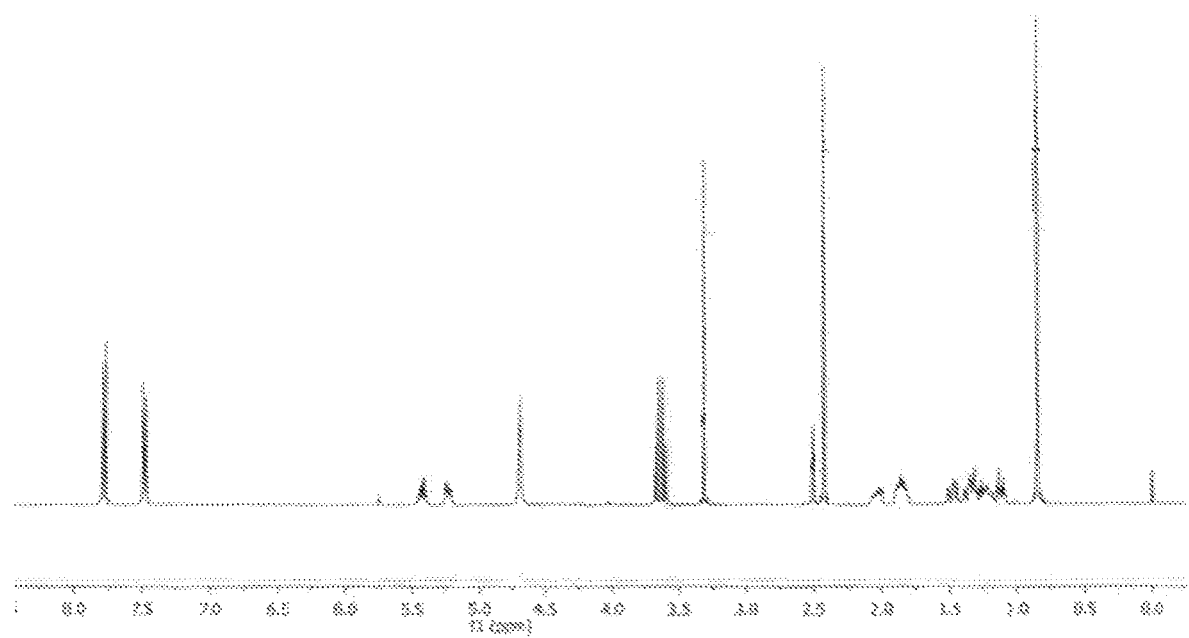

FIG. 29 shows the $^1$H NMR spectrum for the tosyl alcohol 4 of Example 6.

Figure 30:
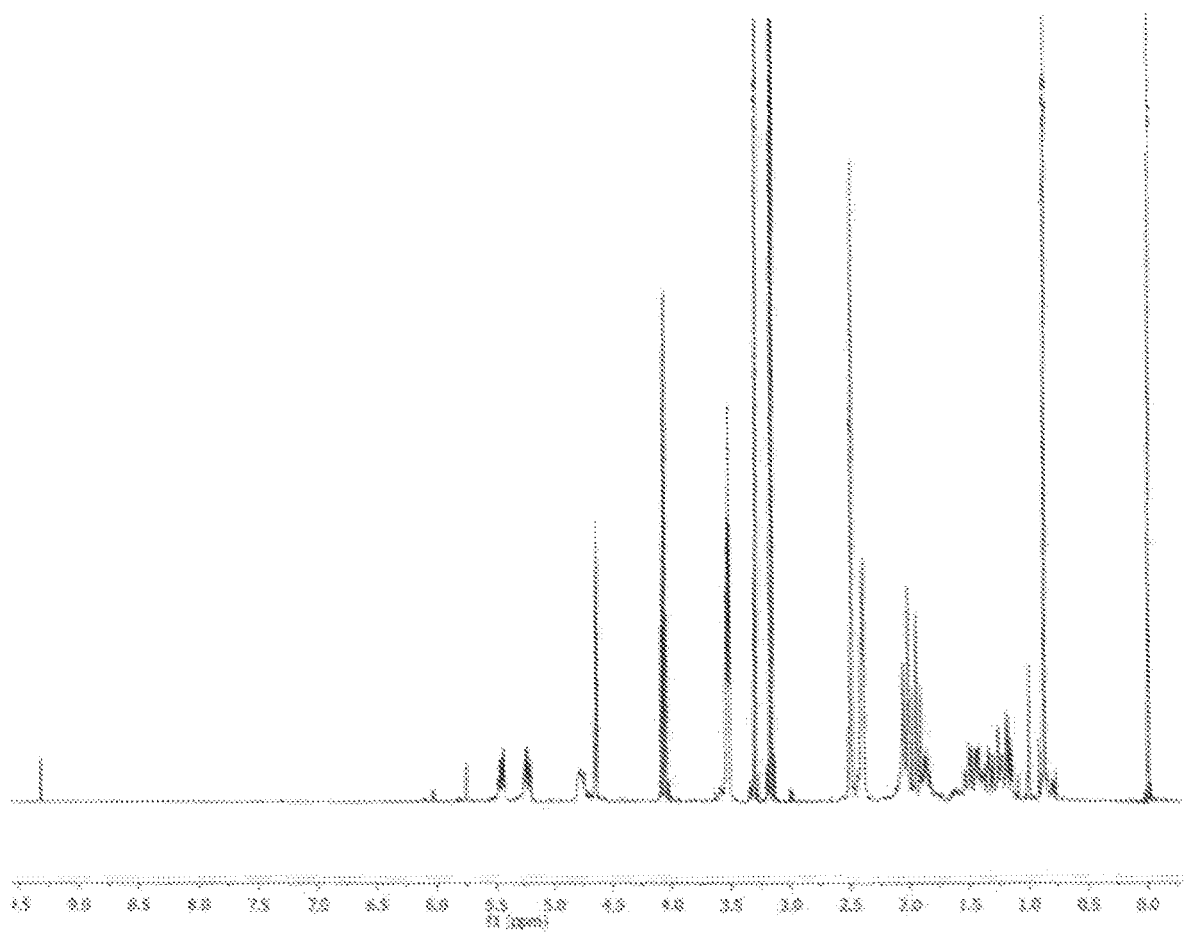

FIG. 30 shows the $^1$H NMR spectrum for the Alcohol 2 of Example 6.

FIG. 31 shows different locations for substitution of a TCO group on daptomycin.

Figure 32A:
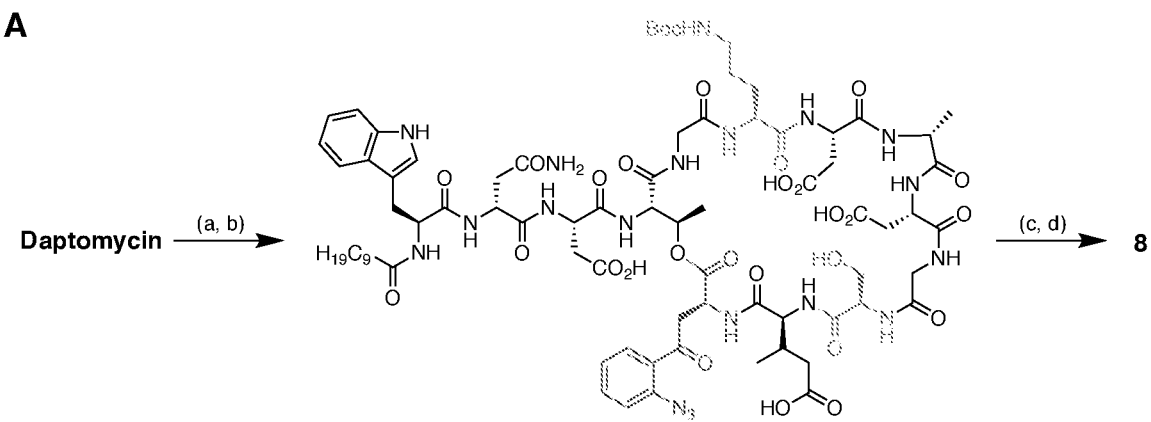
Figure 32B:
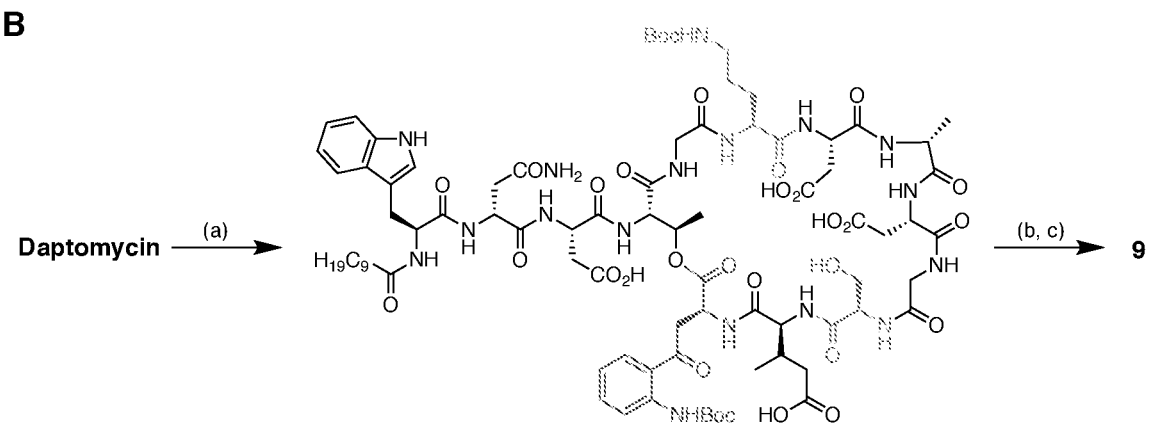

FIGS. 32A and 32B show synthetic protocols for preparing soluble TCO-daptomycin prodrugs of FIG. 31.

Figure 33A:
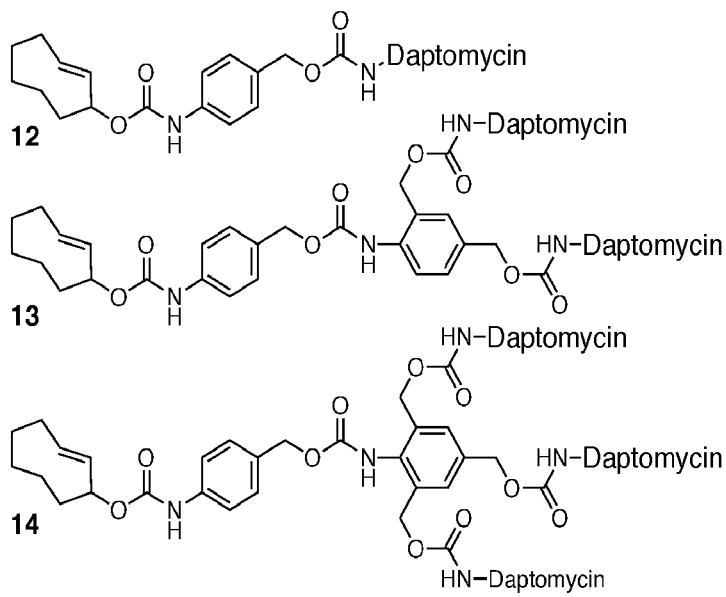

FIG. 33A shows various TCO-daptomycin prodrugs with different linkers.

Figure 33B:
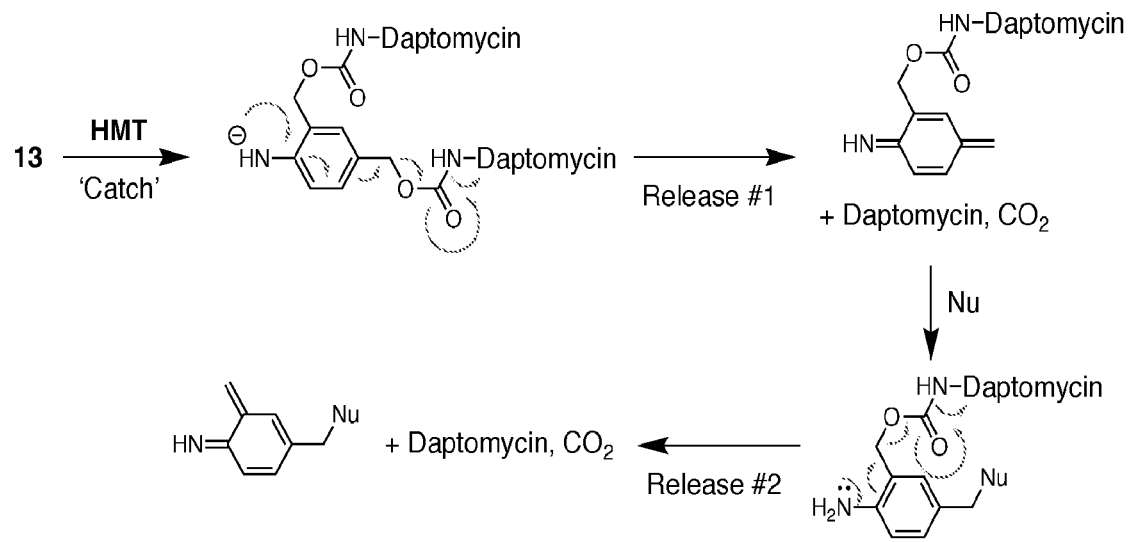

FIG. 33B shows the mechanism for daptomycin release from prodrugs in FIG. 33A.

Figure 34:
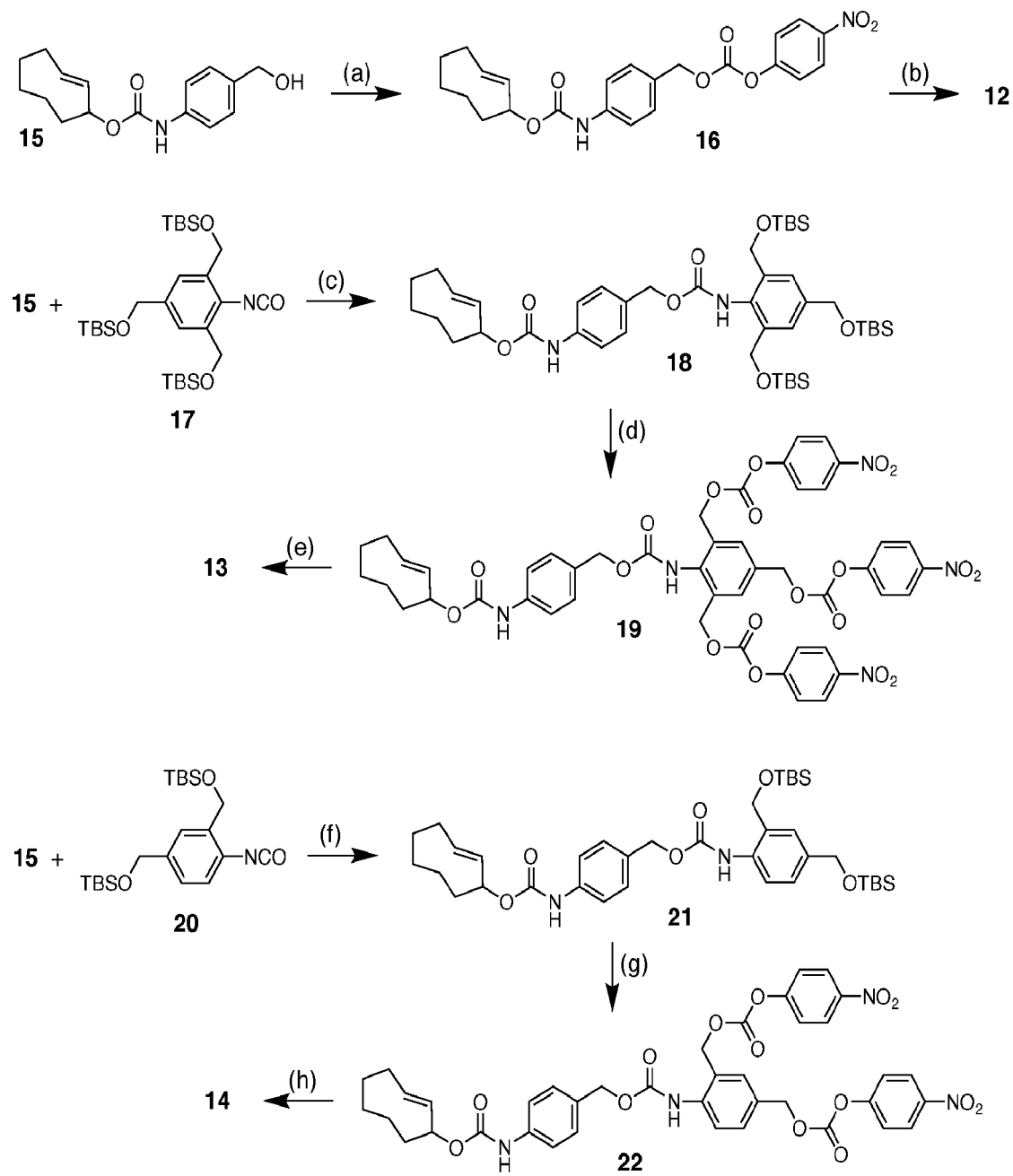

FIG. 34 is a schematic showing the synthesis of the conjugates of daptomycin in FIG. 33A: (a) p-nitrophenyl chloroformate, triethylamine; (b) daptomycin; (c) triethylamin; (d) Amberlyst 15, followed by p-nitrophenyl chloroformate; (e) daptomycin; (f) triethylamine; (g) Amberlyst 15, followed by p-nitrophenyl chloroformate; (h) daptomycin.

Figure 35:
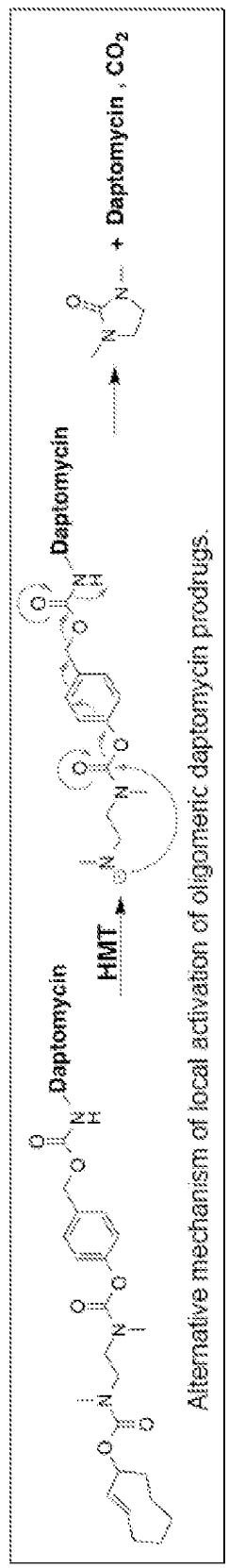

FIG. 35 shows a mechanism of local activation of daptomycin prodrugs.

Figures 36A, 36B:
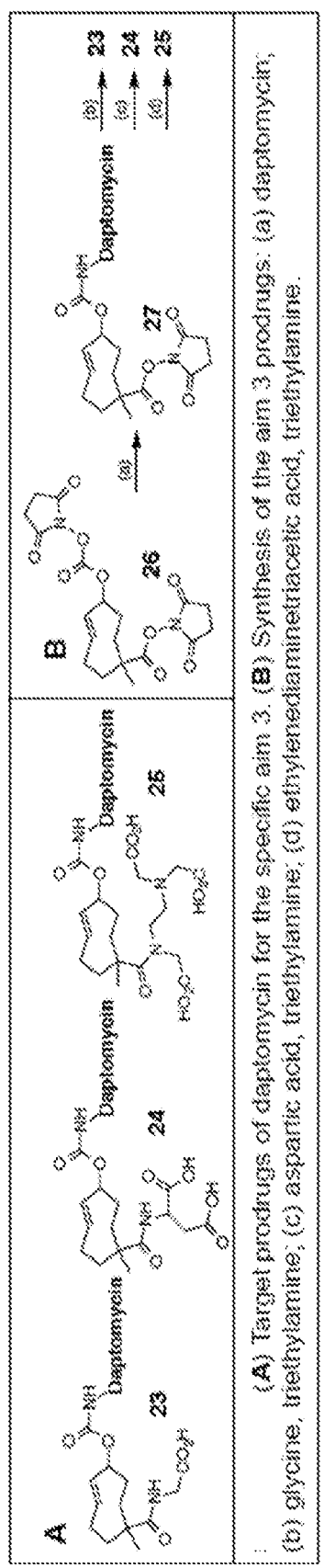

FIG. 36A shows alternate soluble TCO-daptomycin prodrugs.

FIG. 36B shows a synthesis for prodrugs in FIG. 36A.

FIG. 37 shows dosing parameters and adverse events from TCO-dox administration in a dog.

Figure 38:
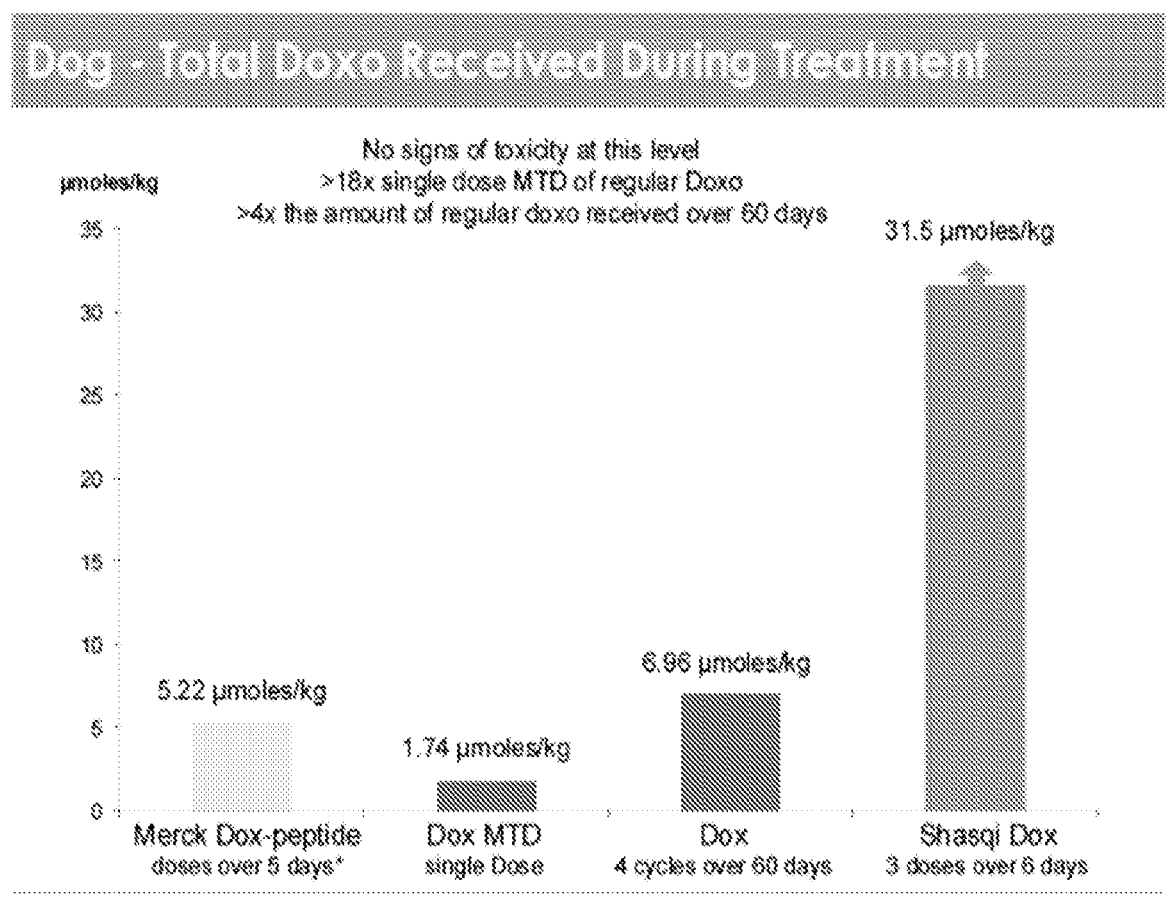

FIG. 38 shows that TCO-doxorubicin is significantly less toxic than existing doxorubicin formulations in a canine model. TCO-doxorubicin was administered to a dog at 18 times the single dose MTD for regular doxorubicin, with no observable adverse effects. This also represents a significant enhancement over the Merck Dox-peptide described by DeFeo-Jones et al. in Mol. Cancer Therap. 2002, 451-459 and Nat. Med., 2000, 1248-1252, based on reported use of 3 times the MTD of doxorubicin in dogs. Data presented is extrapolated from the published MTD.

Figure 39:
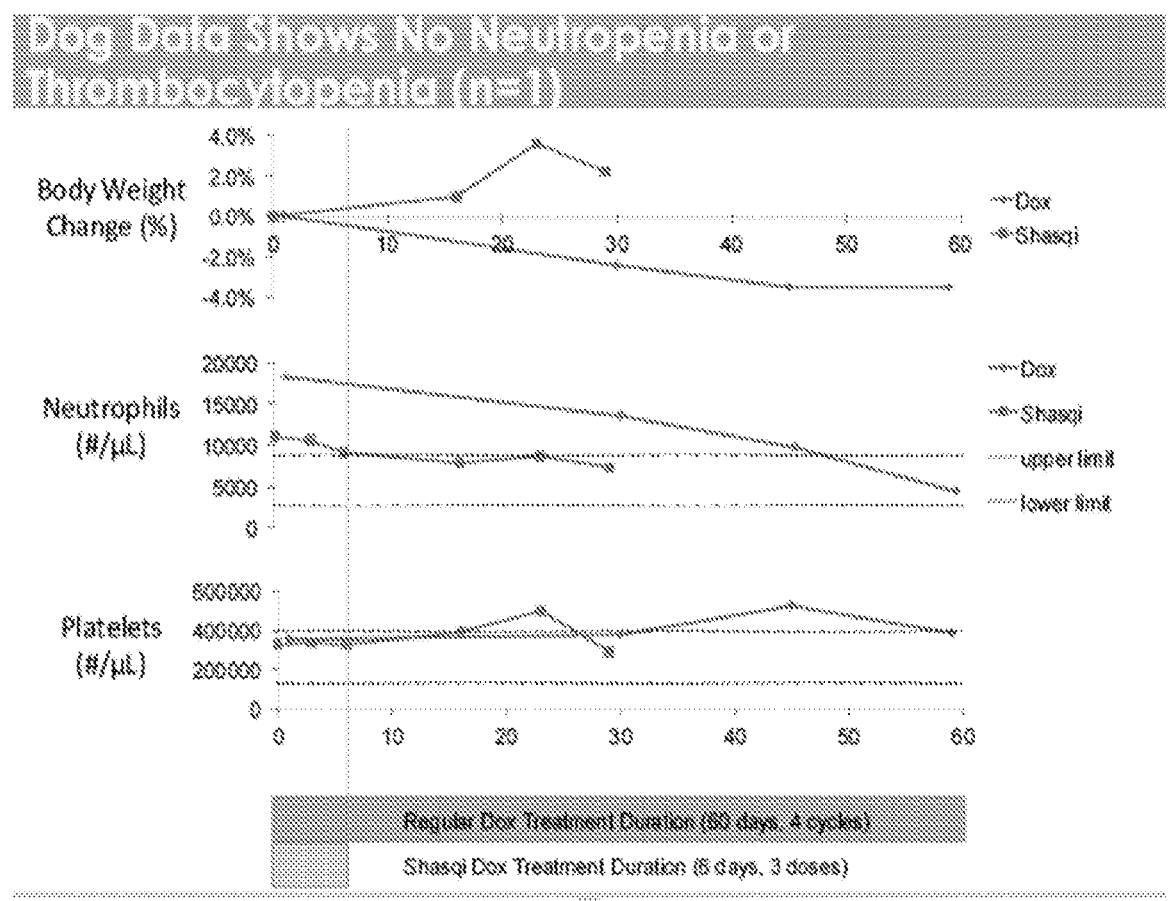

FIG. 39 shows a dog treated with TCO-doxorubicin or doxorubicin at the doses indicated in FIG. 38 experienced a drop in body weight of 3.5% during the course of doxorubicin treatment. Subsequently, the same animal gained 3.6% body weight after TCO-doxorubicin treatment. FIG. 39 also shows neutrophil count and platelet levels following treatment. Dashed lines represent the upper and lower limit of normal values. Treatment time frames are indicated by bars below chart.

Figure 40:
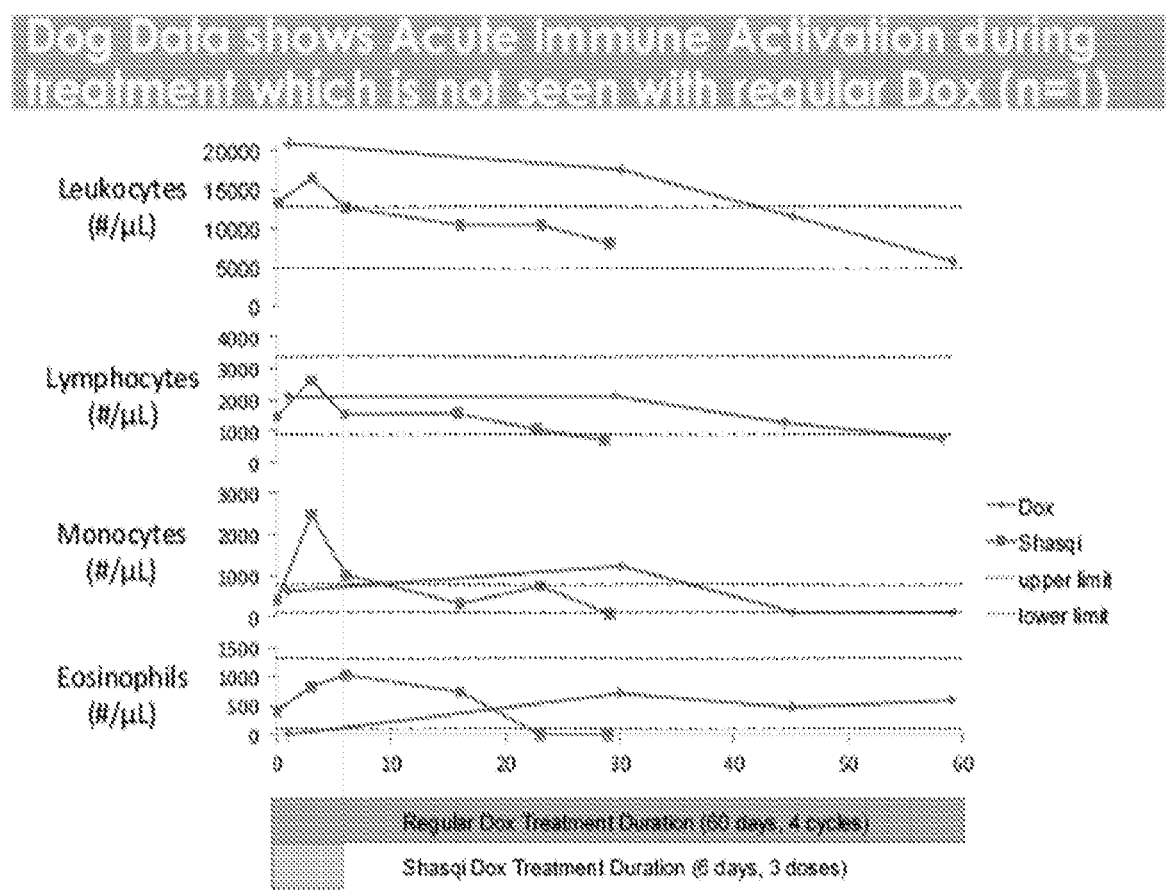

FIG. 40 shows effects on leukocytes, lymphocytes, monocytes, and eosinophils in a dog following administration of TCO-doxorubicin or doxorubicin.

Figures 41A, 41B:
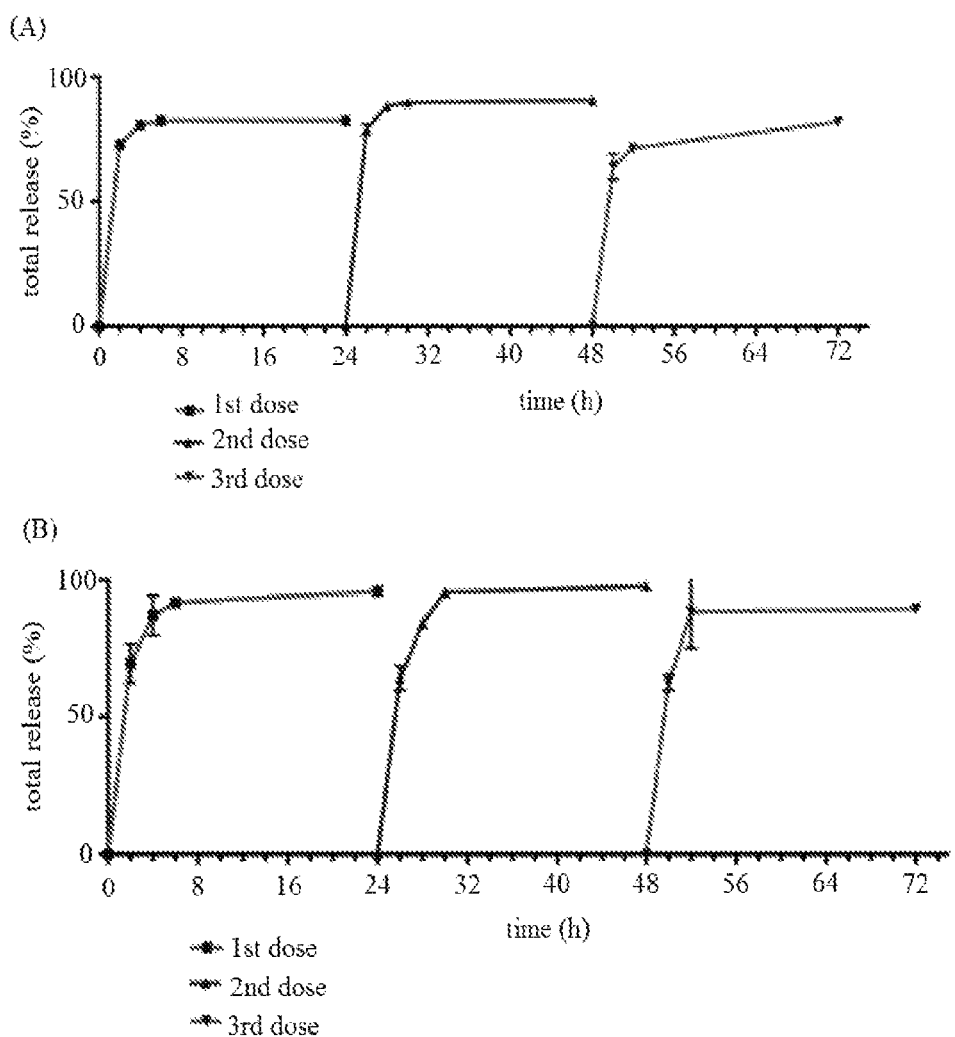

FIG. 41A shows release of daptomycin from the daptomycin-TCO-glycine conjugate of Example 13B upon contact with alginate TAG in PBS following three separate doses.

FIG. 41B shows release of vancomycin from the Vanco-Bis-TCO-glycine conjugate of Example 13C upon contact with alginate TAG in PBS following three separate doses.

Figure 42:
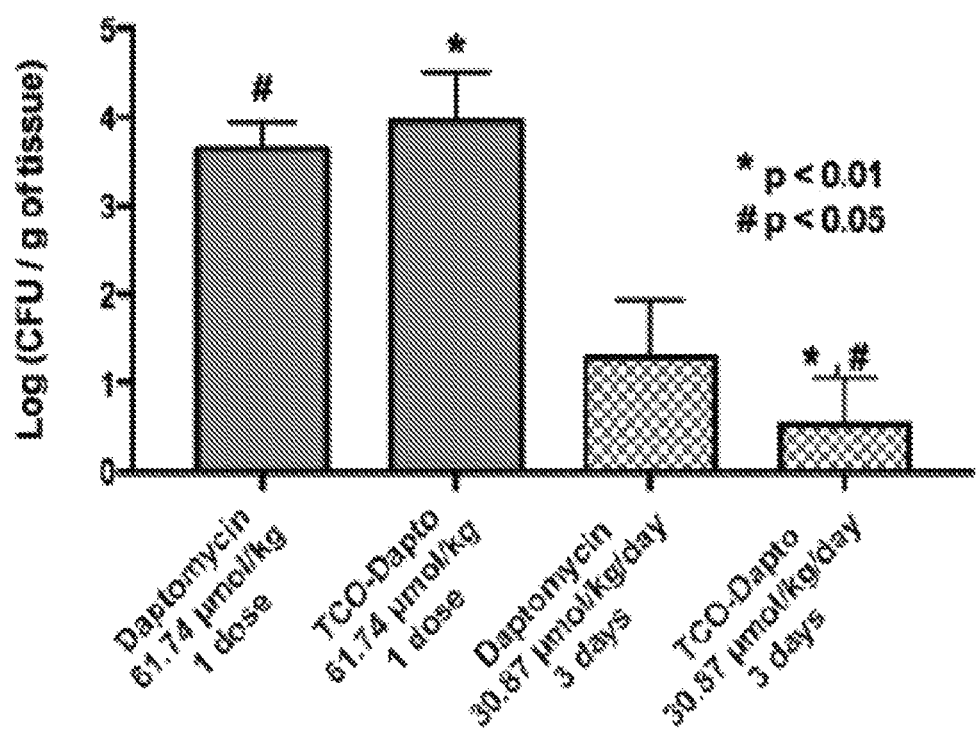

FIG. 42 shows the results in vivo for single or multiple dose treatment of MRSA infection with daptomycin or the daptomycin-TCO-glycine of Example 13B.

DETAILED DESCRIPTION

The present disclosure provides bioorthogonal compositions for delivering agents in a subject. The disclosure also provides methods of producing the compositions, as well as methods of using the same. Embodiments of each are described in more detail in the sections below.

The bioorthogonal compositions of the present disclosure may be used to deliver a payload to a target location in a subject, such as selectively delivering a payload to a specific target location in the subject. In certain embodiments, the bioorthogonal compositions include a support composition having different bioorthogonal functional groups, which may be administered to a subject (e.g., injected or implanted) at a desired target location in the subject, or may be administered systemically and targeted to a specific location or targeted to specific cells in the subject via a targeting agent.

The present disclosure also provides functionalized payload compositions that include a payload linked to a bioorthogonal functional group, which is complementary to one of the bioorthogonal functional groups of the support composition. Upon administration of the functionalized payload to the subject (e.g., systemic administration), selective binding between complementary bioorthogonal binding partners (e.g., between a bioorthogonal functional group of the support composition and its complementary bioorthogonal functional group of a functionalized payload) may occur, thus localizing the payload to the desired target location or cells in the subject.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry, 5$^{th}$ Edition*, John Wiley & Sons, Inc., New York, 2001; Larock, *Comprehensive Organic Transformations*, VCH Publishers, Inc., New York, 1989; Carruthers, *Some Modern Methods of Organic Synthesis, 3$^{rd}$* Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 30 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 30 carbon atoms with at least one carbon-carbon double bond. The alkenyl group may be substituted or unsubstituted. For example, the alkenyl group may be substituted with an aryl group, such as a phenyl.

The term "alkynyl," as used herein, refers to straight or branched monovalent hydrocarbyl groups having from 2 to 30 carbon atoms, such as 2 to 20, or 2 to 10 carbon atoms and having at least 1 site of triple bond unsaturation. The term "alkyne" also includes non-aromatic cycloalkyl groups of from 5 to 20 carbon atoms, such as from 5 to 10 carbon atoms, having single or multiple rings and having at least one triple bond. Examples of such alkynyl groups include, but are not limited to acetylenyl (—C≡CH), and propargyl (—CH$_2$C≡H), and cycloalkynyl moieties, such as, but not limited to, substituted or unsubstituted cyclooctyne moieties.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 30 carbon atoms, for example, of 2 to 10 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "amino acid" refers to both natural and unnatural amino acids. It also includes protected natural and unnatural amino acids.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "azide" as used herein, refers to the functional group —N$_3$.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein, a heteroaryl group as defined herein, or a heterocycle as defined herein.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "cyclooctene" as used herein, refers to a substituted or unsubstituted non-aromatic cyclic alkyl group of 8 carbon atoms, having a single ring with a double bond.

Examples of such cyclooctene groups include, but are not limited to, substituted or unsubstituted trans-cyclooctene (TCO).

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

The term "hydroxyalkyl" as used herein, means an alkyl group, as defined herein, in which one, two, three, four, five, six, seven or eight hydrogen atoms are replaced by a hydroxyl group.

In some instances, the number of carbon atoms in a hydrocarbyl substituent (e.g., alkyl or cycloalkyl) is indicated by the prefix "$C_x$-$C_y$-" or "$C_{x-y}$," wherein x is the minimum and y is the maximum number of carbon atoms in the substituent. Thus, for example, "$C_1$-$C_3$-alkyl" and "$C_{1-3}$alkyl" refer to an alkyl substituent containing from 1 to 3 carbon atoms. The two conventions "$C_x$-$C_y$-" and "$C_{x-y}$" are used interchangeably and have the same meaning.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "tetrazine" refers to a substituted or unsubstituted aromatic cyclic group of 2 carbon atoms and 4 nitrogen atoms, having a single ring with three double bonds. Examples of tetrazine groups include 1,2,3,4-tetrazine and 1,2,4,5-tetrazine. As used herein, 1,2,4,5-tetrazine is referred to as a "Tz" group.

The term "selectively delivering" refers to delivering an agent (e.g., a payload) to an organ or tissue (or portion thereof) in need of treatment or diagnosis, without significant binding to other non-target organs or tissues (or portions thereof).

The term "payload" refers to an agent for delivery to a target site in a subject. Payloads include therapeutic agents, diagnostic agents, targeting agents, and the like.

The term "therapeutic agent" refers to an agent capable of treating and/or ameliorating a condition or disease, or one or more symptoms thereof, in a subject. Therapeutic agents of the present disclosure also include prodrug forms of therapeutic agents.

The term "diagnostic agent" refers to agents that assist in diagnosing conditions or diseases. Representative diagnostic agents include imaging agents such as paramagnetic agents, optical probes, radionuclides, and the like. Paramagnetic agents are imaging agents that are magnetic under an externally applied field. Examples of paramagnetic agents include, but are not limited to, iron particles including iron nanoparticles and iron microparticles. Optical probes are fluorescent compounds that can be detected by excitation at one wavelength of radiation and detection at a second, different, wavelength of radiation. Optical probes of the present disclosure include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo detectable radioactive decay. Radionuclides useful in embodiments of the present disclosure include, but are not limited to, $^3$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

The term "targeting agent" refers to a chemical or biological agent that specifically binds to a target (e.g., a targeted organ or tissue), thereby forming a stable association between the targeting agent and the specific target. By "stably associated" or "stable association" is meant that a moiety is bound to or otherwise associated with another moiety or structure under standard physiological conditions. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. A targeting agent may be a member of a specific binding pair, such as, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like.

The term "targeted organ or tissue" refers to an organ or tissue that is being targeted for delivery of the payload. Representative organs and tissues for targeting include those that can be targeted by chemical or biological targeting agents, as well as those organs and tissues that cannot be targeted by chemical or biological targeting agents.

The term "implanting" refers to surgical implantation into a subject's body.

The term "biocompatible support" refers a support material capable of implantation into a subject's body and supporting binding agents, as well as payloads after the binding agents conjugate. The support is compatible with the subject's body. Representative biocompatible supports include, but are not limited to polymers, viscous or non-viscous liquid materials, gels, hydrogels such as polysaccharide hydrogels, alginate, cellulose, chitosan, hyaluronic acid, chondroitin sulfate, heparin, and the like. Biocompatible supports also include particles, such as nanoparticles, microparticles, and the like.

The term "contacting" or "contact" refers to the process of bringing into contact at least two distinct species such that they can interact with each other, such as in a non-covalent or covalent binding interaction or binding reaction. It should be appreciated, however, the resulting complex or reaction product can be produced directly from an interaction or a reaction between the added reagents or from an intermediate from one or more of the added reagents or moieties, which can be produced in the contacting mixture.

The term "linker", "linked" or "linking" refers to a chemical moiety that attaches two moieties together, such as a compound of the present disclosure to a biological material that targets a specific type of cell, such as a cancer cell, other type of diseased cell, or a normal cell type. The linking can be via covalent bonds, ionic bonds, hydrophobic interactions, hydrogen bonds, van der Waals forces (e.g., London dispersion forces), dipole-dipole interactions, and the like. The linking can be direct linkage between to the two moieties being linked, or indirectly, such as via a linker. Linkers useful in embodiments of the present disclosure include linkers having 30 carbon atoms or less in length. In some embodiments, the linkers are 1-15 carbon atoms in length, such as 1-12 carbon atoms, or 1-10 carbon atoms, or 5-10 carbon atoms in length. The types of bonds used to link the linker to the compound and biological molecule of the present disclosure include, but are not limited to, amides, amines, esters, carbamates, ureas, thioethers, thiocarbamates, thiocarbonate and thioureas. Other types of bonds may also be used in embodiments of the present disclosure. Particular linkers such as L and $L^2$ are specifically defined herein.

The term "binding agent" refers to an agent having a functional group capable of forming a covalent bond to a complementary functional group of another binding agent in a biological environment. Binding between binding agents in a biological environment may also be referred to as bioconjugation. Representative binding agents include, but are not limited to, an amine and an activated ester, an amine and an isocyanate, an amine and an isothiocyanate, thiols for formation of disulfides, an aldehyde and amine for enamine formation, an azide for formation of an amide via a Staudinger ligation. Binding agents also include bioorthogonal binding agents, which are binding agents having bioorthogonal functional groups. Bioorthogonal functional groups of bioorthogonal binding agents selectively react with a complementary bioorthogonal functional group of another bioorthogonal binding partner. Selective reaction between bioorthogonal binding partners can minimize side reactions with other binding agents, biological compounds, or other non-complementary bioorthogonal binding agents or non-complementary bioorthogonal functional groups. Bioorthogonal functional groups of bioorthogonal binding agents include, but are not limited to, an azide and alkyne for formation of a triazole via Click-chemistry reactions, trans-cyclooctene (TCO) and tetrazine (Tz) (e.g., 1,2,4,5-tetrazine), and others. The binding agents useful in the present disclosure may have a high reactivity with the corresponding binding agent so that the reaction is rapid.

The term "functionalized" refers to a moiety having a functional group attached to the moiety, such as for example a moiety having a binding agent functional group (e.g., a bioorthogonal functional group) attached thereto.

The term "administering" refers to any suitable route of administration to a subject, such as, but not limited to, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

The term "parenterally," as used herein, refers to modes of administration which include intravenous, intramuscular, intraperitoneal, intrasternal, subcutaneous and intraarticular injection and infusion.

The term "leaving group" refers to an atom (or a group of atoms) with electron withdrawing ability that can be displaced as a stable species, taking with it the bonding electrons. Examples of suitable leaving groups include halides (e.g., Br, Cl, I), sulfonate esters (e.g., triflate, mesylate, tosylate, and brosylate), and nitrophenols.

The term "pharmaceutically effective amount" and "therapeutically effective amount" refer to an amount of a compound sufficient to treat a specified disorder or disease or one or more of its symptoms and/or to prevent or reduce the risk of the occurrence or reoccurrence of the disease or disorder or symptom(s) thereof. In reference to tumorigenic proliferative disorders, a pharmaceutically or therapeutically effective amount comprises an amount sufficient to, among other things, cause the tumor to shrink or decrease the growth rate of the tumor.

As used herein, the term "subject," "patient," or "organism" includes humans and mammals (e.g., mice, rats, pigs, cats, dogs, and horses). Typical subjects to which an agent(s) of the present disclosure may be administered may include mammals, particularly primates, especially humans. For veterinary applications, suitable subjects may include, for example, livestock such as cattle, sheep, goats, cows, swine, and the like; poultry such as chickens, ducks, geese, turkeys, and the like; and domesticated animals particularly pets such as dogs and cats. For diagnostic or research applications, suitable subjects may include mammals, such as rodents (e.g., mice, rats, hamsters), rabbits, primates, and swine such as inbred pigs and the like.

The term "treating" or "treatment" as used herein means the treating or treatment of a disease or medical condition or symptom(s) thereof in a patient, such as a mammal (particularly a human) that includes: (a) ameliorating the disease or medical condition or symptom(s) thereof, such as, eliminating or causing regression of the disease or medical condition or symptom(s) thereof in a patient; (b) suppressing the disease or medical condition or symptom(s) thereof, for example by, slowing or arresting the development of the disease or medical condition or symptom(s) thereof in a patient; or (c) alleviating a symptom of the disease or medical condition or symptom(s) thereof in a patient.

The term "physiological conditions" is meant to encompass those conditions compatible with living cells, e.g., predominantly aqueous conditions of a temperature, pH, salinity, etc. that are compatible with living cells.

The term "particle" as used herein is used in its broadest sense and it may take the form of any fabricated material, a polymer, a protein, a synthetic hydrogel, a biological hydrogel, an organogel, a ceramic, a composite, a metal, a wood, or a glass material, a molecule, cryptophan, a virus, a phage, etc. Further, a particle may be of any shape, for example, spheres, rods, non-symmetrical shapes, etc. In some examples, the particles may be magnetic and can be formed from a paramagnetic, super-paramagnetic or ferromagnetic material or any other material that responds to a magnetic field. The particles, or a group of several particles in a complex, may be functionalized with a receptor that has a specific affinity to bind to or interact with a clinically relevant substrate. The receptor may be inherent to the particle itself. For example, the particle itself may be a virus or a phage with an inherent affinity for certain substrates. Additionally or alternatively, the particles can be functionalized by covalently or otherwise attaching or associating a receptor that specifically binds or otherwise recognizes a particular clinically relevant substrate. The functionalized receptor can be an antibody, peptide, nucleic acid, phage, bacteria, virus, or any other molecule with a defined affinity for a target substrate. Examples of material that may be used for the "particles" and/or "carrier" include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, poly anhydrides, polyphosphazines, poly(vinyl alcohols), poly(alkylene oxides), poly(allylamines)(PAM), poly(acrylates), modified styrene polymers, pluronic polyols, polyoxamers, poly (uronic acids), poly(vinylpyrrolidone) and copolymers or graft copolymers of any of the above. These examples do not limit their concentration, their cross-linking with different agents, their method of administration, their tailored degradation profiles and other characteristics known to those skilled in the art.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

2. Compositions

The present disclosure provides compositions for delivering agents in a subject. The compositions can include a functionalized payload composition and a support composition. In certain embodiments, the composition is used to selectively deliver one or more agents to a specific location in a subject, for example a targeted organ or tissue (or portion thereof) in a subject. The targeted delivery of the agent may be such that an effective amount of the agent is delivered to the targeted organ or tissue to produce a desired effect on the targeted organ or tissue (or targeted portion thereof). As such, compositions of the present disclosure facilitate selective targeting and treatment of a targeted organ or tissue (or portion thereof) in a subject.

A. Functionalized Payloads

As described above, functionalized payloads of the present disclosure includes a payload, a complementary binding agent, and optionally a linker attaching the payload to the complementary binding agent. A payload is an agent capable of producing a desired effect in a subject. For example, payloads of the present disclosure include therapeutic agents, diagnostic agents, targeting agents, and the like.

A therapeutic agent is an agent capable of treating and/or ameliorating a condition or disease in a subject. The therapeutic agent included of the present disclosure may be any desired therapeutic agent. Selection of a therapeutic agent may depend on various factors, for example, the disease or condition to be treated in the subject, functional groups on the therapeutic agent that may be used to attach a linker or binding agent, compatibility with other components of the compositions (e.g., low cross-reactivity with binding agents or complementary binding agents), and the like.

Representative therapeutic agents include, but are not limited to, therapeutic agents for treating cancer (e.g., paclitaxel, doxorubicin, daunorubicin, etoposide, irinotecan, SN-38, docetaxel, paclitaxel, gemcitabine, podophyllotoxin, Carmustine, Ixabepilone, Patupilone (epothelone class), platinum drugs, and the like), immunosuppressants (e.g., cyclosporin A, rapamycin, and the like), anti-fungal agents (e.g., Amphotericin, and the like), antibiotics (e.g., vancomycin, daptomycin, doxycycline, ceftriaxone, trimethoprim, sulfamethoxazole, acyclovir, nystatin, amphotericin B, flucytosine, emtricitabine, gentamicin, colistin, and the like), etc. Still other therapeutic agents include, but are not limited to, matrix metalloproteinase (MMP) inhibitors, L-dopa, oseltamivir, cefalexin, 5-aminolevulinic acid, cysteine, celecoxib, nimodipine, among others. In some embodiments, the therapeutic agent is vancomycin. In some embodiments, the therapeutic agent is daptomycin. In some embodiments, the therapeutic agent is doxorubicin. In some embodiments, the therapeutic agent is gemcitabine. In some embodiments, the therapeutic agent is docetaxel. In some embodiments, the therapeutic agent is cyclic-adenosine monophosphatidyl (c-AMP).

Therapeutic agents of the present disclosure also include pro drug forms of the therapeutic agent. In some cases, the therapeutic agent may include a functional group for attachment of the therapeutic agent to a linker or binding agent. For example, the therapeutic agent may be attached to the linker or the binding agent through a covalent bond, such as an amide, amine, ester, carbonate, carbamate, urea, thioether, thiocarbamate, thiocarbonate, thiourea, etc. In some instances, the therapeutic agent is covalently attached to the linker or binding agent through an amide bond; e.g., the therapeutic agent may be an amine-containing therapeutic agent for attachment of the therapeutic agent to a carboxyl group of the linker or binding agent, or, in other cases, the therapeutic agent may be a carboxyl-containing therapeutic agent for attachment of the therapeutic agent to an amine group of the linker or binding agent. In some instances, the therapeutic agent is covalently attached to the linker or binding agent through a carbamate group; e.g., the therapeutic agent may be an amine-containing therapeutic agent for attachment of the therapeutic agent to an acyloxy group of the linker or binding agent.

Diagnostic agents suitable for embodiments of the present disclosure are agents that facilitate diagnosing conditions or diseases in a subject. Representative diagnostic agents include imaging agents such as paramagnetic agents, optical probes, radionuclides, and the like. Paramagnetic agents are imaging agents that are magnetic under an externally applied field. For example, paramagnetic agents may produce a detectable magnetic field under an externally applied magnetic field. Examples of paramagnetic agents include, but are not limited to, iron particles including iron nanoparticles and iron microparticles. Optical probes are fluorescent compounds that can be detected by excitation at one wavelength of radiation and detection at a second, different, wavelength of radiation. Optical probes of the present disclosure include, but are not limited to, fluorescein, rhodamine, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo detectable radioactive decay. Radionuclides useful in embodiments of the present disclosure include, but are not limited to, $^{3}$H, $^{11}$C, N, $^{8}$F, $^{1}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am. Other radionucleotide agents that may be used include, for example, DOTA (1,4,7,10-tetraazacyclododecane-1,4,7,10-tetraacetic acid) and TETA (1,4,8,11-tetraazacyclotetradecane-1,4,8,11-tetraacetic acid); e.g., DOTA-$^{64}$Cu, TETA-$^{64}$Cu, DOTA-$^{111}$In, and the like. Diagnostic agents also include detectable labels, which may themselves be detectable or may elicit accumulation of detectable compounds at a target site. For instance, detectable labels include fluorophores or autofluorescent or luminescent markers. An example of a detectable label that elicits accumulation of detectable compounds at a target site is 5-aminolevulinic acid, which elicits accumulation of fluorescent porphyrins (e.g., protoporphyrin IX) in neoplastic tissues.

A targeting agent is a chemical or biological targeting agent that specifically binds to a target (e.g., a targeted organ or tissue), thereby forming a stable association between the targeting agent and the specific target. Stable associations between a targeting agent and its target may include covalent bonds and non-covalent interactions, such as, but not limited to, ionic bonds, hydrophobic interactions, hydrogen bonds, van der Waals forces (e.g., London dispersion forces), dipole-dipole interactions, and the like. Targeting agents may include members of specific binding pairs, such as, but not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like.

Targeting agents include ligands that specifically bind (or substantially specifically bind) a particular clinically-relevant target receptor or cell surface target. The ligand can be an antibody, peptide, nucleic acid, phage, bacteria, virus, or other molecule with a specific affinity for a target receptor or cell surface target. Examples of receptors and cell surface targets include, but are not limited to, PD-1, CTLA-4, HER2/neu, HER1/EGFR, VEGFR, BCR-ABL, SRC, JAK2, MAP2K, EML4-ALK, BRAF V600E, 4-1BB, GITR, GSK3beta, or other cellular receptors or cell surface targets.

As described above, the payload may be attached to the complementary binding agent through a linker. Any suitable linker can be used to link the payload to the complementary binding agent. Representative linkers can have 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms.

In certain embodiments, the linker between the payload and the complementary binding agent is a non-releasable linker. A non-releasable linker is a linker that forms an attachment between at least two moieties, where the attachment is not significantly disrupted under the conditions that compositions using the non-releasable linker are used (e.g., covalent bonds in the linker remain intact and are not cleaved). For instance, a non-releasable linker may include one or more covalent bonds between at least two moieties, such that the moieties are covalently bound to each other and remain covalently bound to each other under the conditions that compositions are used. For example, in certain embodiments, a non-releasable linker may be used with a payload, such as a payload having a prodrug form of a therapeutic agent, where release of the therapeutic agent from the prodrug provides for delivery of the therapeutic agent to the target site in the subject.

In certain embodiments, the linker between the payload and the complementary binding agent is a releasable linker. A releasable linker is a linker that forms an attachment between at least two moieties, where the attachment may be disrupted under releasing conditions such that the moieties are no longer attached to each other (e.g., one or more covalent bonds in the linker may be cleaved). Releasable linkers may have the attachment between the moieties disrupted by exposure of the releasable linker to releasing conditions, such as, but not limited to, light, heat, sound, a releasing agent (e.g., chemical releasing agent (e.g., an acid, a base, an oxidizing agent, a reducing agent), a solvent, an enzyme, etc.), combinations thereof, and the like. In some embodiments, the releasable linker may not require the application of an external stimulus or contact with releasing conditions to disrupt the attachment between the moieties. For example, a releasable linker may include one or more unstable bonds or functional groups in the linker that can be cleaved spontaneously without contact with an external stimulus or releasing conditions, thereby releasing the payload from the support composition. Examples of bonds or functional groups that can be spontaneously cleaved as described above include, but are not limited to, carbamates, which release carbon dioxide upon spontaneous cleavage. Functionalized payloads of the present disclosure that include a releasable linker may facilitate delivery of a payload to a target location in a subject.

In some cases, the payload may be released as described above by contacting the releasable linker to releasing conditions. The releasing conditions can be target specific, such as releasing conditions that are directly applied to a desired target location in a subject (e.g., a target location where the support composition is present). In some embodiments, the releasing conditions may be non-specific, such as by exposure of the releasable linker to an extracellular mechanism (e.g., low pH in tumor tissue, hypoxia, enzymes, and the like). In other instances, release of the payload can be achieved through intracellular, such as lysosomal, release mechanisms (e.g., glutathione, proteases (e.g., cathepsin), catabolism, and the like). In these cases, the support composition may be internalized within a cell and subsequently exposed to releasing conditions present within the cell. Intracellular releasing conditions (e.g., glutathione, cathepsin, and the like) may result in release of the payload from the support composition such that the payload can be dispersed from the cell and provide a therapeutic effect on neighboring cells. Examples of these types of releasable linkers include, but are not limited to, hydrazones (acid labile), peptide linkers (cathepsin B cleavable), disulfide moieties (thiol cleavable), and the like. This type of release mechanism of action may facilitate providing treatment to diseases or conditions, such as tumors (e.g., tumors with heterogeneous receptor expression, or with poor mAb penetration).

In certain embodiments, the linker between the payload and the complementary binding agent is an immolative linker.

In certain embodiments, the linker between the payload and the complementary binding agent is a pH tunable linker.

In certain embodiments, the functionalized payload compositions have formula:

(I)

wherein
D is a payload as defined herein;
L is a linker as defined herein; and
BA is a complementary binding agent as defined herein.

The person skilled in the art will recognize that a payload D bonded to a linker does not refer to a payload molecule per se, but refers to the portion of the payload molecule bonded to the linker. Release of the payload D from a compound herein, releases the payload per se.

In certain embodiments, the functionalized payload compositions comprise a trans-cyclooctene (TCO) as the complementary binding agent. The compounds can include one or more therapeutic agents. The compounds can include one or more cell permeation agents. The compounds can include one or more diagnostic agents. The compounds can optionally include a linker group (e.g., a self-immolative linker) attaching the one or more agents to the trans-cyclooctene.

In one aspect, the functionalized payload is a compound of formula (I-A), wherein D, $R^{1a}$, $R^{1b}$, $L^1$, $L^2$, m and p are as defined herein.

In some embodiments, $R^{1b}$ is selected from the group consisting of $G^1$, OH, $-NR^{1c}-C_{1-4}$ alkylene-$G^1$, $-NR^{1c}-C_{1-4}$alkylene-N$(R^{1d})_2$, $-N(R^{1c})$CHR$^{1e}$CO$_2$H, $-N(R^{1c})$CH$_2$CO$_2$H, and $-N(R^{1f})-$CH$_2$CH$_2-$(N(CH$_2$CO$_2$H)CH$_2$CH$_2)_n-$N(CH$_2$CO$_2$H)$_2$; $R^{1e}$ is $-$CH$_2$CO$_2$H, $-$CH$_2$CH$_2$CO$_2$H, $-$CH$_2$CONH$_2$, $-$CH$_2$CH$_2$CONH$_2$, $-$CH$_2$OH, or $-$CH(CH$_3$)OH; and $R^{1f}$ is hydrogen or CH$_2$CO$_2$H, wherein n, $G^1$ and $R^{1c}$ care as defined herein.

In some embodiments, $R^{1a}$ is $C_{1-4}$alkyl; $R^{1b}$ is selected from the group consisting of $G^1$, OH, $-NR^{1c}-C_{1-4}$alkylene-$G^1$, $-NR^{1c}-C_{1-4}$alkylene-N$(R^{1d})_2$, $-N(R^{1c})$CHR$^{1e}$CO$_2$H, $-N(R^{1c})$CH$_2$CO$_2$H, and $-N(R^{1f})-$CH$_2$CH$_2-$(N(CH$_2$CO$_2$H)CH$_2$CH$_2)_n-$N(CH$_2$CO$_2$H)$_2$; $R^{1e}$ is $-C_{1-4}$ alkylene-CO$_2$H; $R^{1f}$ is hydrogen or $C_{1-4}$alkylene-CO$_2$H; $G^1$ is a 4- to 8-membered monocyclic heterocyclyl containing a first nitrogen and optionally one additional heteroatom selected from nitrogen, oxygen, and sulfur, $G^1$ being attached at the first nitrogen and optionally substituted with 1-4 substituents independently selected from the group consisting of $C_{1-4}$alkyl, $C_{1-4}$ haloalkyl, halo, cyano, OH, $-$OC$_{1-4}$alkyl, and oxo; and n is 0, 1, or 2, wherein $R^{1c}$ and $R^{1d}$ are as defined herein.

In some embodiments, $R^{1a}$ is CH$_3$; $R^{1e}$ is $-$CH$_2$CO$_2$H; $R^{1f}$ is hydrogen or CH$_2$CO$_2$H; and $G^1$ is a piperazinyl (e.g., piperazin-1-yl), morpholinyl (e.g., morpholin-4-yl), piperidinyl (e.g., piperidin-1-yl), azepanyl (e.g., azepan-1-yl), or pyrrolidinyl (e.g., pyrrolidin-1-yl), attached through a ring nitrogen atom and optionally substituted with 1-4 substituents independently selected from the group consisting of $C_{1-4}$alkyl, $C_{1-4}$haloalkyl, halo, cyano, OH, $-$OC$_{1-4}$alkyl, and oxo.

In some embodiments, -$L^2$- is $-$C(O)$-$.

In some embodiments, $R^{1b}$ is selected from the group consisting of OH, N(H)CH$_2$CO$_2$H, $-$N(H)CHR$^{1e}$CO$_2$H, $-$N(H)$-$CH$_2$CH$_2-$(N(CH$_2$CO$_2$H)CH$_2$CH$_2)_n-$N(CH$_2$CO$_2$H)$_2$, and $-$N(CH$_2$CO$_2$H)$-$CH$_2$CH$_2-$N(CH$_2$CO$_2$H)$_2$; and $R^{1e}$ is $-$CH$_2$CO$_2$H.

In certain embodiments, the functionalized payload compositions have formula (I),

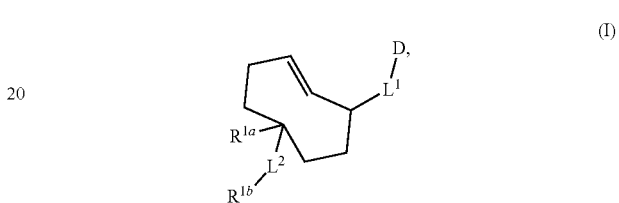

(I)

wherein
D is a payload as defined herein;
L is a linker as defined herein;
$R^{1a}$ is selected from the group consisting of $C_{1-4}$alkyl, $C_{1-4}$haloalkyl, and OC$_{1-4}$alkoxy;
$L^2$ is selected from the group consisting of $-$C(O)$-$ and $C_{1-3}$alkylene (e.g., $-$CH$_2-$); and
$R^{1b}$ is selected from the group consisting of $G^1$, OH, $-$NR$^{1c}-C_{1-4}$alkylene-$G^1$, and $-$NR$^{1c}-C_{1-4}$alkylene-N$(R^{1d})_2$;
$G^1$ is an optionally substituted heterocyclyl; and
$R^{1c}$ and $R^{1d}$, at each occurrence, are independently hydrogen or $C_{1-4}$alkyl.

In some embodiments, the $G^1$ is optionally substituted morpholino or piperazinyl (e.g., N-methylpiperazine).

In some embodiments, -$L^1$- is

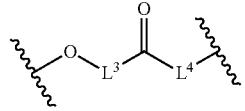

or $-$O$-$; -$L^3$- is a bond or $C_{1-6}$ alkylene; -$L^4$- is a bond, $-$NHN, $-$N(R$^{10}$)$-$C$_{2-6}$alkylene-N(R$^{11}$)$-$, $-$N(R$^{12}$)$-$C$_{2-3}$alkylene-N(R$^{13}$)C(O)$-$, $-$N(R$^{10}$)$-$C$_{1-6}$alkylene-C(O)NHN, $-$NHNHC(O)C$_{1-6}$alkylene-C(O)NHN, $-$CH(NHC(O)R$^{14}$)C$_{1-4}$alkylene-S$-$S$-$C$_{1-4}$alkylene-OC(O)$-$, $-$NHNHC(O)CH(NHC(O)R$^{15}$)CH$_2$C(O)$-$, $-$C$_{1-6}$alkylene-CH(G$^X$)OC(O)$-$,

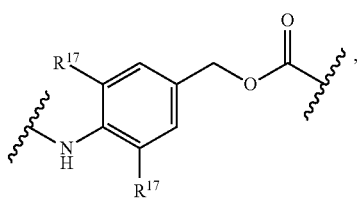

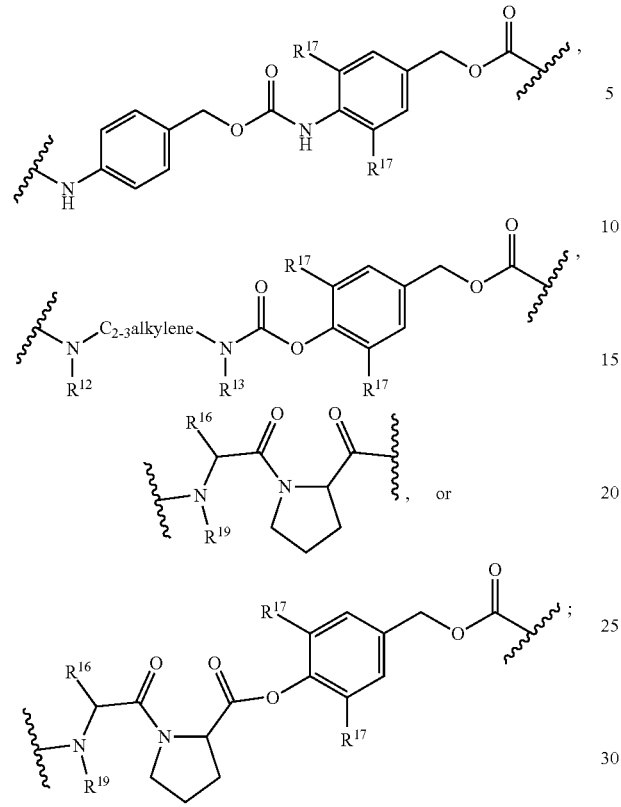

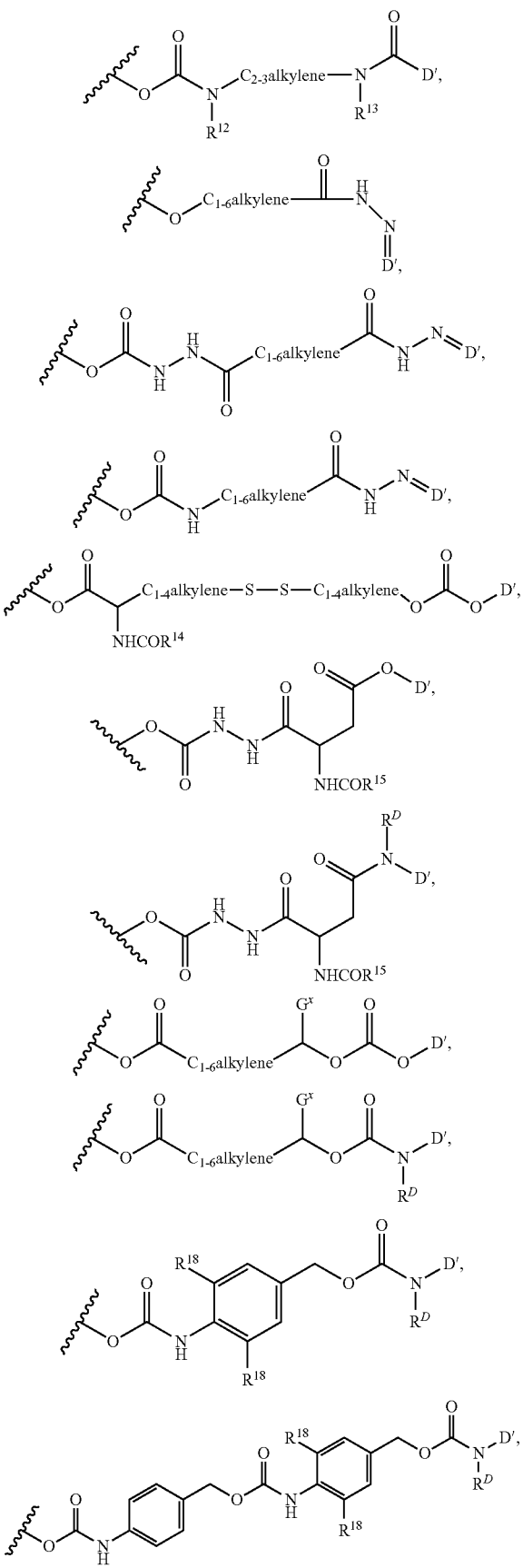

$R^{10}$, $R^{11}$, $R^{12}$, $R^{13}$, $R^{14}$, $R^{15}$, and $R^{19}$ are each independently hydrogen or $C_{1-4}$alkyl; $R^{16}$ is hydrogen, $C_{1-4}$alkyl, —$C_{1-4}$alkylene-OH, —$C_{1-4}$ alkylene-O$C_{1-4}$alkyl, —$C_{1-4}$alkylene-$CO_2$H, or —$C_{1-4}$alkylene-$CONH_2$; $R^{17}$, at each occurrence, is independently hydrogen or —$CH_2OC(O)$—; and $G^X$ is phenyl optionally substituted with 1-5 substituents independently selected from the group consisting of halogen, $C_{1-4}$alkyl, $C_{1-4}$haloalkyl, $C_{1-4}$alkoxy, cyano, and nitro.

In some embodiments, m is 1. In some embodiments where m is 1, is

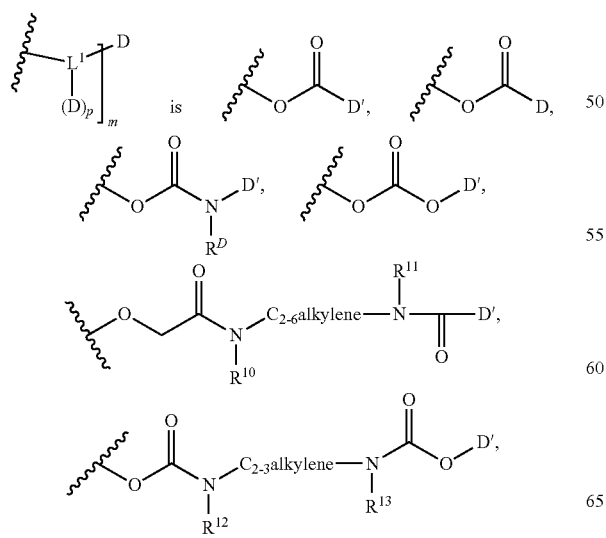

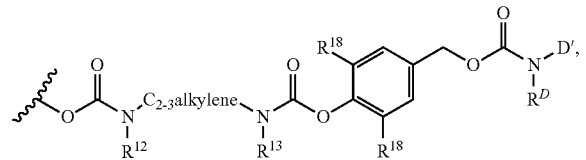

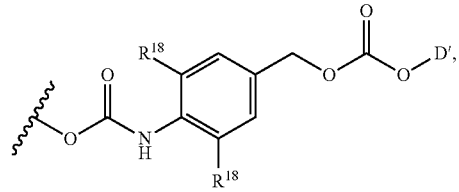

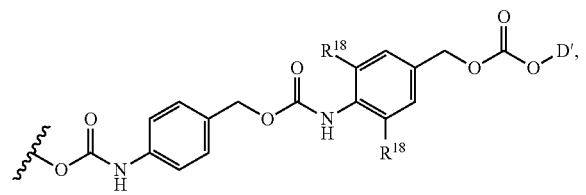

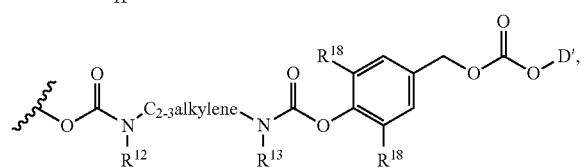

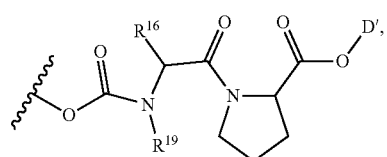

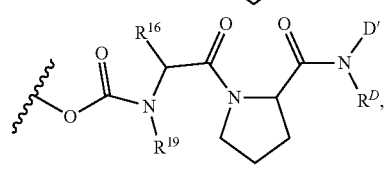

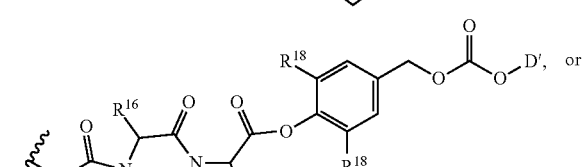

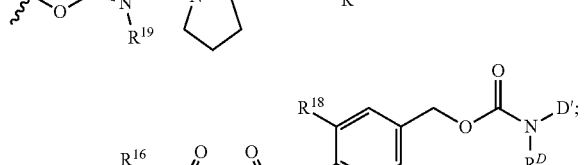

$R^{18}$, at each occurrence, is independently hydrogen or —CH$_2$OC(O)ND; $R^D$ is hydrogen or C$_{1-4}$alkyl on a nitrogen atom of the payload; and D' is a payload moiety.

A "payload moiety" as used herein refers to a payload D minus its nucleophilic group such as NH, NC$_{1-4}$alkyl, O, or S that attaches to a linker or minus its electrophilic group such as C(O) that attaches to a linker, i.e., the remainder of the payload. For example, a compound of formula

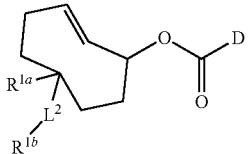

includes a compound such as

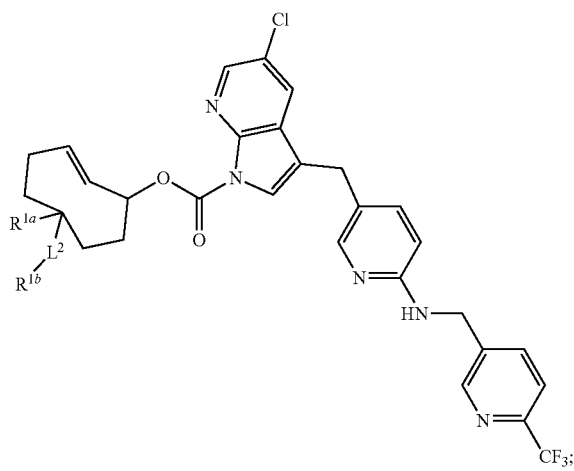

a compound

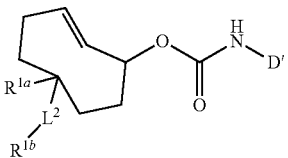

includes a compound such as

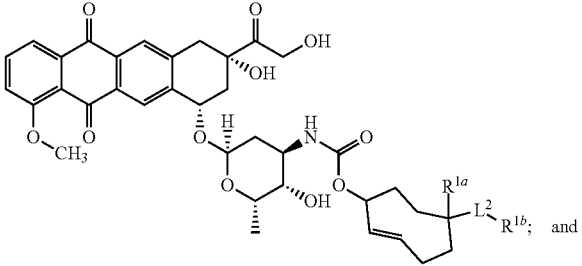

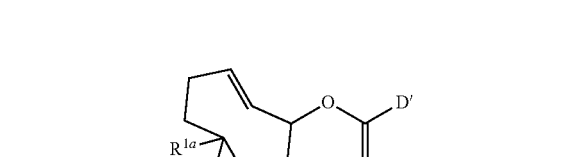

includes a compound such as

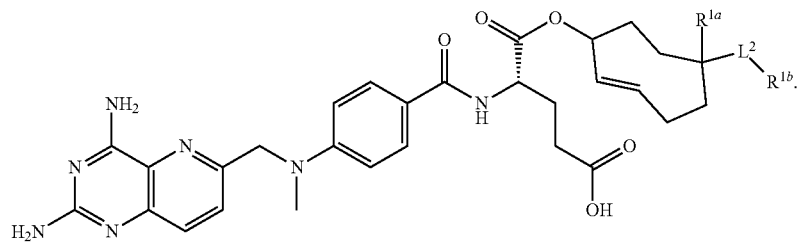

Release of DH, NH$_2$-D', or HOOC-D' releases the payload molecule per se.

In some embodiments, p is 0.

In some embodiments, m is 2 or 3. In some embodiments where m is 2 and

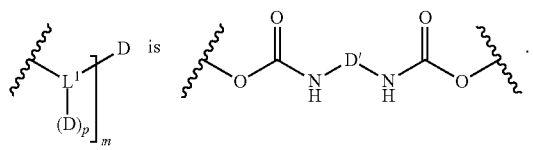

In these embodiments, the payload may be vancomycin.

In some embodiments, the payload is a therapeutic agent, such as an antibiotic agent, antifungal agent, antiviral agent, anticancer agent, cardiovascular agent, CNS agent, anti-inflammatory/anti-arthritic agent, anti-TB/anti-leprosy agent, anti-histaminic/respiratory disorder agent, a corticosteroid agent, immunosuppressant agent, or anti-ulcer agent. Particular therapeutic agents include paclitaxel, doxorubicin, daunorubicin, etoposide, irinotecan, SN-38, docetaxel, gemcitabine, podophyllotoxin, carmustine, ixabepilone, patupilone, cyclosporin A, rapamycin, amphotericin, vancomycin, daptomycin, doxycycline, ceftriaxone, trimethoprim, sulfamethoxazole, acyclovir, nystatin, amphotericin B, flucytosine, emtricitabine, gentamicin, colistin, L-dopa, oseltamivir, cefalexin, 5-aminolevulinic acid, cysteine, celecoxib, and nimodipine.

Particular

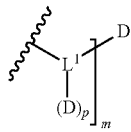

include

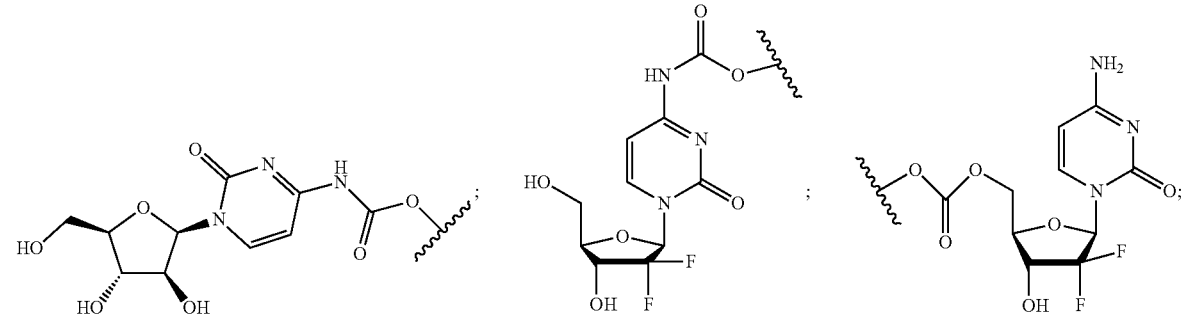

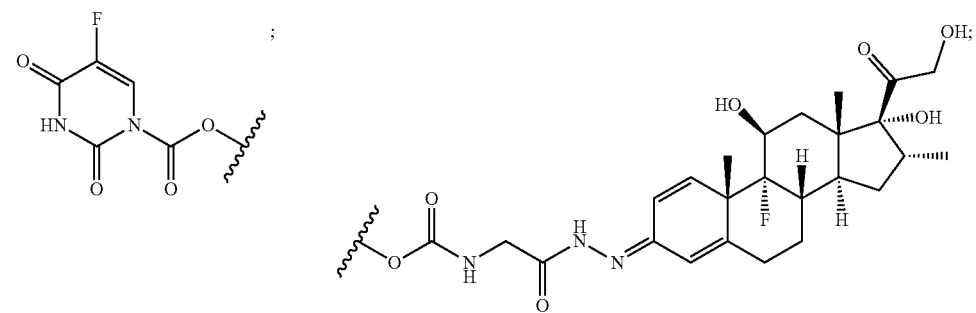

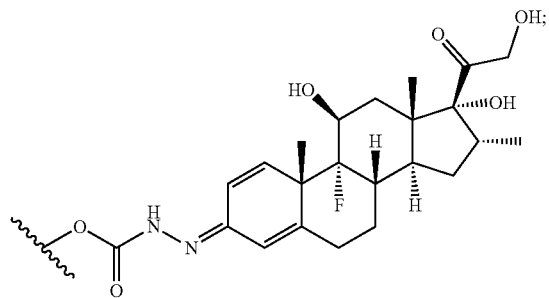
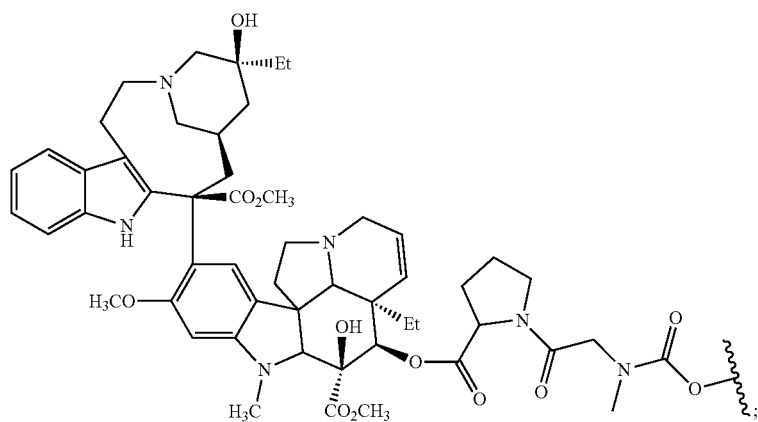
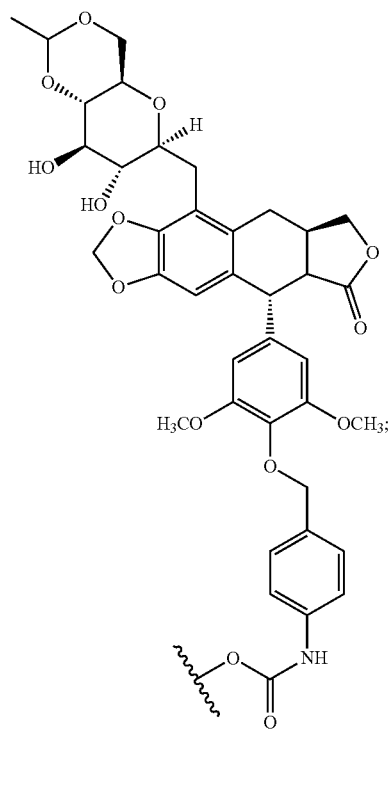
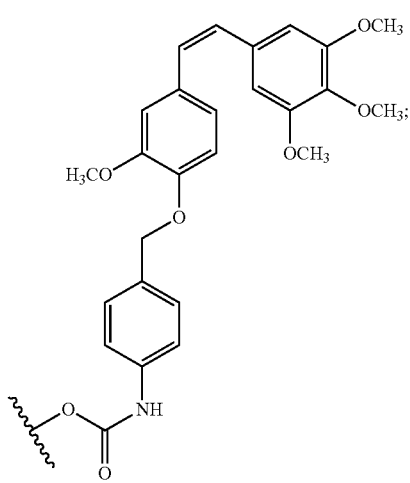
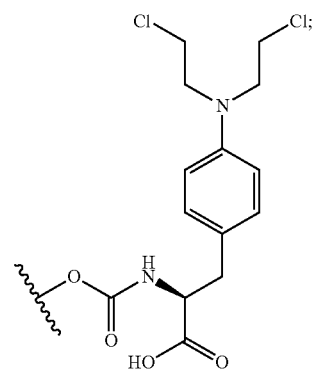

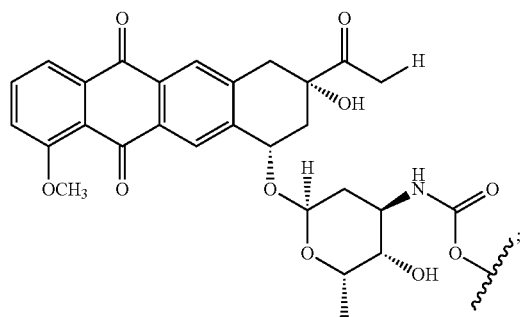
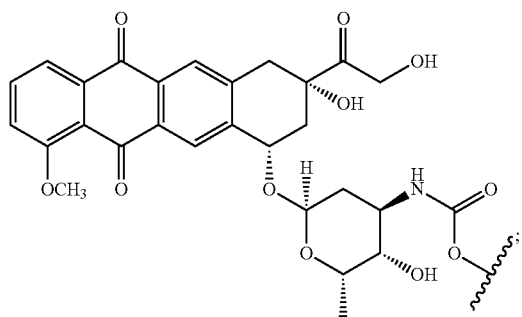
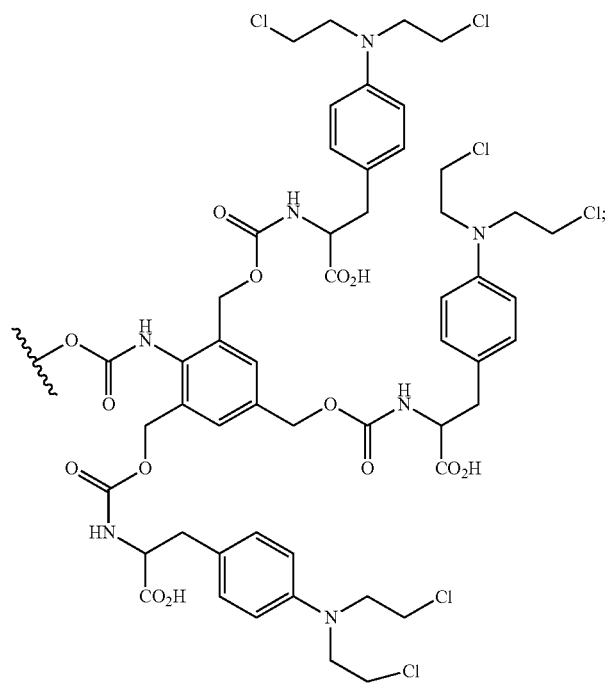
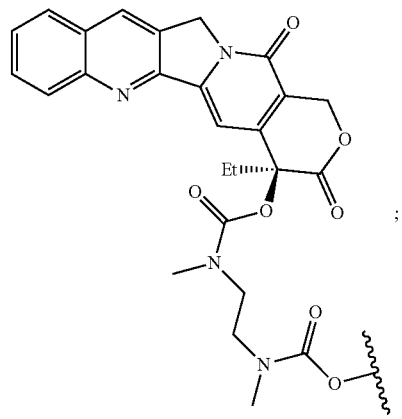
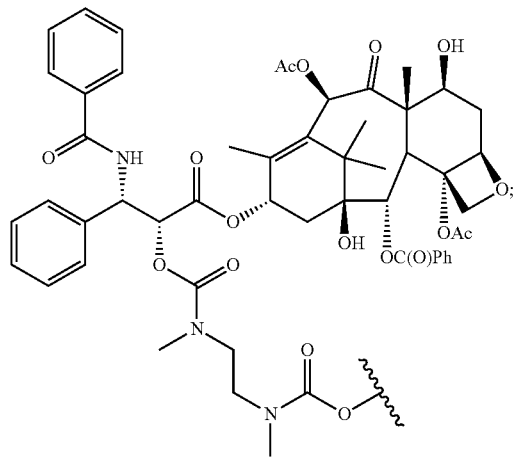
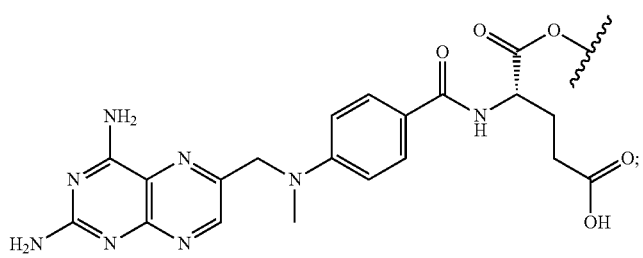

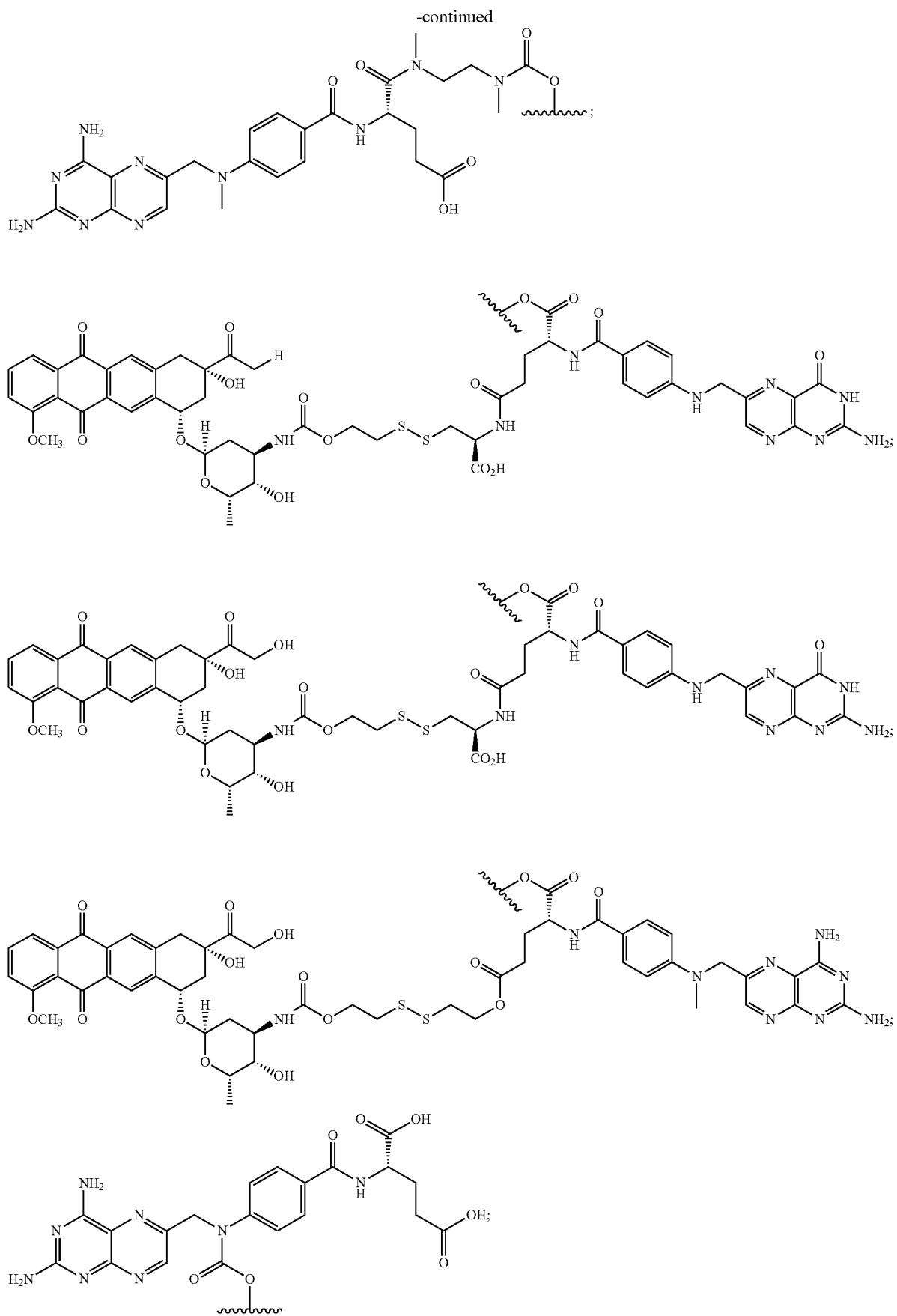

-continued
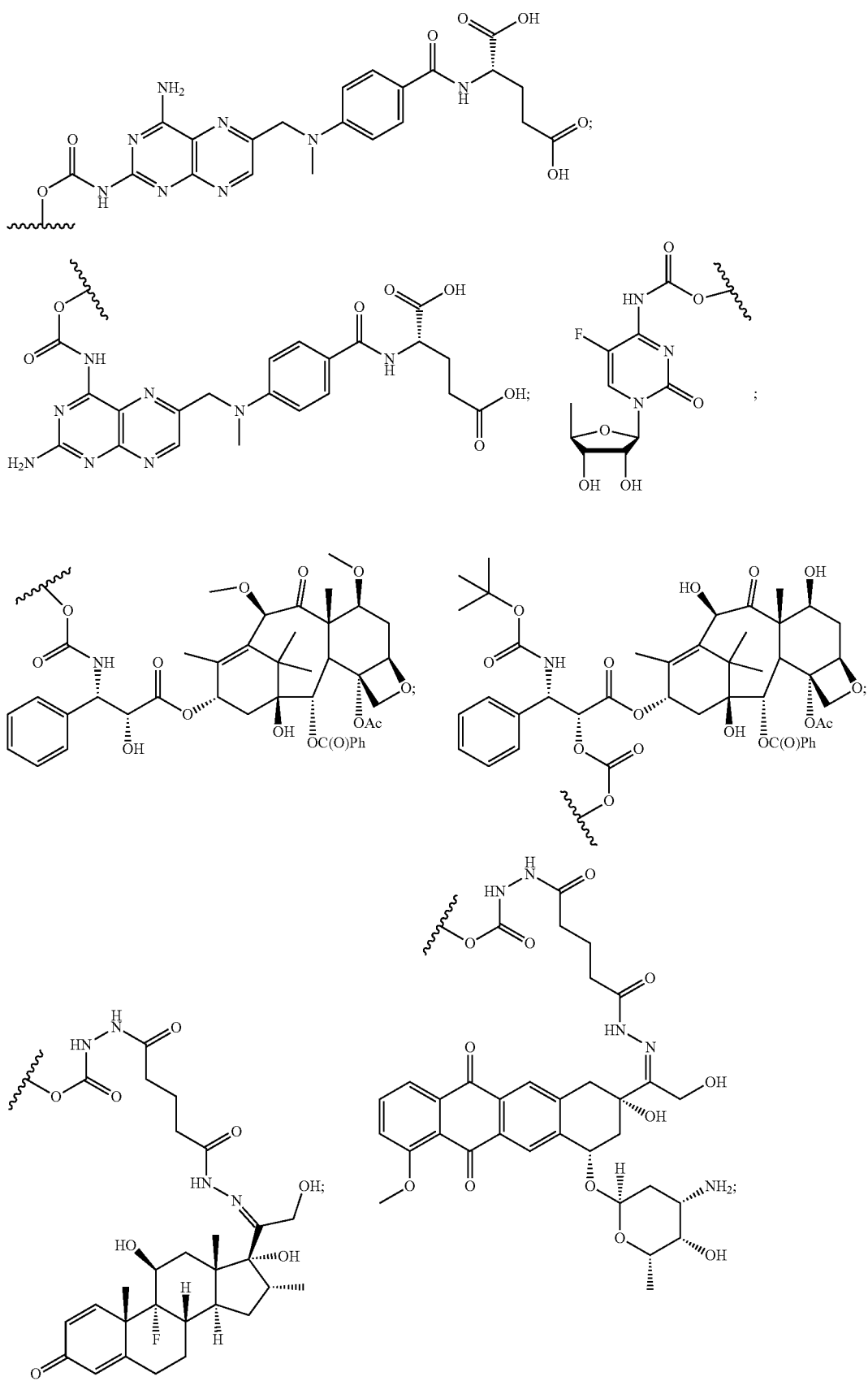

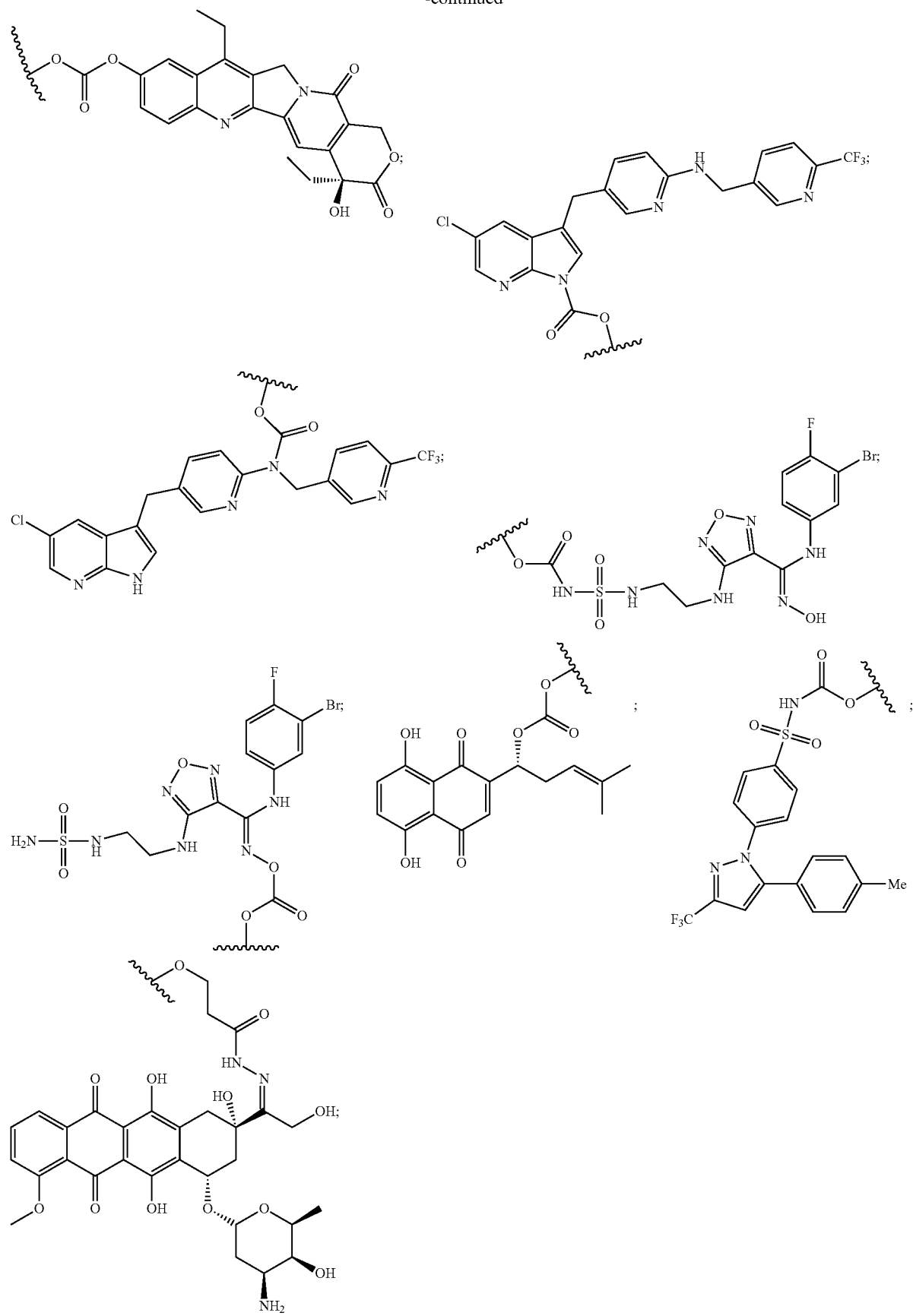

-continued
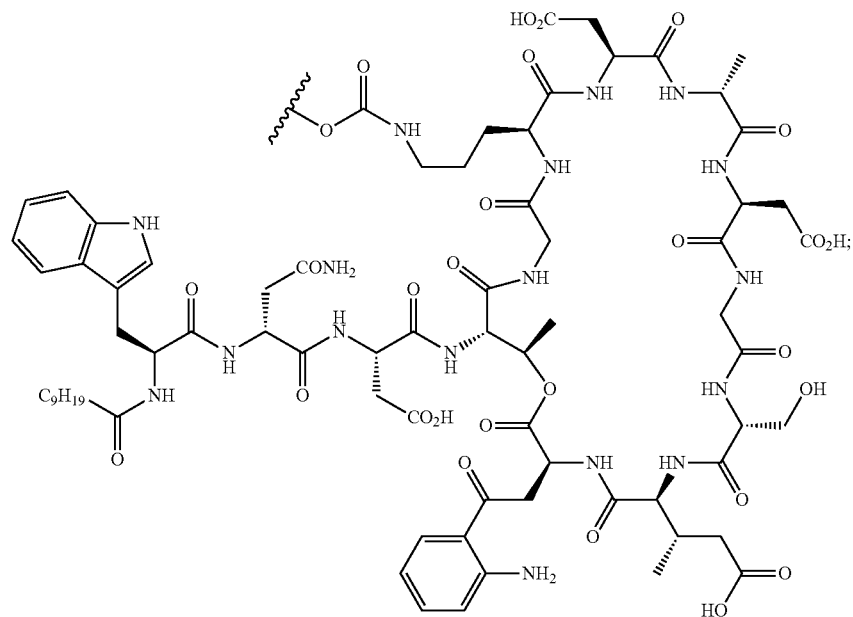
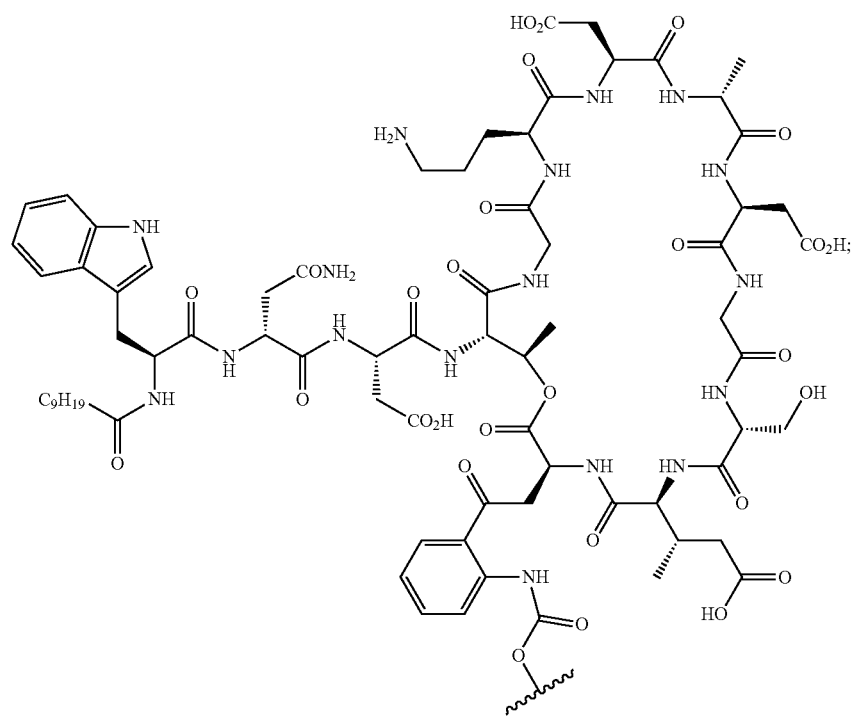

-continued
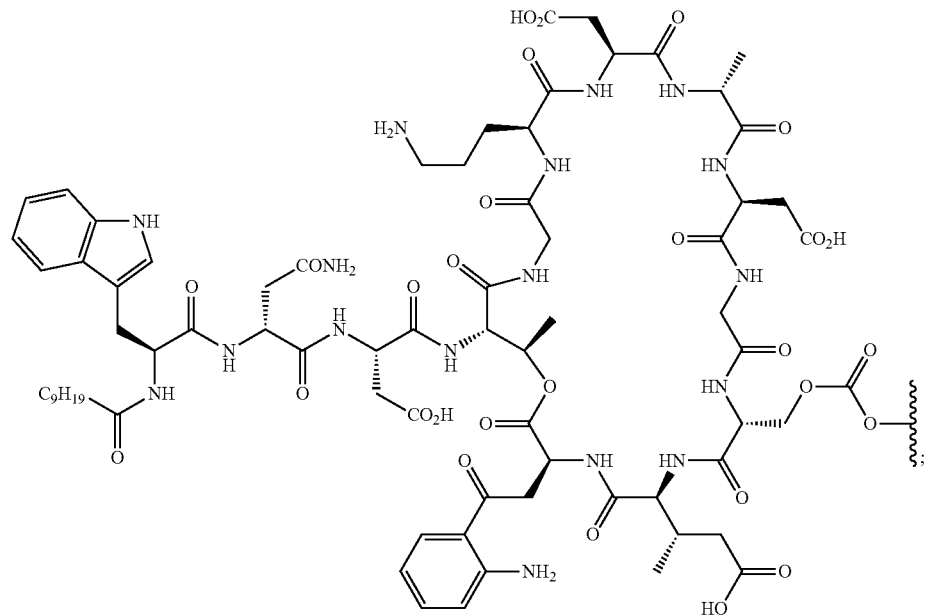
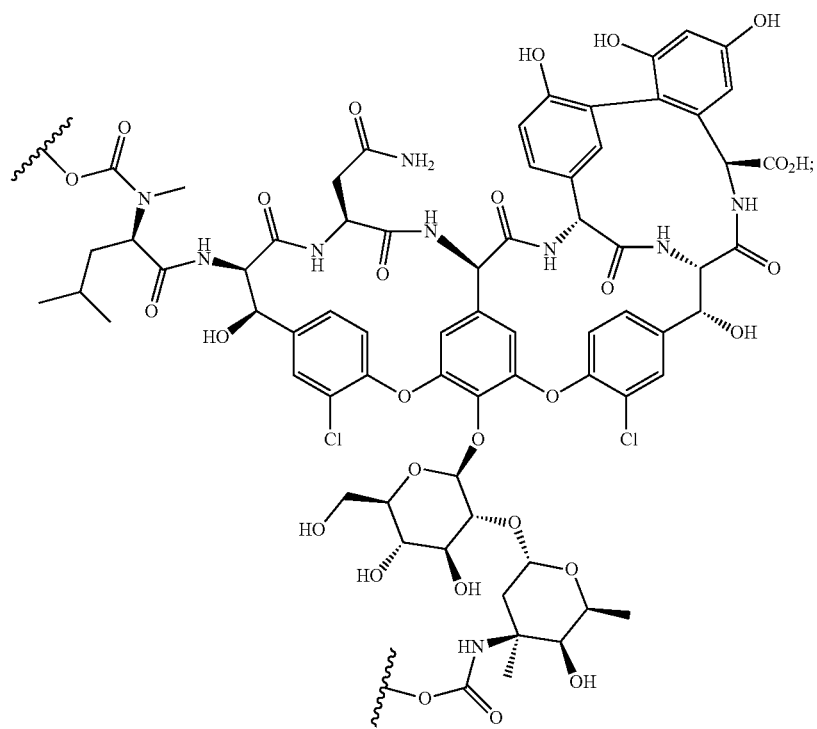

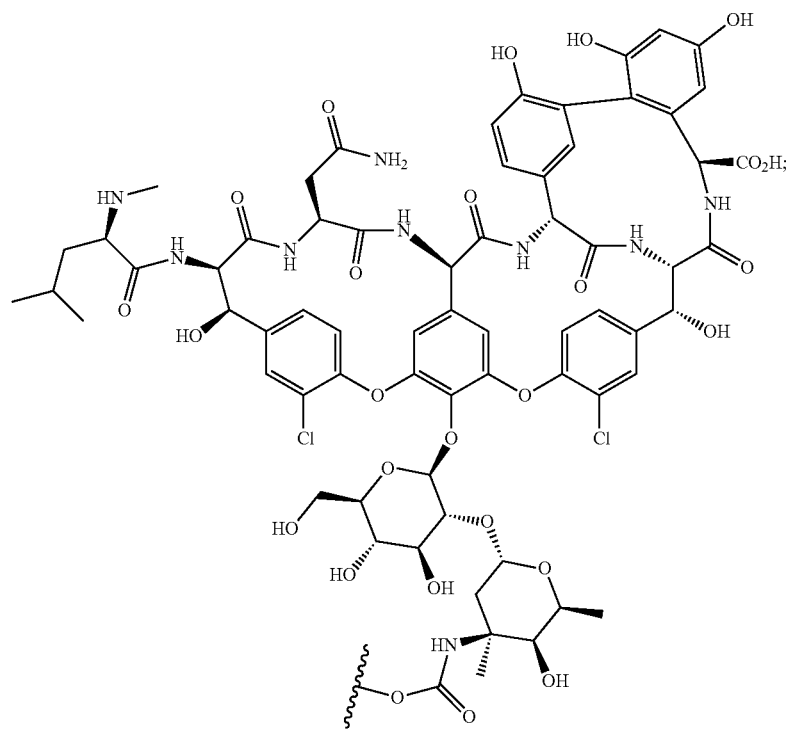
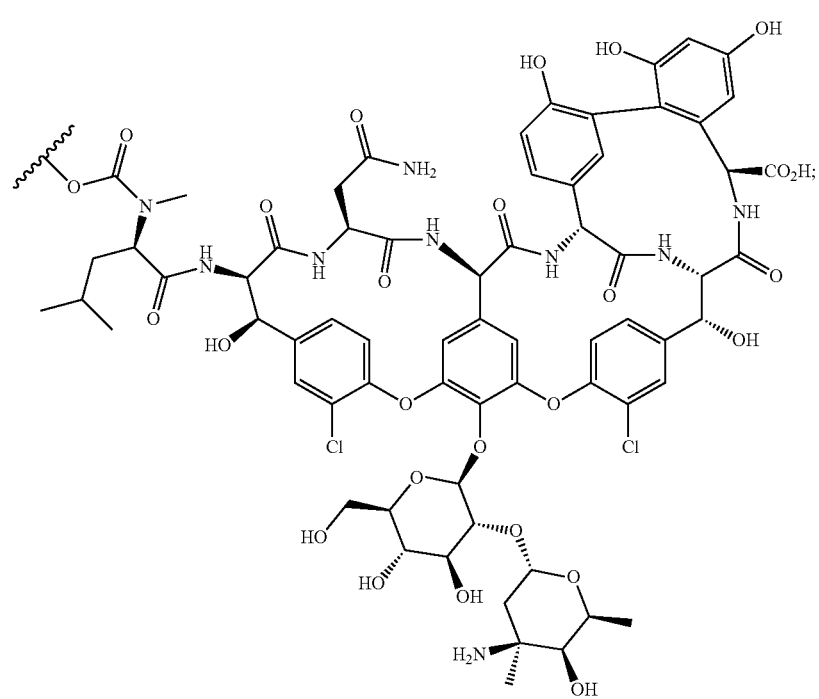

-continued
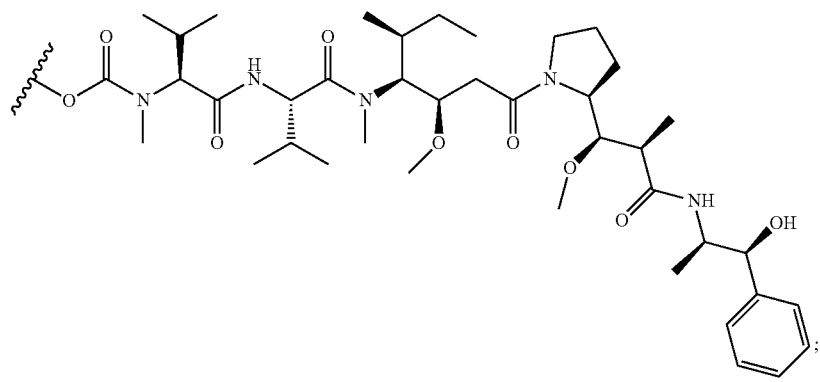
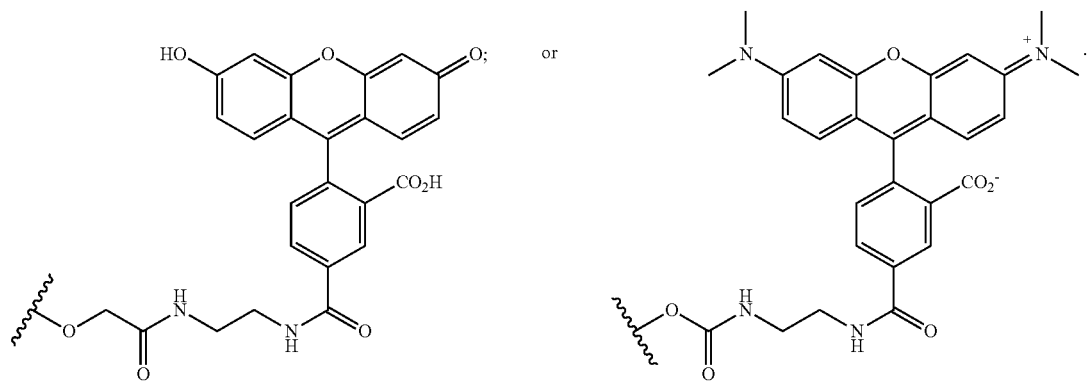
In any of the embodiments described herein are further embodiments wherein
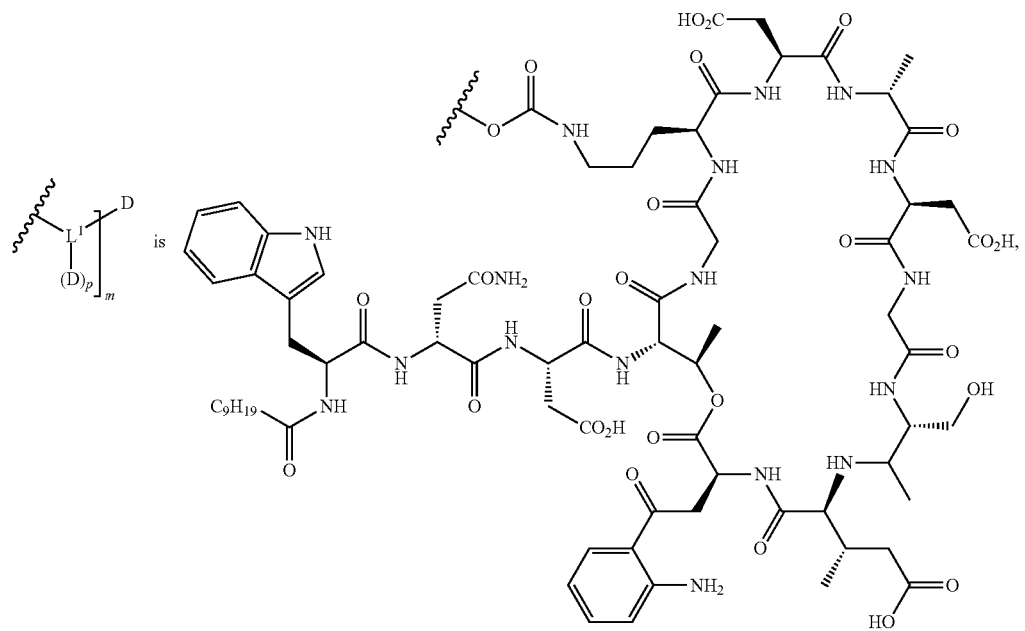

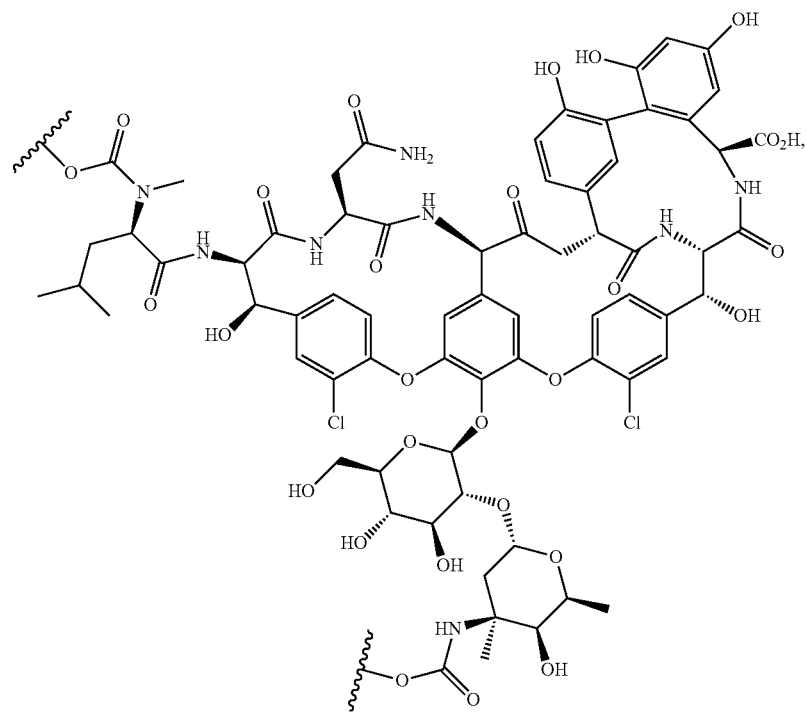
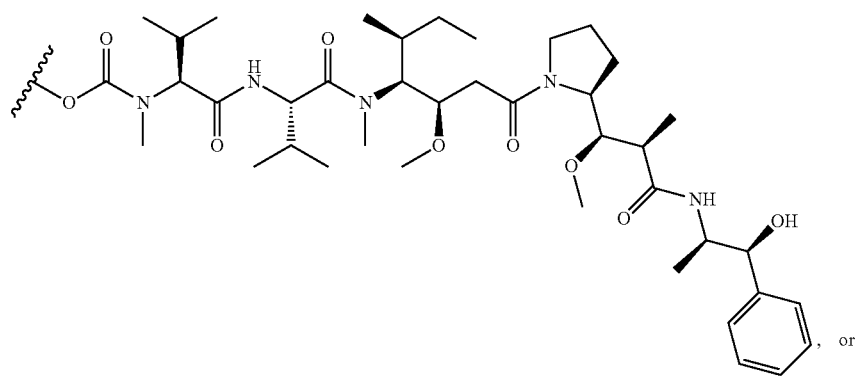
, or
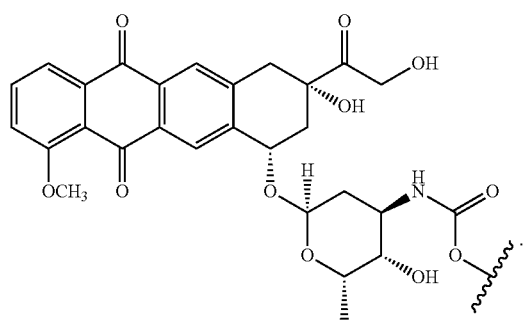
.
The functionalized payloads according to the invention have improved aqueous solubility compared with payloads linked to an unsubstituted cyclooctene and therefore are more easily formulated and administered according to the methods disclosed herein. Structures of functionalized payloads are shown below. Solubility data are shown in FIG. 1.

The numerical values for mouse and dog show calculated doses possible based on a typical injection volume for each species and the thermodynamic solubility of each drug.

Acid, Morpholine & Piperazine Doxorubicin Amide Derivatives

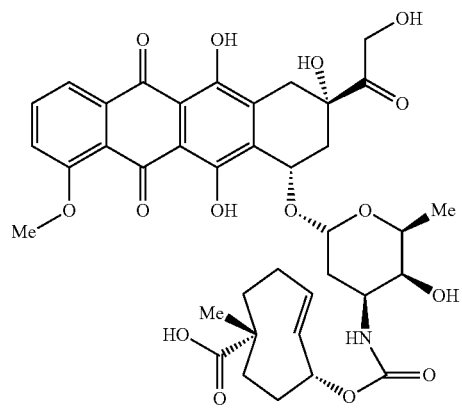

Exact Mass: 753.28
Exact Mass: 113.99
TCO-Dox-acid-TFA (MW 867)

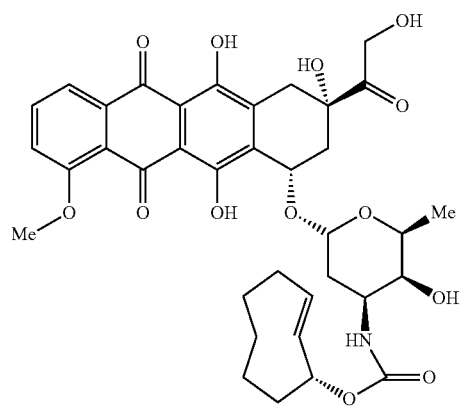

Exact Mass: 695.26
TCO-Dox

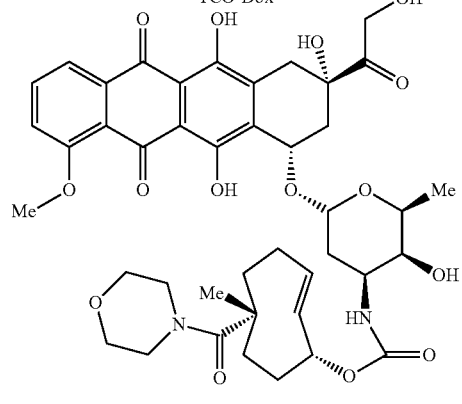

Exact Mass: 822.32
Exact Mass: 113.99
TCO-Dox-Mor-TFA (MW 935.8)

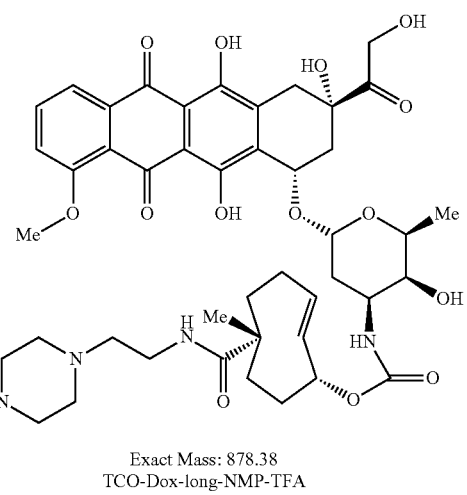

Exact Mass: 878.38
TCO-Dox-long-NMP-TFA

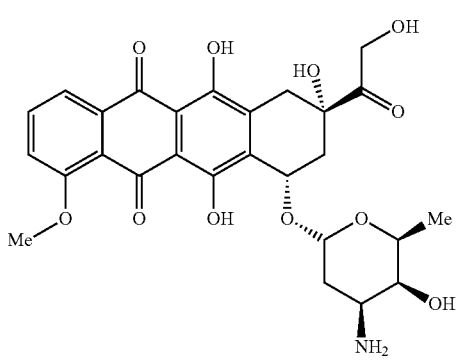

Exact Mass: 543.17
HCl
Exact Mass: 35.98
Dox-HCl (MW 579.15)

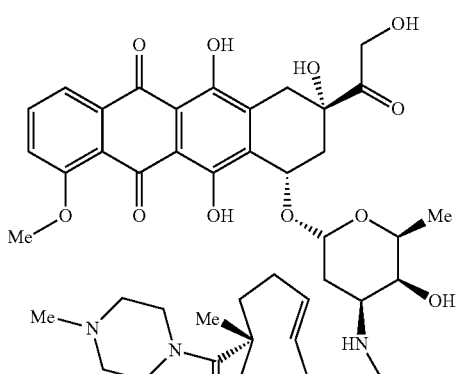

Exact Mass: 835.35
TCO-Dox-short-NMP

The invention further provides substituted cyclooctyne of the following formula for use in the preparation of functionalized payloads, wherein $R^{1a}$, $R^{1b}$, and $L^2$ are as defined above.

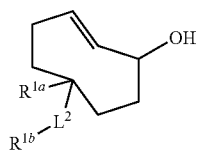

In certain embodiments, D is an antibiotic agent, antifungal agent, antiviral agent, anticancer agent, cardiovascular agent, CNS agent, anti-inflammatory/anti-arthritic agent, anti-TB/anti-leprosy agent, anti-histaminic/respiratory disorder agent, a corticosteroid agent, immunosuppressant agent, or anti-ulcer agent.

In certain embodiments, D is an antibiotic. Suitable antibiotics include, but are not limited to β-lactams, including penicillins and cephalosporins, such as thienamycins, monobactams, β-lactamade inhibitors and methoxypeniciuins; aminoglycosides, including streptomycin, gentamicin, kanamycin, tobramycin, amikacin, neomycin, ribostamycin, micronomicin and astromicin; tetracyclines, including tetracycline, oxytetracycline, chlortetracycline and doxycycline; chloramphenicols, including chloramphenicol and thiamphenicol; macrolides, including erythromycin, albomycin, erythromycin estolate, erythromycin ethylsuccinate, azithromycin, acetylspiramycin, midecamycin and josamycin; other antibiotics acting on Gram-positive bacteria, such as lincomycin, clindamycin, vancomycin and bacitracin; other antibiotics acting on Gram bacteria, such as polymyxin, fosfomycin, ciramycin, cycloserine and rifampicin; antifungal antibiotics, such as griseofulvin; anticancer antibiotics, such as mitomycin, actinomycin D, bleomycin and Adriamycin; and immunosuppressive antibiotics, such as cyclosporine.

In certain embodiments, D is an anticancer drug, an anticoagulant, a microbial immunosuppressive drug, or an anti-restenosis drug. The anticancer drug may be one or more selected from methotrexate, purines, pyrimidines, plant alkaloids, epothilones, triptolide compounds, antibiotics (notably actinomycin D), hormones and antibodies. From among the plant alkaloids, mention may notably be made of paclitaxel, doxorubicin, maytansin, auristatin, calicheamycin, duocarmycin, tubulysin and camptothecin. The anticoagulant may be one or more selected from heparin, aspirin, hirudin, colchicine and platelet GPIIb/IIIa receptor antagonists. The platelet GPIIb/IIIa receptor antagonists may be one or more selected from tirofiban, abciximab and eptifibatide. The microbial immunosuppressive drug may be one or more selected from cyclosporin A, tacrolimus and its analogues, despergualin, mycophenolate esters, rapamycin and its derivatives, FR-900520 substance from *Streptomyces* strains, FR-900523 substance from *Streptomyces* strains, daclizumab, pentanamide, kanglemycin C, spergualin, prodigiosin-25C, tranilast, myriocin, cyclosporin C, bredinin, mycophenolic acid, brefeldin A and ketosteroids. The anti-restenosis drug may be one or more selected from batimastat, metalloproteinase inhibitors, 17β-estradiol, NO donors, 2-chlorodeoxyadeno sine, 2-deoxycoformycin, fingolimod, mycophenolate sodium, $ISA_{rx}247$ (a cyclosporin A derivative), elsibucol, daclizumab, basiliximab, anti-thymocyte globulin, everolimus, methotrexate, neoral, cyclophosphamide, brequinar sodium, leflunomide and mizoribine.

In certain embodiments, D is an anticancer drug. Exemplary anti-cancer drugs include, but are not limited to, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Bendamustine Hydrochloride, BEP, Bevacizumab, Bexarotene, Bexxar (Tositumomab and 1131 Iodine Tositumomab), Bicalutamide, Bleomycin, Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, Carboplatin-Taxol, Carfilzomib, Casodex (Bicalutamide), CeeNU (Lomustine), Cerubidine (Daunorubicin Hydrochloride), Cervarix (Recombinant HPV Bivalent Vaccine), Cetuximab, Chlorambucil, Chlorambucil-Prednisone, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), Folfiri, Folfiri-Bevacizumab, Folfiri-Cetuximab, Folfirinox, Folfox (Leucovorin, Fluorouracil, Oxaliplatin), Folotyn (Pralatrexate), FU-LV, Fulvestrant, Gardasil (Recombinant HPV Quadrivalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Hyper-CVAD, Ibritumomab Tiuxetan, Ibrutinib, ICE, Iclusig (Ponatinib Hydrochloride), Ifex (Ifosfamide), Ifosf amide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OPPA, Oxaliplatin, Paclitaxel, Paclitaxel Albumin-stabilized Nanoparticle Formulation, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Radium 223 Dichloride, Raloxifene Hydrochloride, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), Stanford V, Sterile Talc Powder (Talc), Steritalc (Talc), Stivarga (Regorafenib), Sunitinib Malate, Sutent (Sunitinib Malate), Sylatron (Peginterferon Alfa-2b), Synovir (Thalidomide), Synribo (Omacetaxine Mepesuccinate), Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and 1 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VelP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), Xelox, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), and Zytiga (Abiraterone Acetate).

In certain embodiments, D is a PBD dimer, calicheamicin, speromycin, tubulysin B, rhizoxin, dolastatin, didemnin B, camptothecin, CBI, temsirolimus, actinomycin D, epothilone B, taxol, cryptophycin, SN38, velcade, bruceantin, DAVLBH, DM1, Phyllanthoside, Alimta, T2 Toxin, MMC, vantalanib, vinorelbine, brefeldin, sunitinib, daunomycin, semaxanib, tarceva, iressa, irinotecan, LY-541503, geldanomycin, gemcitabine, methotrexate, gleevec, topotecan, bleomycin, doxorubicin, cisplatin, N-mustards, etoposide, or 5-FU.

In certain embodiments, D is an anthracycline. In certain embodiments, D is a taxane. In certain embodiments, D is gemcitabine. In certain embodiments, D is doxorubicin. In certain embodiments, D is docetaxel. In certain embodiments, D is SN38. In certain embodiments, D is monomethyl auristatin E. In certain embodiments, D is dexamethasone. In certain embodiments, D is celecoxib. In certain embodiments, D is gentamicin.

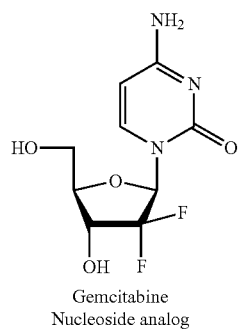

Gemcitabine
Nucleoside analog

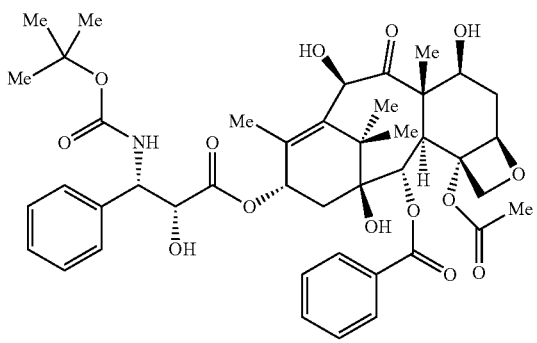

Docetaxel
Microtubule inhibitor

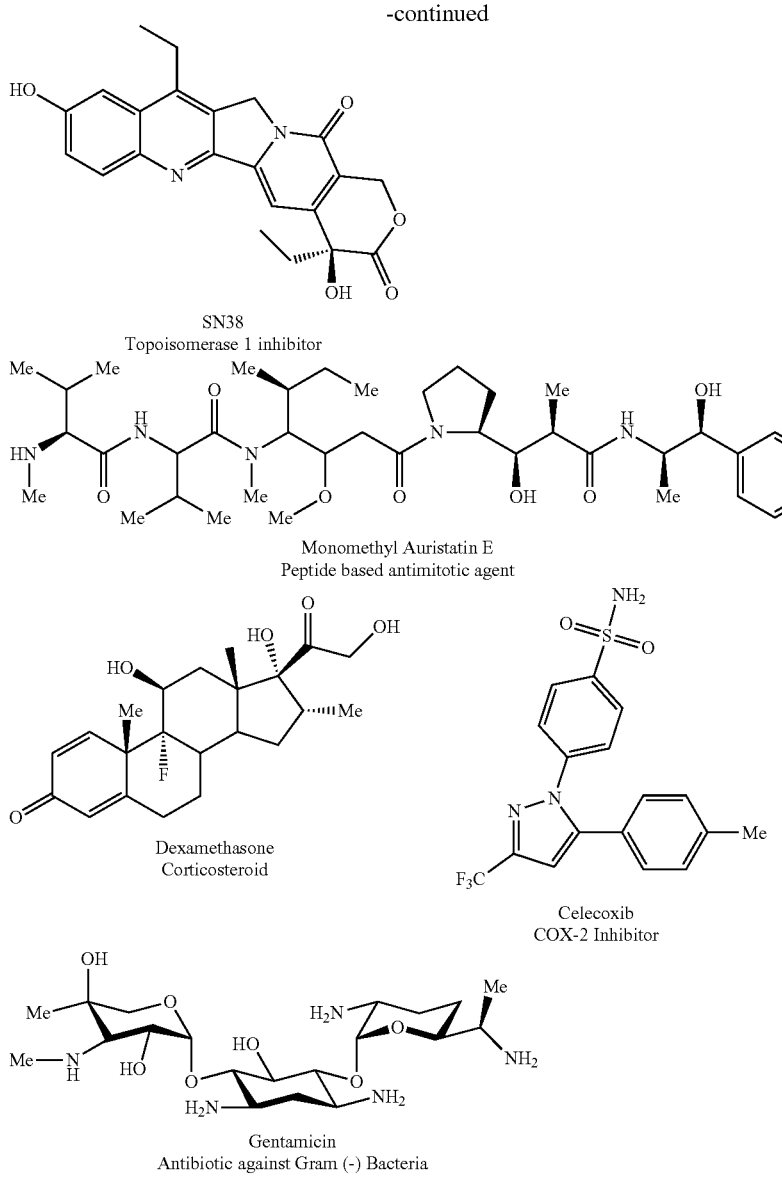

SN38
Topoisomerase 1 inhibitor

Monomethyl Auristatin E
Peptide based antimitotic agent

Dexamethasone
Corticosteroid

Celecoxib
COX-2 Inhibitor

Gentamicin
Antibiotic against Gram (-) Bacteria

In certain embodiments, D is an intracellular permeation enhancing agent. For example, D may be a functionalized ketoacid, 6-Oxo-6-phenylhexanoic acid, 8-Oxo-8-phenyloctanoic acid, 8-(2,5-Dichlorophenyl)-8-oxooctanoic acid, a functionalized ketoester or aldehyde, a modified amino acid, modified amino acids, N-[8-(2-hydroxybenzoyl)aminooctanoic acid, N-[8-(2-hydroxybenzoyl)aminodecanoic acid, N-(5-chlorosalicyloyl)-8-aminocaprylic acid, N-[4-(4-chloro-2hydroxybenzoyl)aminol butanoic acid, 2-ethylhexyl 2-hydroxybenzoate, 5-Cyclohexyl-5-oxovaleric acid, 6-Cyclohexyl-6-oxohexanoic acid, 7-Cyclohexyl-7-oxoheptanoic acid, 8-Cyclohexyl-8-oxooctanoic acid, 4-Cyclopentyl-4-oxobutyric acid, 5-Cyclopentyl-5-oxovaleric acid, 6-Cyclopentyl-6-oxohexanoic acid, 7-Cyclopentyl-7-oxoheptanoic acid, 8-Cyclopentyl-8-oxooctanoic acid, 4-Cyclobutyl-4-oxobutyric acid, 5-Cyclobutyl-5-oxovaleric acid, 6-Cyclobutyl-6-oxohexanoic acid, 7-Cyclobutyl-7-oxoheptanoic acid, 8-Cyclobutyl-8-oxooctanoic acid, 4-Cyclopropyl-4-oxobutyric acid, 5-Cyclopropyl-5-oxovaleric acid, 6-Cyclopropyl-6-oxohexanoic acid, 7-Cyclopropyl-7-oxoheptanoic acid, 8-Cyclopropyl-8-oxooctanoic acid, 8-[(3-methylcyclohexyl)oxy]octanoic acid, 7-[(3-methylcyclohexyl)oxy]heptanoic acid, 6-[(3-methylcyclohexyl)oxy]hexanoic acid, 5-[(3-methylcyclohexyl)oxy]pentanoic acid, 4-[(3-methylcyclohexyl)oxy]butanoic acid, 3-[(3-methylcyclohexyl)oxy]propanoic acid, octisalate, a diketopiperazines, saponin, an acylcarnitine, an alkanoylcholine, a taurodihydrofusidate, a sulphoxide, an oxazolidinone, a pyrrolidone, an alcohol or alkanol, a benzoic acid, a glycol, a surfactant, a terpene, a functionally effective salt of any of the foregoing, a derivative of any of the foregoing, or combinations thereof.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited herein, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds disclosed herein can generally be prepared by conventional techniques known to those skilled in the art or by processes analogous to those described in the accompanying Examples using appropriate isotopically-labeled reagent in place of non-isotopically-labeled reagent.

B. Support Compositions

In certain embodiments, the composition is a support composition. The support composition may be a biocompatible support composition. Biocompatible support compositions are compatible with the subject's body. In some instances, a biocompatible support composition is non-toxic to the subject and does not substantially react with tissue or biological compounds in the subject. Any suitable biocompatible support can be used. For example, the biocompatible support can be a hydrogel, a cross-linked polymer matrix, a metal, a ceramic, a plastic, a bone graft material, among others.

Hydrogels include, but are not limited to, polysaccharide hydrogels, alginate, cellulose, hyaluronic acid, chitosan, chitosin, chitin, hyaluronic acid, chondroitin sulfate, heparin, and the like. Other suitable sugar-based biomaterials include those described in Polymer Advanced Technology, 2014, 25, 448-460. Polymers that may be used as the biocompatible support can include, but are not limited to, polyphosphazenes, polyanhydrides, polyacetals, poly(ortho esters), polyphosphoesters, polycaprolactones, polyurethanes, polylactides, polycarbonates, polyamides, and polyethers, and blends/composites/co-polymers thereof. Representative polyethers include, but are not limited to, poly(ethylene glycol) (PEG), polypropylene glycol) (PPG), triblock Pluronic ([PEG]n-[PPG]m-[PEG]n), PEG diacrylate (PEGDA), and PEG dimethacrylate (PEGDMA). The biocompatible support can also include proteins and other poly(amino acids), such as collagen, gelatin, elastin and elastin-like polypeptides, albumin, fibrin, poly(gamma-glutamic acid), poly(L-lysine), poly(L-glutamic acid), poly (aspartic acid), and the like.

In some embodiments, the support is a hydrogel. In some embodiments, the support is alginate. In some embodiments, the support is chitin. In some embodiments, the support is hyaluronic acid. In some embodiments, the support is chitosin.

In certain embodiments, the support is a particle. Particles of the present disclosure can have a diameter that is 2 cm or less, such as 1.5 cm or less, or 1 cm or less, or 0.5 cm or less. For example, the particles can be nanoparticles or microparticles. Nanoparticles include particles having average dimensions in the nanometer scale (e.g., 1000 nm or less). Microparticles are particles having average dimensions in the micrometer scale (e.g., 1000 μm or less). By "average" is meant the arithmetic mean. In some embodiments, the nanoparticles have a diameter ranging from 1 nm to 1 μm, such as from 10 nm to 1 μm, or 25 nm to 1 μm, or 50 nm to 1 μm, or 75 nm to 1 μm, or 100 nm to 1 μm, or 150 nm to 1 μm, or 200 nm to 1 μm, or 250 nm to 1 μm, or 300 nm to 1 μm, or 350 nm to 1 μm, or 400 nm to 1 μm, or 450 nm to 1 μm, or 500 nm to 1 m. In other embodiments, the microparticles have a diameter ranging from 1 μm to 1 mm, such as from 10 μm to 1 mm, or 25 μm to 1 mm, or 50 μm to 1 mm, or 75 μm to 1 mm, or 100 μm to 1 mm, or 150 μm to 1 mm, or 200 μm to 1 mm, or 250 μm to 1 mm, or 300 μm to 1 mm, or 350 μm to 1 mm, or 400 μm to 1 mm, or 450 μm to 1 mm, or 500 μm to 1 mm. In further embodiments, small particles on the order of 10-100 nm in diameter may be assembled to form larger complexes, such as clusters or assemblies on the order of 1-10 μm. Particles of the present disclosure may be substantially spherical, such that the particles have a substantially circular cross-section. Other particle shapes may also be used, such as, but not limited to, ellipsoid, cubic, cylindrical, conical, needle, or other irregular shapes.

A "particle" may take the form of any fabricated material, a molecule, cryptophan, a virus, a phage, etc. The particle may be composed of a material, such as, but not limited to, a metal, a ceramic, a plastic, a polymer, a hydrogel, and the like. For example, the particles may be made of an inert material, such as alginate or iron oxide. In some examples, the particles may be magnetic and can be formed from a paramagnetic, super-paramagnetic or ferromagnetic material, or other material that responds to a magnetic field.

The particles, or a group of several particles in a complex, may be functionalized with a targeting agent (e.g., a ligand or antibody) that specifically binds (or substantially specifically binds) to a target (e.g., a target receptor or a cell surface target, such as a clinically relevant receptor or cell surface target (e.g., antigen)). The targeting agent may be attached directly to the particle itself. The targeting agent can be an antibody, peptide, nucleic acid, phage, bacteria, virus, or any other molecule with a specific affinity for a target receptor or cell surface target. In some instances, the receptor or cell surface target is PD-1, CTLA-4, HER2/neu, HER1/EGFR, VEGFR, BCR-ABL, SRC, JAK2, MAP2K, EML4-ALK, BRAF V600E, 4-1BB, GITR, GSK3beta, or other cellular receptors or cell surface targets. Other compounds or molecules, such as fluorophores or autofluorescent or luminescent markers, which may assist in detecting the particles (e.g., in vivo detection), may also be attached to the particles. The ligands and/or detectable labels may be attached directly to the particle or attached to the particle through bioorthogonal functional groups as described herein.

In certain embodiments, the support is a bone graft material, such as a bone graft substitute material. A bone graft substitute material is a biocompatible material structurally similar to bone. In some instances, a bone graft substitute material is bioresorbable such that the bone graft substitute material can dissolve or be absorbed in the body over time. A bone graft substitute material can be osteoconductive, such that it facilitates blood vessel and new bone formation into the bone graft substitute material. In some instances, the bone graft substitute material is osteoinductive, such that facilitates the formation of new bone through active recruitment of mesenchymal stem cells from the surrounding tissue. For example, growth factors, such as bone morphogenetic proteins, may be included in the bone graft substitute material. Bone graft substitute materials include, but are not limited to, hydroxyapatite, tricalcium phosphate, demineralized bone matrix, bovine collagen, calcium sulfate, calcium phosphate, cancellous bone chips, and the like, and combinations thereof.

As described above, support compositions of the present disclosure include a support and a first binding agent covalently linked to the support. The binding agent may be attached to the support on a surface of the support, such as a solvent-accessible surface of the support (e.g., a surface of the support that is in contact with the surrounding solvent). In some cases, the binding agent is attached directly to the support. For example, the binding agent may be covalently attached to the surface of the support, e.g., through a covalent bond, such as an amide, amine, ester, carbamate, urea, thioether, thiocarbamate, thiocarbonate, thiourea, etc. In some instances, the binding agent is covalently attached to the support through an amide bond. In other instances, the binding agent may be linked to the support via a linker. Any suitable linker can be used to link the binding agent to the support. Representative linkers can have from 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms. Representative linkers include, but are not limited to, those shown below:

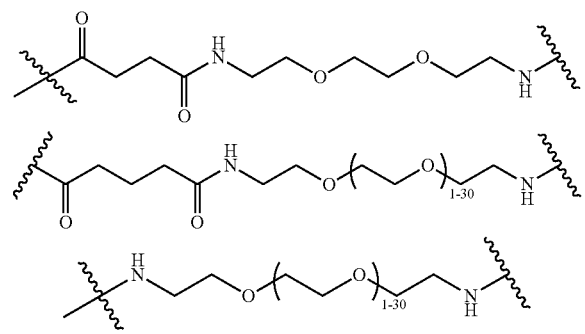

In certain embodiments, the support compositions comprise a tetrazine-containing group of formula:

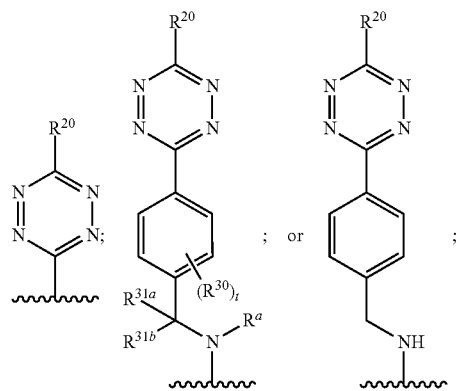

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S) R'R''', SC(=S)R'R'', NR'C(=O)NR''R''', and NR'C(=S)NR''R'''; R' and R'' at each occurrence are independently selected from hydrogen, aryl and alkyl; and R''' at each occurrence is independently selected from aryl and alkyl; $R^{30}$ is halogen, cyano, nitro, hydroxy, alkyl, haloalkyl; alkenyl, alkynyl, alkoxy; halalkoxy; heteroalkyl, aryl, heteroaryl, heterocycle, cycloalkyl, or cycloalkenyl; $R^a$, $R^{31a}$ and $R^{31b}$ are each independently hydrogen, $C_1$-$C_6$-alkyl, or $C_1$-$C_6$-haloalkyl; and t is 0, 1, 2, 3, or 4.

In certain embodiments, the support compositions have formula:

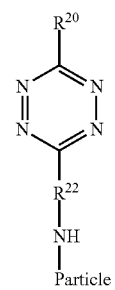

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S) R'R''', SC(=S)R'R'', NR'C(=O)NR''R''', and NR'C(=S)NR''R'''; R' and R'' at each occurrence are independently selected from hydrogen, aryl and alkyl; R''' at each occurrence is independently selected from aryl and alkyl; and $R^{22}$ is a linker of 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms.

In certain embodiments, the support compositions have formula:

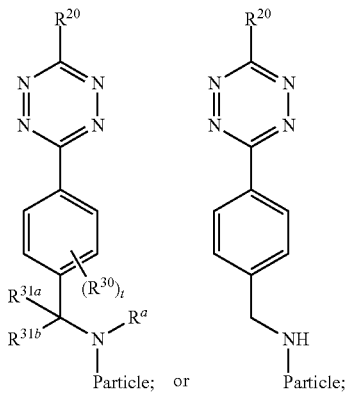

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S) R'R''', SC(=S)R'R'', NR'C(=O)NR''R''', and NR'C(=S)NR''R'''; R' and R'' at each occurrence are independently selected from hydrogen, aryl and alkyl; R''' at each occurrence is independently selected from aryl and alkyl; $R^{30}$ is halogen, cyano, nitro, hydroxy, alkyl, haloalkyl; alkenyl, alkynyl, alkoxy; halalkoxy; heteroalkyl, aryl, heteroaryl, heterocycle, cycloalkyl, or cycloalkenyl; $R^a$, $R^{31a}$ and $R^{31b}$ are each independently hydrogen, $C_1$-$C_6$-alkyl, or $C_1$-$C_6$-haloalkyl; and t is 0, 1, 2, 3, or 4.

In certain embodiments, the support compositions comprise substituted alginate having units of formula:

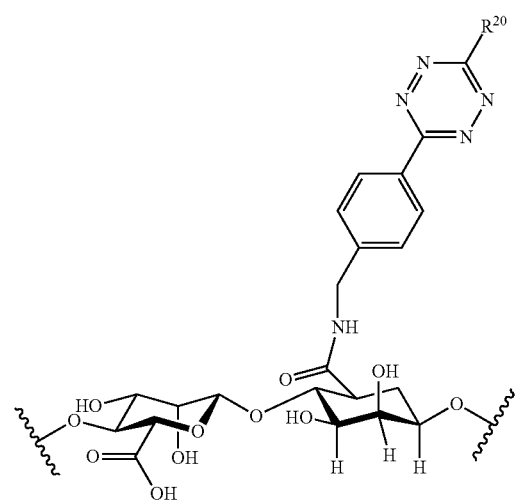

and/or

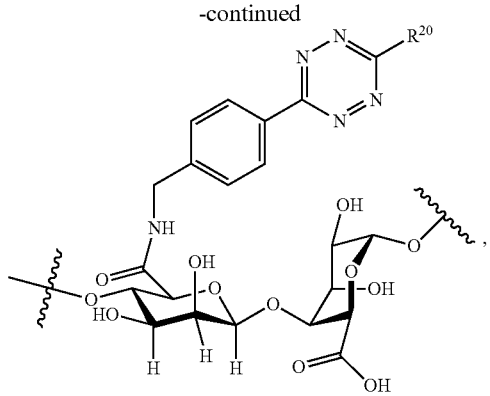

salt thereof, wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)$_2$R''', S(=O)$_2$NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S) R'R''', SC(=S)R'R'', NR'C(=O)NR''R''', and NR'C(=S)NR''R'''; R' and R'' at each occurrence are independently selected from hydrogen, aryl and alkyl; and R''' at each occurrence is independently selected from aryl and alkyl.

In certain embodiments, the support compositions comprise units of formula:

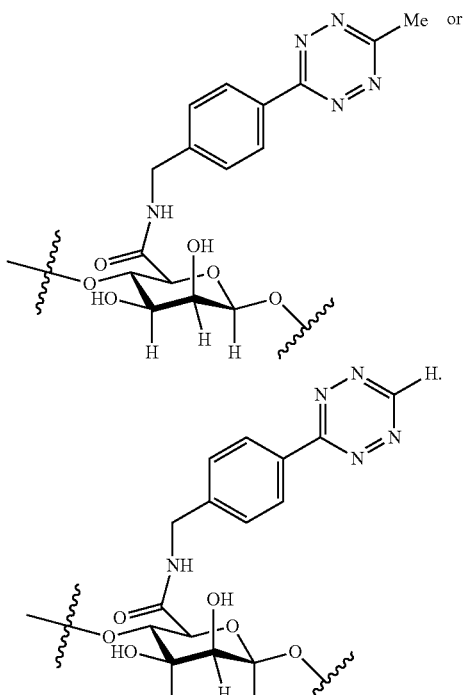

In some embodiments, the support compositions comprise units of formula:

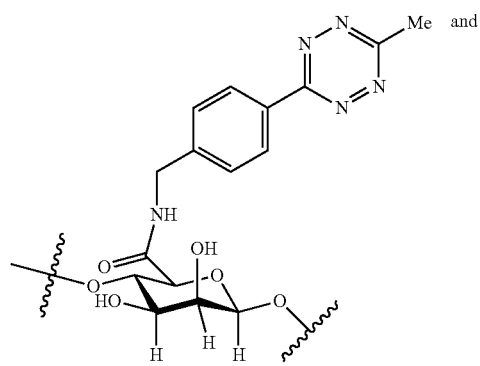
and
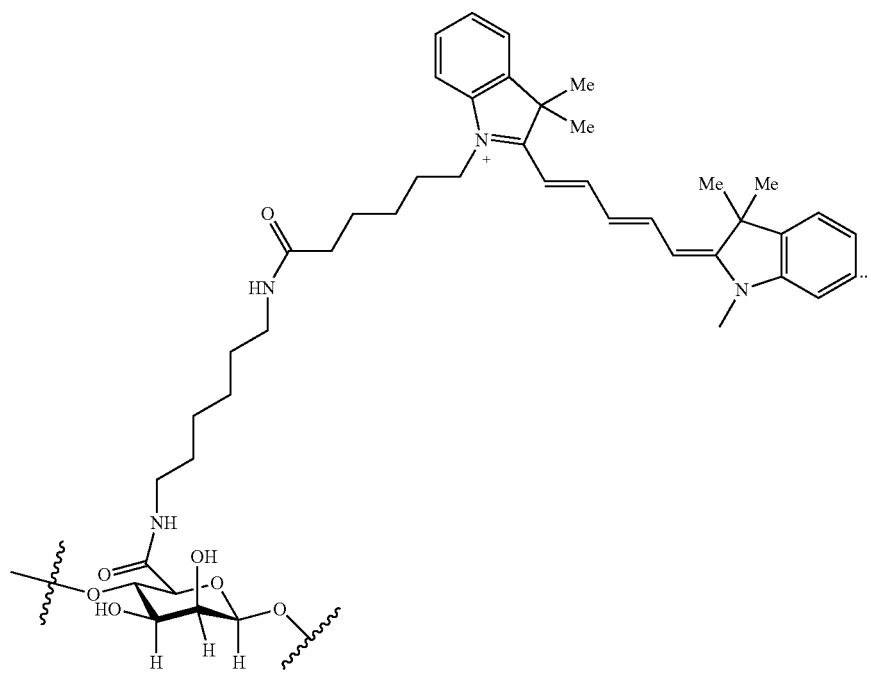
In some embodiments, the support compositions comprise units of formula:
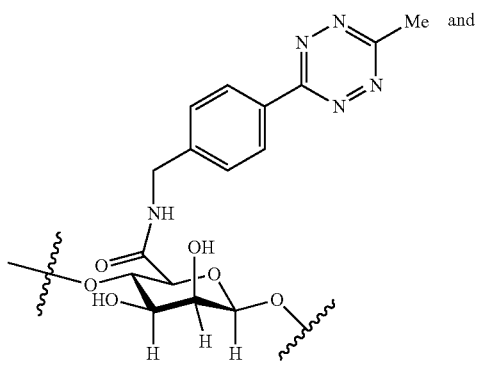
and
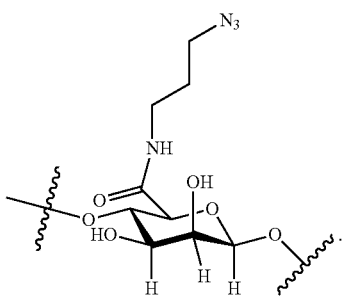
In some embodiments, the support compositions comprise substituted hyaluronic acid having units of formula (II):

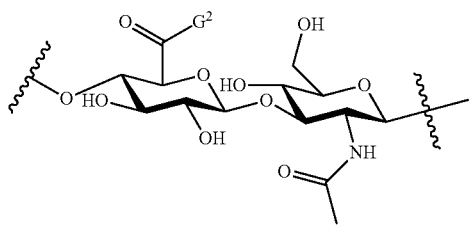

(II)

wherein G² is

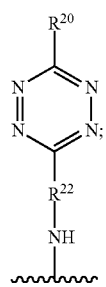

R²² is a linker of 1 to 100 linking atoms; and R²⁰ is as defined herein. In further embodiments, G² is

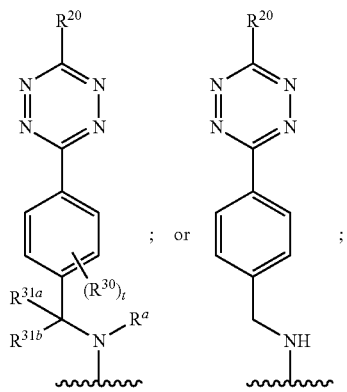

In still further embodiments, G² is

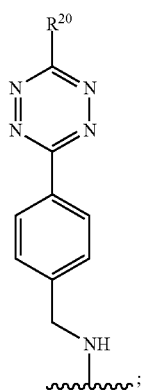

and R²⁰ is hydrogen or $C_{1-4}$ alkyl.

Compounds of formula (II) include compounds of formula (III):

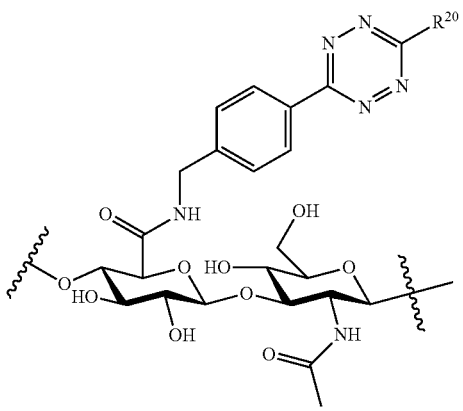

(III)

wherein R²⁰ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R''', SC(=O)R''', OC(=S)R''', SC(=S)R''', S(=O)R', S(=O)₂R''', S(=O)₂NR'R'', C(=O)O—R', C(=O)S—R', C(=S)O—R', C(=S)S—R', C(=O)NR'R'', C(=S)NR'R'', NR'R'', NR'C(=O)R'', NR'C(=S)R'', NR'C(=O)OR'', NR'C(=S)OR'', NR'C(=O)SR'', NR'C(=S)SR'', OC(=O)NR'R'', SC(=O)NR'R'', OC(=S) R'R''', SC(=S)R'R'', NR'C(=O)NR''R''', and NR'C(=S)NR''R'''; R' and R'' at each occurrence are independently selected from hydrogen, aryl and alkyl; and R''' at each occurrence is independently selected from aryl and alkyl. In further embodiments according to formula (III), R²⁰ is hydrogen or $C_{1-4}$ alkyl.

In some embodiments, the support compositions comprise units of formula:

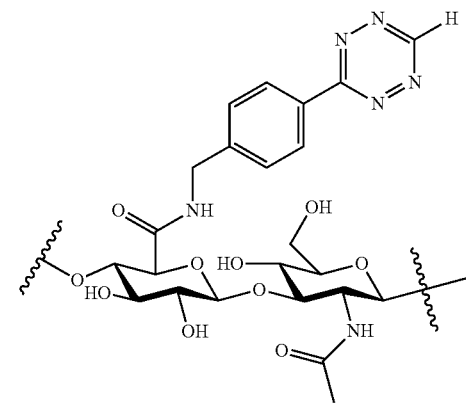

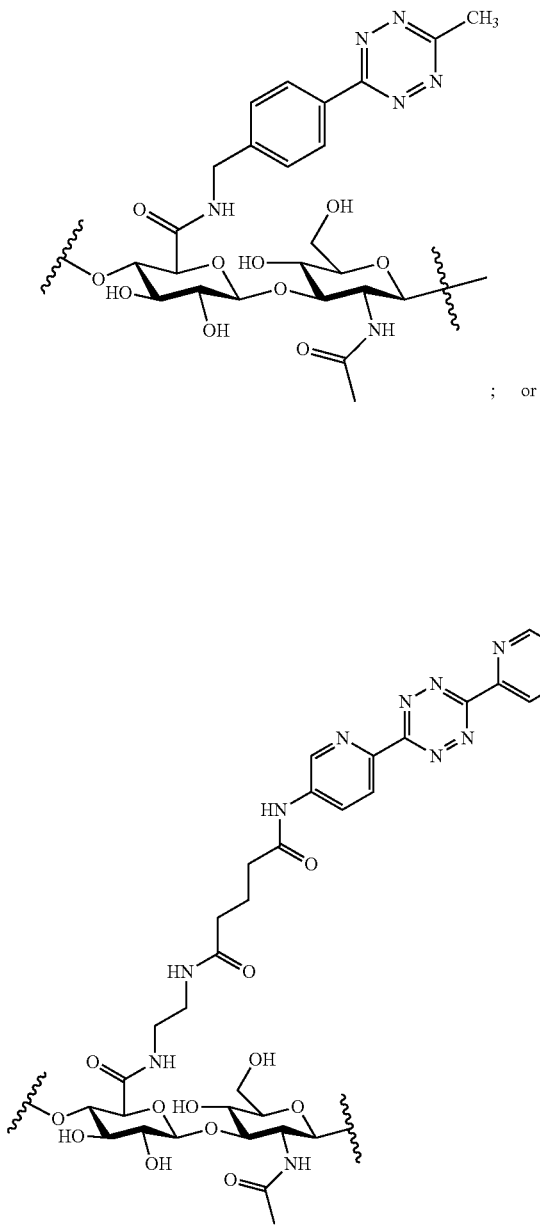

; or

Additional support compositions are exemplified in WO2017/044983, WO/2015/139025A1, and WO/2014/205126A1, the entire contents of each of which is incorporated herein by reference in their entirety.

The hyaluronic acid derivative includes a hyaluronic acid having a plurality of glucuronic acid units and a tetrazine-containing group linked or directly bonded to a glucuronic acid unit of the hyaluronic acid. The hyaluronic acid may also have a plurality of N-acetylglucosamine units. In certain embodiments, the N-acetylglucosamine units of the hyaluronic acid are not linked or conjugated to the tetrazine-containing group.

The tetrazine-containing group can be linked or directly bonded through a carboxylic acid of a glucuronic acid unit. The tetrazine-containing group can be incorporated into the hyaluronic acid from about 0.1% to about 80% as measured by the % of carboxylic acids being linked or conjugated to the tetrazine-containing group, such as about 1% to about 75%, about 5% to about 75%, about 10% to about 50%, or about 40% to about 75% as measured by the % of carboxylic acids being linked or conjugated to the tetrazine-containing group.

3. Synthetic Methods

The compounds of the present disclosure can be better understood in connection with the following synthetic schemes and methods which illustrate a means by which the compounds can be prepared.

In another aspect, disclosed are methods of preparing the disclosed compositions.

In general, compounds of formula (I) or (I-A) can be prepared by reacting a payload having a primary amine, secondary amine, or a hydroxyl group with a suitably activated linker either before or after the linker is attached to the cyclooctene portion. It is to be understood that a reactive group on a linker (e.g., ester, carbonate, acyl chloride, carboxylic acid) can be located on any selected position of the linker group. Conversely, the linker may have a nucleophilic amine or hydroxyl group that may be reacted with a suitable group on the payload such as an aldehyde, ketone, ester, carbonate, carboxylic acid, or acyl chloride.

In certain embodiments, as shown below, a trans-cyclooctene activated for nucleophilic addition can be reacted with a suitable payload (D), or a payload attached to a linker $L^4$-H, in the presence of a base to provide a functionalized payload. The payload or linker can include a primary amine, secondary amine, or hydroxyl group that reacts with the activated TCO. In certain embodiments, the leaving group (LG) is a chloro leaving group, a p-nitrophenol leaving group, or an N-hydroxysuccinimide leaving group. Exemplary bases for use in the reaction include organic and inorganic bases, such as for example, triethylamine, pyridine, sodium hydroxide, and sodium bicarbonate.

As shown in Scheme 1, a trans-cyclooctene having an activated carbonate ester may be coupled with D-$L^4$-H to provide an intermediate 4, which may be further hydrolyzed to an acid 5 or coupled with $R^{1b}$—H or $G^1$-H under basic conditions to provide 6 or 7. Suitable $R^{1b}$—H reactants for the method of Scheme 1 include, for example, $HNR^{1c}$—$C_{1-4}$alkylene-$G^1$, $HN(R^{1c})CHR^{1c}CO_2H$, $HN(R^{1c})$—$C_{1-6}$alkylene-$CO_2H$, $HN(R^{1f})$—$C_{2-4}$alkylene-$(N(C_{1-4}$alkylene-$CO_2H)$—$C_{2-4}$alkylene$)_n$-$N(C_{1-4}$alkylene-$CO_2H)_2$, $HN(R^{1c})CHR^{1c}C(O)OC_{1-6}$alkyl, $HN(R^{1c})$—$C_{1-6}$alkylene-$C(O)OC_{1-6}$alkyl, and $HN(R^{1f})$—$C_{2-4}$alkylene-$(N(C_{1-4}$alkylene-$C(O)OC_{1-6}$alkyl)-$C_{2-4}$alkylene$)_n$-$N(C_{1-4}$alkylene-$C(O)OC_{1-6}$alkyl$)_2$. Suitable $G^1$-H reactants for the method of Scheme 1 include N-containing heterocycles having an available NH group that may be substituted.

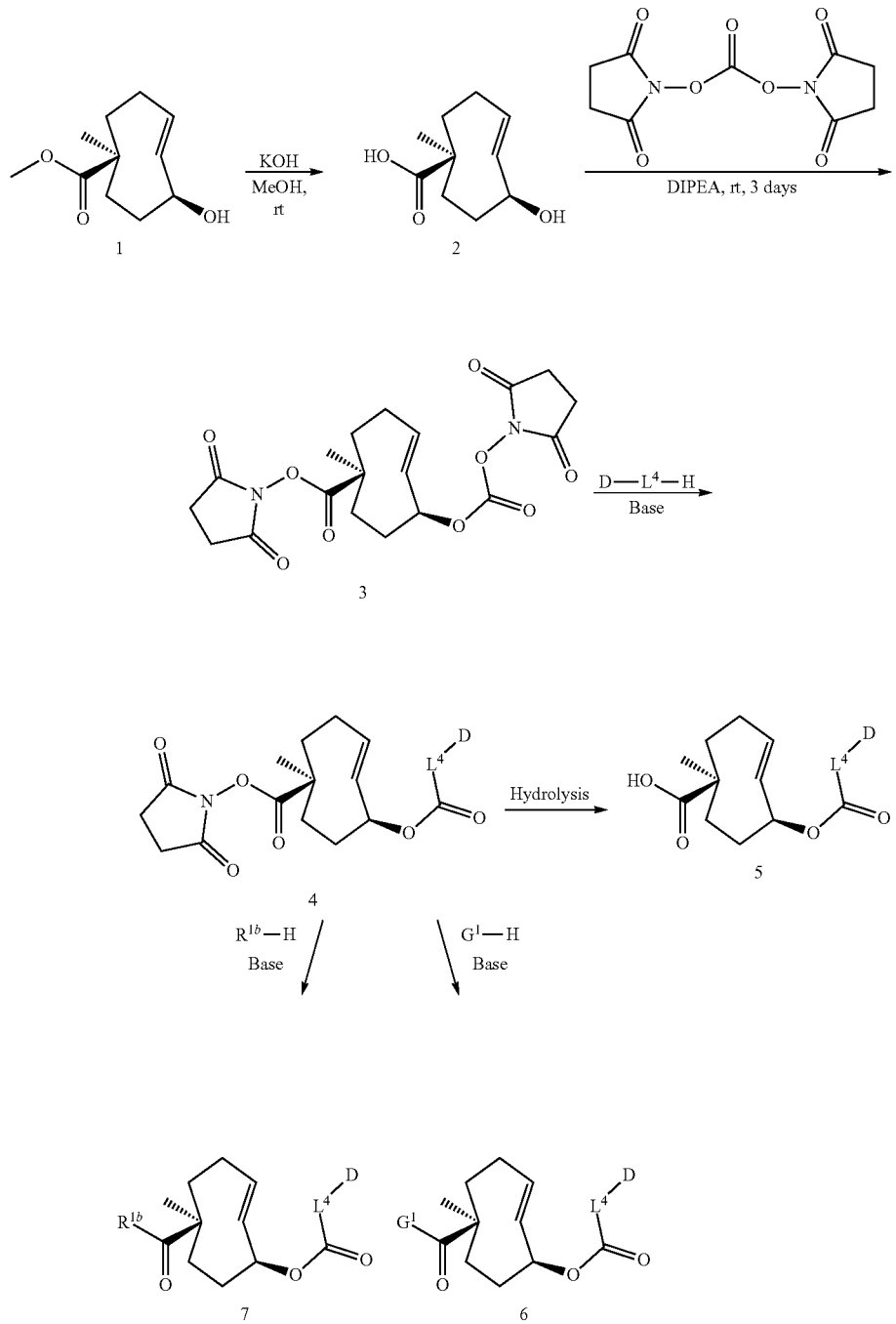

Scheme 1

As shown in Scheme 2 below, a trans-cyclooctene having an activated carbonate ester may be coupled with a payload (e.g., doxorubicin, abbrev. as doxo) having an amine. The intermediate 4 may be further coupled with amine containing groups or hydrolyzed to the acid to provide functionalized payloads of the invention. The synthetic methods of Scheme 2 may be used to prepare compounds of formula (I), wherein $L^2$ is C(O) and $R^{1b}$ is an optionally substituted heterocyclyl $G^1$ (e.g., morpholino, piperazinyl), —$NR^{1c}$—$C_{1-4}$alkylene-$G^1$, or OH. The general procedure of Scheme 2 may also be applied to the synthesis of additional $R^{1b}$ groups, for example —N($R^{1c}$)CHR$^{1c}$CO$_2$H, —N($R^{1c}$)—C$_{1-6}$alkylene-CO$_2$H, —N($R^{1f}$)—C$_{2-4}$alkylene-(N(C$_{1-4}$alkylene-CO$_2$H)—C$_{2-4}$alkylene)$_n$-N(C$_{1-4}$alkylene-CO$_2$H)$_2$, —N($R^{1c}$)CHR$^{1c}$C(O)OC$_{1-6}$alkyl, —N($R^{1c}$)—C$_{1-6}$alkylene-C(O)OC$_{1-6}$alkyl, and —N($R^{1f}$)—C$_{2-4}$alkylene-(N(C$_{1-4}$alkylene-C(O)OC$_{1-6}$alkyl)-C$_{2-4}$alkylene)$_n$-N(C$_{1-4}$alkylene-C(O)OC$_{1-6}$alkyl)$_2$. Likewise the methods of Scheme 1 are applicable to other payload groups bearing a reactive amine group.

Scheme 2
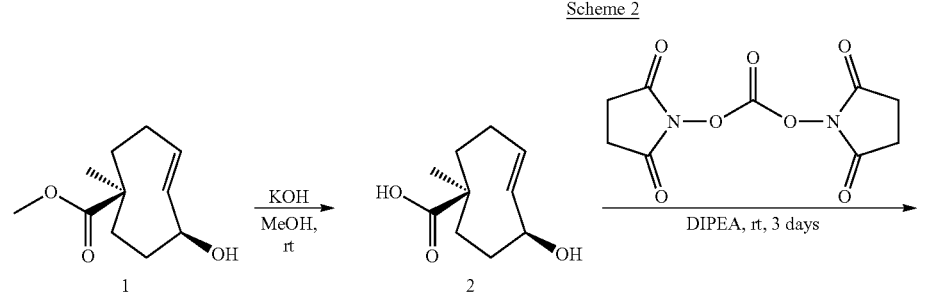
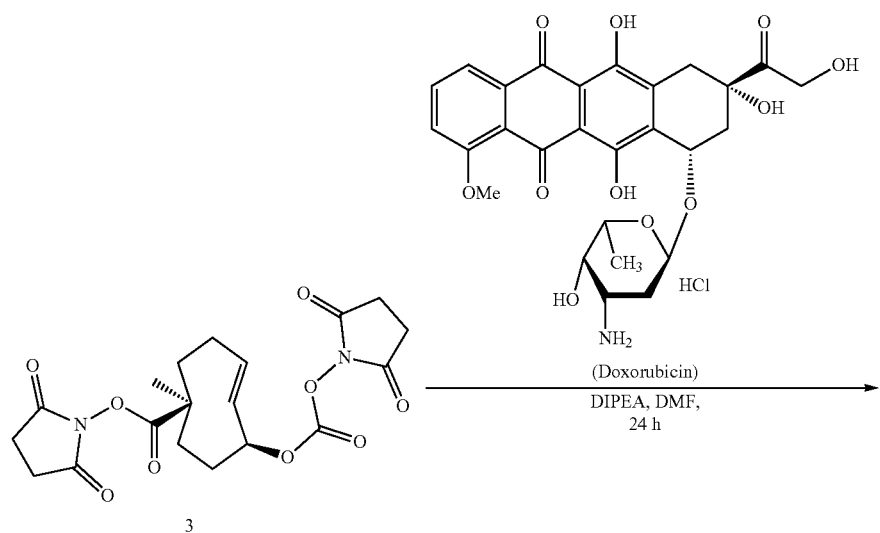
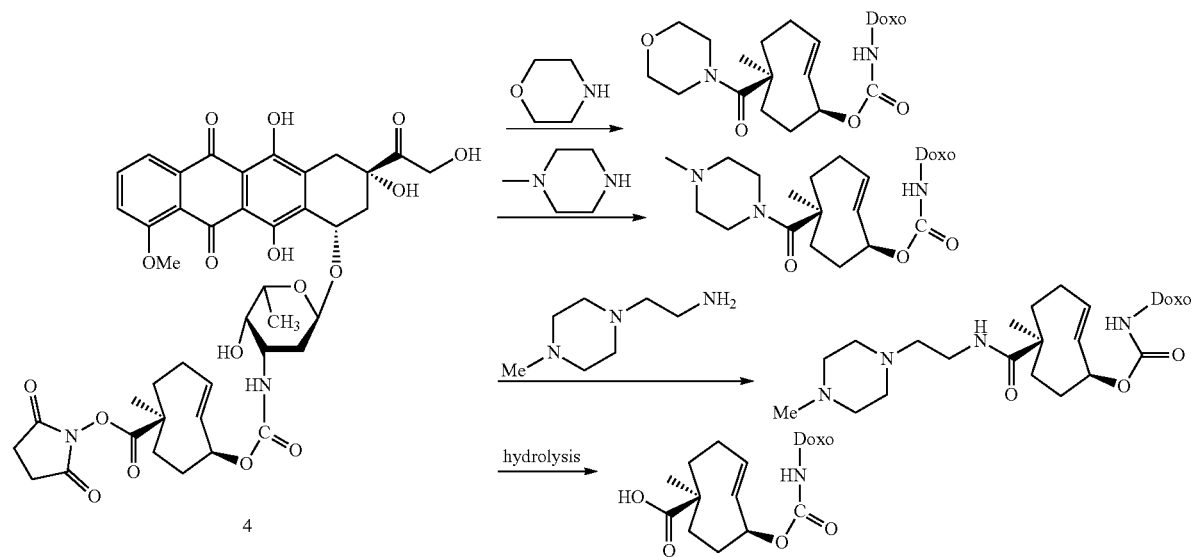

Scheme 3 illustrates further applications of the foregoing chemistry where the intermediate carbonate ester may be reacted with the ornithine side chain of daptomycin and further coupled with an amino-containing groups $R^{1b}$—H under basic conditions.
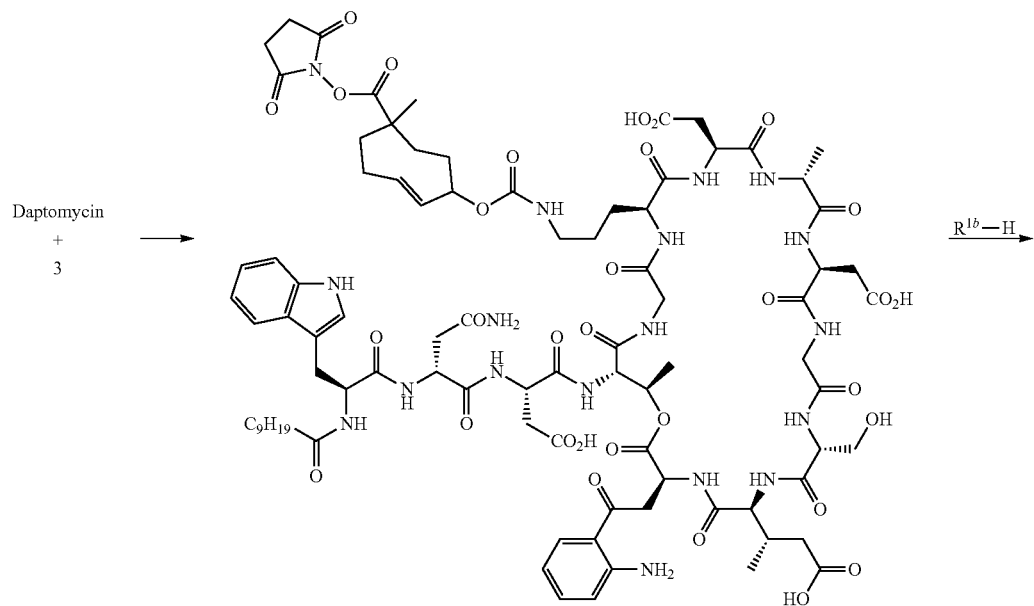
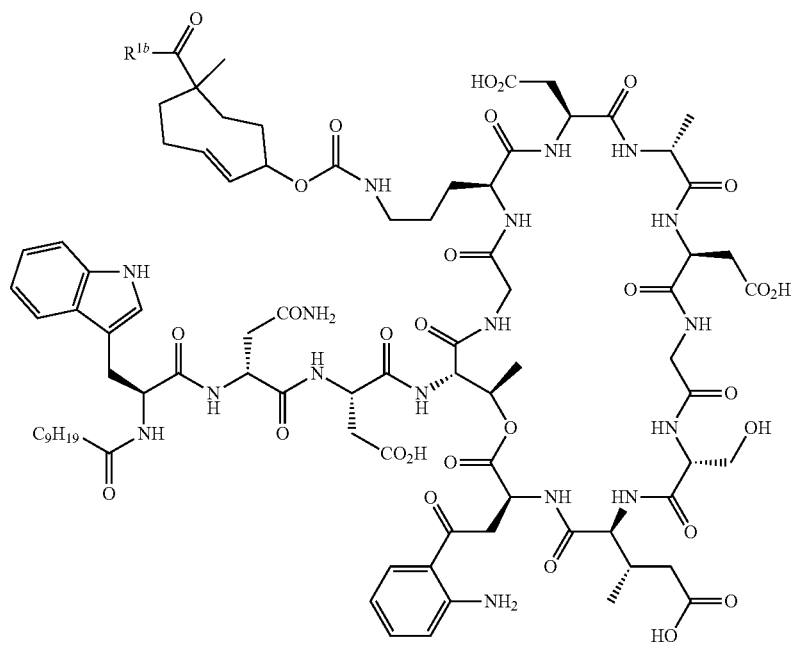

Scheme 4 shows a synthetic sequence to convert an intermediate 10 to an intermediate 11. Either 10 or 11 may be used to elaborate a linker, a protected linker, or a linker attached to a payload

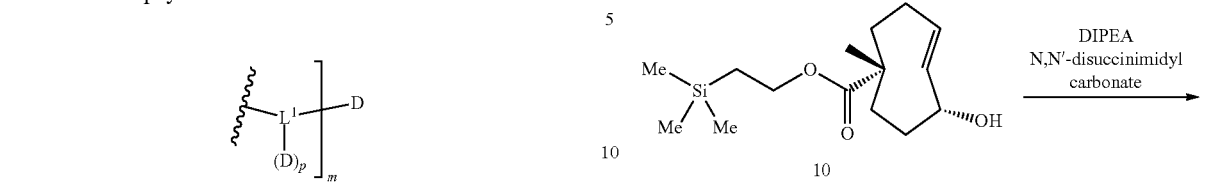

using general synthetic methods disclosed in WO2017/044983. The trimethylsilylethyl group may be removed at an appropriate point in the synthetic sequence to provide the carboxylic acid, which may optionally be further converted to other solubilizing $R^{1b}$ groups. The skilled artisan would be able to adapt the synthetic routes and protecting group strategies to arrive at compounds of the invention.

Scheme 4

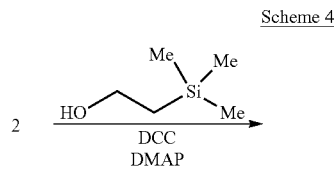

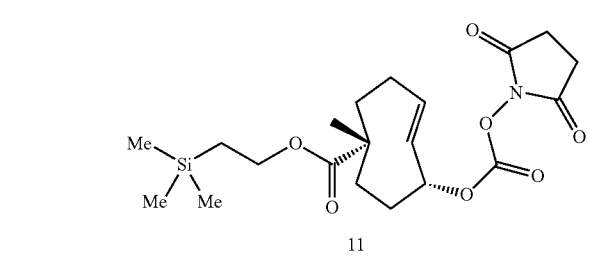

For example, Scheme 5 illustrated conversion of 11 to a carboxylic acid intermediate that may be further converted to payload-bearing products 13 and 14.

Scheme 5

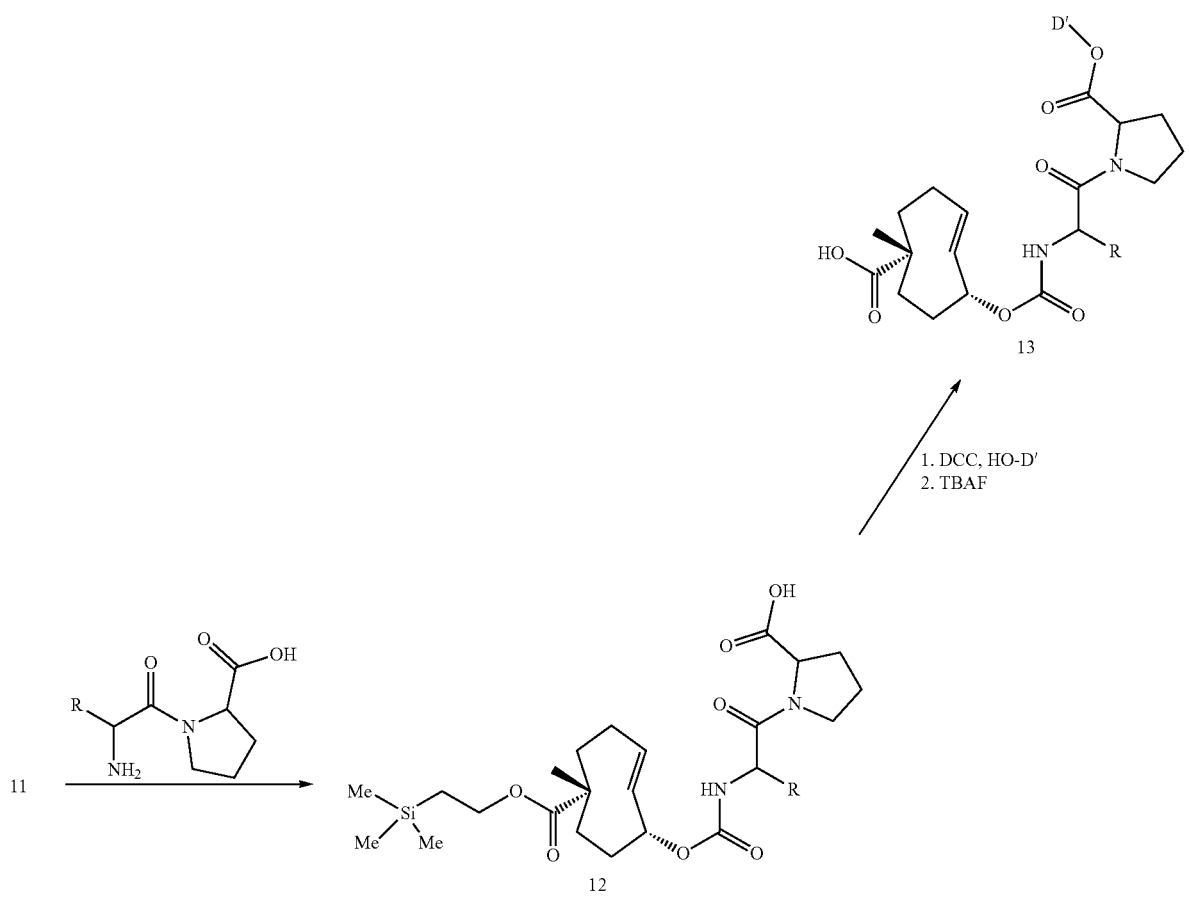

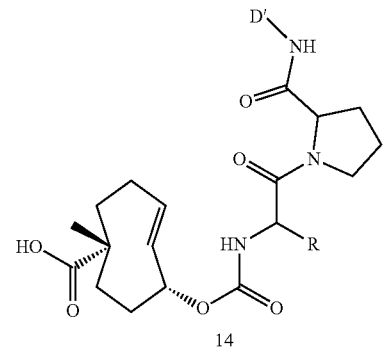
Other carboxylic acids that may be prepared using 11 include those shown in Scheme 6.
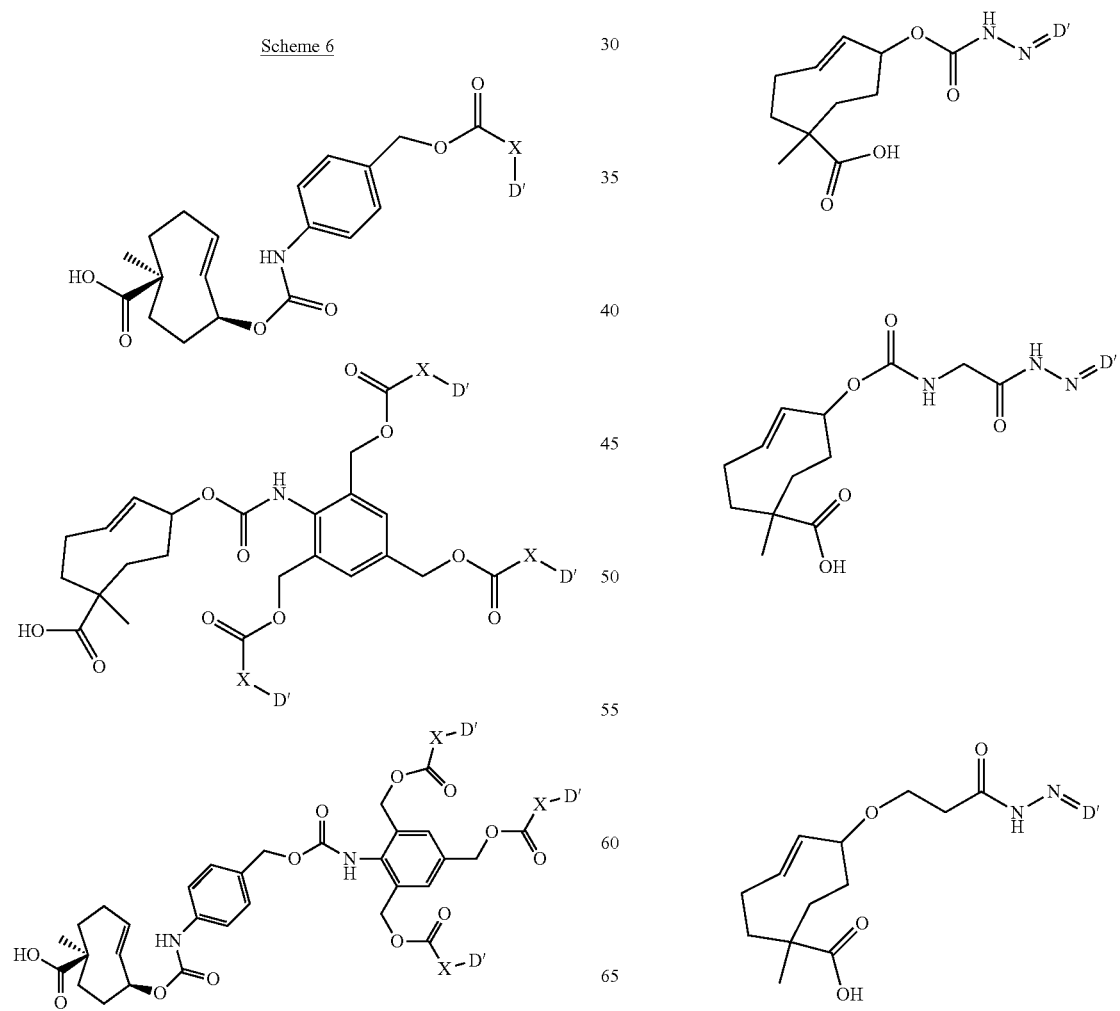

81
-continued
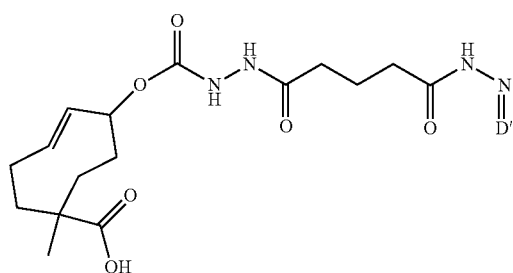
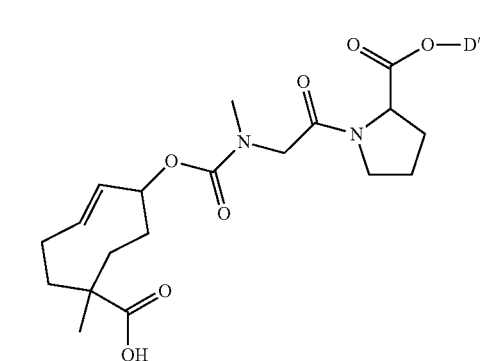
82
-continued
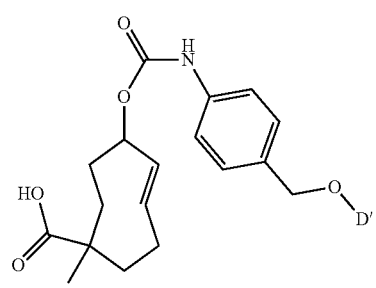
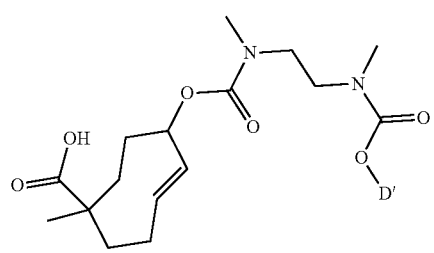
Scheme 7 illustrates general methods to prepare TCO conjugates with amide substitution on the TCO.
Scheme 7
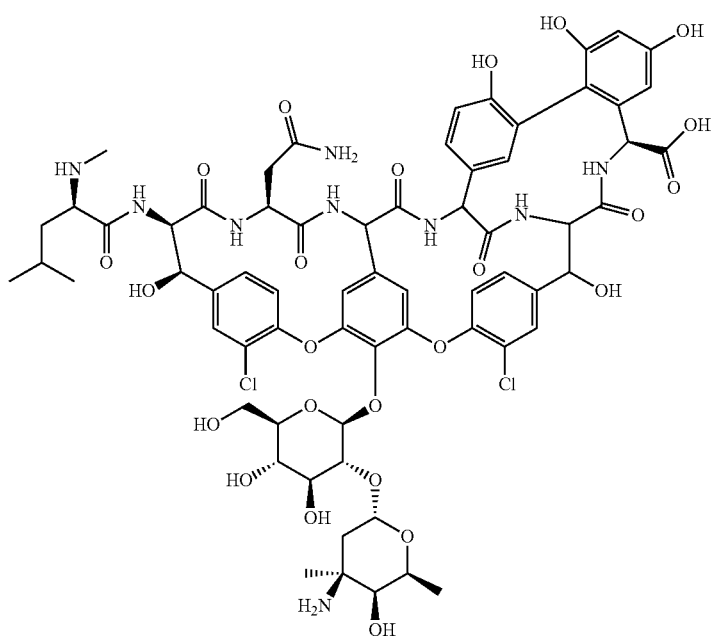
Vancomycin
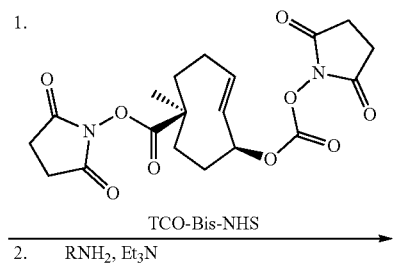

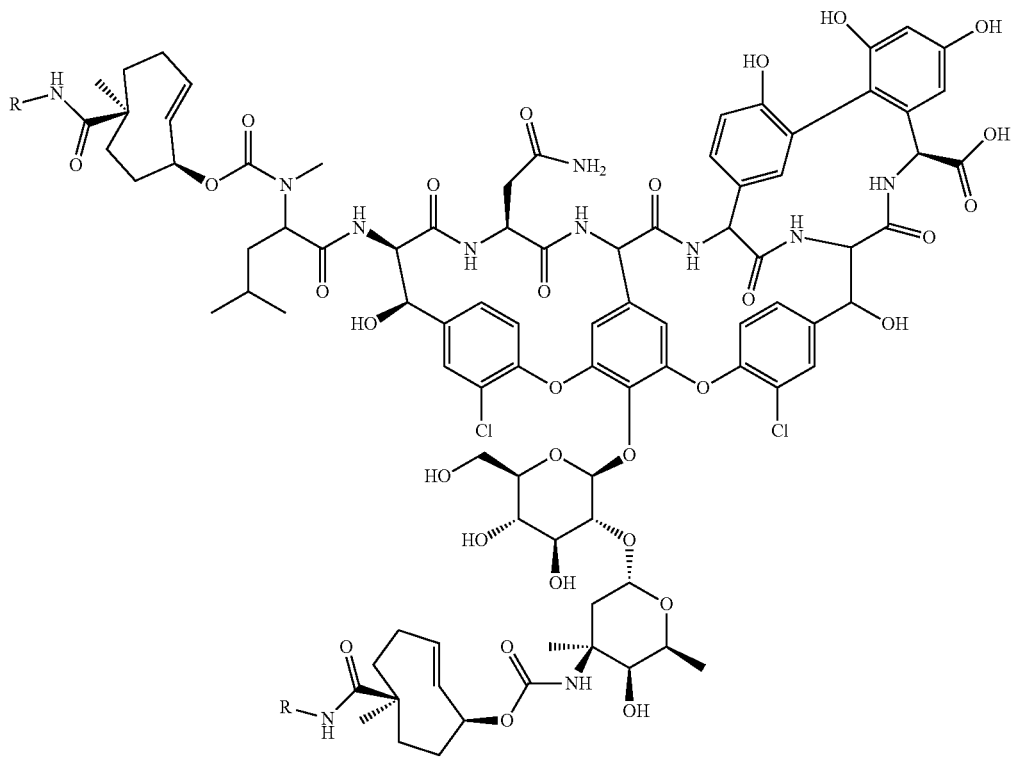
Vanco-Bis-TCO-conjugates
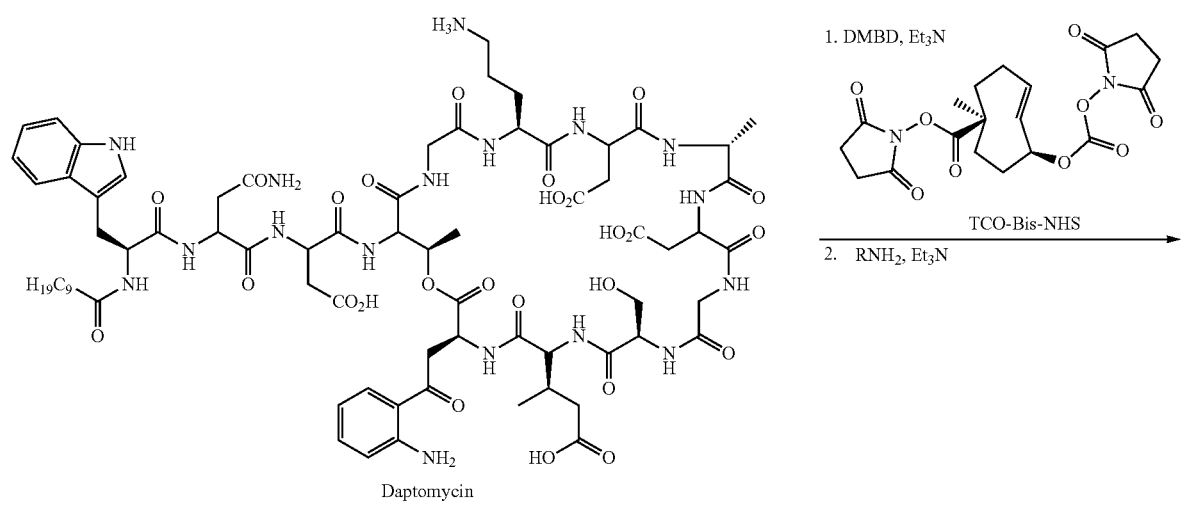
Daptomycin

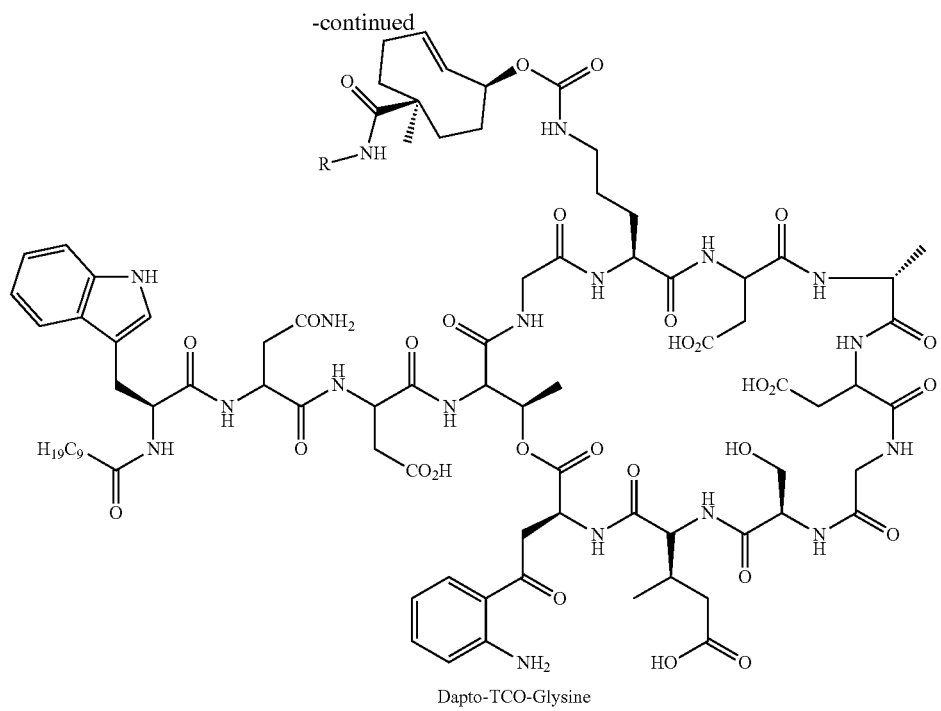

Dapto-TCO-Glysine

The disclosed compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." J. Pharm. Sci. Vol. 66, pp. 1-19.

For example, if the compound is anionic, or has a functional group which may be anionic (e.g., —COH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchep tonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C=O) is converted to a diether (R$_2$C(OR)$_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases (e.g., cyclic amines), as a nitroxide radical (>N-0«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—CH$_2$NHC(O)CH$_3$).

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

4. Formulations

The compositions of the present disclosure can be formulated in a variety of different ways. In general, compositions that include one or more binding agents or complementary binding agents are formulated in a manner compatible with the binding agents and complementary binding agents, the condition to be treated, and the route of administration to be used. In addition, where the composition includes a payload, the composition is formulated in a manner compatible with the payload, the condition to be treated, and the route of administration to be used.

The composition (e.g., support composition and/or functionalized payload) can be provided in any suitable form, e.g., in the form of a pharmaceutically acceptable formulation, and can be formulated for any suitable route of administration, e.g., oral, topical or parenteral administration. Where the composition is provided as a liquid injectable (such as in those embodiments where they are administered intravenously or directly into a tissue), the composition can be provided as a ready-to-use dosage form, or as a reconstitutable storage-stable powder or liquid that may include pharmaceutically acceptable carriers and excipients.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and includes an excipient, diluent, carrier, and adjuvant that are acceptable for veterinary use and/or human pharmaceutical use. "A pharmaceutically acceptable excipient, diluent, carrier and/or adjuvant" as used herein includes one or more such excipients, diluents, carriers, and adjuvants.

Methods for formulating compositions can be adapted from those readily available. For example, compositions can be provided in a pharmaceutical formulation that includes a therapeutically effective amount of a composition and a pharmaceutically acceptable carrier (e.g., saline). The pharmaceutical formulation may optionally include other additives (e.g., buffers, stabilizers, preservatives, and the like). In some embodiments, the formulations are suitable for administration to a mammal, such as those that are suitable for administration to a human.

The compositions of the present disclosure can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the subject. The compositions of the present disclosure can also be administered by injection, that is, intravenously, intramuscularly, intracutaneously, subcutaneously, intraduodenally, or intraperitoneally. In some instances, the compositions described herein can be administered by inhalation, for example, intranasally. In some instances, the compositions of the present disclosure can be administered transdermally. In some instances, the compositions can be administered by intraocular, intravaginal, and intrarectal routes including suppositories, insufflation, powders and aerosol formulations (for examples of steroid inhalants, see Rohatagi, J. Clin. Pharmacol. 35: 1187-1193, 1995; Tjwa, Ann. Allergy Asthma Immunol. 75: 107-111, 1995). Accordingly, the present disclosure also provides pharmaceutical formulations including a composition as described herein and a pharmaceutically acceptable carrier or excipient.

For preparing pharmaceutical formulations from the compositions of the present disclosure, pharmaceutically acceptable carriers can be solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are found, for example in Remington's Pharmaceutical Sciences, Maack Publishing Co, Easton Pa. ("Remington's").

5. Methods of Treatment

Aspects of the present disclosure include methods for delivering a payload to a target location in a subject. In certain embodiments, the method includes selectively delivering a payload to the target location in a subject. Selective delivery of the payload includes delivering the payload to the target location (e.g., an organ or tissue, or portion thereof), without targeting other locations in the subject (e.g., other organs or tissues, or portions thereof) that do not need administration of the payload. Selective delivery of the payload may be achieved through use of the support compositions and the functionalized payloads described herein.

In some instances, a support composition of the present disclosure may be localized to a desired target location in a subject. For example, methods of the present disclosure may include administering to a subject a support composition as described herein. The support composition may be administered to the subject at a desired target location in the subject. In some instances, the support composition may be implanted into the subject at the desired target location in the subject. In some embodiments, the support composition may be attached to a targeting agent as described herein, and the method may include administering the support composition to the subject (e.g., administered systemically). In these embodiments, the support composition that is attached to a targeting agent may localize at a desired target location in the subject through specific binding of the targeting agent to its target (e.g., antibody-antigen interaction, and the like), or may localize on the surface of a desired target (e.g., a cell surface) through specific binding of the targeting agent to its target (e.g., antibody-antigen interaction, and the like).

As described herein, selective binding between bioorthogonal binding partners (e.g., between a binding agent of the support composition and its complementary binding agent of a functionalized payload) may occur. Due to the localized administration of the support composition to a desired location in the subject as described above, the selective binding between the binding agent of the support composition and its complementary binding agent of the functionalized payload will localize the payload to the desired target location. Accordingly, in certain embodiments, the method includes administering to the subject a functionalized payload such that the functionalized payload binds to the support composition to form a support complex. For example, the functionalized payload may be administered systemically to the subject. Upon administration of the functionalized payload to the subject, contact between the binding agent of the support composition and the complementary binding agent of the functionalized payload may occur, such that the binding agent and its complementary binding agent bind to one another to form a support complex, thereby selectively delivering the payload to the target location in the subject. In some embodiments, selective delivery of the functionalized payload results in a concentration of the payload at the target location that is greater than the concentration of the payload elsewhere in the subject (e.g., at non-targeted areas in the subject).

Indications for this approach, include cancer, both hematological and solid cancers, infections, wound healing, stenosis, ischemia, re-vascularization, myocardial infarction, arrhythmias, vascular occlusion (thrombi, through anticoagulants), inflammation through anti-proliferative drugs, corticosteroids and derivatives, and/or NSAIDS, autoimmune disorders, transplants, macular degeneration, rheumatoid arthritis, osteoarthritis, peri-prosthetic infections, through coating of implants, paste, wax, polymethylmethacrylate (PMMA) constructs, and others. In certain embodiments, the approach can be used for the treatment and/or diagnosis of soft tissue sarcomas: rhabdomyosarcoma, fibrosarcoma, Ewing's sarcoma, and all the different subtypes of soft tissue sarcoma as well as osteosarcoma. The compositions can be for the treatment and/or diagnosis of pigmented vilonodular synovitis.

The compositions of the present disclosure find use in treatment and/or diagnosis of a condition or disease in a subject that is amenable to treatment or diagnosis by administration of the payload (e.g., the parent drug (i.e., the drug prior to conjugation to the composition)). By "treatment" is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition. Treatment may include inhibition, that is, arresting the development or further development of clinical symptoms, e.g., mitigating or completely inhibiting an active disease. Treatment may include relief, that is, causing the regression of clinical symptoms. For example, in the context of cancer, the term "treating" includes any or all of: reducing growth of a solid tumor, inhibiting replication of cancer cells, reducing overall tumor burden, prolonged survival and ameliorating one or more symptoms associated with a cancer.

The subject to be treated can be one that is in need of therapy, where the subject to be treated is one amenable to treatment using the parent drug. Accordingly, a variety of subjects may be amenable to treatment using the compositions disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of composition administered to a subject can be initially determined based on guidance of a dose and/or dosage regimen of the parent drug. In general, the compositions can provide for targeted delivery and/or enhanced serum half-life of the bound drug, thus providing for at least one of reduced dose or reduced administrations in a dosage regimen. Thus, the compositions can provide for reduced dose and/or reduced administration in a dosage regimen relative to the parent drug prior to being conjugated in a composition of the present disclosure.

The compositions of the present disclosure can be delivered by any suitable means, including oral, parenteral and topical methods. For example, transdermal administration methods, by a topical route, can be formulated as applicator sticks, solutions, suspensions, emulsions, gels, creams, ointments, pastes, jellies, paints, powders, and aerosols.

The pharmaceutical formulation may be provided in unit dosage form. In such form the pharmaceutical formulation may be subdivided into unit doses containing appropriate quantities of the compositions of the present disclosure. The unit dosage form can be a packaged preparation, the package containing discrete quantities of the preparation, such as packeted tablets, capsules, and powders in pouches, vials or ampoules. Also, the unit dosage form can be a capsule, tablet, dragee, cachet, or lozenge, or it can be the appropriate number of any of these in packaged form.

Compositions of the present disclosure can be present in any suitable amount, and can depend on various factors including, but not limited to, weight and age of the subject, state of the disease, etc. Suitable dosage ranges for the composition of the present disclosure include from 0.1 mg to 10,000 mg, or 1 mg to 1000 mg, or 10 mg to 750 mg, or 25 mg to 500 mg, or 50 mg to 250 mg. For instance, suitable dosages for the composition of the present disclosure include 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg or 1000 mg.

In some embodiments, multiple doses of a composition are administered. The frequency of administration of a composition can vary depending on any of a variety of factors, e.g., severity of the symptoms, condition of the subject, etc. For example, in some embodiments, a composition is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The compositions of the present disclosure can be administered at any suitable frequency, interval and duration. For example, the composition of the present disclosure can be administered once an hour, or two, three or more times an hour, once a day, or two, three, or more times per day, or once every 2 days, 3 days, 4 days, 5 days, 6 days, or 7 days, so as to provide the desired dosage level to the subject. When the composition of the present disclosure is administered more than once a day, representative intervals include 5 min, 10 min, 15 min, 20 min, 30 min, 45 min and 60 minutes, as well as 1 hr, 2 hr, 4 hr, 6 hr, 8 hr, 10 hr, 12 hr, 16 hr, 20 hr, and 24 hours. The composition of the present disclosure can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The compositions of the present disclosure can be co-administered with another active agent. Co-administration includes administering the composition of the present disclosure and active agent within 0.5 hr, 1 hr, 2 hr, 4 hr, 6 hr, 8 hr, 10 hr, 12 hr, 16 hr, 20 hr, or 24 hours of each other. Co-administration also includes administering the composition of the present disclosure and active agent simultaneously or approximately simultaneously (e.g., within about 1 min, 5 min, 10 min, 15 min, 20 min, or 30 minutes of each other), or sequentially in any order. In addition, the composition of the present disclosure and the active agent can each be administered once a day, or two, three, or more times per day so as to provide the desired dosage level per day.

In some embodiments, co-administration can be accomplished by co-formulation, e.g., preparing a single pharmaceutical formulation including both the composition of the present disclosure and the active agent. In other embodiments, the composition of the present disclosure and the active agent can be formulated separately and co-administered to the subject.

The composition of the present disclosure and the active agent can be present in a formulation in any suitable weight ratio, such as from 1:100 to 100:1 (w/w), or 1:50 to 50:1, or 1:25 to 25:1, or 1:10 to 10:1, or 1:5 to 5:1 (w/w). The composition of the present disclosure and the other active agent can be present in any suitable weight ratio, such as 1:100 (w/w), 1:75, 1:50, 1:25, 1:10, 1:5, 1:4, 1:3, 1:2, 1:1, 2:1, 3:1, 4:1, 5:1, 10:1, 25:1, 50:1, 75:1, or 100:1 (w/w). Other dosages and dosage ratios of the composition of the present disclosure and the active agent are suitable in the formulations and methods described herein.

The functionlized payloads, therapeutics support compositions, and methods can be used for the treatment, prevention, and/or diagnosis of any targeted disease. Indications for this approach, include cancer, both hematological and solid cancers, infections, wound healing, stenosis, ischemia, revascularization, myocardial infarction, arrhythmias, vascular occlusion (thrombi, through anticoagulants), inflammation through anti-proliferative drugs, corticosteroids and derivatives, and/or NSAIDS, autoimmune disorders, transplants, macular degeneration, rheumatoid arthritis, osteoarthritis, peri-prosthetic infections, through coating of implants, paste, wax, polymethylmethacrylate (PMMA) constructs, and others. In certain embodiments, the functionlized payloads, therapeutics support compositions, and methods can be used for the treatment, prevention, and/or diagnosis of soft tissue sarcomas: rhabdomyosarcoma, fibrosarcoma, Ewing's sarcoma, and all the different subtypes of soft tissue sarcoma as well as osteosarcoma. The compositions can be for the treatment and/or diagnosis of pigmented vilonodular synovitis.

In certain embodiments, the functionlized payloads, therapeutics support compositions, and methods can be used for the treatment, prevention, and/or diagnosis of solid tumors, including but not limited to, melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), glioblastoma, and lung cancer (e.g., non-small cell lung cancer), soft tissue sarcoma, fibrosarcoma, osteosarcoma, pancreatic cancer, among others. The disclosed approach lends itself well as an adjuvant/neoadjuvant system. For example, particles as disclosed herein could be placed during the biopsy, once the results from the study come back, the practitioner could deliver the appropriate cocktail to the desired site in the body. This would minimize the size of the tumor particularly in the context of a surgically resectable tumor. Then at the end of the surgery, the surgeon could place more particles around the surgical cavity and treat the patient with further doses of treatment (e.g. chemotherapy through the disclosed approach) to minimize the risk of any cancer cells that may have been missed in the surgical margins.

In certain embodiments, the disclosed methods provide the ability to place particles as disclosed herein at the time of the biopsy. When the results return, the practitioner can deliver through to the biopsy site chemokines (agents that attract cancerous cells and/or immune cells) and adjuvants to enhance the immune system with fewer side effects as well as the chemotherapeutics agents combined with immunotherapy agents. This combination approach would be beneficial to patients. The chemotherapy agent would treat the solid tumor or specific location, while the enhanced response of the immunotherapy would help with distant metastatic sites. For example, in certain embodiments, the disclosed compositions and methods could employ or be used with anthracyclines, taxanes, gemcitabine and other agents to enhance the efficacy of ipilimunab, nivolumab, pembrolizumab, avelumab (also known as MSB0010718C; Pfizer) and other checkpoint inhibitors.

The disclosed compounds and compositions may be used in methods of treatment. The methods of treatment disclosed herein may be used to treat bacterial infections. The methods of treatment disclosed herein may be used to treat or prevent MRSA infections. The methods of treatment disclosed herein may be used to treat cancer. The methods of treatment disclosed herein may be used to treat pigmented villonodular synovitis. The methods of treatment disclosed herein may be used to treat diseases or disorders related to inflammation. The methods of treatment disclosed herein may be used to treat arthritis.

a. Bacterial Infections

The disclosed methods may be used to treat or prevent bacterial infections. Although bacteria may not be harmful, and in some cases may be beneficial, bacteria may also lead to infection. Bacterial infections can affect multiple organs and body systems including, but not limited to, skin, mucous membranes, blood, lungs, kidneys, urinary tract, eyes, heart, intestines, meninges, respiratory tract, genitals, stomach, bone, connective tissue, and tissue surrounding organs. Bacterial infections may affect more than one organ or body system. Bacterial infections may be systemic. Bacterial infections may be asymptomatic. Bacterial infections may cause a variety of symptoms including, but not limited to, fever, inflammation, wounds that do not heal, weeping wounds, skin rash, red bumps on the skin, abscesses, swollen lymph nodes, nausea, diarrhea, headaches, earaches, sore throat, fatigue, low blood pressure, hyperventilation, weak and rapid pulse, local or systemic pain, and muscle aches. Bacterial infections may cause death. Subjects with co-morbidities or a compromised immune system may be more susceptible to bacterial infections. Bacterial infections may occur at surgical sites. Bacterial infections may be related to catheter placement.

The diagnosis of a bacterial infection may include, but are not limited to, symptomatic diagnostics, microbial culture, microscopy, biochemical tests, PCR based diagnostics, and metagenomics sequencing. A microbial examination may include sample collection, microbial cultivation, identification, and test of antibiotic susceptibility. The diagnosis may include gram staining of the bacterial culture. The diagnosis may include a coagulase test of the bacterial culture. The diagnosis may include a catalase test of the bacterial culture. The diagnosis may include blood tests. The blood tests may include, but are not limited to, a full blood count, measurement of C-reactive protein, measurement of procalcitonin, and measurement of rapid plasma reagin. The diagnosis may include ELISA. The diagnosis may include PCR. A rapid latex agglutination test that detects the PBP2a protein may be conducted to identify MRSA. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The determination of bacteria growing on an agar plate or in a nutrient broth may determine the bacteria responsible for the subject's infection. Discs containing antibiotic compounds may be placed on the agar plates. The antibiotic compounds may kill the bacteria growing on the plate. The greater the zone of dead bacteria around the disc (zone of inhibition) may indicate a more effective antibiotic.

Samples for diagnosing a bacterial infection may be obtained from the subject in need of treatment. The sample for testing may be from the site of the infection. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and/or other body fluids. Multiple samples may be taken from the subject. Multiple samples may be taken around the site of a prosthesis or medical device.

Bacterial infections may be treated with the compounds and compositions disclosed herein. Bacterial infections that may be treated by the compounds and compositions disclosed herein include, but are not limited to, *Staphylococcus aureus*, methicillin-resistant *Staphylococcus aureus* (MRSA), methicillin-sensitive *Staphylococcus aureus* (MSSA), *Enterococcus faecalis, Enterococcus faecium, Escherichia coli, Salmonella, Neisseria, Bacillus, Brucella, Nocardia, Listeria monocytogenes, Lactobacillus plantarum, Lactococcus lactis, Francisella, Legionella, Yersinia pestis, Pseudomonas aeruginosa, Burkholderia cenocepacia, Mycobacterium avium*, vancomycin-resistant Enterococci (VRE), and vancomycin-resistant *Staphylococcus aureus* (VRSA). The bacterial infection to be treated may be resistant to one or many antibiotics. Bacterial infections treated herein may be caused by Gram-positive bacteria. Bacterial infections treated herein may be caused by Gram-positive bacterial strains that are resistant to vancomyocin. Bacterial infections treated herein may be caused by multi-drug-resistant Gram-positive bacteria.

i. MRSA Infections

The disclosed methods may be used to treat MRSA. MRSA is any strain of *Staphylococcus aureus* that has developed multi-resistance to beta-lactam antibiotics, which include the penicillins (methicillin, dicloxacillin, nafcillin, oxacillin, etc.) and the cephalosporins. MRSA evolved from horizontal gene transfer of the mecA gene to at least five distinct *S. aureus* lineages. MRSA infections can quickly cause serious and life threatening internal infections including, but not limited to, sepsis, endocarditis, MRSA pneumonia bone infections, and infections of implants. MRSA may cause infections of the skin. The MRSA skin infections may lead to boils or abscesses. MRSA may cause systemic or internal infections. Some MRSA infections are untreatable with currently available antibiotics, usually resulting in severe, debilitating infection, or death. The MRSA infection may occur in subjects who have been hospitalized, which is known as health care-associated MRSA (HA-MRSA). The MRSA infection may be spread by skin-to-skin contact, which is known as community-associated MRSA (CA-MRSA). Cases of MRSA have increased in livestock animals. CC398, a variant of MRSA, has emerged in animals and is found in intensively reared production animals (e.g., pigs, cattle, and poultry), where it can be transmitted to humans as LA-MRSA (livestock-associated MRSA).

The strains of MRSA to be treated by the compounds and compositions disclosed herein may include, but are not limited to, CBD-635, ST250 MRSA-1, ST2470-MRSA-I, ST239-MRSA-III, ST5-MRSA-II, ST5-MRSA-IV, ST239-MRSA-III, EMRSA15, EMRSA16, MRSA252, ST5: USA100, EMRSA 1, ST8:USA300, ST1:USA400, ST8: USA500, ST59:USA1000, USA1100, USA600, USA800, USA300, ST30, ST93, ST80, ST59, CC22, CC8, CC425, and CC398.

ii. Catheter-Related Bloodstream Infections

The disclosed methods may be used to treat catheter-related bloodstream infections. Catheter-related bloodstream infection (CRBSI) is defined as the presence of bacteremia originating from an intravenous catheter. CRBSI may occur frequently, may be lethal, and may be a common cause of nosocomial bacteremia. Intravascular catheters are integral to the modern practices and are inserted in critically-ill patients for the administration of fluids, blood products, medication, nutritional solutions, and for hemodynamic monitoring. Central venous catheters (CVCs) may pose a greater risk of device-related infections than any other types of medical device and may be major causes of morbidity and mortality. They may be a source of bacteremia and septicemia in hospitalized patients. CRBSIs may be associated with CVCs.

The disclosed methods may be used to deliver molecular payloads to an implanted biomaterial (e.g., polymer or hydrogel substituted with a bioorthogonal group). The material may be implanted at a desired location of the body during any local manipulation even if the specific pathogen or problem has not been determined yet such as a surgical implant or indwelling device insertion ("local injection"). For example, a suitably modified polymer or hydrogel such as hyaluronic acid modified with a tetrazine (HAT) may be used to coat catheter materials or other implanted medical device using known procedures for coating plastic materials with hyaluronic acid. Coating procedures can be optimized on small sections of polyurethane (PU) or polyvinyl chloride (PVC) tubing. PU or PVC tubing can be treated with 3-aminopropyltriethoxysilane in distilled water to incorporate amine groups for covalent functionalization with hyaluronic acid (HA). A base layer of HAT or unmodified HA can then be bonded to the surface using carbodiimide chemistry conditions as detailed in the literature. Additional layers of HAT or HA can be deposited through repeated manual dip coating procedures using similar carbodiimide chemistry conditions until a total of 10 additional layers have been applied. The final coated tubing can be characterized by scanning electron microscopy to examine surface morphology, confocal microscopy to determine coating thickness, and contact angle measurement to evaluate surface hydrophilicity.

Figures 8A, 8B, 8C, 8D:
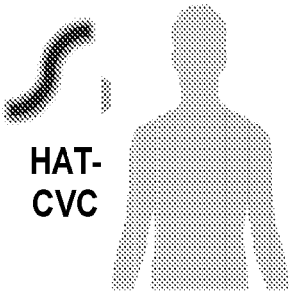
FIG. 8A-8D shows in vivo bioorthogonal chemistry for the concentration and activation of systemic prodrugs.
Figures 10A, 10B, 10C, 10D:
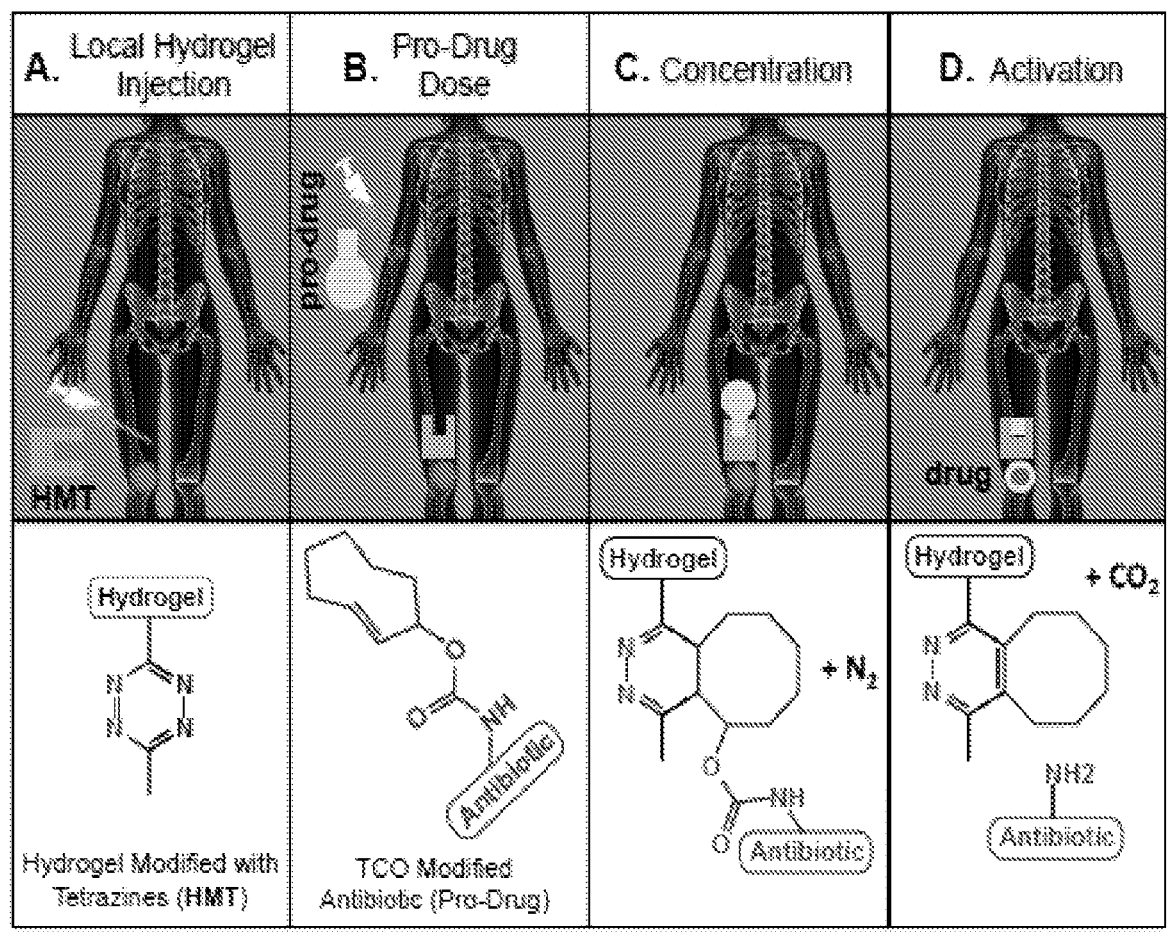
FIG. 10A-10D is a schematic showing a bio-orthogonal chemistry-based strategy for concentration and activation of systemically administered antibiotic prodrugs.
Figure 11:
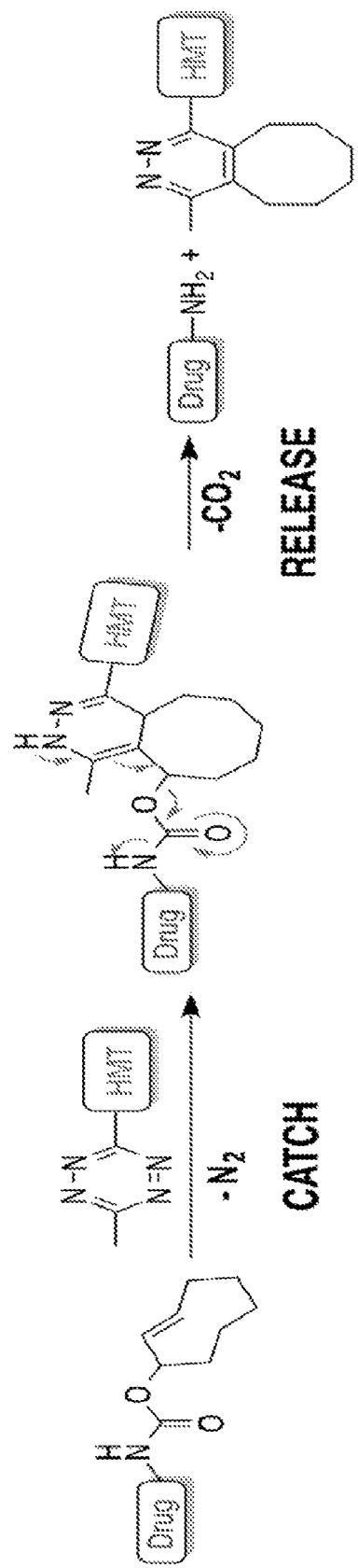
FIG. 11 is a schematic showing the underlying molecular mechanism of a 'Catch and Release' strategy.

Following implantation of a biomaterial-coated device, an inactive prodrug, created by modifying a drug with the reaction partner, is injected into the blood stream whenever it is needed ("systemic exposure"). The inactive prodrugs spread throughout the body, but when they come near the biomaterial, whether in the form of a coating or gel, they quickly attach to it ("catch"), thus concentrating the prodrug at the desired location. Finally, the active drug is spontaneously released from the biomaterial to perform its function ("release"). This provides a system with the temporal control of systemic drug delivery, and effectively turns systemic drugs into localized medicines (FIG. 8).

Due to the limited systemic activity of the prodrug, problems related to the disruption of the body's natural microbiome, such as drug-resistant bacteria or the development of infections will be prevented. A supratherapeutic dose may be given, thus increasing the drug's therapeutic index and reducing the likelihood of bacteria at the site of infection developing resistance. Having the gel coat the surface of a CVC or other implanted device, the drug will be able to accumulate deep into tissues that systemic drugs in their usual doses cannot reach.

The disclosed methods may lead to "reloading" by a prodrug, ensuring local release and improved efficacy. This will lead to better utilization of antimicrobials and reduction of the emergence of resistant bacteria. If a bacterial or fungal infection turned out to be resistant to the first prodrug, then a second prodrug could be "caught and released" by the already-implanted gel or coated device. Standard technologies require implant removal and placement to achieve similar results. The disclosed biodegradable coating would not require an additional invasive procedure to implant or remove it.

b. Cancer

The disclosed methods may be used to treat or prevent cancer. Cancer is a group of related diseases that may include sustained proliferative signaling, evasion of growth suppressors, resistance to cell death, enablement of replicative immortality, induction of angiogenesis, and the activation of invasion and metastasis. The disclosed methods may enhance or elicits an immune response against a cancer in the subject. The immune response may lead to an increase in one or more of leukocytes, lymphocytes, monocytes, and eosinophils.

Cancer that may be treated by the disclosed methods, includes, but is not limited to, astrocytoma, adrenocortical carcinoma, appendix cancer, basal cell carcinoma, bile duct cancer, bladder cancer, bone cancer, brain cancer, brain stem cancer, brain stem glioma, breast cancer, cervical cancer, colon cancer, colorectal cancer, cutaneous T-cell lymphoma, diffuse intrinsic pontine glioma, ductal cancer, endometrial cancer, ependymoma, Ewing's sarcoma, esophageal cancer, eye cancer, fibrosarcoma, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, soft tissue carcinoma, soft tissue sarcoma, solid tumor, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor.

In some embodiments, the cancer that may be treated by the disclosed methods is melanoma, renal cancer, prostate cancer, ovarian cancer, breast cancer, glioma, lung cancer, soft tissue carcinoma, soft tissue sarcoma, osteosarcoma, or pancreatic cancer. In some embodiments, the cancer is a solid tumor. In some embodiments, the cancer is a soft tissue carcinoma. In some embodiments, the cancer is afibrosarcoma. In some embodiments, the cancer is diffuse intrinsic pontine glioma.

Without being bound by a particular theory, local release of certain anti-cancer agents using the compounds and methods of the invention may produce or contribute to immunogenic cell death (ICD). For example, certain anti-cancer agents (e.g., anthracyclines, cyclophosphamide, oxaliplatin) have been reported to induce ICD. Kroemer et al. Annu. Rev. Immunol. 2013 (31), 51-72. Immunogenic apoptosis of cancer cells can induce an effective antitumour immune response through activation of dendritic cells (DCs) and consequent activation of specific T cell response. ICD is characterized by secretion of damage-associated molecular patterns (DAMPs). Three important DAMPs which are exposed to the cell surface during ICD. Calreticulin (CRT), one of the DAMP molecules, which is normally in the lumen of endoplasmic reticulum (ER), is translocated after the induction of immunogenic apoptosis to the surface of dying cell where it functions as an "eat me" signal for professional phagocytes. Other important surface exposed DAMPs are heat-shock proteins (HSPs), namely HSP70 and HSP90, which are under stress condition also translocated to the plasma membrane. On the cell surface they have an immunostimulatory effect, based on their interaction with number of antigen-presenting cell (APC) surface receptors like CD91 and CD40 and also facilitate crosspresentation of antigens derived from tumour cells on MHC class I molecule, which than leads to the CD8+ T cell response. Other important DAMPs, characteristic for ICD are secreted amphoterin (HMGB1) and ATP. HMGB1 is considered to be late apoptotic marker and its release to the extracellular space seems to be required for the optimal release and presentation of tumour antigens to dendritic cells. It binds to several pattern recognition receptors (PRRs) such as Toll-like receptor (TLR) 2 and 4, which are expressed on APCs. The most recently found DAMP released during immunogenic cell death is ATP, which functions as a "find-me" signal for monocytes when secreted and induces their attraction to the site of apoptosis. Kroemer et. al. Curr. Op. Immunol. 2008 (20), 504-511.

Thus, local release of ICD inducers using the compounds and methods of the invention may be beneficially combined with other immuno-oncology drug classes, including immune checkpoint inhibitors (e.g., PD-1, PD-L1 inhibitors).

i. Diffuse Intrinsic Pontine Gliomas

The disclosed methods may be used to treat diffuse intrinsic pontine gliomas. Diffuse intrinsic pontine gliomas (DIPG) are pediatric brainstem tumors that may be highly malignant and may be difficult to treat. There is no known curative treatment for DIPG, and survival odds have remained dismal over the past four decades. DIPG patients have a median overall survival of just 11 months, with a two-year survival rate below 10%. DIPG account for 75-80% of brainstem tumors in children, affecting an estimated 200-300 children in the U.S. each year. The rarity of this devastating disease and previous lack of experimental model systems has impeded research, and over the past four decades survival odds have remained the same. Diagnosis of DIPG may begin with clinical symptoms and may be confirmed by MRI. The disease may begin with several months of generalized symptoms, including behavioral changes and difficulties in school, double vision, abnormal or limited eye movements, an asymmetric smile, loss of balance, and weakness. Alternately, severe neurologic deterioration may happen more quickly, with symptoms present for less than a month prior to diagnosis. Clinical examination may reveal the triad of multiple cranial neuropathies, long tract signs such as hyperreflexia and clonus, as well as ataxia. Expansion of the pons section of the brainstem may cause obstructive hydrocephalus and increased intracranial pressure.2

Nuclei critical for life-sustaining function such as breathing and heartbeat in are located in the pons and without treatment, breathing and heartbeat may be damaged by DIPG.

The disclosed methods may be used to deliver molecular payloads to the site of a DIPG (e.g., an HDAC inhibitor such as panobinostat). The disclosed methods may include delivering drugs systemically that are only activated at the tumor site. The disclosed methods may be used as a neoadjuvant or adjuvant therapy. The biomaterial may be placed during a biopsy. The results of the biopsy may indicate the amount and type of treatment to deliver to the site of a tumor. The disclosed compounds and compositions may be administered prior to surgical resection. The disclosed methods may minimize the size of the tumor prior to surgical resection. The disclosed compounds and compositions may be administered during surgical resection. The disclosed compounds and compositions may be administered after surgical resection. Biomaterial may be placed around the surgical cavity at the end of surgical resection and the subject may then be treated with further doses of a treatment (e.g., pro-doxorubicin). The disclosed biodegradable gel may be implanted at the time of biopsy or surgery. The disclosed methods may not require an additional invasive procedure to deliver additional doses of the disclosed compounds and compositions.

The disclosed methods may include multiple systemic doses of prodrug that focus at one location. The disclosed methods may be used to deliver a second prodrug. The disclosed methods may be used to administer a second prodrug if the tumor is resistant to the first prodrug. A second prodrug may be a TCO-labeled prodrug of gemcitabine or docetaxel. The TCO-labeled prodrug of gemcitabine or docetaxel may be administered in combination with doxorubicin. The second prodrugs may be activated by the implanted gel used for the first prodrug.

The in vivo efficacy of TAG and TCO-doxorubicin may be determined in a mouse xenograft model of DIPG. The efficacy of Shasgi's local activation platform to treat DIPG xenografts may be evaluated in mice. Nude mice can be injected stereotactically into the cerebrum with a suspension of luciferase-expressing DIPG cells (SU-DIPG-V1-luc and SF7761 patient derived cell lines) and TAG. The cerebrum, rather than the pons, would be used to improve xenograft consistency for these preliminary experiments. The xenografts models chosen have been shown to have replicated the histopathological features, invasive phenotypes and major genetic abnormalities of the original primary tumors. TAG and cells can be premixed prior to injection in order to limit the number of injections into this sensitive region for this proof-of-concept study. This study would employ 6 groups of 5 mice each, testing TCO-doxorubicin, doxorubicin, or saline control administered through intravenous (IV) and intracranial (IC) injection, as outlined in Table 1.

DIPG Animal Study Matrix (Per Cell Line)

| Group # | # Mice | Agent   | Delivery mode | Treatment Initiation | Measurements             | Endpoint         |
|---------|--------|---------|---------------|----------------------|--------------------------|------------------|
| 1       | 5      | TCO-dox | IV            | 7 days post implant  | IVIS, body weight, clinical score | 60 days post implant |
| 2       | 5      |         | IC            |                      |                          |                  |
| 3       | 5      | Dox     | IV            |                      | Daily-Week 1             |                  |
| 4       | 5      |         | IC            |                      | Weekly-                  |                  |
| 5       | 5      | Saline  | IV            |                      | endpoint                 |                  |
| 6       | 5      |         | IC            |                      |                          |                  |
| Total   | 30     | —       | —             | —                    | —                        | —                |

Seven days post cell implantation, mice can be administered a course of TCO-doxorubicin or doxorubicin at MTD levels. Through 60 days post-transplantation, response to treatment can be determined by bioluminescence signal and mouse survival. Toxicity of the treatment may be measured by clinical observations, including neuropathology clinical score, body condition score, and weight loss. If none of the clinical scores are met, mice are to be sacrificed 60 days after xenotransplantation. Upon reaching any study endpoint, mice are to be sacrificed and subjected to tissue histology of brain slices to determine the degree of disease progression and inflammation or tissue damage resulting from TAG or drugs. The amount of doxorubicin present in the brain tumor after treatment with TAG and pro-doxorubicin may also be analyzed by reverse phase high pressure liquid chromatography (RP-HPLC) to measure the ability of the drug to penetrate and be retained within the tumor.

c. Inflammation Related Diseases or Disorders

The disclosed methods may be used to treat or prevent disease and disorders related to inflammation. Diseases and/or disorders which may be treated and/or prevented by the disclosed methods include, but are not limited to, asthma, arthirtis, rheumatoid arthritis, osteoarthritis, autoimmune diseases, autoinflammtory diseases, celiac disease, chronic prostatis, diverticulitis, glomerulonephritis, otitis, necrotizing enterocolitis, inflammatory bowel disease, Crohn's disease, ulcerative colitis, colitis, Behcet's disease, vasculitis, transplant rejection, and autoimmune thyroid disease.

i. Pigmented Villonodular Synovitis

The disclosed methods may be used to treat pigmented villonodular synovitis. Pigmented villonodular synovitis (PVNS), also known as tenosynovial giant cell tumor (TGCT), is a chronic, progressive neoplastic process that causes the synovial lining of a joint, bursa, or tendon sheath to thicken and overgrow in an aggressive manner with a very low risk of metastasis. This condition affects approximately 1.8 people per million, or about 600, per year in the U.S. and most commonly appears in those aged 20 to 45 years old. PVNS may be focal or diffuse. In the diffuse form, the disease process may accelerate tendon and joint wear and may have a 40-50% rate of local recurrence with traditional treatment strategies. The benign but aggressive behavior of PVNS makes treatment challenging as clinicians have to weigh the morbidity of treatment relative to the natural history of the disease process. Methods that locally deliver and activate therapeutics may be the solution to conditions such as diffuse PVNS. This limits systemic side effects of medications. Diffuse pigmented villonodular synovitis (PVNS) which synonymously goes by the name of tenosynovial giant cell tumor (TGCT) in extraarticular manifestations of the disease, is a primarily localized, aggressive neoplastic process affecting the synovial lining of a joint, bursa, or tendon sheath, causing it to thicken overgrow, and induce a destructive inflammatory process.

In both localized and diffuse types of PVNS, the majority of cases have a genetic rearrangement in chromosome 1p11-13, a site for the macrophage colony stimulating factor (CSF-1). The translocation leads to CSF-1 overexpression, attracting inflammatory cells expressing CSF-1 receptor (CSF1R) and driving the formation of PVNS.13 CSF-1, a secreted cytokine and hematopoietic growth factor, plays an essential role in the proliferation, differentiation, and survival of monocytes, macrophages, and related cells.

Within tissue affected by PVNS, only a small population of mononuclear stromal cells (2-16%) have been demonstrated to overexpress CSF-1, and these neoplastic cells constitute a minor component within the tumor. However, most of the cells are non-neoplastic, have high levels of receptor (CSFR1) expression and are recruited and activated by the CSF1 produced by the neoplastic cells. Because CSFR1 is a group III receptor tyrosine kinase, it has been theorized that a tyrosine kinase receptor inhibitor (TKI) targeting CSF1R (e.g., imatinib, nilotinib, emactuzumab, and PLX3397) might inhibit PVNS progression and reduce surgical morbidity and preserve patient quality of life.

There are at least two forms of the disease, which may be histologically identical. A first, focal PVNS/GCTTS may appear in joints or around tendon sheaths that support the joint. It may manifest as a localized extraarticular process, usually affecting the small joints of the hand or wrist (65%-89%) and the foot and ankle (5%-15%), or as localized intraarticular disease, usually affecting the knee, hip, or ankle. The disclosed methods may be used to treat the first form of PVNS/GCTTS. A second type of PVNS is the diffuse form that affects the entire synovial lining. This is most common in large joints usually the hip (4-16%) and knee (66-80%), but can occur in other joints as well (ankle, shoulder, elbow, spine, etc.). This form of the disease is more invasive and more difficult to successfully treat with surgical excision. The disclosed methods may be used to treat the second form of PVNS.

Patients with symptomatic, aggressive PVNS, especially the diffuse form, currently undergo treatments with long-term consequences. The contemporary approach of surgery and radiation is too morbid for a condition that is ultimately benign. The recent development of systemic medication with an effect on the CSF-1R pathway has created an exciting new approach to this frustrating condition. Use as an adjuvant to surgery has demonstrated promising early results, however, side effects continue to be a limitation. The disclosed methods that locally deliver and activate therapeutics will be readily beneficial to treat PVNS while avoiding the long-term sequelae of the treatment itself. The disclosed methods may eliminate the need for surgery in patients with PVNS. The disclosed methods may eliminate the need for surgery in the focal form of PVNS. The disclosed methods may reduce the recurrence of PVNS. The disclosed methods may reduce local recurrence in the diffuse form of PVNS.

ii. Arthritis

The disclosed methods of treatment may be used to treat arthritis. Arthritis is a term that may mean any disorder that affects joints. Symptoms may include joint pain and stiffness. Other symptoms may include redness, warmth, swelling, and decreased range of motion of the affected joints. In some types of arthritis, other organs may also be affected. Onset may be gradual or sudden. There may be over 100 types of arthritis. The most common forms are osteoarthritis and rheumatoid arthritis. Osteoarthritis may occur with aging and may affect the fingers, knees, and hips. Rheumatoid arthritis is an autoimmune disorder that may affect the hand joints, feet joints, skin, lungs, heart and blood vessels, blood, kidneys, eyes, liver, bones and neurological system.

In some embodiments, the disclosed compounds and compositions may be used to treat infections, tissue injury, stenosis, ischemia, re-vascularization, myocardial infarction, arrhythmias, vascular occlusion, inflammation, autoimmune disorders, transplant rejection, macular degeneration, rheumatoid arthritis, osteoarthritis, peri-prosthetic infections, and pigmented villonodular synovitis.

b. Modes of Administration

Methods of treatment may include any number of modes of administering a disclosed compound or composition. Modes of administration may include tablets, pills, dragees, hard and soft gel capsules, granules, pellets, skin patches, skin creams, skin gels, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the compound or compositions disclosed herein may be admixed with adjuvants and excipients, such as gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the compound or compositions disclosed herein may also be dispersed in a microparticle, e.g. a nanoparticulate composition.

For parenteral administration, the compounds or compositions disclosed herein may be dissolved or suspended in a physiologically acceptable diluent, such as water, buffer, oils with or without solubilizers, surface-active agents, dispersants or emulsifiers. Suitable oils may include, for example, olive oil, peanut oil, cottonseed oil, soybean oil, castor oil and sesame oil. For parenteral administration, the compound or compositions disclosed herein may be administered in the form of an aqueous, lipid, oily or other kind of solution or suspension, or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

The compounds and compositions disclosed herein may be administered topically. A topical composition disclosed herein may be applied to the skin of a subject in need thereof. The area of skin selected for treatment may be the site of a bacterial infection. The area of skin selected for treatment may be skin surrounding the infection site. The area of skin selected for treatment may be the site of a bacterial infection and the skin surrounding the infection site. The infection of the skin may be caused by MRSA. A topical composition disclosed herein may be applied to a mucous membrane of a subject in need thereof. The mucous membrane selected for treatment may be the site of a bacterial infection. The area of the mucous membrane selected for treatment may be the mucous membrane surrounding the bacterial infection. The mucous membrane selected for treatment may be the site of a bacterial infection and the mucous membrane surrounding the site of the infection. The infection of the mucous membrane may be caused by MRSA.

The topical administration may be with a patch containing the compounds and compositions disclosed herein. The topical administration may be with a dissolvable patch containing the compound and compositions disclosed herein. The topical administration may be with a cream containing the compound and compositions disclosed herein. The topical administration may be with foam containing the compound and compositions disclosed herein. The topical administration may be with lotion containing the compound and compositions disclosed herein. The topical administration may be with an ointment containing the compound and compositions disclosed herein. The topical administration may be with gel containing the compound and compositions disclosed herein. The topical administration may have fewer side effects than systemic administration of antibiotics.

In some embodiments, a topical composition comprising a therapeutically effective amount of the compounds and compositions disclosed herein may be applied to the infected skin and/or mucous membrane of a subject to reduce or eliminate the infection, and/or improve healing of the wounded skin and/or mucous membrane. In particular embodiments, a topical composition comprising a therapeutically effective amount of the compounds and compositions disclosed herein may be applied to an area of the skin and/or mucous membrane infected by MRSA, including infections caused by MRSA biofilm. In these embodiments, the compounds and compositions disclosed herein may be administered alone or in combination of one or more other active agents to reduce infection and/or promote skin and/or mucous membrane healing.

c. Combination Therapies

Additional therapeutic agent(s) may be administered simultaneously or sequentially with the disclosed compounds and compositions. Sequential administration includes administration before or after the disclosed compound and compositions. An additional therapeutic agent may be administered before the disclosed compounds and compositions. An additional therapeutic agent may be administered after the disclosed compounds and compositions. An additional therapeutic agent may be administered at the same time as the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds or compositions. In some embodiments, administration of an additional therapeutic agent with a disclosed compound or composition may allow lower doses of the other therapeutic agents and/or administration at less frequent intervals. When used in combination with one or more other active ingredients, the compounds or compositions of the present invention and the other active ingredients may be used in lower doses than when each is used singly. Accordingly, the pharmaceutical compositions of the present invention include those that contain one or more other active ingredients, in addition to a compound of the present disclosure.

For the treatment of bacterial infection, the compounds and compositions may be combined with a variety of antibiotics. The antibiotics include, but are not limited to, vancomycin, linezolid, teicoplanin, ceftaorline, clindamycin, mupirocin, trimethoprim-sulfamethoxazole, tetracyclines, daptomycin, sulfa drugs, ceftobiprole, ceftaroline, dalbavancin, telavancin, torezolid, iclaprim, nemonoxacin, platensimycin, and oxadiazoles.

The compounds and compositions may be combined with agents that inhibit bacterial biofilm formation. The agents that inhibit bacterial biofilm formation include, but are not limited to, imidazole derivatives, indole derivatives, emodin, flavonoids, ginger extracts, *Hypericum perforatum*, 7-epiclusianone, isolimonic acid, tannic acid, chelerythrine, carvacrol, bgugaine, resveratrol, garlic extracts, natural halogenated furanones, brominated alkylidene lactams, and AHLs-based inhibitors.

The compounds and compositions may be combined with lysine-conjugated aliphatic norspermidine analogues. The compounds and compositions may be combined with phage therapy. In the case of infection involving a medical device or prosthesis, the compounds and compositions may be administered in combination with the removal of the medical device or prosthesis. A new, sterile medical device or prosthesis may be implanted in the subject.

The compounds and compositions may be combined with agents to modify potential side effects from antibacterial agents. Agents that may mediate or treat side effects include, but are not limited to, probiotics, anti-diarrheal agents, anti-emetic agents, and analgesics.

The subject may also be undergoing a variety of treatments for co-morbidities.

5. Examples

The present disclosure has multiple aspects, illustrated by the following non-limiting examples. The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

The following abbreviations are used herein:
ACN acetonitrile
Boc tert-butoxycarbonyl
Cy5 cyanine 5
Cy5.5 cyanine 5.5
dapto daptomycin
DCC N,N'-dicyclohexylcarbodiimide
DCM dichloromethane
dd doubly distilled
DIBAL diisobutylaluminum hydride
DIPEA diisopropylethylamine
DMAP 4-dimethylaminopyridine
DMF N,N-dimethylformamide
DMSO dimethylsulfoxide
doxo doxorubicin
EDCI N-(3-dimethylaminopropyl)-N'-ethylcarbodiimide-hydrochloride
Et ethyl
EtOAc ethyl acetate
FCC flash column chromatography
Fmoc fluorenylmethyloxycarbonyl h or hr hour
HA hyaluronic acid
HAT hyaluronic acid modified with tetrazine
HATU 1-[Bis(dimethylamino)methylene]-1H-1,2,3-triazolo[4,5-b]pyridinium 3oxide hexafluorophosphate
HBTU hexafluorophosphate benzotriazole tetramethyl uronium
HMT hydrogel modified tetrazine
HOAt 1-hydroxy-7-azabenzotriazole
HOBt 1-hydroxybenzotriazole
HPLC high performance liquid chromatograph
iPrOH isopropyl alcohol
LCMS liquid chromatography-mass spectrometry
Me methyl
MeCN acetonitrile
MeOH methanol
MES 2-(N-morpholino)ethanesulfonic acid
MeTz methyltetrazine
min minutes
MTD maximum tolerated dose
NHS N-hydroxysuccinimide
NMP N-methylpiperazine
PBS phosphate buffered saline
Ph phenyl
ppm parts per million
pyr pyridine
rt/RT room temperature
SEM standard error of the mean
sulfo-NHS N-hydroxysulfosuccinimide
TAG tetrazine-modified activating gel
TBAF tetrabutylammonium fluoride
TBME tert-butyl methyl ether
TCO trans-cyclooctene
TEA triethylamine
THF tetrahydrofuran
TLC thin-layer chromatography
TFA trifluoroacetic acid
TsCl tosyl chloride or toluenesulfonyl chloride
UV LVG ultrapure low viscosity guluronic acid
Vanco vancomycin Example 1

Morpholine-TCO-Doxorubicin rel-(1R,4E,6R,pS)-6-hydroxy-1-methylcyclooct-4-ene-1-carboxylic acid (Axial Isomer 2)

A solution of 5.34 g (95.2 mmol) potassium hydroxide in 16.7 mL water was added over a 5 min period to a water-cooled solution of the trans-cyclooctene ester 1 isomer mixture (Rossin et. al., Bioconjugate Chem., 2016, 27, 1697-1706) (1.64 g, 8.28 mmol, ratio of the axial/equatorial isomer ca. 1.2:1 for this particular batch) in 37 mL methanol. The solution was stirred for 18 h at room temperature. Water (51 mL) was added and the mixture was extracted with 3×150 mL TBME. The combined organic layers were washed with 100 mL water and then dried in vacuo to give the non-hydrolyzed equatorial ester 1b. The combined aqueous layers were treated with 300 mL TBME, and then with 15 g citric acid. The layers were separated and the aqueous layer was extracted with TBME (3×150 mL). The combined organic layers were dried and rotary evaporated at 25° C. to afford 873 mg (57%) of the pure axial isomer 2 of the trans-cyclooctene acid as a colorless oil. $^1$H-NMR (CDCl$_3$): δ=6.15-5.95 (m, 1H), 5.6 (d, 1H), 4.45 (bs, 1H), 2.4-1.7 (m, 7H), 1.6 (dd, 1H), 1.18 (s, 3H). $^{13}$C-NMR (CDCl$_3$): δ=185.4 (C=O), 134.8 (=CH), 130.7 (=CH), 69.8 (CH), 44.8, 38.2, 31.0, 29.8 (CH$_2$), 18.1 (CH$_3$).

rel-(1R,4E,6R,pS)-2,5-dioxopyrrolidin-1-yl-6-((((2,5-dioxopyrrolidin-1-yl)oxy)carbonyl)oxy)-1-methylcyclooct-4-ene-1-carboxylate (Axial Isomer 3)

To a solution of compound 2 (873 mg, 4.74 mmol) in 24.0 mL MeCN was added DIPEA (4.59 g, 35.6 mmol), followed by N,N'-disuccinimidyl carbonate (5.22 g, 20.4 mmol). The mixture was stirred for 3 days at RT, and subsequently evaporated in vacuo at 25° C. The residue was chromatographed on 40 g silica, with dichloromethane as eluent, followed by elution with dichloromethane containing an increasing amount of TBME (0-20%). The product fractions were combined and dried in vacuo. The resulting residue was stirred with TBME until a homogeneous suspension was obtained. Filtration and washing gave 761 mg of product 3 as a white solid (38%); $^1$H-NMR (CDCl$_3$): δ=6.07 (ddd, J=16.8, 10.7, 3.5 Hz, 1H), 5.62 (dd, J=16.7, 2.5 Hz, 1H), 5.25 (s, 1H), 2.83 (2 s, 8H), 2.5-2.25 (m, 4H), 2.2-1.9 (m, 4H), 1.28 (s, 3H).

NHS-TCO-Doxorubicin (Axial Isomer 4)

Doxorubicin hydrochloride (53.7 mg; 0.093 mmol) and 3 (39.1 mg; 0.093 mmol) were dissolved in DMF (2.0 mL), and DIPEA (60.1 mg; 0.465 mmol) was added. The solution was stirred under an atmosphere of argon at room temperature for 22 h. HPLC analysis indicated about 60% of the desired product with double peaks. The crude product was split into two portions.
One portion was treated with morpholine (4.0 mg, 0.047 mmol, 5 eq) at room temperature for 24 h. Starting material was still present and the reaction was allowed to stir at room temperature for another 20 h. The conversion rate was about 71%. The product was also shown double peaks. The product was purified by Preparative HPLC to afford a fairly pure product. The product was confirmed by LCMS with m/z 935.9 (M+114-1)
Another portion was treated with 1-methylpiperazine (4.7 mg, 0.047 mmol, 5 eq) at room temperature for 24 h. Starting material was still present and the reaction was allowed to stir at room temperature for another 20 h. The conversion rate was about 64%. The product was also shown double peaks. The product was purified by Preparative HPLC to afford a fairly pure product. The product was confirmed by LCMS with m/z 948.9 (M+114-1)

NHS-TCO-Doxorubicin (Axial Isomer 4)

Doxorubicin hydrochloride (1.05 g; 1.8 mmol) and 3 (761 mg; 1.8 mmol) were dissolved in DMF (18 mL), and DIPEA (1.16 g; 9.0 mmol) was added. The solution was stirred under an atmosphere of nitrogen at room temperature for 22 h. HPLC analysis indicated the reaction went well and the product has a single peak. The rest of the crude product was concentrated to dryness on rotavapor to remove DMF. The residue was purified by FCC (iPrOH/DCM: 0%-23%) to afford a pure product 4 (1.015 g, 66%) as a red solid. $^1$H-NMR (CDCl$_3$): δ=13.97 (s, 1H), 13.22 (s, 1H), 8.03 (d, J=7.9 Hz, 1H), 7.78 (t, J=8.0 Hz, 1H), 7.38 (d, J=8.6 Hz, 1H), 5.85 (m, 1H), 5.59 (m, 1H), 5.51 (s, 1H), 5.29 (s, 1H). 5.16 (d, J=8.4 Hz, 1H), 5.12 (s, 1H), 4.75 (d, J=4.8 Hz, 2H), 4.52 (d, J=5.8 Hz, 1H), 4.15 (q, J=6.5 Hz, 1H), 4.08 (d, J=3.6

Hz, 3H), 3.87 (m, 1H), 3.69 (m, 1H), 3.26 (d, J=18.8 Hz, 1H), 3.00 (m, 2H), 2.81 (s, 4H), 2.4-1.7 (br. m, 13H), 1.62 (s, 2H), 1.30 (d, J=6.5 Hz, 3H), 1.23 (s, 3H) ppm.

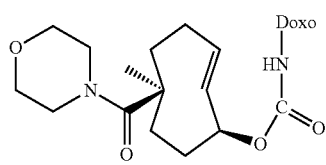

Morpholine-TCO-Doxorubicin (Axial Isomer AB12547)

Morpholine (215 mg, 2.47 mmol, 6 eq) was added into a solution of NHS-TCO-Doxorubicin 4 (350 mg, 0.41 mmol) in DMF (4.1 mL). The resulting mixture was stirred at room temperature for 15 h. TLC analysis indicated the starting material 4 was gone and one major spot was observed (iPrOH/DCM=1/9). HPLC analysis also indicated one major peak. LCMS analysis was also shown the desired m/z 935.8 (M+114-H). The reaction mixture was concentrated to dryness and the residue was purified by FCC (iPrOH/DCM: 0-40%) to yield a fairly pure product (~120 mg). The $^1$H NMR spectrum is shown in FIG. 25.

Example 2

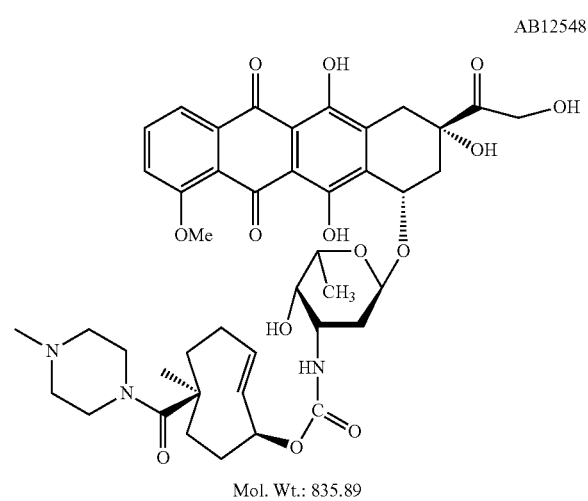

NMP-TCO-Doxorubicin (Axial Isomer AB12548)

N-Methylpiperazine (247 mg, 2.47 mmol, 6 eq) was added into a solution of NHS-TCO-Doxorubicin 4 (350 mg, 0.41 mmol) in DMF (4.1 mL). The resulting mixture was stirred at room temperature for 15 h. TLC analysis indicated the starting material 4 was gone and many spots were observed (iPrOH/DCM=1/9). HPLC analysis also indicated multi-peak. LCMS analysis was also shown the desired m/z 951.8 (M+114-H). The reaction mixture was concentrated to dryness and the residue was stored in −20° C. The crude product was attempted to be purified by FCC (5% NEt$_3$ in iPrOH/DCM: 0% to 30%). The fractions containing product were combined and concentrated to dryness. The fractions are impure.

Another testing reaction was carried out: about 2.4 mg of the intermediate 4 in DMF (0.2 mL) was treated with N-methylpiperazine solution in DMF. It was gradually increasing equivalents of the amine. After adding 4 eq in 3 days, the starting material was nearly consumed. The reaction was still complicated even though the major peak is attributed to the desired product with a double-peak.

Example 3

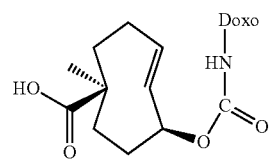

Acid-TCO-Doxorubicin (Axial Isomer AB12549)

The intermediate 4 (~2.4 mg) in DMF (0.10 mL) could be treated with saturated sodium bicarbonate (0.10 mL) at room temperature. After 18 h, the starting material was nearly consumed and the reaction was still complicated. The crude product could be purified by Prep HPLC to get a fairly pure product. The $^1$H NMR spectrum is shown in FIG. 26.

When intermediate 4 (10 mg) in DMF was treated with sodium hydroxide (0.25 N), a side reaction was dominated to generate a side product 5.

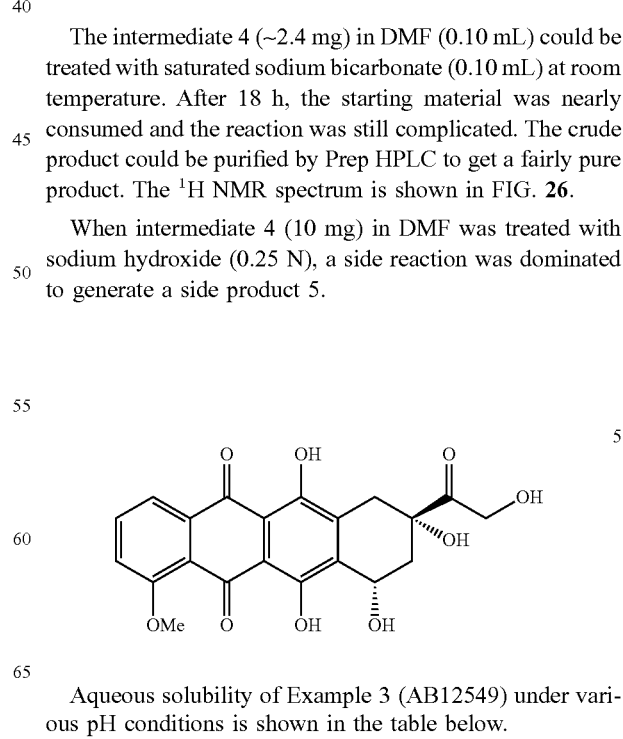

Aqueous solubility of Example 3 (AB12549) under various pH conditions is shown in the table below.

| | AB12549 | | | | |
|---|---|---|---|---|---|
| | Solubility, mg/mL | | | Precipitate after supernatant settling | Visual inspection after |
| Cycle | Value | Mean | Final pH | undisturbed for 1 hr? | centrifugation |
| 1 | 1.08<br>1.09<br>1.08 | 1.08 | 5.07 | No | Pellet |
| 2 | 11.56<br>11.52<br>11.47 | 11.52 | 5.25 | No | A smaller pellet |
| 3 | 22.76<br>22.97<br>22.89 | 22.87 | 5.62 | No | A very small pellet |
| 4 | 61.41<br>60.67<br>60.33 | 60.80 | 7.23 | No | A very small pellet |
| 5 | 49.55<br>48.57<br>48.32 | 48.81 | 8.00 | No | A very small pellet |

Example 4

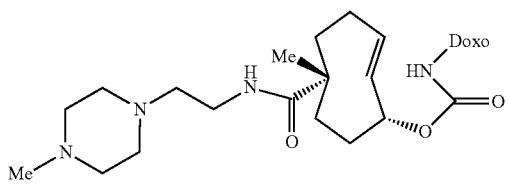

N-Methylpiperazinylethyl-TCO-doxorubicin

N-Methylpiperazinylethyl-TCO-doxorubicin may be prepared using the foregoing methods. The $^1$H NMR spectrum for Example 4 is shown in FIG. 27.

Substituted cyclooctenes may be further prepared according to the following schemes and procedures. Cis-cyclooctenes may be isomerized to trans-cyclooctenes using methods known to those skilled in the art (e.g., UV, heat).

Example 5

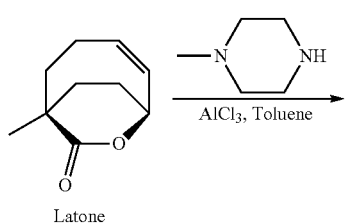

Latone

-continued

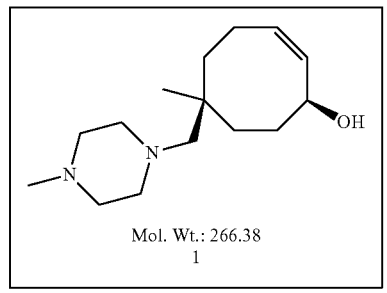

Mol. Wt.: 266.38
1

To a solution of starting material Lactone (1.5 g) and 1-methylpiperazine (3 ml) in toluene (10 ml) was added AlCl$_3$ (2 eq, 2.5 g) at 0° C. with vigorously stirring in three portions. The mixture was heated at 110° C. for six hours under argon. LC/MS indicated a complete reaction. Reaction solution was cooled down to rt. Water (5 ml) and MeOH (50 ml) was added to dissolve the black tar solid. The resulting solution was mixed with silica gel and concentrated to dryness. The silica gel powder was loaded to a silica gel column and the column was eluted with water in MeCN 10% to 20%. The collections were pooled and concentrated. The residue was dissolved in 10% of MeOH in DCM and filtered out silica gel. Filtrate was concentrated and dissolved in 10% of MeOH in DCM again to remove AlCl$_3$. The product 1 was obtained (1 g) as brown solid. NMR shows the product was not pure.

Example 6

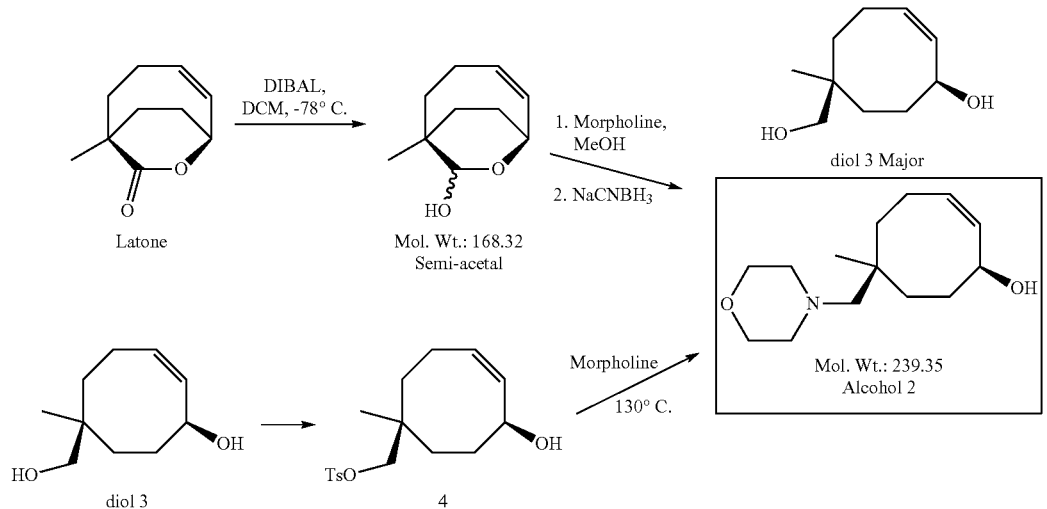 [SMILES: C[C@]12CC/C=C\[C@H](CC1)OC2=O ; C[C@]12CC/C=C\[C@H](CC1)OC2O ; C[C@]1(CN2CCOCC2)CC/C=C\[C@@H](O)CC1 ; C[C@]1(CO)CC/C=C\[C@@H](O)CC1 ; C[C@]1(CO)CC/C=C\[C@@H](O)CC1 ; Cc1ccc(S(=O)(=O)OC[C@@]2(C)CC/C=C\[C@@H](O)CC2)cc1]

To a stirred solution of lactone 1 (1.3 g) in CDM (30 ml) was added DIBAL (3 eq, 23.5 ml, 1M in toluene) in dropwise at −78° C. under nitrogen. After one hour, another 23.5 ml of DIBAL was added. The reaction was done in four hours and quenched with water at −78° C. and diluted with 50 ml of DCM. The resulting solution was washed with 10% HCl and brine (1:1), sat. NaHCO$_3$, and then brine, dried with MgSO$_4$, filtered and concentrated. The residue was coevaperated with toluene and taken to next reaction.

To a solution of crude semi-acetal obtained from above in MeOH (30 ml) was added morpholine (3 eq, 2 ml). The resulting solution was stirred at rt for one hour, heated at 60° C. for three hours and then cooled down to rt. To the reaction solution, a solution of NaCNBH$_3$ (4 eq, about 2 g) in MeOH (10 ml) was added slowly at rt under nitrogen. Reaction solution was stirred at rt for overnight. After FCC (EtOAc in Hex 1:1 to 2:1+1% TEA), diol 3 was obtained as major product (1 g) and desired product (220 mg) was isolated. The $^1$H NMR spectrum of diol 3 is shown in FIG. 28.

The diol 3 (500 mg) was treated with TsCl (1.2 eq) in DCM/Pyr at rt overnight and at 50° C. for 5 h. Solvent was removed and the residue was purified with FCC. The tosylated primary alcohol product 4 (510 mg) was obtained. LC/MS and NMR were recorded, as shown in FIG. 29.

Compound 4 was heated with morpholine at 130° C. for one day and converted to Alcohol 2. TLC and LC/MS showed a messy reaction, but the desired product Alcohol 2 was major one. The $^1$H NMR spectrum of Alcohol 2 is shown in FIG. 30.

Example 7

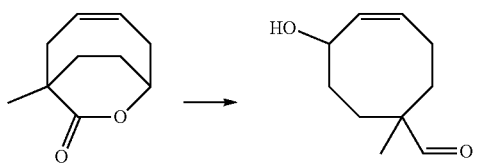

(Z)-6-hydroxy-1-methylcyclooct-4-ene-1-carbaldehyde

To a solution of starting material 1.3 g (7.82 mmol) in 13 mL of THF at −78° C., was added a 1M solution of DIBAL-H (7.43 mL, 7.43 mmol). The reaction mixture was stirred for 15 min at −78° C. and was quenched by addition of 1M aqueous HCl solution before warming up to room temperature. The layers were separated and the aqueous phase was washed with EtOAc (3*25 mL). The combined organic phase was washed with brine, dried over Na$_2$SO$_4$, filtered and concentrated under reduced pressure. The product was purified by flash chromatography using EtOAc/Hexane. (0.89 g, 67.6% yield).

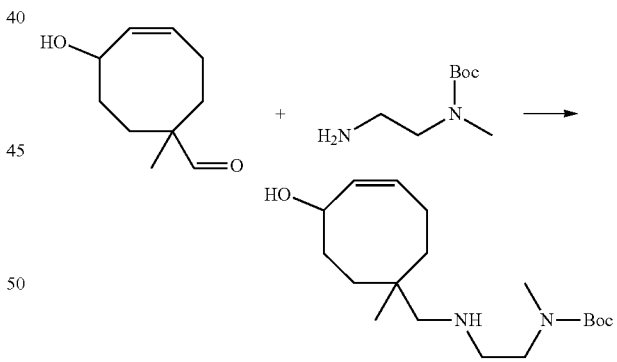

Tert-butyl (Z)-(2-(((6-hydroxy-1-methylcyclooct-4-en-1-yl)methyl)amino)ethyl)(methyl)carbamate To a solution of starting material 1.1 g (6.54 mmol) in 5.5 mL of DCM, was added acetic acid 0.393 g (6.54 mmol) and N-Boc-N-methylethylenediamine 1.14 g (6.54 mmol). The reaction mixture was stirred at room temperature for 20 min. Then sodium triacetoxyborohydride 2.77 g (13.1 mmol) was added into the reaction mixture and stirred for 4 hours at room temperature. The reaction was quenched add pouring into saturated sodium bicarbonate solution and the pH of aqueous phase was adjusted to 8~9 before extracting with chloroform (3*25 mL). The combined organic phase was washed with brine and dried over Na$_2$SO$_4$. The solvent was removed under vacuum and took it forward for the next step reaction without further purification. (2.09 g, 97.9% yield) LCMS (+esi): calc. M+H+=327.3; Found 327.4.

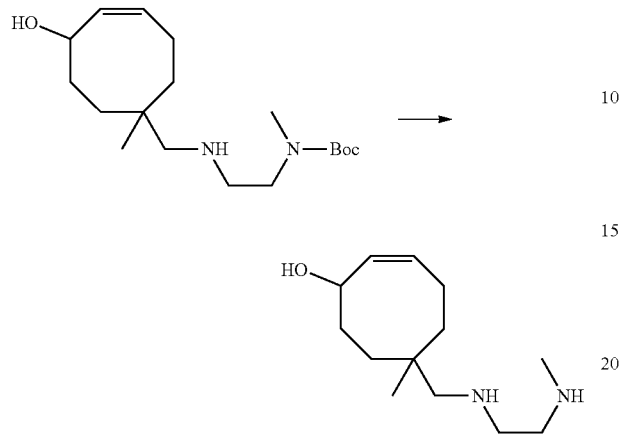

(Z)-6-methyl-6-(((2-(methylamino)ethyl)amino)methyl)cyclooct-2-en-1-ol

The starting material was dissolved in 40 mL of formic acid/water (80/20) mixture and stirred at room temperature overnight until the completion of the reaction. Then formic acid was removed under reduced pressure. The aqueous phase was basified by 1M NaOH solution and extracted with chloroform/isopropyl alcohol (3/1). The combined organic phase was washed with brine, dried over Na$_2$SO$_4$. The solvent was removed under vacuum and took it forward for the next step reaction without further purification. (1.47 g, 96.4% yield) LCMS (+esi): calc. M+H+=227.2; Found 227.2.

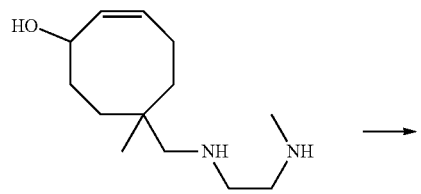

(Z)-6-methyl-6-((4-methylpiperazin-1-yl)methyl)cyclooct-2-en-1-ol

To a solution of starting material 1.66 g (7.33 mmol) and acetic acid 0.44 g (7.33 mmol) in 50 mL DCM, was add 1.06 g of 40% aqueous glyoxal solution (7.33 mmol). The reaction mixture was stirred at room temperature for 20 min before adding sodium triacetoxyborohydride 4.66 g (22.0 mmol). The reaction mixture was stirred at room temperature for 4 hours. The reaction was quenched add pouring into saturated sodium bicarbonate solution and the pH of aqueous phase was adjusted to 8~9 before extracting with chloroform/isopropyl alcohol (3/1) (3*40 mL). The combined organic phase was washed with brine, dried over Na$_2$SO$_4$, filtered and concentrated under reduced pressure. The product was purified by flash chromatography using DCM/MeOH:DCM (20:80). (0.385 g, 20.8% yield) LCMS (+esi): calc. M+H+=253.2; Found 253.3. $^1$H NMR (400 MHz, DMSO-d$_6$) δ=5.51-5.39 (m, 1H), 5.23 (m, J=5.7, 11.9 Hz, 1H), 4.78 (m, J=5.4, 10.3 Hz, 1H), 3.75-3.41 (br, 1H), 2.44 (br s, 4H), 2.32 (br s, 4H), 2.16 (s, 3H), 2.05 (br d, J=13.9 Hz, 2H), 1.94-1.81 (m, 2H), 1.57-1.07 (m, 6H), 0.86 (s, 3H). $^{13}$C NMR (100 MHz, DMSO-d$_6$) δ=134.08, 128.61, 68.95, 66.54, 55.85, 55.51, 46.04, 39.45, 35.18, 34.50, 31.31, 25.87, 23.45. Obtained the byproduct (Z)-4-((6-hydroxy-1-methylcyclooct-4-en-1-yl)methyl)-1-methylpiperazin-2-one. (0.85 g) LCMS (+esi): calc. M+H+=266.2; Found 267.1.

Example 8

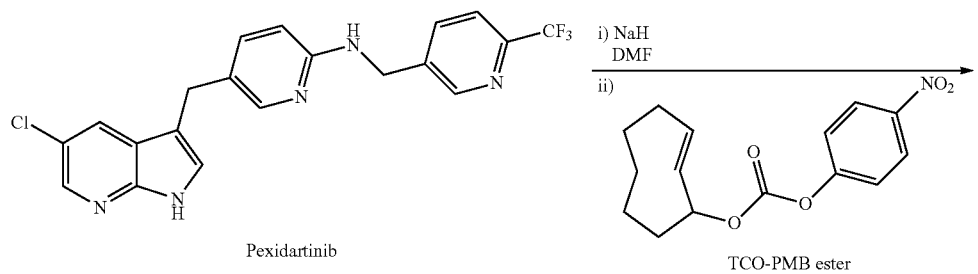

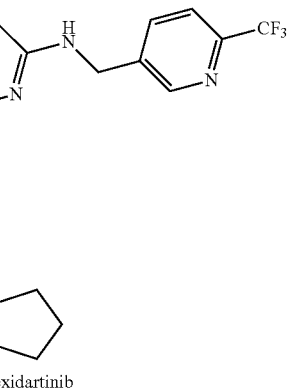

TCO-pexidartinib

General Procedure for the Preparation of TCO-pexidartinib To a solution of Pexidartinib (PLX3397) (373 mg, 0.89 mmol) in DMF (4.0 mL) 0° C. was added sodium hydride (ca. 60%, 39 mg, ca. 0.96 mmol); and reaction mixture was stirred under nitrogen for 1 h before TCO-PNB ester (200 mg, 0.68 mmol) was added. The resulting mixture was stirred at rt overnight and evaporated in vacuo. The reaction mixture was diluted with water (30 mL) and extracted with ethyl acetate (2×30 mL). The combined organic layers were washed with brine, dried ($Na_2SO_4$) and evaporated in vacuo. The residue was purified by flash chromatography on silica gel eluting with dichloromethane followed by MeOH—$CH_2Cl_2$ (0-5%) to give TCO-pexidartinib (145 mg, 37%). LC-MS: 571 [M+H]+H NMR (300 MHz, $CDCl_3$) δ 8.72 (s, 1H), 8.41 (s, 1H), 8.05 (s, 1H), 7.85 (d, J=6.9 Hz, 1H), 7.66 (s, 1H), 7.62 (d, J=7.8 Hz, 1H), 7.56 (s, 1H), 7.29 (d, J=2.4 Hz, 1H), 6.37 (d, J=8.4 Hz, 1H), 6.15 (m, 1H), 5.74 (s, 1H), 5.60 (d, J=6.0 Hz, 1H), 4.88 (t, J=6.0 Hz, 1H), 4.67 (d, J=6.0 Hz, 2H), 3.87 (s, 1H), 2.50 (m 1H), 2.30 (m, 1H), 2.10-0.80 (m, 8H).

Example 9

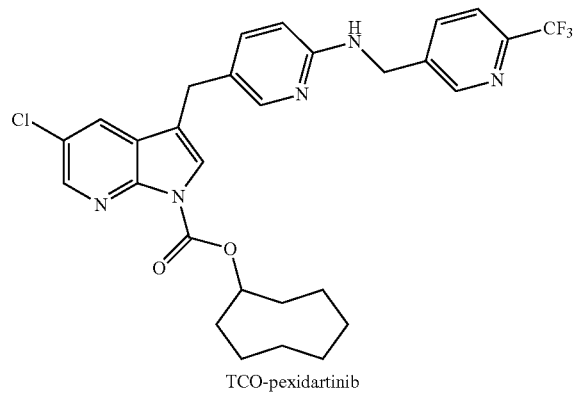

TCO-valdecoxib

General Procedure for the Preparation of TCO-valdecoxib. To a solution of Valdecoxib (157 mg, 0.5 mmol) in DMF (4 mL) was added TCO-PNB ester (129 mg, 0.44 mmol), DMAP (106 mg, 0.88 mmol). The mixture was stirred at rt for 40 h, and diluted with ethyl acetate (100 mL), washed with brine (40 mL), dried over sodium sulfate, and evaporated in vacuo. The product was purified by flash chromatography on silica gel eluting with DCM followed by MeOH-DCM (5%) to give compound TCO-valdecoxib (201 mg, 97%) as white solid. LC-MS: 467 [M+H]+. H NMR (300 MHz, $CDCl_3$) δ 8.03 (d, J=8.7 Hz, 2H), 7.65 (m, 1H), 7.43-7.32 (m, 7H), 5.73 (m, 1H), 5.64 (d, J=16.5 Hz, 1H), 5.33 (s, 1H), 2.50 (s, 3H), 2.43 (m, 1H), 2.09-0.77 (m, 9H).

Example 10

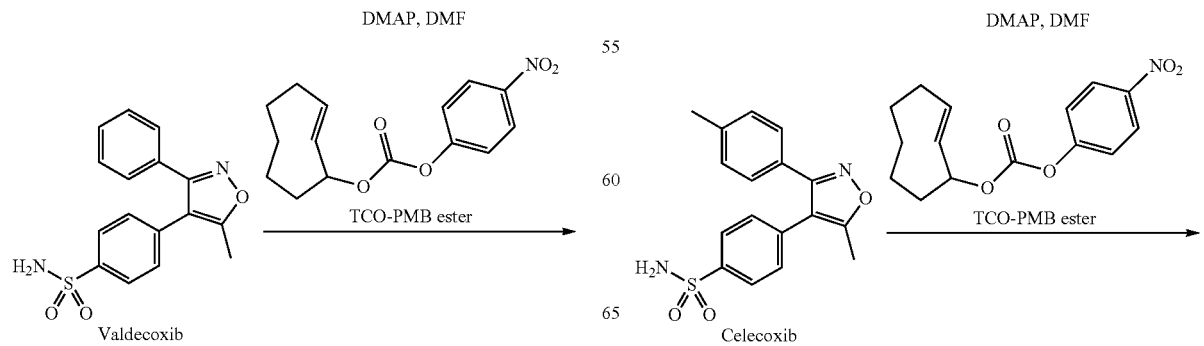

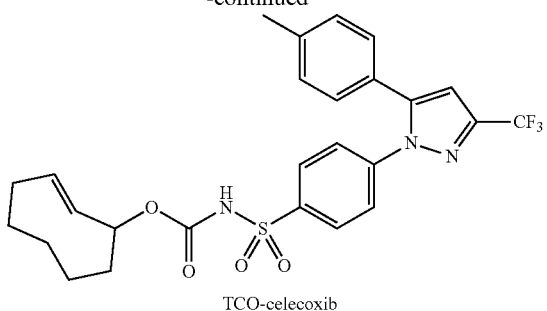

TCO-celecoxib

General Procedure for the Preparation of TCO-celecoxib. To a solution of Celecoxib (141 mg, 0.37 mmol) in DMF (4 mL) was added TCO-PNB ester (100 mg, 0.34 mmol), DMAP (106 mg, 0.88 mmol). The mixture was stirred for 40 h and diluted with ethyl acetate (100 mL), and washed with water (30 mL) and brine (30 mL), dried over sodium sulfate, and concentrated in vacuo. The product was purified by flash chromatography on silica gel eluting with methanol (5%) in DCM to afford the product TCO-celecoxib (162 mg, 88%). LC-MS: 534 [M+H]+

$^1$H NMR (300 MHz, CDCl$_3$) δ 8.01 (d, J=8.7 Hz, 2H), 7.60 (br, 1H), 7.50 (d, J=8.7 Hz, 2H), 7.18 (d, J=8.1 Hz, 2H), 7.14 (d, J=8.1 Hz, 2H), 6.74 (s, 1H), 5.69 (m, 1H), 5.45 (d, J=12.0 Hz, 1H), 5.30 (s, 1H), 2.44 (m, 1H), 2.38 (s 3H), 2.03-0.76 (m, 9H).

Example 11

Synthesis of TCO-Monomethyl Auristatin E (TCO-MMAE) Conjugate

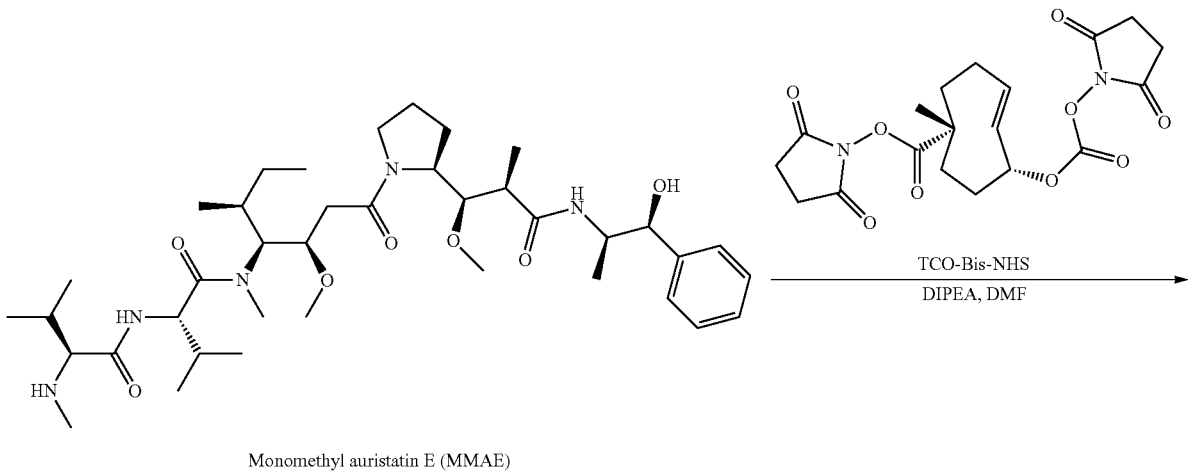

Monomethyl auristatin E (MMAE)

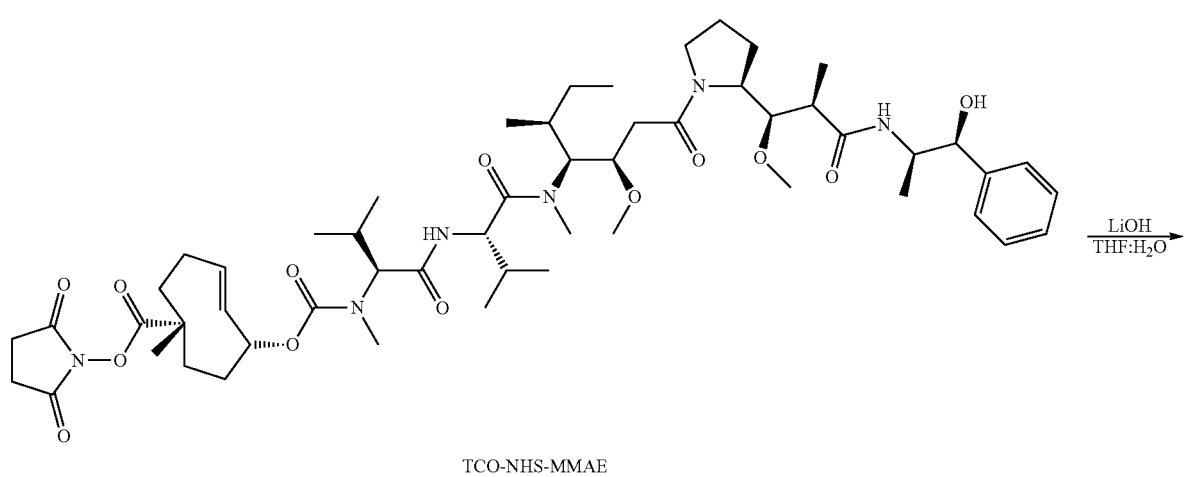

TCO-NHS-MMAE

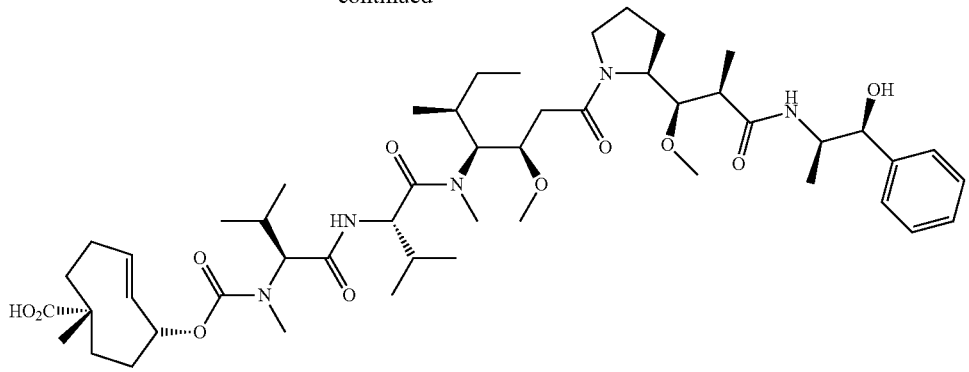

TCO-Acid-MMAE

Preparation of TCO-MMAE Conjugate

To monomethyl auristatin E (170 mg, 0.24 mmol) in DMF (2 mL) at rt, TCO-Bis-NHS (100 mg, 0.24 mmol) and DIPEA (93 mg, 0.72 mmol) were added. The solution was stirred at rt for 20 h, acetonitrile (ACN, 8 mL) was added and the mixture was purified by prep-HPLC (ACN/water from 0 to 100%, formic acid 0.1%) to give TCO-NHS-MMAE (88 mg, 36%). To TCO-NHS-MMAE (78 mg, 0.076 mmol) in THF (2 mL) and $H_2O$ (2 mL) at rt was added LiOH (9.2 mg, 0.38 mmol). The solution was stirred at rt for 20 h. After removal of solvent, HCl (aq, 0.5 N) was added to pH ~3. The mixture was purified by prep-HPLC (ACN/water from 0 to 100%, formic acid 0.1%) to give TCO-Acid-MMAE (54 mg, 76%, two isomers). LCMS: (ESI+) 928 [M+H].

Example 12

Synthesis of Trans-Cyclooctene(TCO)-Glycine-Doxorubicin Conjugate

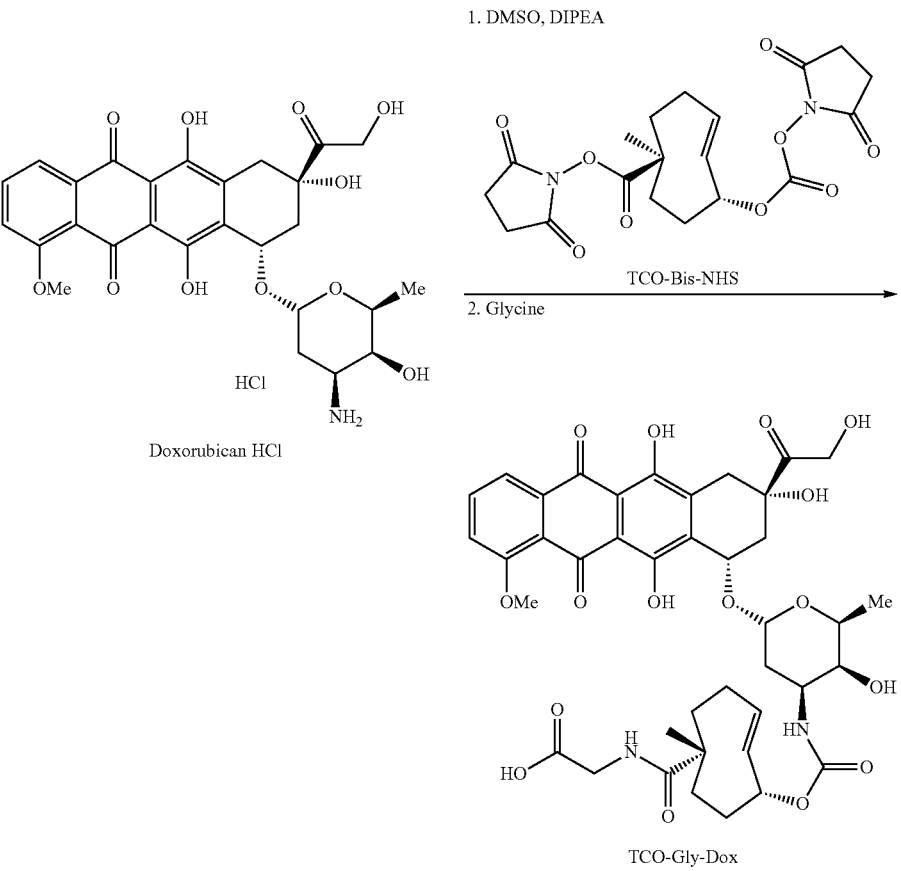

Preparation of TCO-glycine-doxorubicin conjugate. To a solution of doxorubicin hydrochloride (100 mg) in 1 mL DMSO, TCO-Bis-NHS (75 mg) was added. DIPEA (148 µL) was added by injection. The mixture was stirred overnight and then glycine (51 mg) was added to the reaction in one portion, and the reaction was stirred for 24 h. The mixture was diluted with 2 mL H$_2$O and purified by HPLC to yield TCO-Gy-Dox. MS: (ESI+) 833 [M+Na].

Example 13

Antibiotic-TCO Conjugates

Example 13A

Dapto-TCO-Amino Acid synthesis

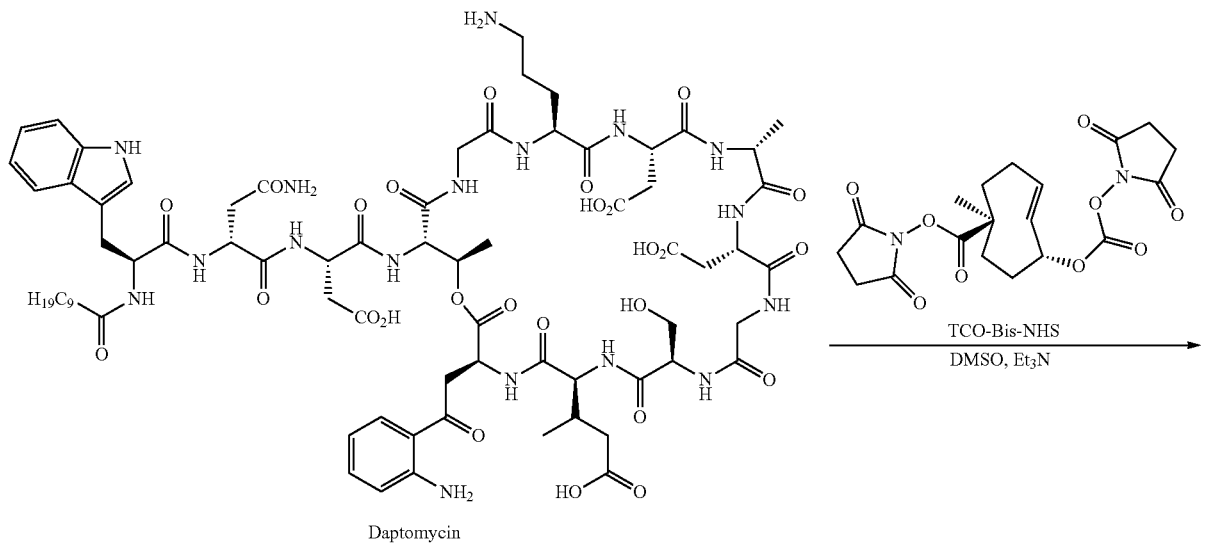

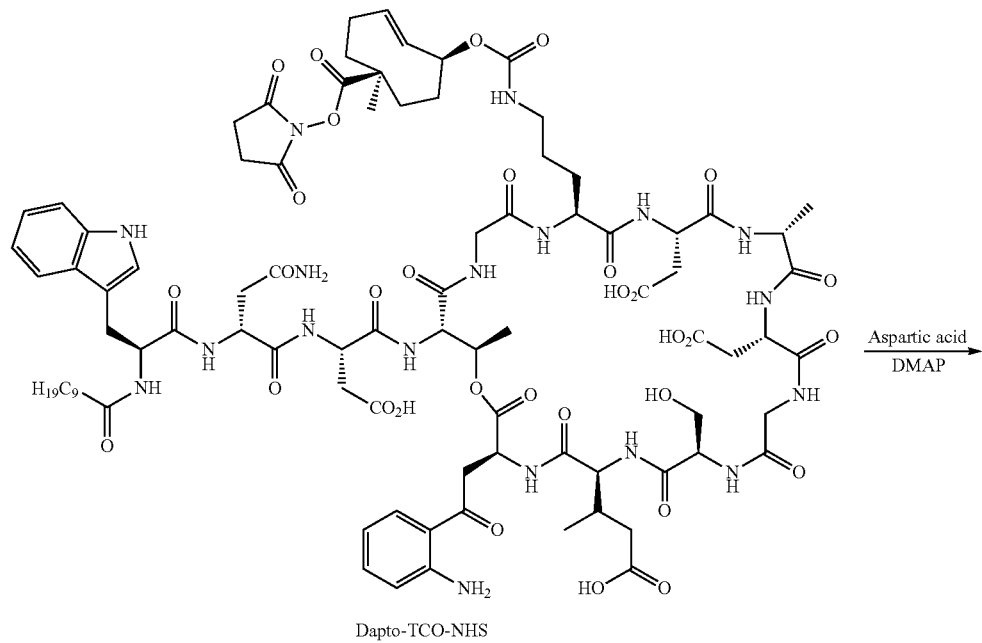

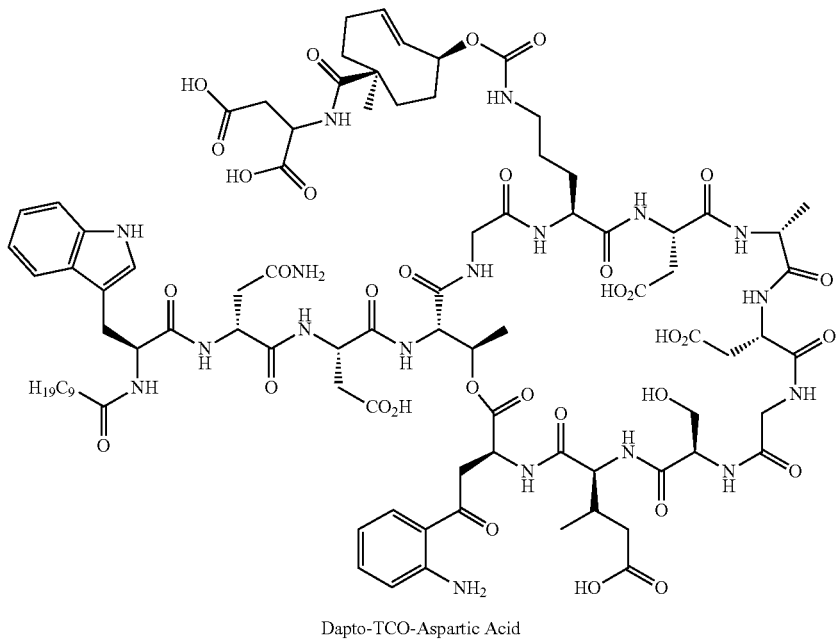

Dapto-TCO-Aspartic Acid

Example protocol: Add daptomycin (100 mg, 0.062 mmol), TCO-Bis-NHS (62.5 mg, 0.149 mmol), and triethylamine (62.5 μL, 45.3 mg, 0.448 mmol) to DMSO and stir at RT overnight to produce Dapto-TCO-NHS. LCMS: (ESI−) 1926.8 [M−H]. To Dapto-TCO-NHS (126.1 mg, 0.0654 mmol), add aspartic acid (104.5 mg, 0.785 mmol) and 4-dimethylaminopyridine (150.9 mg, 1.235 mmol), and stir for 18 h at 37° C. Purify by HPLC to obtain Dapto-TCO-Aspartic Acid. Yield: 100 mg, 0.0514 mmol. LCMS: (ESI−) 1944.8 [M−H].

This approach has been used to produce glycine and aspartic acid-modified TCO-prodrugs, and can be generally applied to for the incorporation of other amino acid cargos as well.

Example 13B

Daptomycin-TCO-Glycine Conjugate

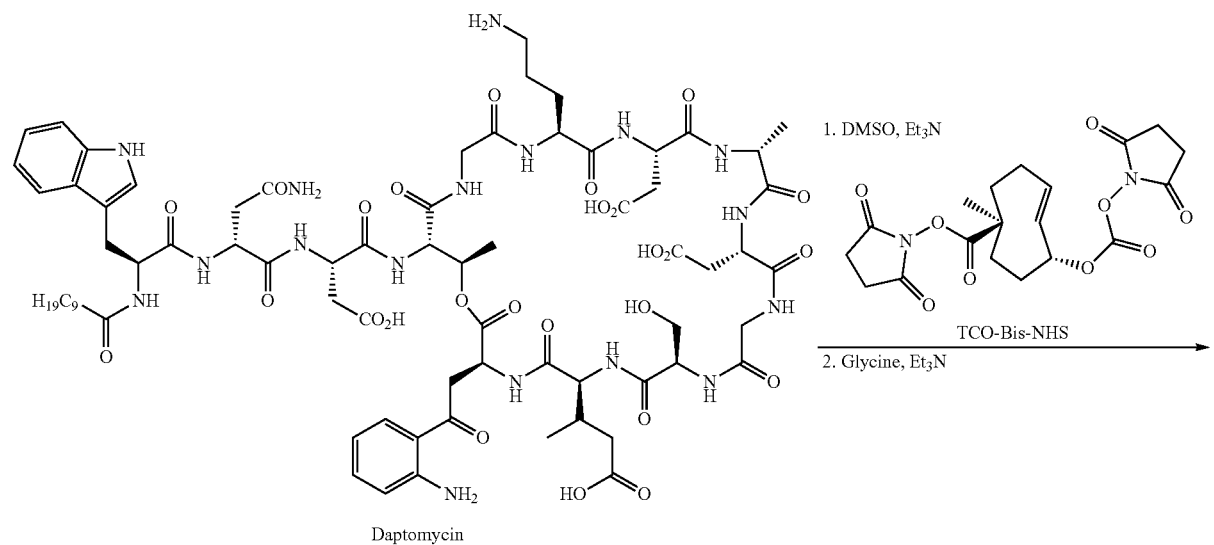

Daptomycin

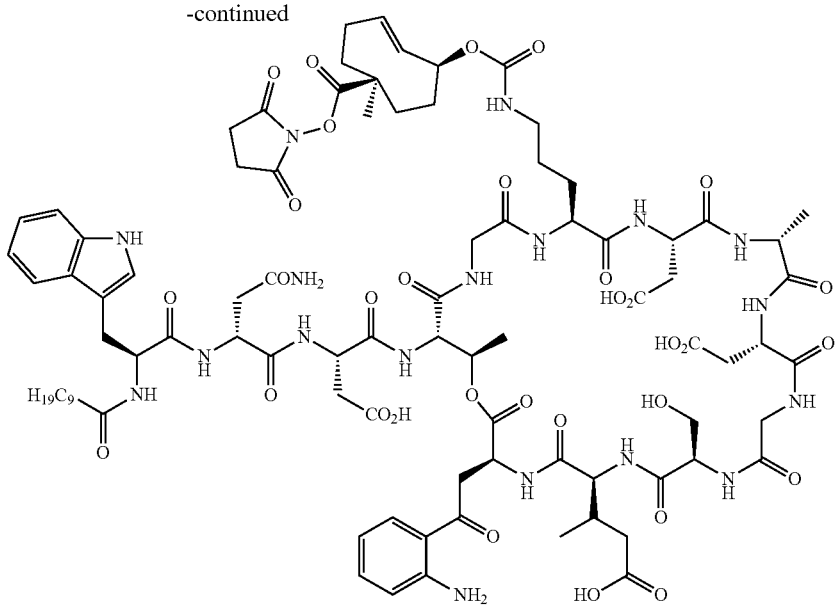

Dapto-TCO-Glycine

Daptomycin (537 mg, 0.33 mmol), TCO-Bis-NHS (350 mg, 0.83 mmol), and triethylamine (0.350 mL, 2.51 mmol) in DMSO (11 mL). Stir at RT overnight. Then heat to 37° C. Add glycine (300 mg, 4.00 mmol) and triethylamine (1.8 mL, 13 mmol), and stir for 18 h. Add 8 mL water and purify by HPLC. Yield: Dapto-TCO-Glycine-373 mg, 0.20 mmol, 59.6%.

Aqueous solubility for Example 13B is shown in the table below under different buffer conditions.

| Example 13B | | | | |
|---|---|---|---|---|
| | Solubility, mg/mL | | | Visual |
| Buffer | Value | Mean | Final pH | Inspection |
| Water | 0.15 | 0.15 | 3.4 | Turbid |
| | 0.14 | | | |
| | 0.15 | | | |
| Phosphate Buffer pH 6.5 | 10.8 10.9 10.9 | 10.9 | 6.1 | Clear |
| Phosphate Buffer pH 7.5 | 38.1 38.3 38.3 | 38.3 | 5.4 | Clear |

Example 13C

Vanco-Bis-TCO-Glycine Conjugate

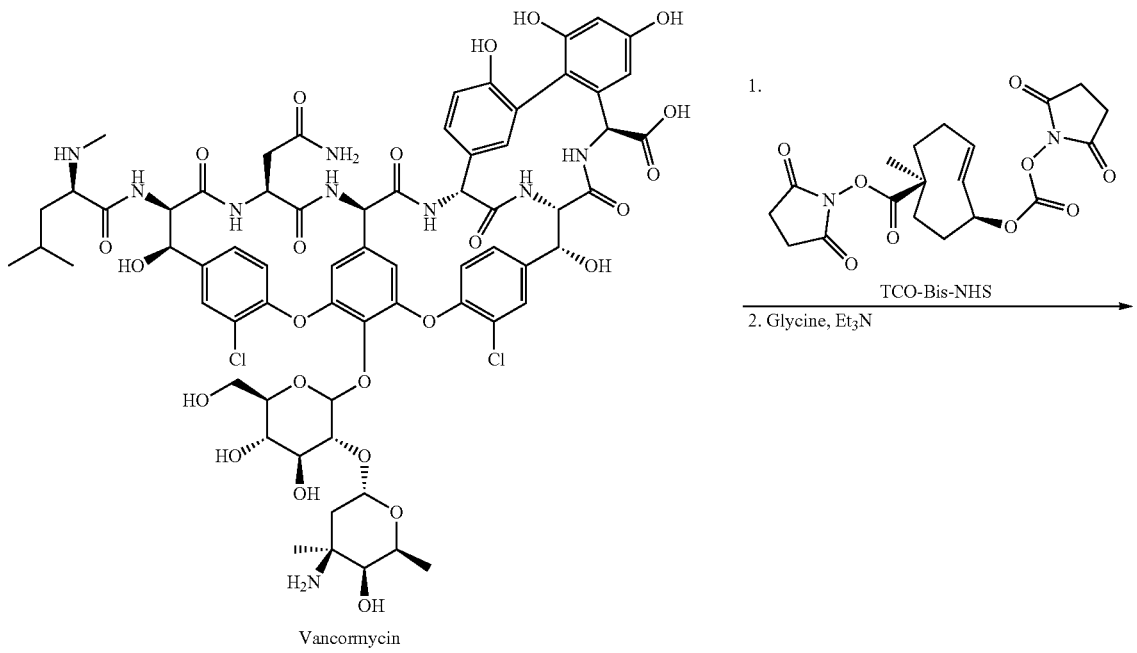

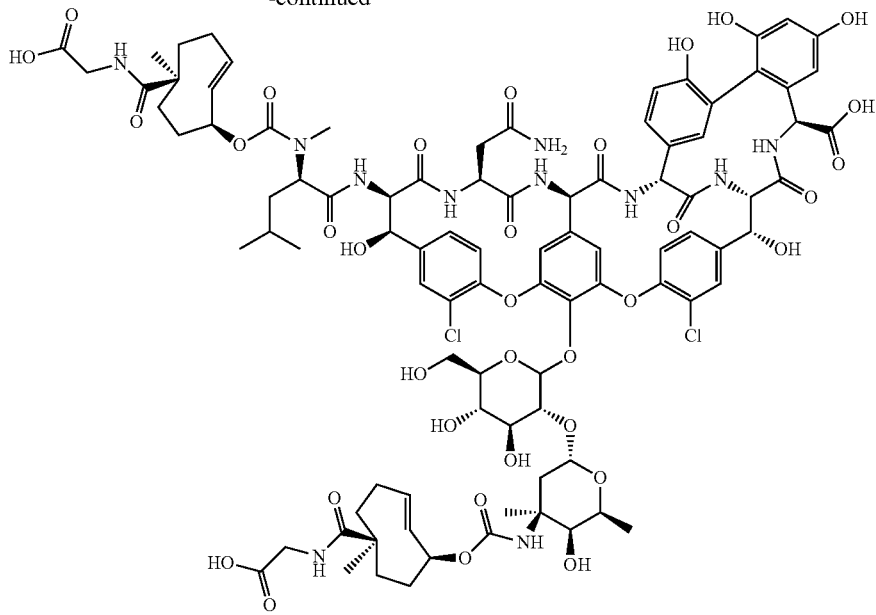

Vanco-Bis-TCO-Glycine

Example 13C can be synthesized using a protocol analogous to Example 13B. Vanco-Bis-TCO-Glycine tested up to 64 µg/ml (32 µM) shows no activity against bacteria as measured by microcalorimetry, indicating the drug deactivation after modification.

General HPLC purification conditions for TCO amino acid conjugates are as follows: Column: Higgins Cat #PS-253C-C185, 250×30 mm, Phalanx C18 5 µm Solvent A: water (0.1% formic acid)

Solvent B: acetonitrile (0.1% formic acid)

| Min | % B |
| --- | --- |
| 0.01 | 10 |
| 2.00 | 10 |
| 3.00 | 30 |
| 30.00 | 90 |
| 31.00 | 10 |
| 34.00 | 10 |

Example 14 (Prophetic Example)

Prodrug Synthesis Using TCO Modified with Other Solubilizing Groups

Figure 7:
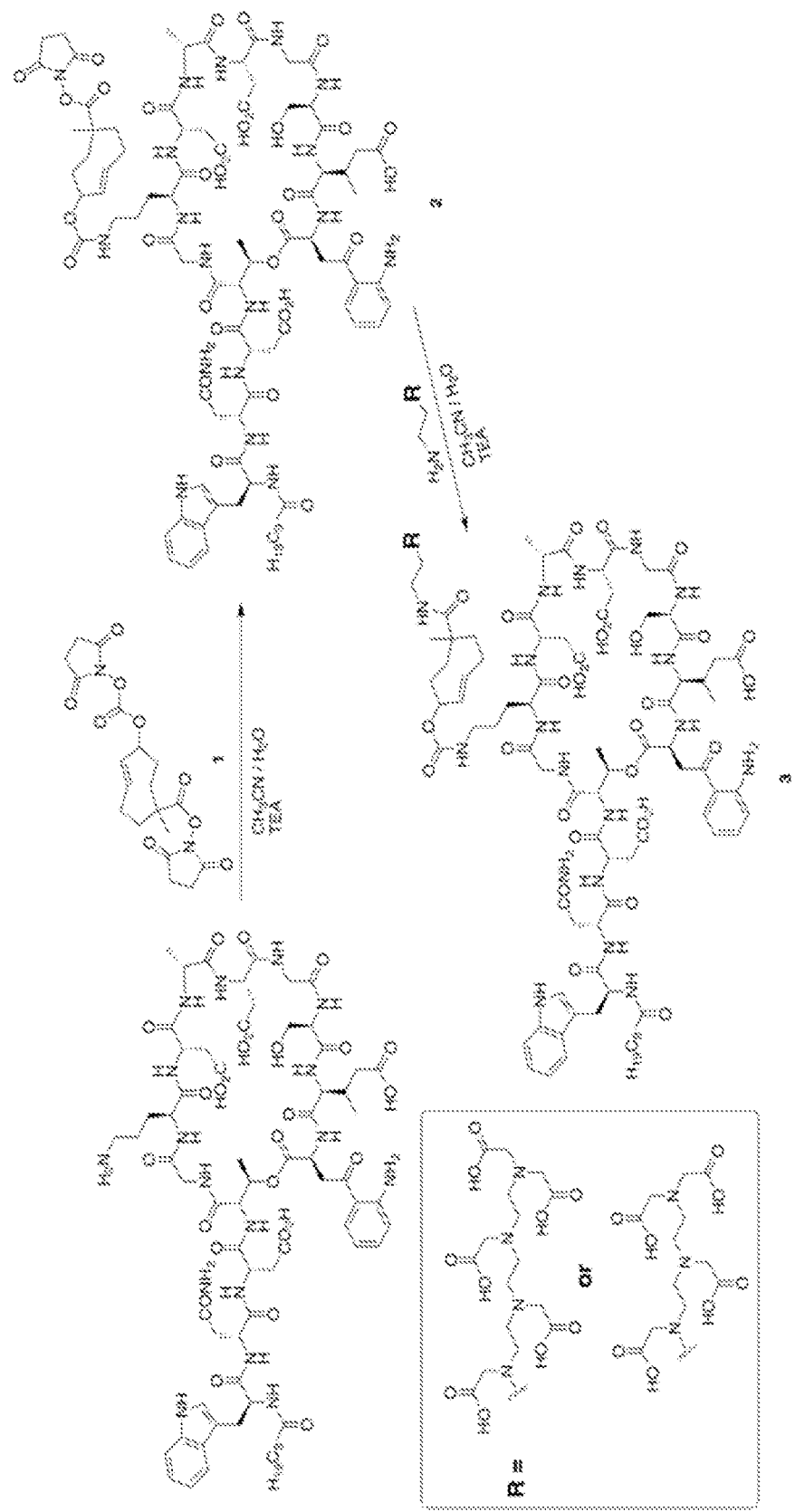
FIG. 7 shows synthesis of TCO-daptomycin (3) bearing multiple carboxyl groups.

Other prodrugs with carboxyl solubilizing groups that may be accessed using the foregoing chemistry are shown in FIG. 7. The presence of multiple hydrophilic carboxylic acid moieties should enhance the aqueous solubility, and the incorporation large structural perturbations is expected to attenuate activity. Upon prodrug activation using TAG, the carboxylate groups should be detached thus restoring antibiotic activity of daptomycin.

Example 15

Hyaluronic Acid Modified Tetrazine

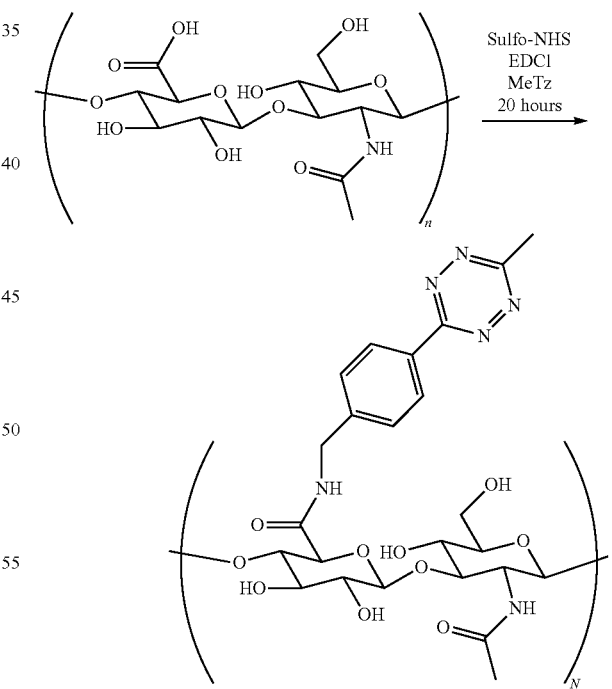

To 5 mL of MES buffer (0.1 M MES, 0.3 M NaCl, pH=6.5) was added 0.0500 grams of Sodium Hyaluronate (200 kDa) and stirred until it dissolved (4 hours). To this, was added N-hydroxysulfosuccinimide (23.3 mg, 0.107 mmols), N, N'-dicyclohexylcarbodiimide (42.0 mg, 0.219 mmols), and (4-(6-methyl-1,2,4,5-tetrazin-3-yl)phenyl)

methanamine hydrochloride (15.9 mg, 0.066 mmols). The reaction mixture was stirred for 20 hours in the absence of light for after which time it was quenched with hydroxylamine (66.2 mg, 0.953 mmols). The hyaluronic acid product was purified in the absence of light against deionized water containing a decreasing salt concentration (NaCl, 0.13 M-0.0 M) over 5 days. The hyaluronic acid product was filtered (0.22 μm) and lyophilized for 5 days.

To 5 mL of MES buffer (0.1 M MES, 0.3 M NaCl, pH=6.5) was added 0.0500 grams of Sodium Hyaluronate (100 kDa) and stirred until it dissolved (4 hours). To this, was added N-hydroxysulfosuccinimide (40.6 mg, 0.19 mmols), N,N'-dicyclohexylcarbodiimide (72.1 mg, 0.38 mmols), and (4-(6-methyl-1,2,4,5-tetrazin-3-yl)phenyl) methanamine hydrochloride (28.4 mg, 0.12 mmols). The reaction mixture was stirred for 20 hours in the absence of light for after which time it was quenched with hydroxylamine (117.1 mg, 1.69 mmols). The hyaluronic acid product was purified in the absence of light against deionized water containing a decreasing salt concentration (NaCl, 0.13 M-0.0 M) over 5 days. The hyaluronic acid product was filtered (0.22 μm) and lyophilized for 5 days.

To 5 mL of MES buffer (0.1 M MES, 0.3 M NaCl, pH=6.5) was added 0.0500 grams of Sodium Hyaluronate (5 kDa) and stirred until it dissolved (4 hours). To this, was added N-hydroxysulfosuccinimide (145.9 mg, 0.670 mmols), N,N'-dicyclohexylcarbodiimide (257.3 mg, 1.34 mmols), and (4-(6-methyl-1,2,4,5-tetrazin-3-yl)phenyl) methanamine hydrochloride (100.3 mg, 0.42 mmols). The reaction mixture was stirred for 20 hours in the absence of light for after which time it was quenched with hydroxylamine (413.4 mg, 5.95 mmols). The hyaluronic acid product was purified in the absence of light against deionized water containing a decreasing salt concentration (NaCl, 0.13 M-0.0 M) over 5 days. The hyaluronic acid product was filtered (0.22 μm) and lyophilized for 5 days.

Example 16

Hyaluronic Acid Modified Tetrazine

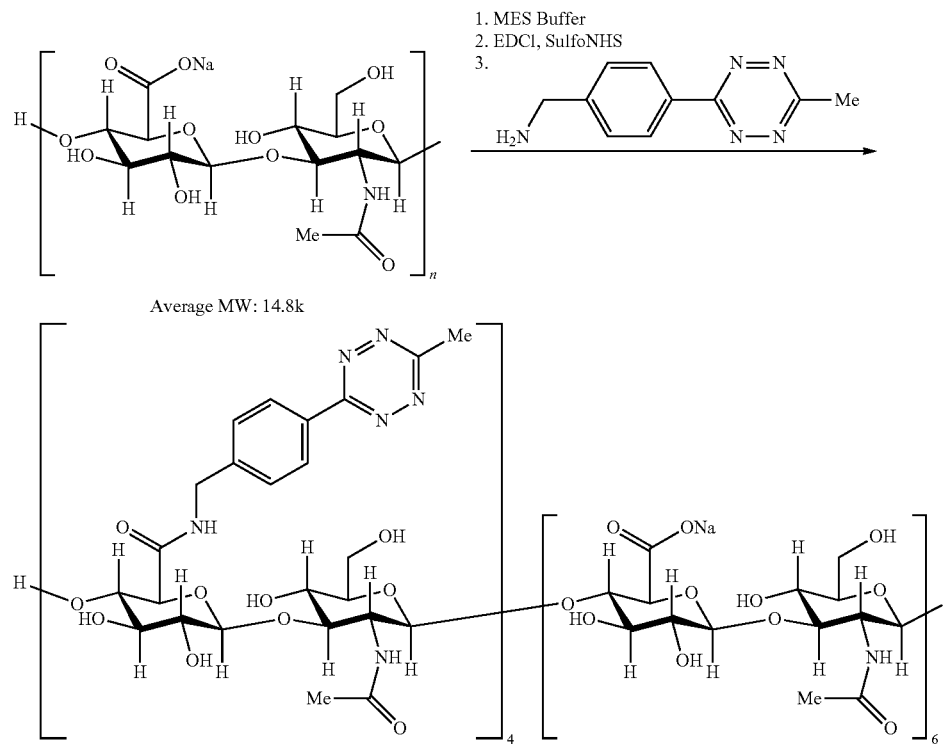

M-0.0 M) over 5 days. The hyaluronic acid product was filtered (0.22 μm) and lyophilized for 5 days.

To 5 mL of MES buffer (0.1 M MES, 0.3 M NaCl, pH=6.5) was added 0.0500 grams of Sodium Hyaluronate (60 kDa) and stirred until it dissolved (4 hours). To this, was added N-hydroxysulfosuccinimide (58.2 mg, 0.27 mmols), N,N'-dicyclohexylcarbodiimide (103.9 mg, 0.54 mmols), and (4-(6-methyl-1,2,4,5-tetrazin-3-yl)phenyl) methanamine hydrochloride (40.4 mg, 0.17 mmols). The reaction mixture was stirred for 20 hours in the absence of light for after which time it was quenched with hydroxylamine (165.7 mg, 2.38 mmols). The hyaluronic acid product was purified in the absence of light against deionized water containing a decreasing salt concentration (NaCl, 0.13

To 5 mL of MES buffer (0.1 M MES, 0.3 M NaCl, pH=4.5) was added 0.5000 grams of Sodium Hyaluronate (14.8 kDa) and stirred until it dissolved. To this, was added N-hydroxysulfosuccinimide (14.2 mg, 0.0625 mmols), N,N'-dicyclohexylcarbodiimide (125.7 mg, 0.625 mmols), and (4-(6-methyl-1,2,4,5-tetrazin-3-yl)phenyl) methanamine hydrochloride (151.2 mg, 0.625 mmols). The reaction mixture was stirred for 4 hours in the absence of light for after which time it is diluted to 1% (w/w) and filtered through a 0.45 μm filter. The hyaluronic acid product was then purified by Tangential flow filtration (TFF), prior to the final sterile filtration (0.22 μm) and lyophilized for 3 days. By elemental analysis, the tetrazine incorporation into the Sodium Hyaluronate starting material is 40%.

Example 17

Hyaluronic Acid Modified with Tetrazine and Cyanine 5

To 5 mL of MES buffer (0.1 M MES, 0.3 M NaCl, pH=6.5) was added 0.0500 grams of Sodium Hyaluronate (5 kDa) and stirred until it dissolved (4 hours). To this, was added N-hydroxysulfosuccinimide (145.9 mg, 0.670 mmols), N,N'-dicyclohexylcarbodiimide (257.3 mg, 1.34 mmols), (4-(6-methyl-1,2,4,5-tetrazin-3-yl)phenyl)methanamine hydrochloride (100.3 mg, 0.42 mmols), and Cyanine 5 (6.25 mg, 0.018 mmols). The reaction mixture was stirred for 20 hours in the absence of light for after which time it was quenched with hydroxylamine (413.4 mg, 5.95 mmols). The hyaluronic acid product was purified in the absence of light against deionized water containing a decreasing salt concentration (NaCl, 0.13 M-0.0 M) over 5 days. The hyaluronic acid product was filtered (0.22 μm) and lyophilized for 5 days.

Example 18

Tetrazine Modified Alginate Gel

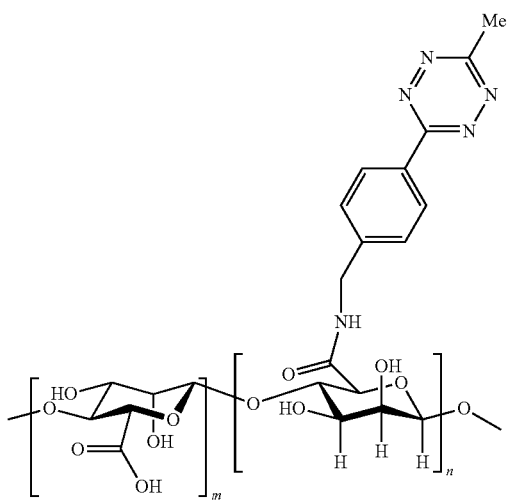

To 5 mL of MES buffer (0.1 M MES, 0.3 M NaCl, pH=6.5) was added 50 mg of UP LVG alginate (75-200 kDa) and stirred until it dissolved (4 hours). To this, was added N-hydroxysulfosuccinimide (34.7 mg, 0.16 mmols), N,N'-dicyclohexylcarbodiimide (61.8 mg, 0.32 mmols), and (4-(6-methyl-1,2,4,5-tetrazin-3-yl)phenyl)methanamine hydrochloride (24.1 mg, 0.10 mmols). The reaction mixture was stirred for 20 hours in the absence of light for after which time it was quenched with hydroxylamine (99.3 g, 1.44 mmols). The alginate product was purified in the absence of light against deionized water containing a decreasing salt concentration (NaCl, 0.13 M-0.0 M) over 4 days. The alginate was filtered (0.22 μm) and lyophilized for 5 days.

Example 19

Reaction of Tetrazine Modified Gel with (E)-Cyclooct-2-Enol

To determine the concentration of available tetrazine in the hydrogel, a titration is performed with (E)-Cyclooct-2-enol (TCO*A-OH) and measured by UV/VIS spectroscopy. Hydrogel modified with tetrazine has a characteristic absorbance of 520 nm, while TCO*A-OH (1.2-3.6 mM) and the product of the tetrazine/TCO*A-OH reaction have no detectable absorbance in the visible spectrum. To perform the titration, the hydrogel was dissolved in ddH$_2$O (0.625%-2.5 w/w). Samples of gel were reacted with equal volumes of increasing concentration of TCO*A-OH (0.6-3.6 mM) and allowed to react for 30 minutes. From the x-intercept of the best-fit line, the concentration of tetrazine in the gel is determined.

|  | Alginate |  | Hyaluronic Acid |  |  |
| --- | --- | --- | --- | --- | --- |
|  |  | MWCO |  |  |  |
| <75 kDa (nmols/100 μL) | 75-200 kDa (nmols/100 μL) | >200 kDa (nmols/100 μL) | 5 kDa (nmols/100 μL) | 100 kDa (nmols/100 μL) | 200 kDa (nmols/100 μL) |
| 1875.49 | 1417.06 | 1050 | 1776 | 1034.61 | 517 |

Example 20

Improving the Physical Properties of TCO-Prodrugs

Figure 6:
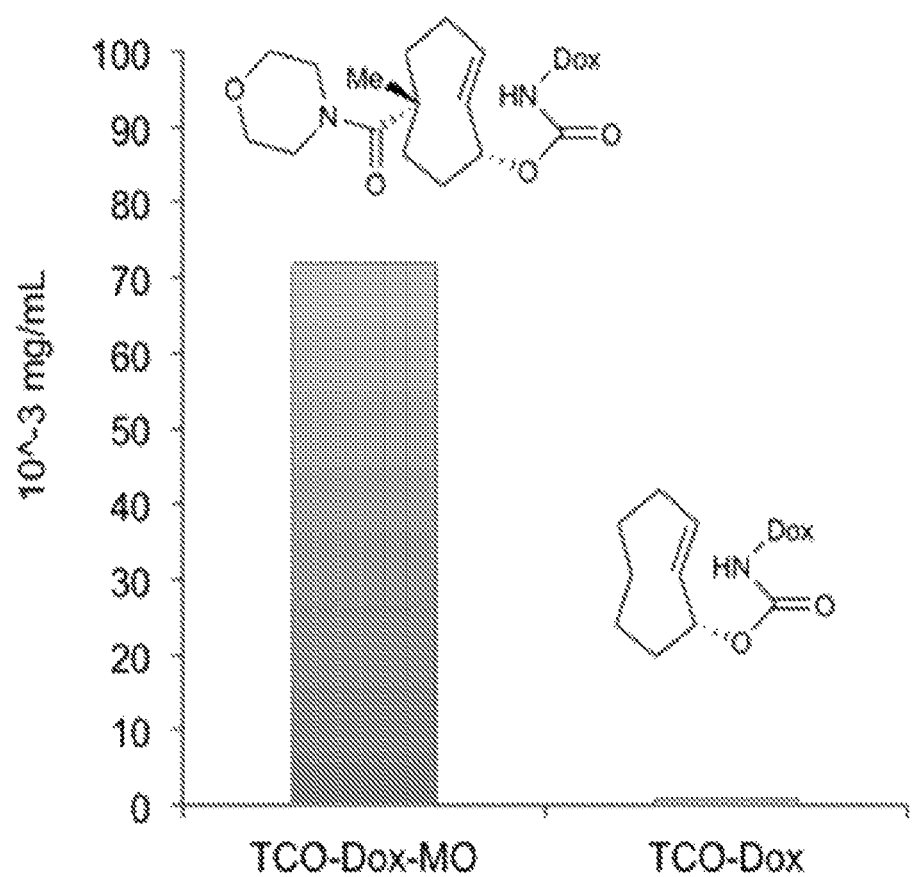
FIG. 6 shows that structural modification increases TCO-dox aqueous solubility. TCO-dox modified with a morpholine group (MO) is over 70 times more soluble in saline than regular TCO-dox.

It was noted that TCO modifications of drugs tended to result in decreased solubility compared to the parent compound. This was especially apparent for daptomycin and doxorubicin. Poor aqueous solubility limited the dosage levels that could feasibly be administered. The ability to delivery the maximum dosage is important for the local activation system, as it significantly expands the therapeutic index to enable supratherapeutic dosing due to diminished side effects. To address this issue, solubilizing chemical groups were attached to the TCO portion. In the case of TCO-doxorubcin, incorporation of a polar morpholine group increased aqueous solubility over 70-fold (FIG. 6).

Example 21

Quantifying the Technology's Ability to Catch a Payload

Figure 3:
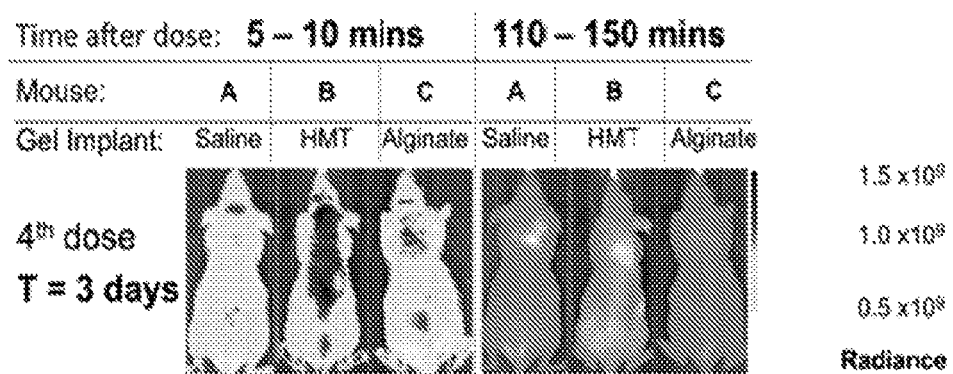
FIG. 3 shows representative images of in vivo proof of concept of catch and release with implanted HNT and a TCO-fluorophore.

The efficacy of the "catch and release" platform technology was demonstrated in mice using rhodamine, a fluorophore, coupled via a carbmate to a TCO moiety. The HMT enhances the local delivery of a rhodamine dye after multiple doses over several days as shown in FIG. 3. Three mice received 100 μL of a local injection in the dorsum at time −2 hrs (A=saline, B=2.5% HMT, C=2.5% alginate). Then starting at time 0, the mice received the same dose of TCO-fluorophore (100 nmoles of TCO-modified rhodamine by tail vein injection) at time 0, 2 h, 5 h and 3 days. After each dose, the mice were imaged after 5-10 mins and 110-150 minutes. These sample images confirm that the largest amount of fluorescence is observed at the dorsum of mouse B and that the effect is transient, suggesting the catch, release and diffusion of the fluorophore. After 5-10 minutes there was a large increase in fluorescence around the site of HMT implantation (Mouse B), while the mice injected with saline (A) or with an unmodified alginate gel (C) did not have a comparable increase in signal. The data supports that the bioorthogonal reaction is able to increase the local concentration of fluorophores. Moreover, the fluorescence signal decreases within two hours to background levels in all cases, supporting the release step. The data shown are selected images after four doses and multiple days of implantation, they confirm the efficiency of the injected biomaterials to catch small molecules modified with TCO and release their cargo at the location of choice, as well as the pharmacokinetics of small molecules to quickly reach the gel site.

Example 22

Therapeutic Efficacy of Doxorubicin Prodrug Against Xenograft Tumors In Vivo A releasable form of doxorubicin was synthesized and tested in mice growing a xenograft of MCF-7 (human breast cancer cell line) or a xenograft of HT1080 (human soft tissue sarcoma). In a breast cancer model, mice (n=4) received two doses of doxorubicin or TCO-doxorubicin at 5 mg/kg every three days in the presence of pre-injected gel at the xenograft site. TCO-doxorubicin resulted in significant tumor shrinkage (p<0.05) compared with vehicle control with less cachexia. TCO-doxorubicin resulted in 40% greater tumor reduction compared to regular doxorubicin after two doses.

Figures 4A, 4B, 4C:
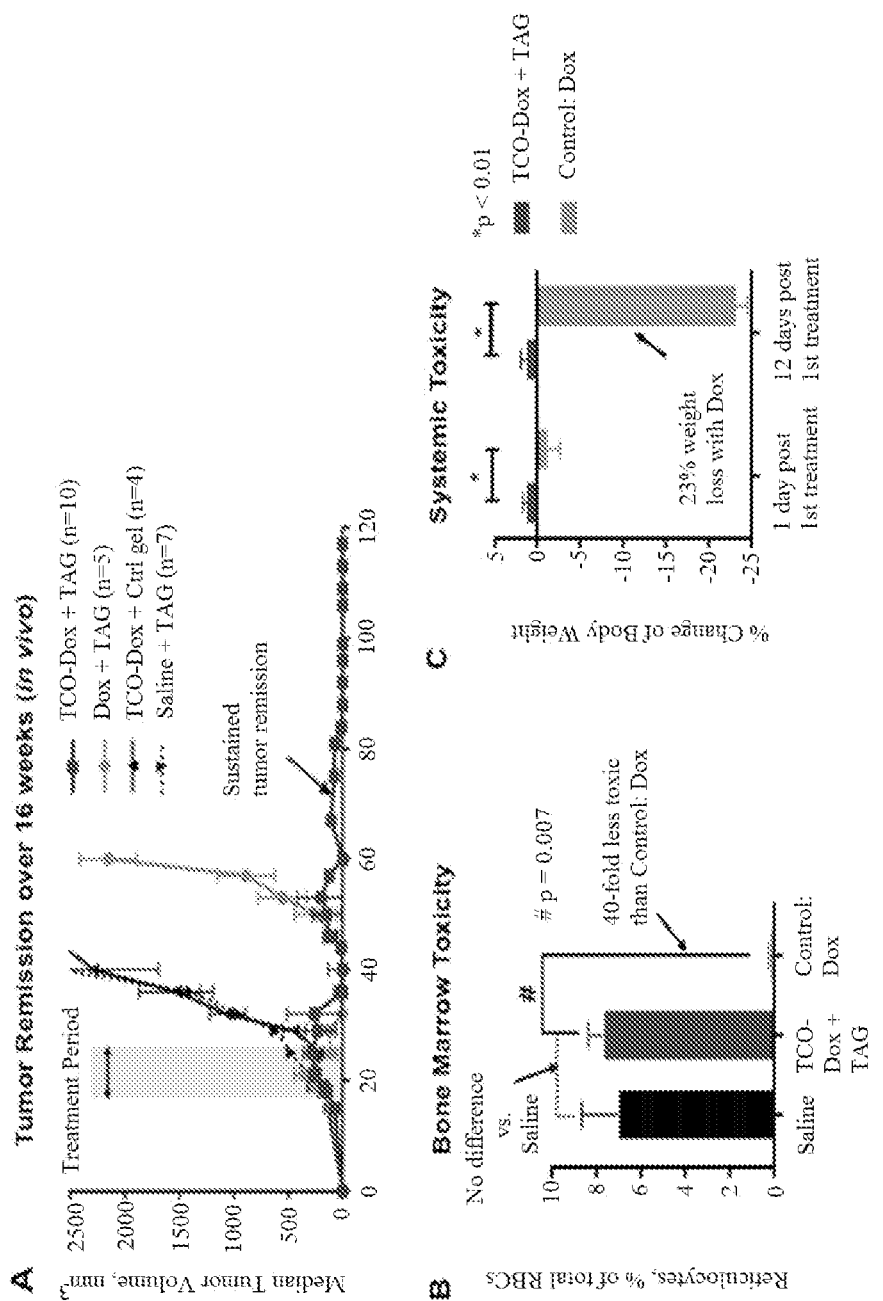
FIGS. 4A, 4B, and 4C show therapeutic effects of doxorubicin pro-drug in a xenograft model of soft tissue sarcoma (HT1080).
Figure 5:
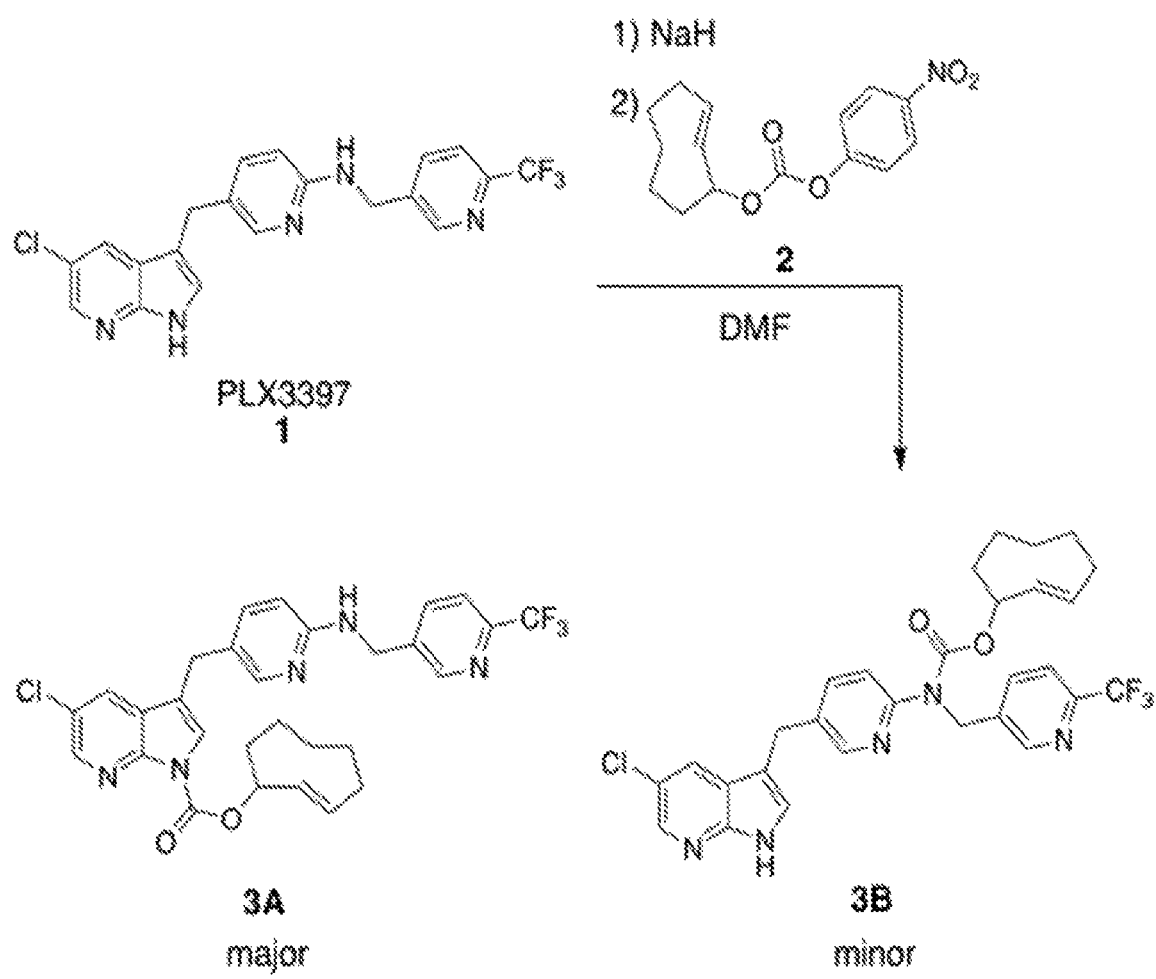
FIG. 5 shows the synthesis of prodrug CSF1R inhibitor TCO-PLX3397 (3A and 3B).

The therapeutic efficacy of the TCO-doxorubicin against HT1080 xenografts are summarized in FIG. 4A. To evaluate the antitumor activity of the doxorubicin prodrug, efficacy studies were performed with athymic nude mice bearing fibrosarcoma (HT-1080) xenografts, a type of human soft tissue sarcoma (STS) often used to evaluate new therapies. Alginate TAG was injected through palpation immediately next to the tumors 18 days after initial implantation when their size reached an average of 195 mm$^3$ (range, 90-500 mm$^3$). There were two treatment cohorts: (i) 3 intravenous doses of 14 µmoles/kg of standard doxorubicin every 4 days (maximum tolerable dose), or (ii) daily doses of 14 µmoles/kg of doxorubicin pro-drug for 10 days. Tumor volumes were measured twice a week for 13 weeks after initiation of therapy (FIG. 4A). No further therapies were given to the subjects 28 days post-tumoral implantation (dpi).

For both therapeutic groups, the median tumor size was undetectable two weeks after the last treatment dose (40 dpi). Thirty days after the last treatment dose (60 dpi), the median tumor size of the systemic doxorubicin cohort was greater than 2000 mm$^3$ and the mice were euthanized shortly thereafter. This is consistent with previous studies evaluating systemic doxorubicin on HT1080. In contrast, the median tumor size of the prodrug cohort remained undetectable (P=0.021). At 88 dpi, half of the mice of the prodrug cohort were euthanized as they reached the endpoint. The other half of the mice in the cohort did not show any detectable signs of tumors and remained that way until the end of the study (118 dpi).

In order to exclude issues such as non-specific in vivo activation of the pro-drug or microenvironment changes due to the placement of an alginate polymer, multiple additional controls were tested. No differences in tumor volume were observed between untreated mice and mice treated with (i) local injection of TAG and i.v. administration of saline, or (ii) local injection of unmodified alginate and doxorubicin pro-drug administration (FIG. 4A). This confirms that the prodrug does not spontaneously turn into the regular doxorubicin without the presence of the gel in clinically meaningful quantities or that an inherent characteristic of the prodrug independent of the bioorthogonal reaction is responsible for the increase in efficacy.

In the control experiments, the growth of the tumor in the presence of saline and TAG gel or pro-drug with an unmodified alginate was identical. This suggests that the TCO modified pro-drug does not have an inherent toxicity that could account for the efficacy observed (FIG. 4A). The data further supports that TAG is necessary for meaningful efficacy.

Example 23

Side Effects Profile of Doxorubicin Prodrug In Vivo

Despite treating mice with more than three times the maximum tolerable dose of regular doxorubicin through our prodrug system, the bioorthogonal approach resulted in substantially fewer side-effects relative to the doxorubicin treatment. Myelosuppression is the main acute dose-limiting toxicity of doxorubicin. A standard measure for this side effect is reticulocyte count, based on short-lived precursors of red blood cells that are easily quantified. The nadir of reticulocytes after systemic doxorubicin occurs 3 days after the end of therapy. The systemic doxorobucin-treated cohort showed a dramatic decrease in reticulocytes (P=0.007) (FIG. 4B). In contrast, the cohort treated with doxorubicin prodrug showed reticulocyte counts similar to mice treated with vehicle (FIG. 4B). Furthermore, mice treated with doxorubicin prodrug did not show any overt signs of toxicity, including weight loss or changes in coat texture, while the regular doxorubicin cohort lost on about 20% of body weight (FIG. 4C).

The safety of TCO-prodrug versions is substantiated by data from a single animal pilot study (n=1), which showed that the doxorubicin prodrug is at least 18-fold less toxic than doxorubicin in a canine model through extrapolation of single-cycle acute toxicity, and nearly six-fold less toxic than a doxorubicin peptide-conjugate (Nat. Med., 2000, 1248-1252). (FIGS. 37 and 38). In this study, a dog treated with 4 doses of doxorubicin (single doses of 1.74 mole/kg) over 60 days experienced a 3.5% loss in body weight. Two months after the final doxorubicin cycle, the same animal was administered 3 doses of TCO-doxorubicin (single doses of 10.1 mole/kg) over a much-shortened treatment course of 6 days, resulting in a gain of body weight of up to 3.6% (FIG. 39). Furthermore, whereas doxorubicin induced a significant drop in neutrophil levels, over the course of treatment, no signs of neutropenia were observed with TCO-doxorubicin (FIG. 39). These studies highlight the safety of the TCO prodrug version over the regular chemotherapeutic.

In the dog study, TCO-doxorubicin treatment led to increases in leukocytes, lymphocytes, monocytes, and eosinophils, indicative of acute immune activation (FIG. 40).

Example 24

Preliminary Pharmacokinetics and Gel Biodegradation

Figure 2:
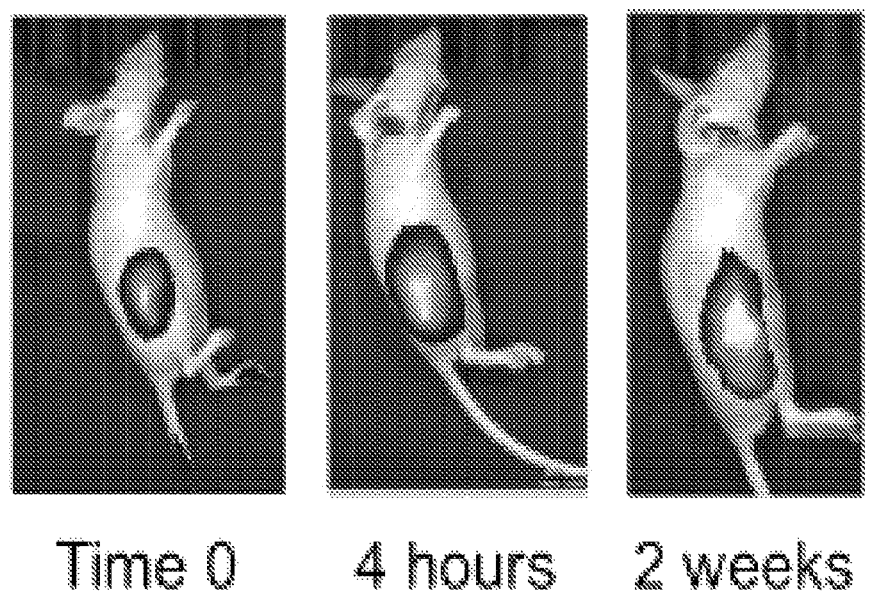
FIG. 2 shows gel immobility after injection. Hydrogel modified with Tz (HMT) covalently modified with Cyanine 5.5, a fluorophore, was injected subcutaneously in the flank of a mouse (100 µL of 2.5% w/w solution). The animal was imaged at different time points (time 0, 4 hrs and 2 wks) confirming the location of the hydrogel.

Preliminary in vitro plasma stability studies were performed on the pro-doxorubicin to help set its preliminary pharmacokinetic stability in mice and human plasma. The prodrug has a half-life in plasma of 6.8 hours in humans and 19.3 hours in mice. These data determine the stability of the prodrug and its suitability for further studies. A hydrogel modified with tetrazine and the fluorophore cyanine 5 was synthesized. From a standard curve for cyanine 5 (absorbance at λ=646 nm), the concentration of cyanine 5 was determined to be 0.732 nmols/mg (n=1). This concentration is sufficient to be able to detect the gel through fluorescent imaging for more than two weeks after in vivo injection (FIG. 2), ensuring the gel does not travel throughout the body to cause systemic side effects.

Example 25

Determine Minimum Inhibitory Concentration (MIC) of TAG and TCO-Prodrugs

In vitro MIC evaluations may be established for each TCO prodrug compound, as well as for vancomycin and daptomycin, using standard methods. Briefly, serial dilutions may be created of the antibiotic agents with either TAG or control gel in ddH$_2$O and allow them to mix for 4 hours. Then luminescent MSSA or MRSA aeruginosa in broth may be added to the mixture. The plates may be placed in the incubator overnight and allowed to grow (n=4 for each prodrug/bacteria combination). Luminescence can be measured with an IVIS imager and reported in radiance. This data can be used to determine inhibition curves.

Example 26

Releasing a Therapeutic Payload Against Bacteria

To demonstrate the applicability to treat bacterial infections, a releasable form of the antibiotic vancomycin was synthesized and tested for its ability to eradicate luminescent methicillin-sensitive *S. aureus* (MSSA). Alginate TAG and a releasable TCO-vancomycin had a minimum inhibitory concentration (MIC) similar to TAG+regular vancomycin (2.0 vs. 0.5 nmoles/mL), whereas 2.0 nmoles of TCO-vancomycin combined with regular alginate gel did not inhibit bacterial growth (FIG. 9A-9B). The mechanism may be that vancomycin gets released once TCO-vancomycin reacts with TAG. The released antibiotic inhibits bacterial growth analogously to vancomycin with no impact on the antibiotic's mechanism of action. These MIC trends are corroborated by isothermal microcalorimetry, where the combination of TAG and TCO-vancomycin eliminated observable bacterial activity, while the control alginate showed a much-reduced affect (FIG. 9C). These results establish proof of concept that the TAG and antibiotic prodrug system is an effective means to kill bacteria.

Example 27

Modification of Alginate Hydrogel with Tetrazine Analogs

Figure 12:
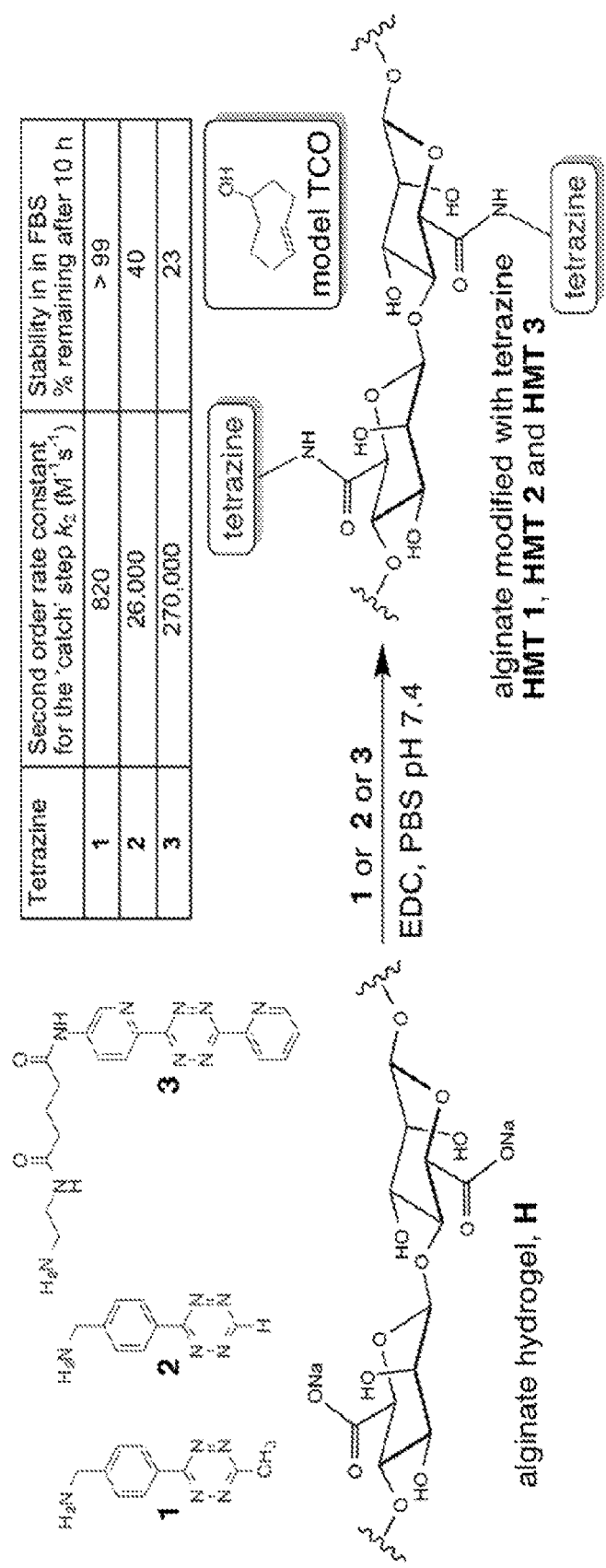
FIG. 12 is a schematic showing that tetrazines 1, 2 and 3 may be used to modify alginate hydrogel, H. Three different hydrogels modified with a tetrazine, HMT 1, HMT 2, and HMT 3 can be synthesized.
Figure 13:
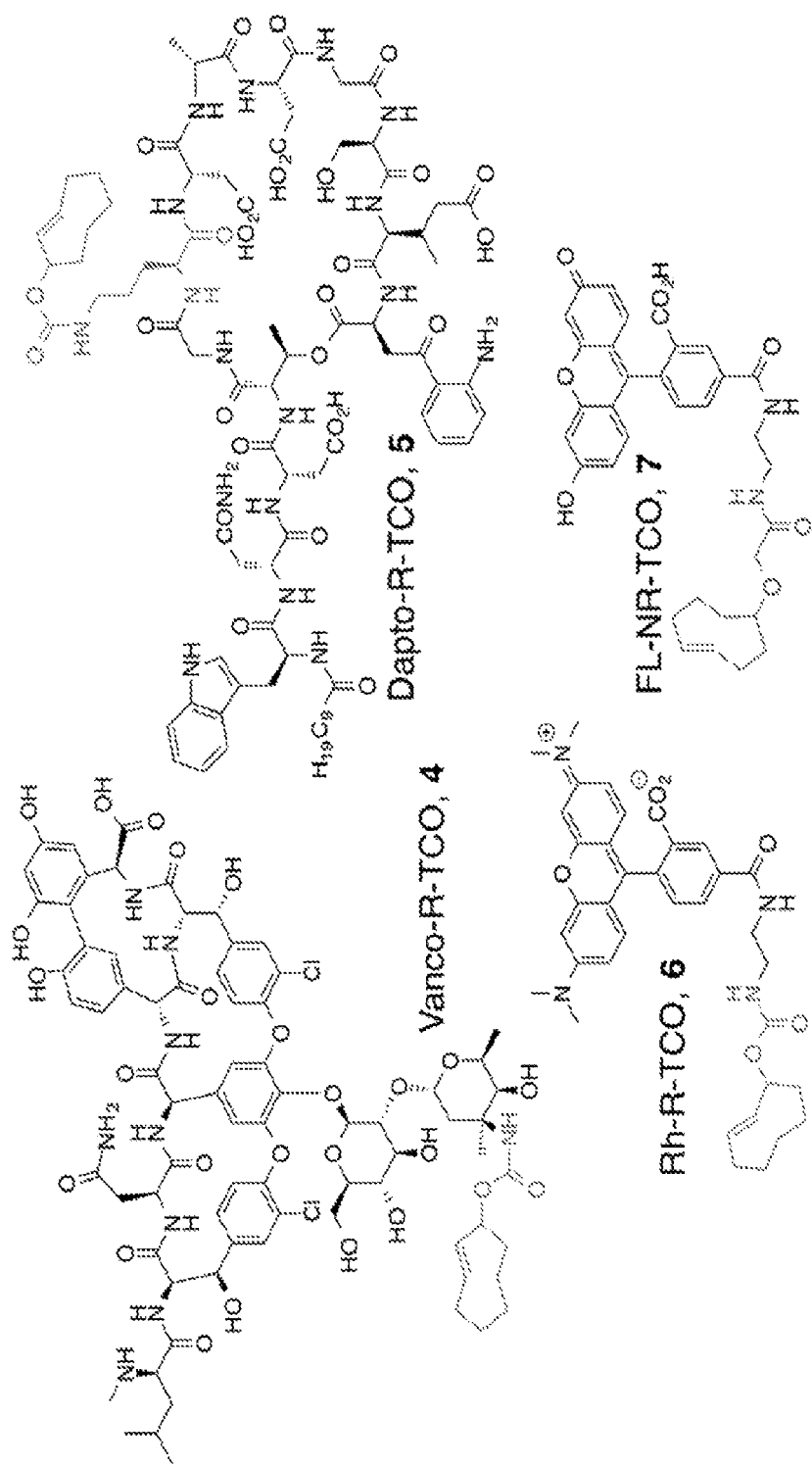
FIG. 13 shows compounds that may be used during preliminary studies: vancomycin-modified with a releasable TCO, Vanco-R-TCO, 4; daptomycin-modified with a releasable TCO, Dapto-R-TCO, 5; rhodamine-modified with a releasable TCO, Rh-R-TCO, 6; and fluorescein-modified with a non-releasable TCO, FL-NR-TCO, 7.

Alginate hydrogel was modified as shown in FIG. 12 with various tetrazines. An ultrapure medium viscosity (>200 mPa s) MVG sodium alginate, H, with a minimum of 60% guluronate monomer units, was purchased from ProNova BioPharma. The three tetrazines were conjugated with H, as shown in FIG. 12, to form a series of hydrogels modified with tetrazine, HMT 1, 2 and 3. Tetrazines 2 and 3 reacted efficiently but had suboptimal physiological stability. Therefore, tetrazine 1 and the resulting HMT 1 were chosen for the rest of the preliminary studies due to their optimal combination of stability plus reactivity. Based on H NMR analysis, shown in FIG. 16A, HMT 1 was determined to contain about 400 nmoles of 1 per milligram of the material. The reaction shown in FIG. 12 was also carried out using a 95:5 mixture of HMT 1 and Cy5.5-mono amine dye to prepare fluorescently labeled HMT 1 for the in vivo studies described in FIG. 16. To characterize hydrogel stability and function, a series of TCO-modified compounds, shown in FIG. 13, was prepared. Two clinically proven antibiotics, vancomycin and daptomycin, were modified with a releasable TCO (Vanco-R-TCO, 4 and Dapto-R-TCO, 5). Modified fluorescent dyes: rhodamine, with a releasable TCO (Rh-R-TCO, 6) and fluorescein with a non-releasable TCO (FL-NR-TCO, 7) were also synthesized.

Example 28

In Vitro Assessment of Antibiotic Release

Figure 14A:
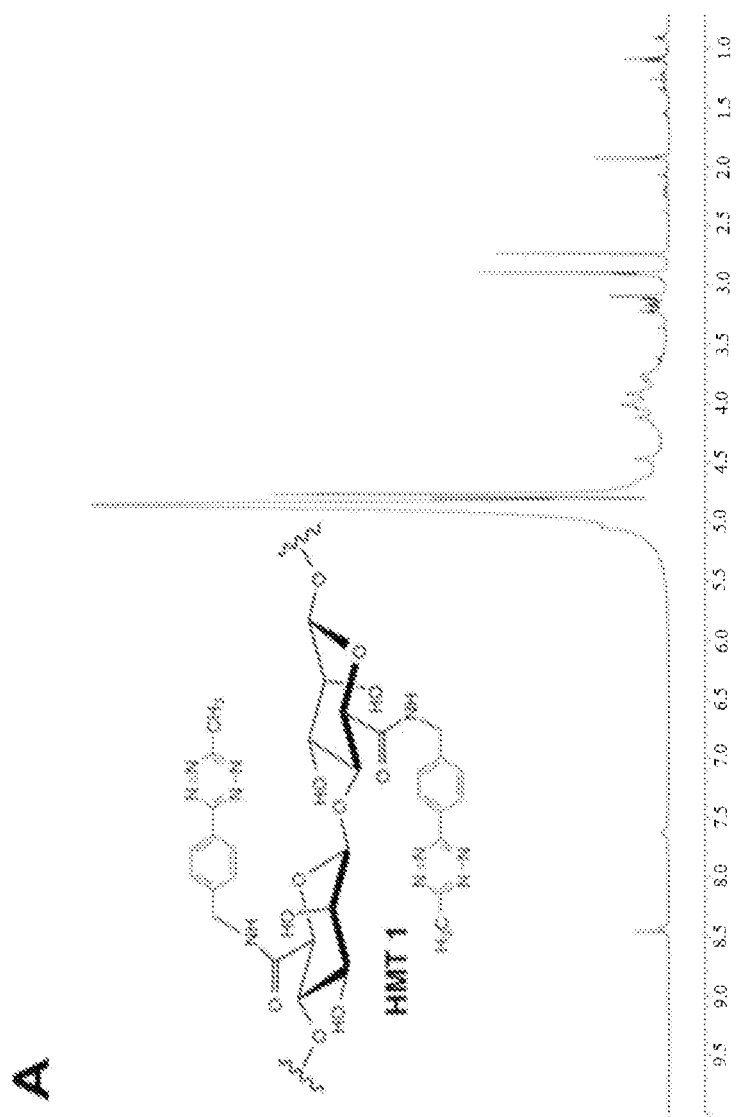
FIG. 14A is $^1$H NMR characterization of HMT 1.
Figure 14B:
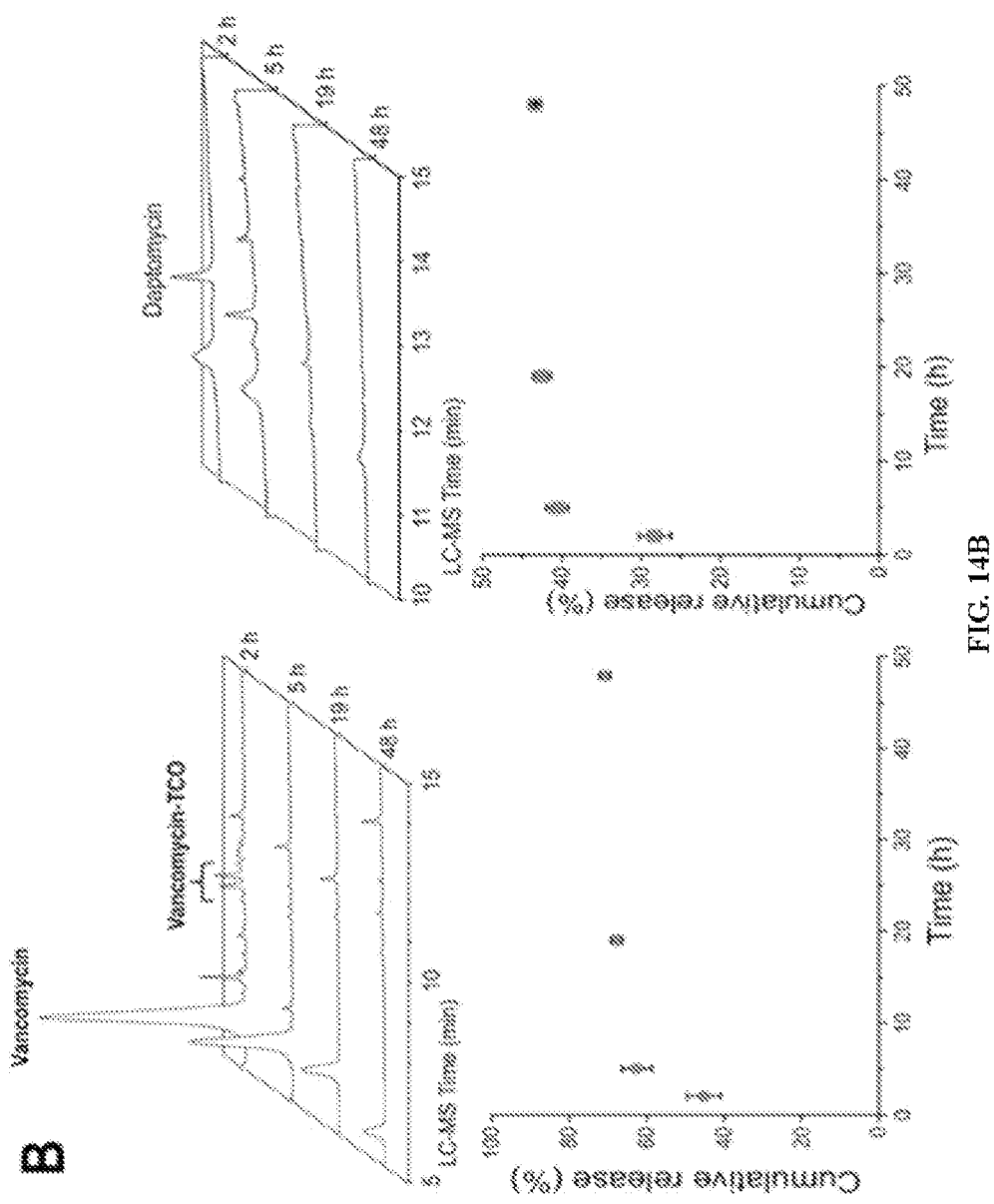
FIG. 14B shows testing of in vitro 'catch and release' process that converts Vanco-R-TCO into vancomycin and Dapto-R-TCO into daptomycin. The in vitro experiments were done in triplicate.

To test the in vitro antibiotic release, HMT 1 was placed inside of spin columns and treated with a PBS solution of either 4, or 5. After 2 h incubation at 37° C., the supernatant was collected by centrifugation. The hydrogels were treated with fresh PBS at regular time intervals. The collected supernatants were analyzed by LC-MS (ESI). The LC-MS spectra (FIG. 14B) shows that HMT 1 efficiently immobilized 4 and 5 after 2 hours of incubation. The activated vancomycin and daptomycin were released over a 2-day period with the total release of over 65% for the former and 43% for the latter. In a separate experiment, it was confirmed that the ability of HMT 1 to capture the prodrug 4 and 5 did not diminish after 7-day incubation in FBS or cell lysate.

Example 29

Functional Stability of HMT 1 in PBS

Figure 15:
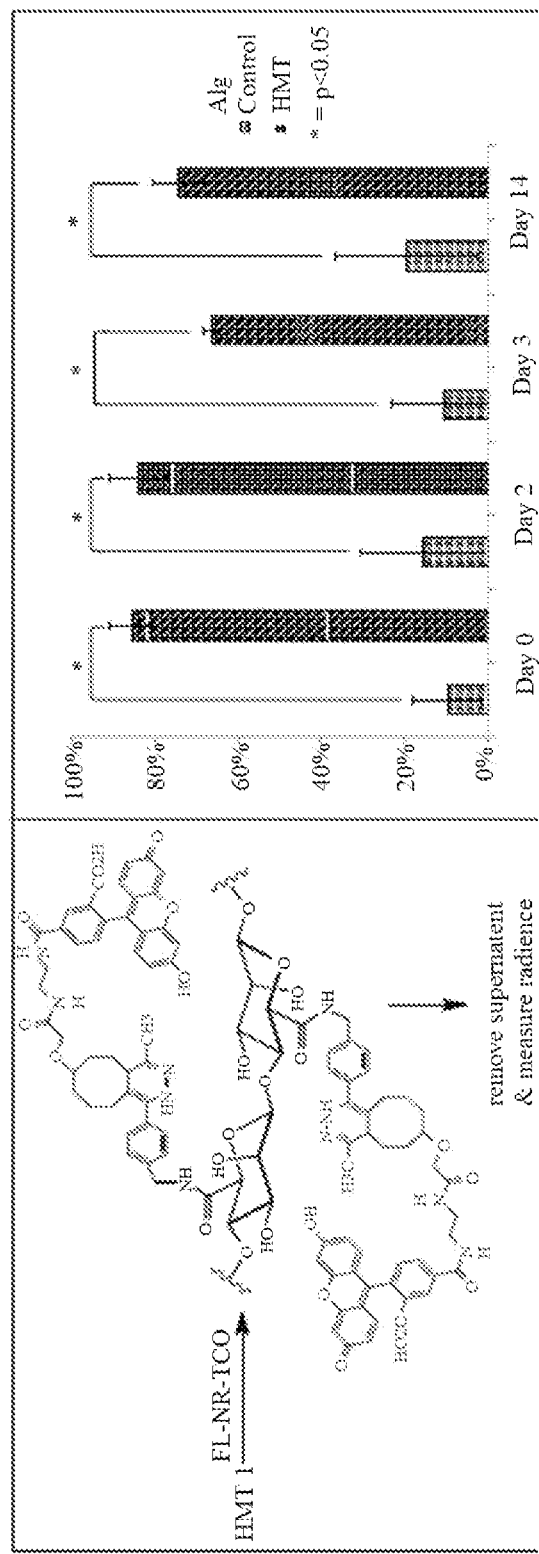
FIG. 15 shows synthesis and assay protocol to determine functional stability of HMT 1 in PBS over 14 days in 37° C.

Functional stability of HMT 1 in PBS was tested using the non-releasable, FL-NR-TCO (FIG. 13), as schematically illustrated in FIG. 15. HMT 1 and unmodified control alginate gel, H, were challenged with FL-NR-TCO, 7, to determine the functional amount of tetrazines that remain active after incubation in PBS at 37° C. for different time periods (0, 2, 3, 14 days). Disks of hydrogel (50 mg) were placed in well plates with 1 mL of PBS and were maintained at a 37° C. incubator for the duration of the experiment. The hydrogels were challenged with 50 nmoles of a solution of 7 for 90 min in a shaker. The resulting supernatant (1 mL) was transferred to another well plate leaving the hydrogel behind. The radiance of the supernatant in each well plate was measured via an IVIS spectrum. The data were averaged SEM, n=3. P values were determined by unpaired t-test. The data, shown in FIG. 15 suggest that more than 70% of the tetrazine moieties remain stable and reactive after a 14-day incubation in PBS at 37° C.

Example 30

Material-Guided Delivery of Antibiotics Against MRSA Bacterial Infection

Figure 16:
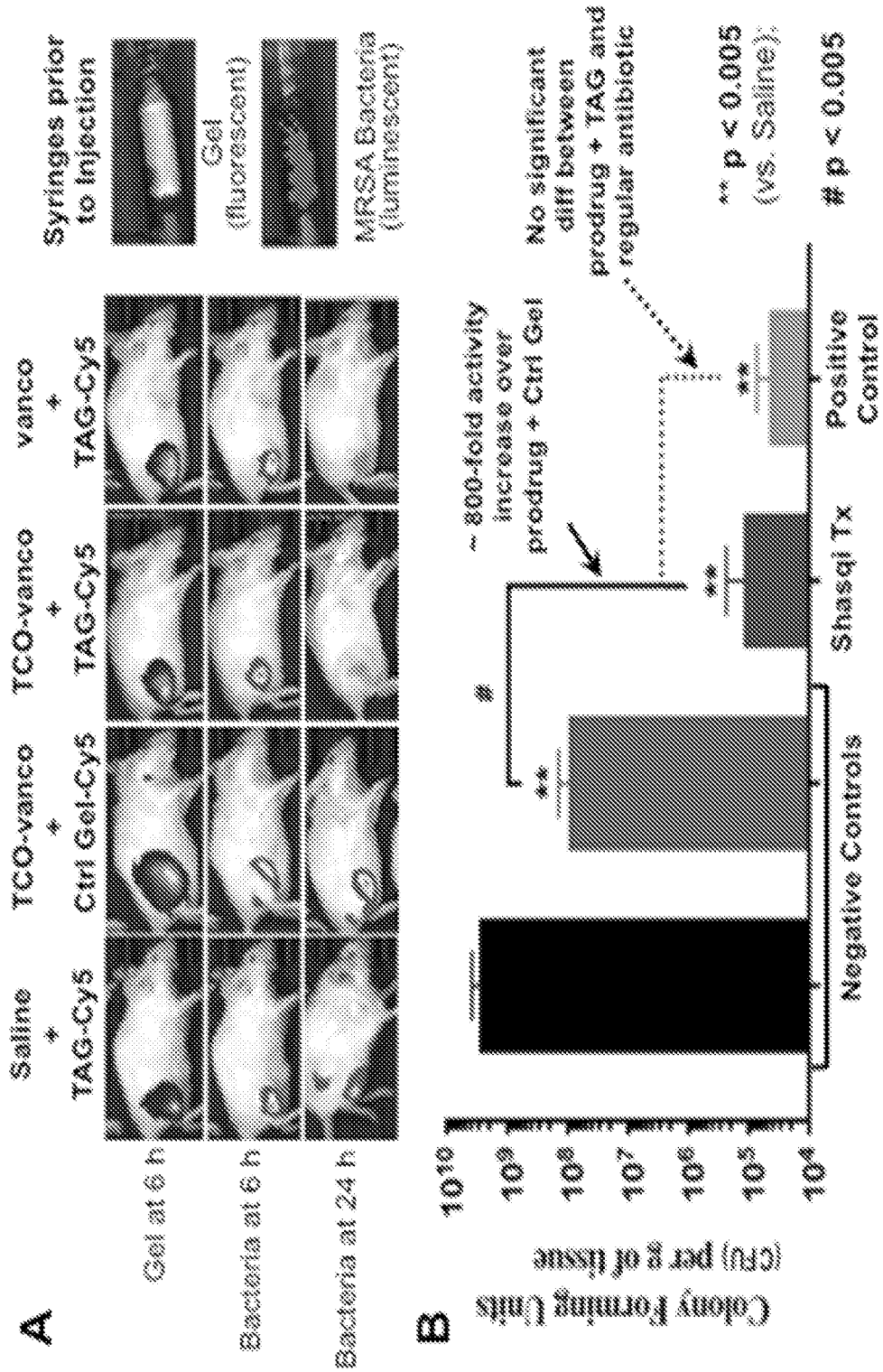
FIG. 16 shows results of material guided delivery of vancomycin against MRSA bacterial infection. In vivo imaging shows that Cy5-modified alginate TAG+TCO-vanco (Shasgi Tx) and Cy5-modified alginate TAG+vanco (positive control) eliminate luminescent bacteria within 24 h while vehicle control does not, and confirms the presence of TAG at the infection site. Culturing of infected tissue confirms that vanco and TCO-vanco reduce bacterial load greater than the control (**p<0.005). No difference was observed between vanco and TCO-vanco in efficacy.

With the antibacterial effect confirmed in vitro, the technology was evaluated to treat *S. aureus* infection in a deep thigh wound infection model in mice. Cy5-modified alginate TAG increases the local concentration of antibiotics at the infection site. Neutropenic (cyclophosphamide-induced) CD-1 mice (n=3) were inoculated intramuscularly (thigh) with TAG or control Cy5-modified control alginate mixed with luminescent methicillin resistant *Staphylococcus aureus* (MRSA). Mice were administered intravenously either saline, Vanco-R-TCO (FIG. 13), or vancomycin 4 hours later. Vanco-R-TCO and vancomycin were each administered at a dose of 69 µmole/kg. In vivo images of gel and luminescent *S. aureus* at 6 and 24 hours post-inoculation are shown in FIG. 16. Bacterial load per gram of tissue is determined by quantitative culture of excised thigh muscle at 24 hours post-inoculation. Unpaired t-test with Welch's correction, 2-tailed (FIG. 16). IVIS in vivo imaging revealed that within 24 hours, bacteria were undetectable after treatment with either Vanco-R-TCO or vancomycin. On the other hand, luminescent bacteria were observed in control experiments involving either gel and a saline injection or gel and Vanco-R-TCO. After 24 hours, efficacy was quantified by culturing of homogenized mouse thighs to measure bacterial load. Despite its 4-fold lower in vitro activity, Vanco-R-TCO exhibited equivalent efficacy to regular vancomycin, a standard treatment for *S. aureus* infection. The control experiment involving gel exhibited significantly attenuated bactericidal activity. These results demonstrate that the 'catch and release' technology is capable of in vivo local activation of antibiotic prodrugs and is an effective approach to deliver antibiotics to local bacterial infections. Lastly, gel covalently modified with a Cy5 dye confirmed that a subcutaneous TAG injection remains at the site of injection for weeks. These results demonstrate that the technology is an effective approach to deliver antibiotics to local bacterial infections.

Example 31

Biodistribution—Rat Joint Study—TCO-Dapto-Glycine with TAG

Figure 17:
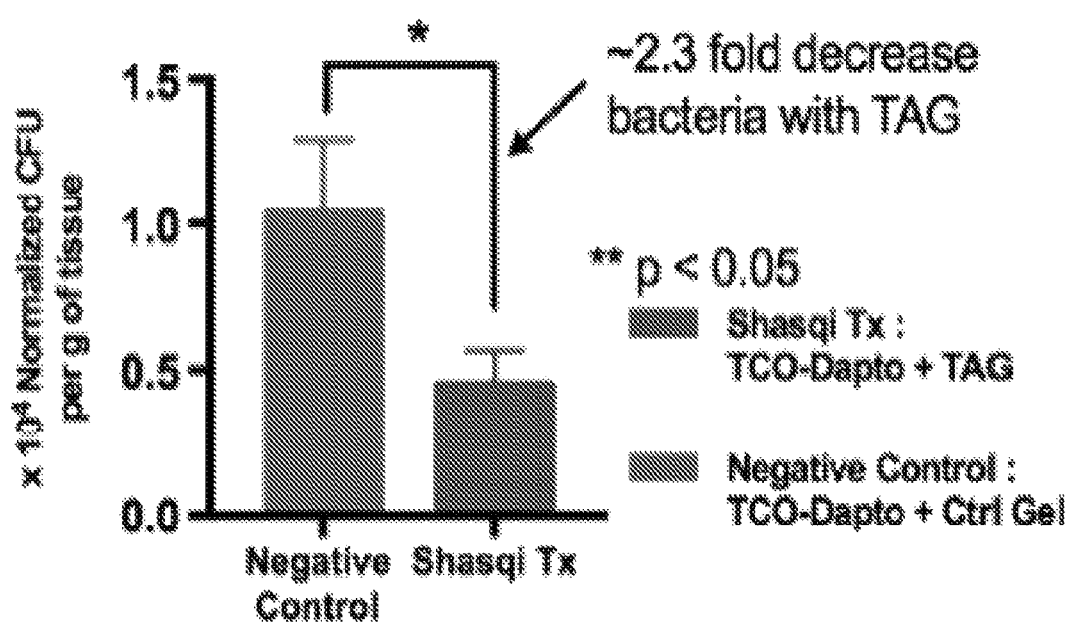
FIG. 17 shows TCO-Dapto+TAG (Shasgi Tx) reduces MRSA infection in vivo in a knee joint.

Female Sprague-Dawley rats of age 6-8 weeks were approved for this study by the Institution of Animal Care and Use Committee (IACUC). Neutropenia was induced with cyclophosphamide intraperitoneally, 4 days (150 mg/kg) and 1 day (100 mg/kg) prior to gel injections. Animals received intra-articular injections of 200 µL of 2.5% w/v of Cy5-modified alginate TAG (right knee) or unmodified alginate-Cy5 gel control (left knee) mixed with 50 µL of $10^8$ CFU/mL of methicillin-resistant *Staphylococcus Aureus* SP231 bacteria. After 2 h, animals received 61 µM of transcyclooctene-modified daptomycin-glycine (TCO-Dapto) via tail vein IV at standard dosing volume. After 24 h of gel injections, knee joints were harvested, homogenized and diluted in Dubelco's Phosphate buffered saline (D-PBS). Homogenized mixture was plated onto trypticase soy agar plates containing 5% sheep's blood duplicate. Bacterial colonies were enumerated following 20 h of incubation and bacterial load as LOG CFU/g of knee joint was determined. Statistical analysis was performed with Welch's two-tailed t-test and * denotes p<0.05. Error bars indicate standard error over means of n=3. FIG. 17 shows antibacterial results for the TCO-dapto and control.

Example 32

Serum and Tissue Levels after TCO-Doxorubicin and Doxorubicin

Figures 18A, 18B:
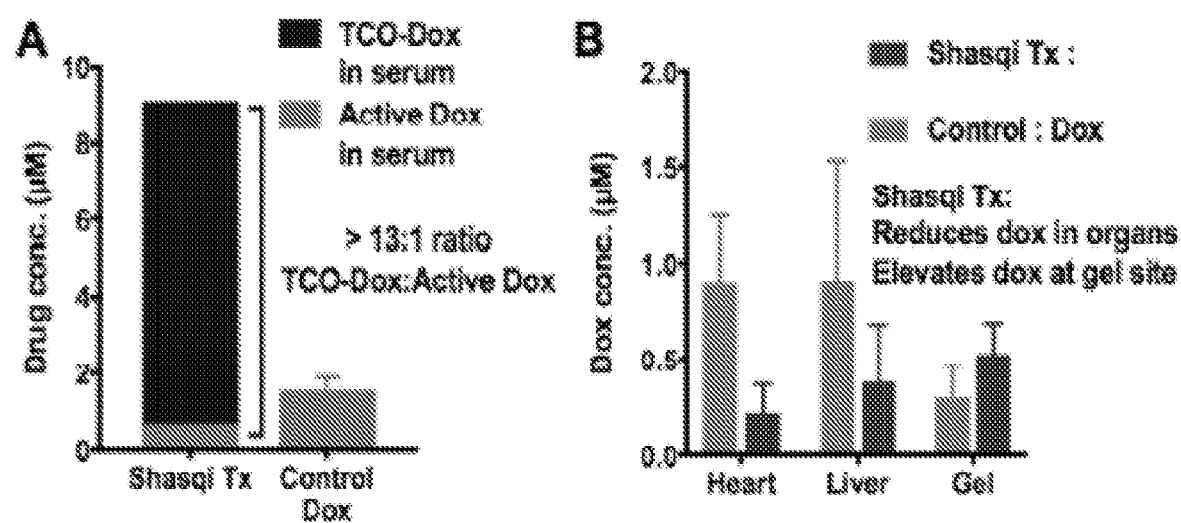
FIGS. 18A and 18B is a set of graphs showing that Shasqi Tx (Tetrazine-modified gel injected locally; followed by TCO-doxorubicin pro-drug injected intravenously) reduces systemic exposure to cytotoxic chemotherapy. Mice injected with tetrazine-modified gel are given TCO-Dox or Doxorubicin intravenously. Serum and tissues are harvested 5 min post-injection to reflect Cmax analyzed by LC-MS/MS.

Serum and tissue bioanalysis suggests that Shasqi Tx (Tetrazine-modified gel injected locally, followed by TCO-doxorubicin pro-drug injected intravenously) reduces systemic exposure to active Dox as anticipated. Balb/C mice injected with tetrazine-modified gel were given TCO-Dox or Dox IV, and serum and organs were harvested 5 minutes post-infusion and analyzed. In serum, the majority of TCO-Dox-Acid remains intact and systemic exposure of active Dox is lower than that of standard treatment (FIG. 18A). Likewise, tetrazine-modified gel injected locally, followed by TCO-doxorubicin pro-drug reduced the amount of activated Dox in the heart and liver, yet increased the amount in the gel, relative to control treatment (FIG. 18B). In sum, these results support the hypothesis that tetrazine-modified gel injected locally, followed by TCO-doxorubicin pro-drug enhances delivery of drug to a target site while limiting exposure in off-target tissues.

Example 33

Gel Residency—Modified Hyaluronic Acid and Alginate

Figure 19:
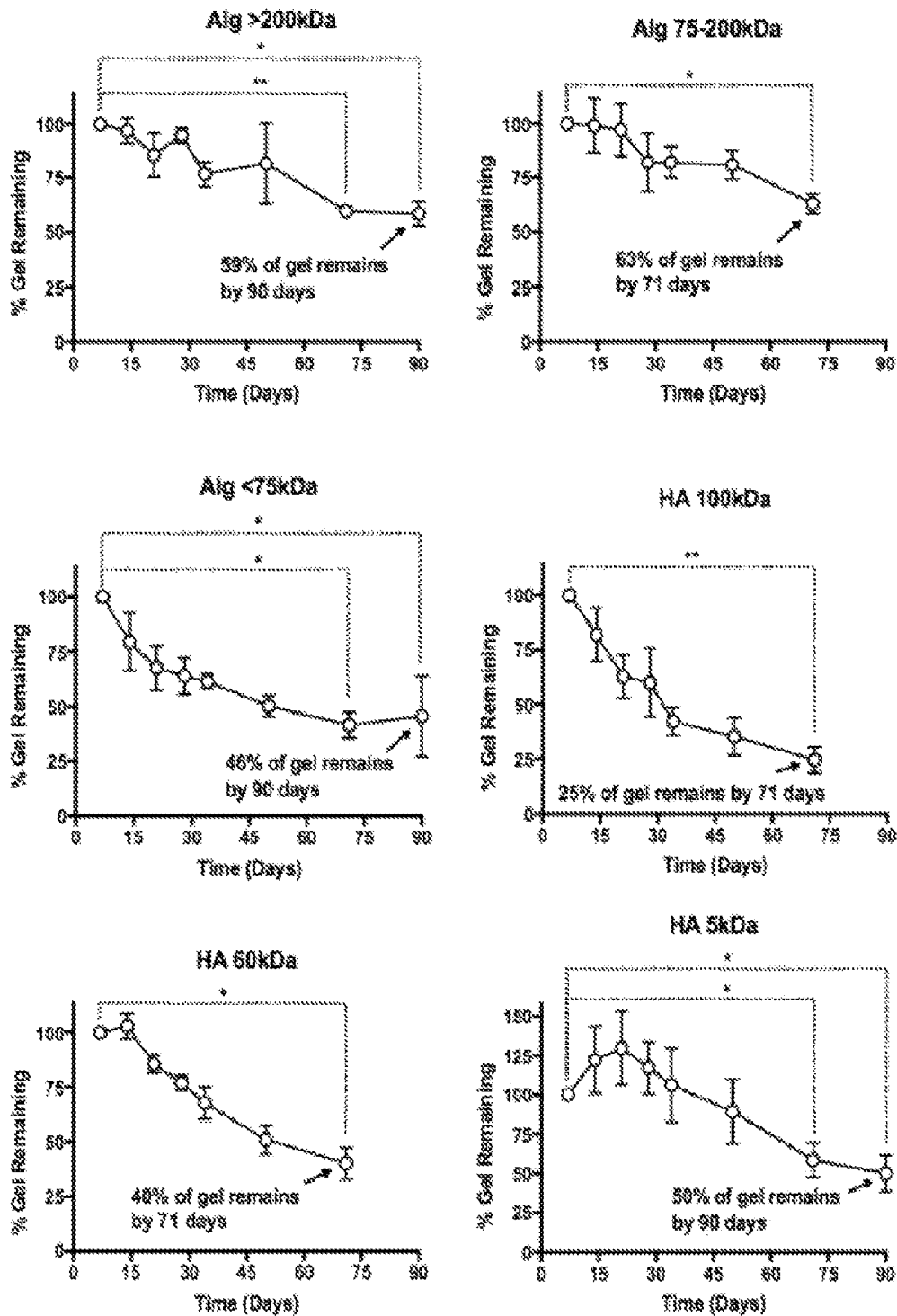
FIG. 19 is a set of graphs showing the percent of gel remaining determined by fluorescence intensity of injection site relative to day 7 post-injection value, mean SEM of n=3, paired one-tail t-test, * p<0.05, ** p<0.005.
Figure 20:
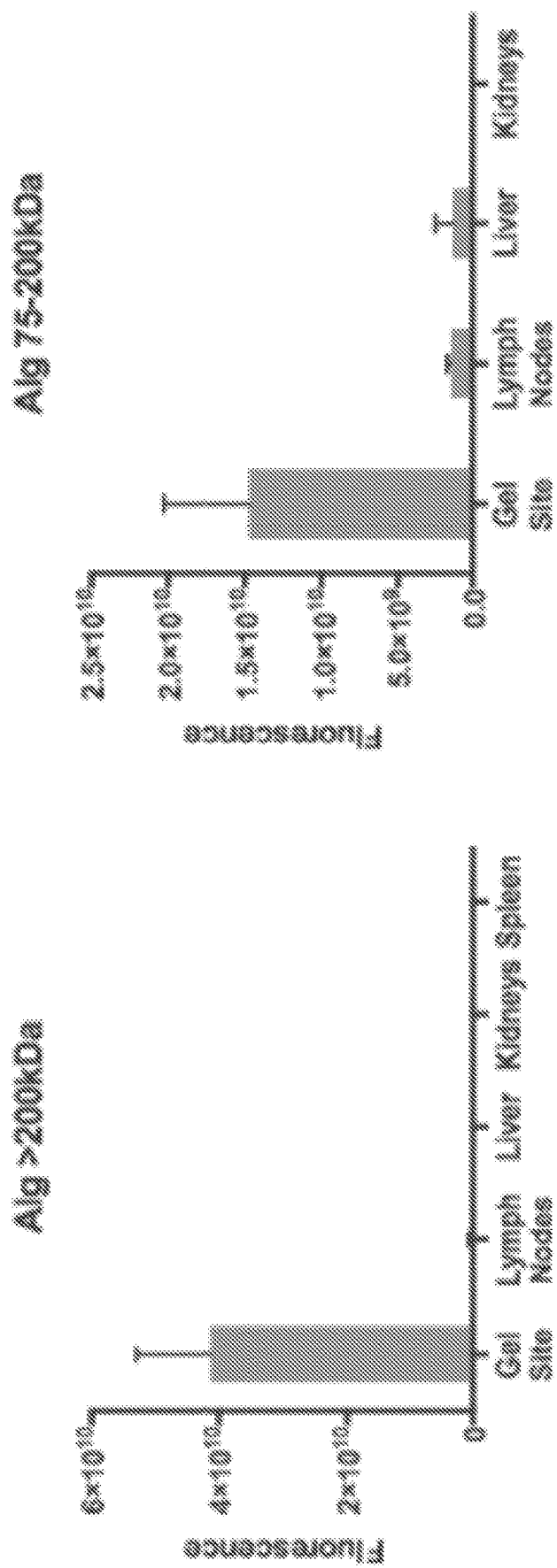
FIG. 20 is a set of graphs showing absolute fluorescence signal of gel injection site tissue and organs collected post-necropsy.

Alginate (Alg; MW=<75 kDa, 75-200 kDa, or >200 kDa) and hyaluronic acid (HA; MW=5 kDa, 60 kDa, or 100 kDa) gel, modified with tetrazine and cyanine 5, was injected as a 10% solution subcutaneously in the flanks of 6-8 week old female CD-1 mice (Charles River Laboratories), n=3/group. In vivo fluorescence imaging was performed on days 1, 2, 4, and 7, once weekly thereafter until day 28, and every other week thereafter until day 90. Fluorescence measured by region-of-interest quantification of flank injection site. Animals were euthanized on day 73 (Alg 75-200 kDa, HA 100 kDa, and HA 60 kDa) or 99 (Alg >200 kDa, Alg <75 kDa, and HA 5 kDa). Fluorescence imaging was performed on harvested liver, kidney, lymph node, spleen, and gel injection site tissue. Fluorescence imaging was performed with 640 nm excitation and 694 nm (Cy5.5) emission filter, and signal was quantified as radiant efficiency [(p/sec/cm$^2$/sr)/ (µW/cm$^2$)] of gel injection site region of interest or whole organ harvested. The results are shown in FIGS. 19, 20, and 21.

Example 34

Tolerability Study in NSG Mice

Five non-tumor bearing animals were used to determine the MTD for the Shasqi gel (tetrazine-modified aliginate) and pro-drug (TCO-doxorubicin-acid) combination in the NSG-H mouse (NOD.Cg-Prkdcscid Hprtem1Mvw Il2rgtm1Wjl/MvwJ, Strain 026222, Jackson Labs). Pre-treatment weight and body conditioning score (BCS) were recorded for each animal. Animals received a dose of Shasgi gel (100 µL) subcutaneously before treatment 1, 2, and 3. Each dose will be provided at a different part of the body. A dose escalation of the prodrug (Pro-Doxorubicin) will be performed as described below.
Treatment 1: 50 mg/kg/day; daily×5
Treatment 2: 75 mg/kg/day; daily×5
Treatment 3: 100 mg/kg×1; 125 mg/kg×1

BCS was recorded daily and body weight recorded every other day. If no clinical signs of toxicity are observed after 5 days of daily treatment, the dose will be escalated to the next Dose Level. In addition to documentation and monitoring of pre- and post-treatment weights and BCS, we will perform a Complete Blood Count (CBC) analysis pre-treatment, after 15 doses of Pro-Doxorubicin, and at the end of the Tolerability study.

Toxicity monitoring for treated animals includes the close monitoring for any signs of distress including neurological symptoms, decreased activity, ruffled fur, weight loss, diarrhea, and dehydration. If such symptoms are observed, treatments will be stopped and will only be restarted after resolution of all symptoms. If symptoms resolve, then the animal will be rechallenged at the same dose level. However, if the same symptoms are observed again, and/or there is ≥10% weight loss from baseline, no further doses will be given and the current dose level deemed the MTD. If animals lose 20% of their body weight or if the signs listed above do not abate within 24 hours, animals will be immediately euthanized and the current dose level will be deemed the MTD. If toxicity resulting in death in any mouse per treatment group occurs, a new drug toxicity study was performed evaluating the tolerability of the drug at 25% of the original dose. If the animals show no appreciable weight loss or decrease in BCS, dose was re-escalated dose by 25% increments every week until the maximal tolerated dose is determined.

Figure 22:
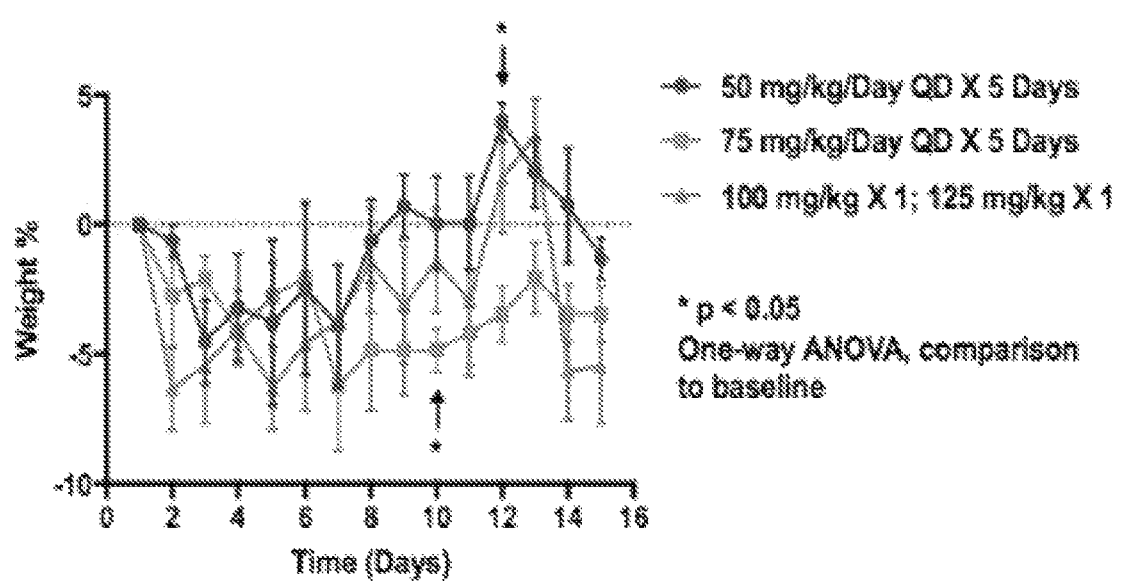
FIG. 22 is a graph showing body weight % change following treatment with alginate TAG and TCO-Dox-Acid.

Effects of TCO-Dox-Acid on body weight are shown in FIG. 22. In FIG. 23 are shown dose equivalent comparisons of tolerability of TCO-Dox-Acid versus doxorubicin. TCO-Dox-Acid was better tolerated than standard doxorubicin alone.

Example 35

Safety and Efficacy in a Canine Model

The safety profile for tetrazine-modified gel injected locally, followed by TCO-doxorubicin pro-drug injected intravenously translates across species, including large animals. In a veterinary pilot study in a canine with local spontaneous adenocarcinoma, standard doxorubicin regimen led to disease progression (tumor growth) well as a drop in body weight (FIG. 24A-B). Subsequently, the lower toxicity of tetrazine-modified gel injected locally, followed by intravenous TCO-doxorubicin pro-drug allowed for multiple cycles of the TCO-Dox pro-drug at higher dosing magnitudes, resulting in a reduction in tumor size followed by stable disease, as well as a gain in body weight and no major side effects (FIG. 24A-B). Serial evaluations by echocardiogram did not reveal any signs of cardiotoxicity, despite providing nearly 12-fold the lifetime MTD (FIG. 24C). This suggests that tetrazine-modified gel injected locally, followed by intravenous TCO-doxorubicin pro-drug can drastically improve the safety of systemic medications, even in large animals.

Example 36

Maximum Tolerated Dose (MTD) and In Vivo Efficacy of TAG and TCO-Prodrug in a Collagen-Induced Arthritis Model in Rats (Prophetic Example)

An acute (single-dose) 7-Day Up or down maximum tolerable dose (MTD) study can be performed in Sprague-Dawley Rats for 3 rounds for TCO-PLX3397 and PLX3397 administered intravenously. Results from this study will help inform dosage levels for subsequent single-dose and repeat-dose studies based on tolerability. Initial dosage is based on the previously examined intravenous concentration of PLX3397 of 1 mg/kg. This study is envisioned to employ 3 groups of 3 male and 3 female rats for each compound (36 animals total). For 7 days following dosage, toxicity may be measured by weight loss and body condition score, with the MTD threshold defined as a 10% drop in body weight at any point during the study. Based on the reported side effects of PLX3397, rats may also be monitored for fatigue and diarrhea and blood draws (200 μL) performed daily to screen for anemia, hyponatremia, and neutropenia. After 7 days, animals may be sacrificed and gross tissue histology to assay for tissue damage and inflammation. At the end of 3 rounds, the highest dose with no overt toxicities is deemed the MTD. The number of animals to be used in each group is consistent with standard protocols for toxicokinetic profiling in rats.

Once basic toxicity profiles have been established, the in vivo efficacy of TAG and CSF1R inhibitor prodrug may be evaluated. Currently, there are no reliable xenograft models of TGCT; thus a collagen-induced arthritis model in rodents is envisioned to be used, based on literature precedent for using this preclinical model to enable clinical trials of a CSF1R inhibitor to treat TGCT8. The disease model can be induced based on established protocols. Briefly, female Lewis rats can be injected (subcutaneously into tail) with collagen in complete Freund's adjuvant on day 1 and day 7. Treatment begins 7 days after the second collagen injection, once animals have developed observable arthritic symptoms. After confirming signs of arthritis in both hind limbs, TAG is injected into one of the hind limb knee joints, and control gel is injected into the opposite knee join. TCO-PLX3397, PLX3397, or saline vehicle is administered intravenously as a single dose at the determined MTD levels. Animals can be monitored for 24 days post treatment, and response quantified by disease scoring twice weekly. At the study endpoint, animals can be sacrificed and the excised limbs assayed by histology for inflammation, cartilage and bone damage, and macrophage infiltration. 7 animals can be used for each treatment arm (21 animals total). This study may demonstrate proof-of-concept for using the TAG platform for the local activation of CSF1R inhibitors to treat joint disorders.

The placement of the TCO-modification on the molecule is expected to significantly impact CSF1R binding interactions, resulting in reduced side effects and a much higher MTD. If MTD values are comparable, the modification site can be reinvestigated. The combination of TAG and TCO-PLX3397 is expected to result in a dramatic reduction of arthritic symptoms as quantified by disease score and histology, with fewer side effects than the parent drug. Unmodified gel can serve as an internal control to confirm the localization of drug activity. No problems with gel placement are expected. In the event that TCO-PLX3397 is comparable to saline control, biodistribution tests can be performed using LC-MS to determine the extent of drug release and accumulation within target and non-target tissues.

Example 37

Multidose Release of Payload from TCO Conjugates

Saturated aqueous calcium sulfate is added to alginate TAG in a tube and transferred to a spin column. A 1 mM stock solution in DMSO of Dapto-TCO-Glycine (Example 13B) or Vanco-Bis-TCO-Glycine (Example 13C) was prepared. The conjugates were added to the TAG solution in PBS at final concentration of 6.25 μM. Daptomycin or vancomycin release is measured by LC-MS. Repeat dosing of TCO-conjugate every 24 hours. The release results are shown in FIGS. 41A and 41B. Multidose release is also envisioned for tetrazine-modified hyaluronic acid and other materials.

Bis-TCO Vanco-Glycine (Example 13C) was tested in vitro for activity against MRSA bacteria using calorimetry both in the presence and absence of TAG. The results presented in the table below show that the MHIC is 8× higher in the absence of TAG, indicating release of active drug on contact with the TAG.

In Vitro Calorimetry (MRSA)

| | MHIC (µM) - MRSA | |
|---|---|---|
| Prodrug | TAG | Ctrl Gel |
| Bis-TCO-vanco | 4 | 32 |

Example 38

Multidose Release of Payload from TCO Conjugate In Vivo

Neutropenic female CD-1 mice were infected with MRSA (ATCC 43300) in the thigh muscle. Mice received tetrazine-modified hyaluronic acid gel mixed with the bacteria. After 2 hours, two groups of mice received a dose of either TCO-Dapto-Glycine (Example 13B) or unconjugated daptomycin at 61.74 µmol/kg (100 mg/kg daptomycin equivalent). A third and fourth group of mice received either TCO-Dapto-Glycine (Example 13B) or unconjugated daptomycin at 30.87 µmol/kg/day (50 mg/kg daptomycin equivalent) for three days. Twenty-four hours after each treatment, the mice were sacrificed, their thigh tissue was harvested and bacterial CFU was counted. The results are shown in FIG. 42. Statistical analysis was done by one-way ANOVA with Sidak's post-test for multiple comparisons. Error bars represent the standard error over mean of n=3, $*p<0.01$, $\#p<0.05$.

Example 39

Biocompatibility and Treatment of Implanted Device-Related Infection (Prophetic Example)

The ability of HAT to activate TCO-prodrugs when coated upon catheter materials may be determined as follows. To sections of HAT-coated PU or PVC tubing may be added a solution of previously synthesized and characterized TCO-vancomycin. Upon incubation with HAT-coated materials, the prodrug will react and release free vancomycin into solution. Release kinetics may be determined by LC-MS analysis. A control using unmodified HA-coated materials will confirm that the release is tetrazine-dependent. These studies will establish that the HAT retains its prodrug activating properties when bonded to a surface.

The antimicrobial effect of HAT-coated PU and PVC can be measured through determining minimum inhibitory concentration (MIC) of prodrugs to kill *S. epidermidis* and methicillin-resistant *S. aureus* (MRSA), two common pathogens responsible for CVC-associated infections, in culture. The antibiotic prodrugs chosen can be TCO-vancomycin or TCO-daptomycin. Serial dilutions of antibiotic prodrugs or corresponding standard antibiotics (vancomycin and daptomycin) would be used as positive controls and allow them to mix in the presence of HAT-coated PU or PVC tubing for 4 hours. Then, MRSA or *S. epidermidis* in broth can be added to the mixture. Plates may be placed in an incubator overnight and allowed to grow (n=4 for each test condition). Bacterial suspensions may then be plated on *staphylococcus*-selective mannitol salt agar plates and growth inhibition determined by counting of colony forming units (CFU). Controls utilizing unmodified-HA or no antibiotic can be included to ensure that antibacterial effects are due to activate of prodrugs by the gel.

Efficacy of the HAT-coated PU and PVC tubing in rats may be determined as follows using a central venous catheter model in specific-pathogen-free Sprague-Dawley rats. Rats would undergo HAT-coated catheter implantation into the jugular vein using established surgical protocols. Catheters coated with unmodified HA will serve as controls. After catheterization, rats can be inoculated with *S. epidermidis* or *S. aureus* through injection of 104-106 CFU into the catheter lumen. A pilot study can be performed to determine the infectious dose of the infectious agent chosen. Prodrugs or conventional antibiotics can be administered intravenously (tail vein) at established maximum tolerated dose levels 24 hours after infection, with saline injection as a negative control. Rats can be monitored daily for body weight, body condition score, and behavior. After 7 days, animals can be sacrificed. Explanted catheters are to be transected and sonicated to deadhere any attached bacteria, which will be measured by quantitative culture on *staphylococcus*-selective agar plate. Tissue surrounding the implant can be homogenized and bacterial burden assessed by the same method.

Biocompatibility of HAT-coated materials and TCO prodrugs can be determined through measuring the morbidity in Sprague-Dawley rats implanted with HAT-coated catheters. HAT-coated catheters can be implanted as described above. Unmodified HA-coated catheters would be used as control implants. Prodrug, standard antibiotic, or saline can then be administered intravenously at the concentrations used in the infection study. Rats can again be monitored daily for body weight, body condition score, and behavior. A loss of 10% body weight at any point will constitute the study endpoint. After 7 days, animals are to be sacrificed, and gross tissue histology, particularly of the region surrounding the implant, performed to determine the presence of irritation, tissue damage or inflammation.

7. Kits

Aspects of the present disclosure include kits that have a composition as described herein. For example, a kit may include a support composition as described herein. Embodiments of the kit may also include a functionalized payload as described herein. In certain embodiments, the kit may include a composition (e.g., support composition and/or functionalized payload) and a packaging configured to contain the composition (e.g., support composition and/or functionalized payload). The support composition and the functionalized payload may be in separate containers in the packaging. One or more support compositions may be provided in a kit. Similarly, one or more functionalized payloads may be provided in a kit. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

In certain embodiments, the kit includes a reagent that may be used as the releasing agent for a releasable linker as described herein. The releasing reagent may be any one of the releasing agents described herein, such as, but not limited to, a chemical releasing agent (e.g., an acid, a base, an oxidizing agent, a reducing agent, etc.), a solvent, and the like. The releasing reagent in the kit may be provided in any convenient form, such as, but not limited to, a gas, a solution, a solid, granules, a powder, a suspension, and the like. The releasing reagent may be packaged in a separate container from the composition(s) in the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another form for the instructions would be a computer readable medium, e.g., CD, DVD, Blu-Ray, computer-readable memory (e.g., flash memory), etc., on which the information has been recorded or stored. Yet another form for the instructions that may be present is a website address which may be used via the Internet to access the information at a removed site. Any convenient means may be present in the kits.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A compound of formula (I-A), or a salt thereof wherein

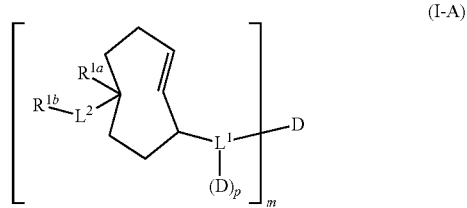

(I-A)

$R^{1a}$ is selected from the group consisting of $C_{1-4}$alkyl, $C_{1-4}$haloalkyl, and $C_{1-4}$alkoxy;
$R^{1b}$ is selected from the group consisting of $G^1$, OH, —$NR^{1c}$—$C_{1-4}$alkylene —$G^1$, —$NR^{1c}$—$C_{1-4}$alkylene —$N(R^{1d})_2$, —$N(R^{1c})CHR^{1e}CO_2H$, —$N(R^{1c})$—$C_{1-6}$alkylene —$CO_2H$, —$N(R^{1f})$—$C_{2-4}$alkylene —$(N(C_{1-4}$alkylene —$CO_2H)$—$C_{2-4}$alkylene$)_n$—$N(C_{1-4}$alkylene —$CO_2H)_2$, —$N(R^{1c})CHR^cC(O)OC_{1-6}$alkyl, —$N(R^{1c})$—$C_{1-6}$alkylene —$C(O)OC_{1-6}$alkyl, and —$N(R^{1f})$—$C_{2-4}$alkylene —$(N(C_{1-4}$alkylene —$C(O)OC_{1-6}$alkyl)—$C_{2-4}$alkylene$)_n$—$N(C_{1-4}$alkylene —$C(O)OC_{1-6}$alkyl)_2$;

$R^{1c}$ and $R^{1d}$, at each occurrence, are independently hydrogen or $C_{1-4}$alkyl;
$R^{1e}$ is —$C_{1-4}$alkylene —$CO_2H$, —$C_{1-4}$alkylene —$CONH_2$, or —$C_{1-4}$alkylene —$OH$;
$R^{1f}$ is hydrogen, $C_{1-6}$alkyl, or $C_{1-4}$alkylene —$CO_2H$;
D, at each occurrence, is independently a payload comprising a therapeutic agent or a diagnostic agent;
-$L^1$- is a linker;
-$L^2$- is selected from the group consisting of —C(O)— and $C_{1-3}$alkylene;
$G^1$ is an optionally substituted heterocyclyl;
m is 1, 2, or 3
n is 0, 1, 2, or 3; and
p is 0, 1, or 2.

2. The compound of claim 1, or a salt thereof, wherein
$R^{1b}$ is selected from the group consisting of $G^1$, OH, —$NR^{1c}$—$C_{1-4}$alkylene —$G^1$, —$NR^{1c}$—$C_{1-4}$alkylene —$N(R^{1d})_2$, —$N(R^{1c})CHR^{1c}CO_2H$, —$N(R^{1c})CH_2CO_2H$, and —$N(R^{1f})$—$CH_2CH_2$—$(N(CH_2CO_2H)CH_2CH_2)_n$—$N(CH_2CO_2H)_2$;
$R^{1e}$ is —$CH_2CO_2H$, —$CH_2CH_2CO_2H$, —$CH_2CONH_2$, —$CH_2CH_2CONH_2$, —$CH_2OH$, or —$CH(CH_3)OH$; and
$R^{1f}$ is hydrogen or $CH_2CO_2H$.

3. The compound of claim 1, or a salt thereof, wherein
$R^{1a}$ a is $C_{1-4}$alkyl;
$R^{1b}$ is selected from the group consisting of $G^1$, OH, —$NR^{1c}$—$C_{1-4}$alkylene —$G^1$, —$NR^{1c}$—$C_{1-4}$alkylene —$N(R^{1d})_2$, —$N(R^{1c})CHR^{1c}CO_2H$, —$N(R^{1c})CH_2CO_2H$, and —$N(R^{1f})$—$CH_2CH_2$—$(N(CH_2CO_2H)CH_2CH_2)_n$—$N(CH_2CO_2H)_2$;
$R^{1e}$ is —$C_{1-4}$alkylene —$CO_2H$;
$R^{1f}$ is hydrogen or $C_{1-4}$alkylene —$CO_2H$;
$G^1$ is a 4- to 8-membered monocyclic heterocyclyl containing a first nitrogen and optionally one additional heteroatom selected from nitrogen, oxygen, and sulfur, $G^1$ being attached at the first nitrogen and optionally substituted with 1-4 substituents independently selected from the group consisting of $C_{1-4}$alkyl, $C_{1-4}$haloalkyl, halo, cyano, OH, —$OC_{1-4}$alkyl, and oxo; and
n is 0, 1, or 2.

4. The compound of claim 3, or a salt thereof, wherein
$R^{1a}$ is $CH_3$;
$R^{1e}$ is —$CH_2CO_2H$;
$R^{1f}$ is hydrogen or $CH_2CO_2H$; and
$G^1$ is a piperazinyl, morpholinyl, piperidinyl, azepanyl, or pyrrolidinyl, attached through a ring nitrogen atom and optionally substituted with 1-4 substituents independently selected from the group consisting of $C_{1-4}$alkyl, $C_{1-4}$haloalkyl, halo, cyano, OH, —$OC_{1-4}$alkyl, and oxo.

5. The compound of claim 1, or a salt thereof, wherein -$L^2$- is —C(O)—.

6. The compound of claim 5, or a salt thereof, wherein $R^{1b}$ is selected from the group consisting of OH, N(H)$CH_2CO_2H$, —$N(H)CHR^{1c}CO_2H$, —$N(H)$—$CH_2CH_2$—$(N(CH_2CO_2H)CH_2CH_2)_n$—$N(CH_2CO_2H)_2$, and —$N(CH_2CO_2H)$—$CH_2CH_2$—$N(CH_2CO_2H)_2$; and
$R^{1c}$ is —$CH_2CO_2H$.

7. The compound of claim 6, or a salt thereof, wherein $R^{1b}$ is OH.

8. The compound of claim 6, or a salt thereof, wherein $R^{1b}$ is N(H)$CH_2CO_2H$.

9. The compound of claim 1 of formula (I), or a pharmaceutically acceptable salt thereof
wherein

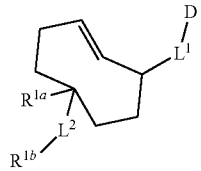
(I)

$R^{1a}$ is selected from the group consisting of $C_{1-4}$alkyl, $C_{1-4}$haloalkyl, and $C_{1-4}$alkoxy;
-$L^2$- is selected from the group consisting of —C(O)— and $C_{1-3}$alkylene;
$R^{1b}$ is selected from the group consisting of $G^1$, OH, —NR$^{1c}$—$C_{1-4}$alkylene —$G^1$, and —NR$^{1c}$—$C_{1-4}$alkylene —N(R$^{1d}$)$_2$;
$G^1$ is an optionally substituted heterocyclyl; and
$R^c$ and $R^{id}$, at each occurrence, are independently hydrogen or $C_{1-4}$alkyl.

10. The compound of claim 1, or a salt thereof, wherein:
-$L^1$- is

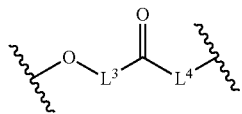

or —O—;
-$L^3$- is a bond or $C_{1-6}$alkylene;
-$L^4$- is a bond, —NHN:,—N(R$^{10}$) —$C_{2-6}$alkylene-N(R$^{11}$)—, —N(R$^{12}$)—$C_{2-3}$ alkylene —N(R$^{13}$)C(O)—, —N(R$^{10}$)—$C_{1-6}$alkylene —C(O)NHN:, —NHNHC(O)$C_{1-6}$alkylene-C(O)NHN:, —CH(NHC(O)R$^{14}$) $C_{1-4}$alkylene-S—S—$C_{1-4}$alkylene —OC(O)—, —NHNHC(O)CH(NHC(O)R$^{15}$)CH$_2$C(O)—, —$C_{1-6}$alkylene —CH(G$^x$)OC(O)—,

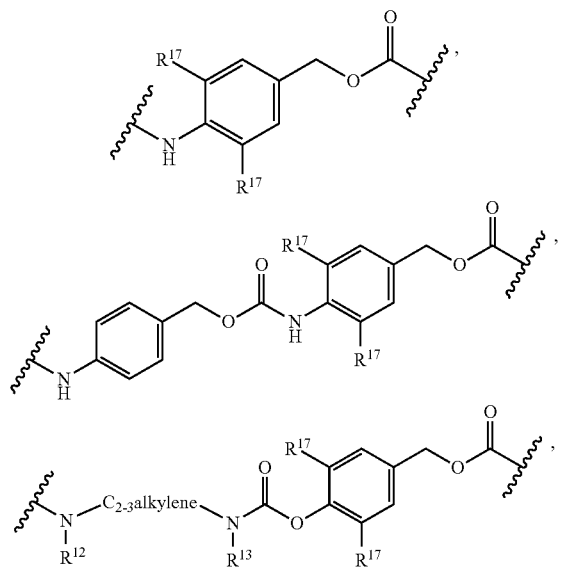

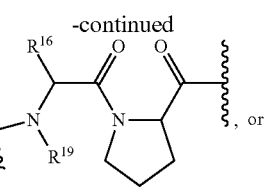, or

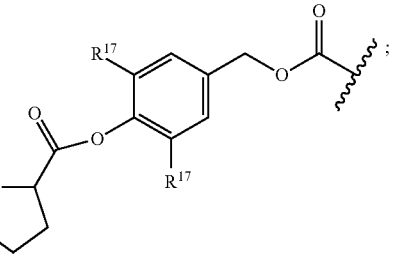;

$R^{10}$, $R^{11}$, $R^{12}$, $R^{13}$, $R^{14}$, $R^{15}$, and $R^{19}$ are each independently hydrogen or $C_{1-4}$alkyl;
$R^{16}$ is hydrogen, $C_{1-4}$alkyl, —$C_{1-4}$alkylene —OH, —$C_{1-4}$alkylene —OC$_{1-4}$alkyl, —$C_{1-4}$alkylene —CO$_2$H, or —$C_{1-4}$alkylene —CONH$_2$;
$R^{17}$, at each occurrence, is independently hydrogen or —CH$_2$OC(O)—; and
$G^X$ is phenyl optionally substituted with 1-5 substituents independently selected from the group consisting of halogen, $C_{1-4}$alkyl, $C_{1-4}$haloalkyl, C1-4alkoxy, cyano, and nitro.

11. The compound of claim 1, or a salt thereof, wherein:

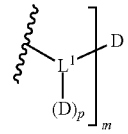

is

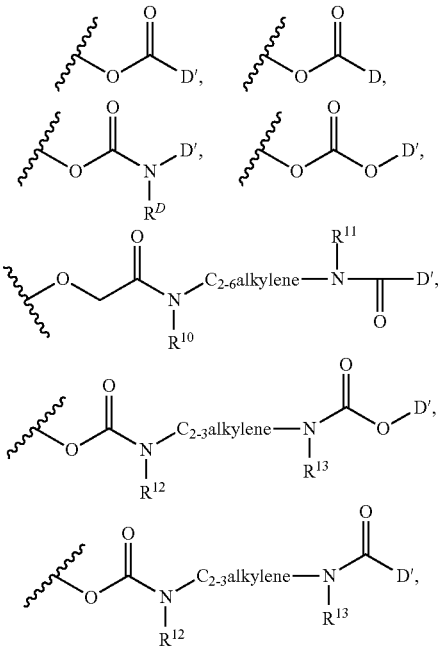

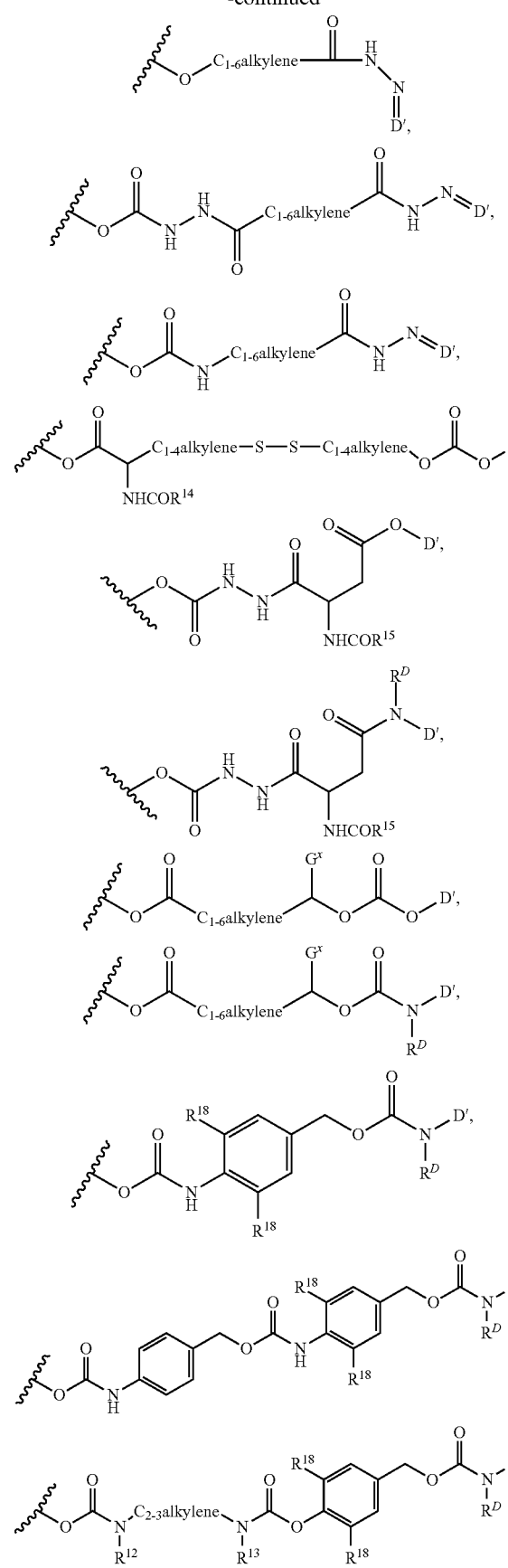
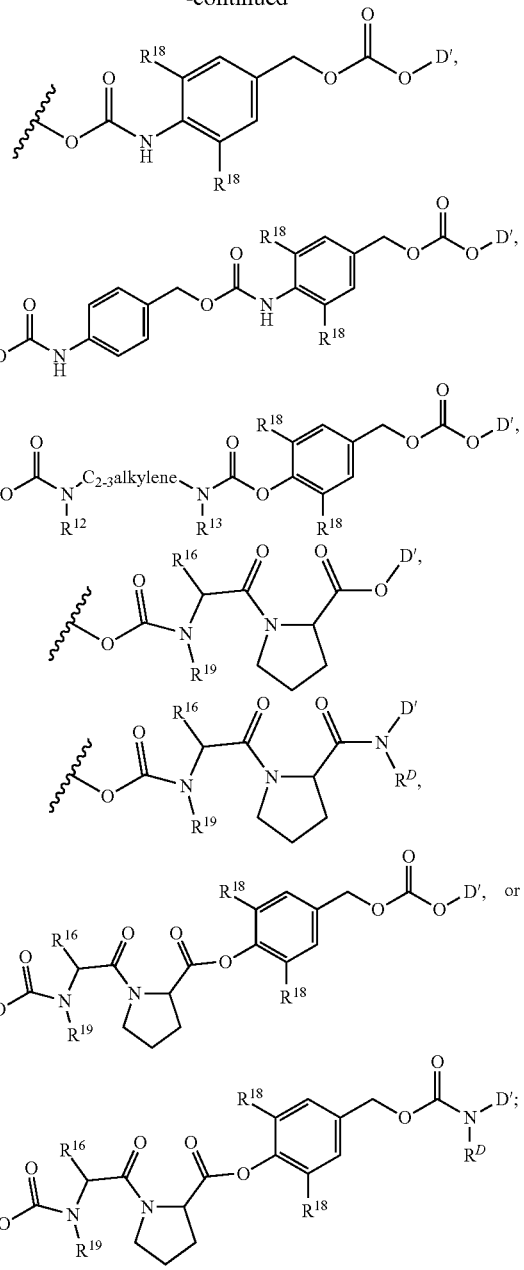
$R^{18}$ at each occurrence, is independently hydrogen or —CH$_2$OC(O)NHD';
$R^D$ is hydrogen or C$_{1-4}$alkyl on a nitrogen atom of the payload; and
D' is a payload moiety.
12. The compound of claim 1, or a salt thereof, wherein
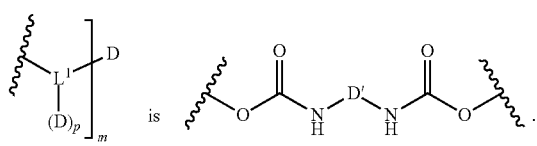
13. The compound of any of claim 1, or a pharmaceutically acceptable salt thereof, wherein the payload is a therapeutic agent.

14. The compound of claim 13, or a pharmaceutically acceptable salt thereof, wherein the therapeutic agent is an antibiotic agent, antifungal agent, antiviral agent, anticancer agent, cardiovascular agent, CNS agent, anti-inflammatory/anti-arthritic agent, anti-TB/anti-leprosy agent, anti-histaminic/respiratory disorder agent, a corticosteroid agent, immunosuppressant agent, or anti-ulcer agent.

15. The compound of claim 14, or a pharmaceutically acceptable salt thereof, wherein the therapeutic agent is selected from at least one of paclitaxel, doxorubicin, daunorubicin, etoposide, irinotecan, SN-38, docetaxel, gemcitabine, podophyllotoxin, carmustine, ixabepilone, patupilone, cyclosporin A, rapamycin, amphotericin, vancomycin, daptomycin, doxycycline, ceftriaxone, trimethoprim, sulfamethoxazole, acyclovir, nystatin, amphotericin B, flucytosine, emtricitabine, gentamicin, colistin, L-dopa, oseltamivir, cefalexin, 5-aminolevulinic acid, cysteine, celecoxib, and nimodipine.

16. The compound or pharmaceutically acceptable salt thereof of claim 15, wherein the compound is

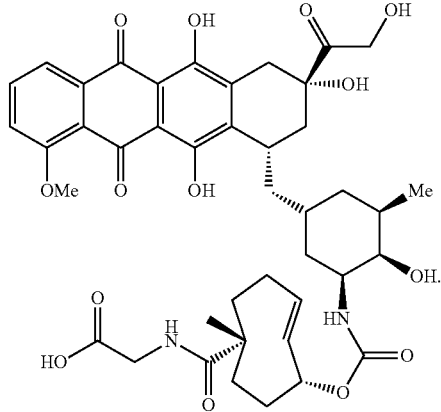

17. A pharmaceutical composition comprising the compound of claim 11, or a pharmaceutically acceptable salt thereof, and a pharmaceutically acceptable carrier.

18. A method of enhancing or eliciting an immune response comprising administering to a subject in need thereof, a therapeutically effective amount of the compound of claim 13, or a pharmaceutically acceptable salt thereof, wherein the therapeutically effective amount enhances or elicits an immune response against a cancer in the subject.

19. A kit comprising the compound of claim 13, or a pharmaceutically acceptable salt thereof, and instructions for use thereof.

20. The compound of any of claim 1, or a salt thereof, wherein the payload is a diagnostic agent.

21. A diagnostic composition comprising the compound of claim 20, or a salt thereof, and a pharmaceutically acceptable carrier.

22. A kit comprising the compound of claim 20, or a salt thereof, and instructions for use thereof.

23. The compound of claim 20, or a salt thereof, wherein the diagnostic agent is a fluorescein or a rhodamine.

24. The compound of claim 1, or a salt thereof, wherein: $R^{1b}$ is selected from the group consisting of OH, —$NR^{1c}$—$C_{1-4}$alkylene—$N(R^{1d})_2$, —$N(R^{1c})$CHR$^{1e}$CO$_2$H, —$N(R^{1c})$—$C_{1-6}$alkylene—CO$_2$H, —$N(R^{1f})$—$C_{2-4}$alkylene—(N($C_{1-4}$alkylene—CO$_2$H)—$C_{2-4}$alkylene)$_n$—N($C_{1-4}$alkylene—O$_2$H)$_2$, —$N(R^{1c})$CHR$^{1e}$C(O)OC$_{1-6}$alkyl, —$N(R^{1c})$C$_{1-6}$alkylene—C(O)OC$_{1-6}$alkyl, and —$N(R^{1f})$—$C_{2-4}$alkylene—N($C_{1-4}$alkylene—C(O)OC$_{1-6}$alkyl)—$C_{2-4}$alkylene)$_n$—N($C_{1-4}$alkylene—C(O)OC$_{1-6}$alkyl)$_2$; and —$L^2$— is —C(O)—.

25. The compound of claim 24, or a salt thereof, wherein: $R^{1b}$ is selected from the group consisting of OH, —$NR^{1c}$—$C_{1-4}$alkylene—$N(R^{1d})_2$, —$N(R^{1c})$CHR$^{1e}$CO$_2$H, —$N(R^{1c})$CH$_2$CO$_2$H, and —$N(R^{1f})$—CH$_2$CH$_2$—(N(CH$_2$CO$_2$H)CH$_2$CH$_2$)$_n$—N(CH$_2$CO$_2$H)$_2$;

$R^{1e}$ is —CH$_2$CO$_2$H, —CH$_2$CH$_2$CO$_2$H, —CH$_2$CONH$_2$, —CH$_2$CH$_2$CONH$_2$, —CH$_2$OH, or —CH(CH$_3$)OH; and $R^{1f}$ is hydrogen or CH$_2$CO$_2$H.

26. The compound of claim 24, or a salt thereof, wherein: $R^{1a}$ is $C_{1-4}$alkyl;

$R^{1b}$ is selected from the group consisting of OH, —$NR^{1c}$—$C_{1-4}$alkylene—$N(R^{1d})_2$, —$N(R^{1c})$CHR$^{1e}$CO$_2$H, —$N(R^{1c})$CH$_2$CO$_2$H, and —$N(R^{1f})$—CH$_2$CH$_2$—(N(CH$_2$CO$_2$H)CH$_2$CH$_2$)$_n$—N(CH$_2$CO$_2$H)$_2$;

$R^{1e}$ is —$C_{1-4}$alkylene—CO$_2$H;

$R^{1f}$ is hydrogen or $C_{1-4}$alkylene—CO$_2$H; and n is 0, 1, or 2.

27. The compound of claim 26, or a salt thereof, wherein: $R^{1a}$ is CH$_3$;

$R^{1e}$ is —CH$_2$CO$_2$H; and $R^{1f}$ is hydrogen or CH$_2$CO$_2$H.

* * * * *

UNITED STATES PATENT AND TRADEMARK OFFICE
CERTIFICATE OF CORRECTION

PATENT NO. : 11,253,600 B2  
APPLICATION NO. : 16/603471  
DATED : February 22, 2022  
INVENTOR(S) : Jose Manuel Mejia Oneto et al.

Page 1 of 1

It is certified that error appears in the above-identified patent and that said Letters Patent is hereby corrected as shown below:

In the Claims

At Column 149, at Lines 21-39 in Claim 16, replace the chemical drawing as follows:

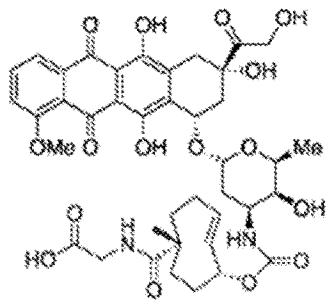

Signed and Sealed this  
Fourth Day of March, 2025

Coke Morgan Stewart  
*Acting Director of the United States Patent and Trademark Office*